(12) United States Patent
Eide et al.

(10) Patent No.: US 11,272,841 B2
(45) Date of Patent: Mar. 15, 2022

(54) INDICATOR FLUIDS, SYSTEMS, AND METHODS FOR ASSESSING MOVEMENT OF SUBSTANCES WITHIN, TO OR FROM A CEREBROSPINAL FLUID, BRAIN OR SPINAL CORD COMPARTMENT OF A CRANIO-SPINAL CAVITY OF A HUMAN

(71) Applicant: BRAINWIDESOLUTIONS AS, Oslo (NO)

(72) Inventors: Per Kristian Eide, Oslo (NO); Geir Andre Ringstad, Oslo (NO)

(73) Assignee: BRAINWIDESOLUTIONS AS, Oslo (NO)

( * ) Notice: Subject to any disclaimer, the term of this patent is extended or adjusted under 35 U.S.C. 154(b) by 206 days.

(21) Appl. No.: 16/577,227

(22) Filed: Sep. 20, 2019

(65) Prior Publication Data
US 2020/0170509 A1    Jun. 4, 2020

Related U.S. Application Data

(63) Continuation-in-part of application No. 16/495,542, filed as application No. PCT/NO2018/050082 on Mar. 20, 2018, now abandoned.

(30) Foreign Application Priority Data

Mar. 23, 2017  (NO) .................................. 20170454
Mar. 23, 2017  (NO) .................................. 20170455
(Continued)

(51) Int. Cl.
*A61B 5/00*       (2006.01)
*A61B 6/00*       (2006.01)
(Continued)

(52) U.S. Cl.
CPC .......... *A61B 5/0035* (2013.01); *A61B 5/4088* (2013.01); *A61B 6/481* (2013.01);
(Continued)

(58) Field of Classification Search
CPC ........................... A61B 5/0036; A61B 5/4088
See application file for complete search history.

(56) References Cited

U.S. PATENT DOCUMENTS

2007/0016016 A1    1/2007  Haras et al.
2012/0179028 A1    7/2012  Caravan et al.
(Continued)

FOREIGN PATENT DOCUMENTS

EP      0793114 A1       9/1997
WO      WO-2009146388 A1  12/2009
(Continued)

OTHER PUBLICATIONS

Absinta M., et al., "Human and Nonhuman Primate Meninges Harbor Lymphatic Vessels That Can Be Visualized Noninvasively by MRI," *Elife*, 6:e29738, eLife Sciences Publications, Ltd., England, (Oct. 2017).
(Continued)

*Primary Examiner* — Joseph M Santos Rodriguez
(74) *Attorney, Agent, or Firm* — Sterne, Kessler, Goldstein & Fox P.L.L.C.

(57) ABSTRACT

The present invention discloses indicator fluids, reference indicator fluid, and usage thereof, and systems and methods for assessing movement of molecular substances within, to or from a cerebrospinal fluid, brain or spinal cord compartment of a human cranio-spinal cavity. Indicator fluid moving from the cerebrospinal fluid compartment enables measurements of levels of indicator fluid in blood or urine and assessment of the cranio-spinal cavity's ability to remove molecular substances. The indicator fluids may be contrast
(Continued)

agents used for imaging, such as by computed tomography imaging, and magnetic resonance imaging, or imaging utilizing radioactive substances by positron emission tomography, single-photon emission computed tomography or scintigraphy. Using these imaging modalities, the invention describes indicator fluids, systems and methods enabling assessment of movement of substances within, to or from a cerebrospinal fluid, brain or spinal cord compartment of a cranio-spinal cavity, and from the human cranio-spinal cavity to lymphatic pathways or kidneys.

27 Claims, 61 Drawing Sheets

(30) Foreign Application Priority Data

| Mar. 23, 2017 | (NO) | 20170456 |
|---|---|---|
| Mar. 23, 2017 | (NO) | 20170457 |
| Mar. 23, 2017 | (NO) | 20170460 |
| Mar. 23, 2017 | (NO) | 20170461 |
| Mar. 23, 2017 | (NO) | 20170462 |
| Mar. 23, 2017 | (NO) | 20170463 |
| Mar. 23, 2017 | (NO) | 20170464 |
| Mar. 23, 2017 | (NO) | 20170465 |
| Mar. 23, 2017 | (NO) | 20170466 |
| Mar. 23, 2017 | (NO) | 20170467 |
| Mar. 23, 2017 | (NO) | 20170468 |
| Mar. 23, 2017 | (NO) | 20170469 |
| Mar. 23, 2017 | (NO) | 20170470 |
| Mar. 23, 2017 | (NO) | 20170471 |
| Mar. 23, 2017 | (NO) | 20170472 |
| Mar. 23, 2017 | (NO) | 20170473 |
| Mar. 23, 2017 | (NO) | 20170474 |
| Mar. 23, 2017 | (NO) | 20170475 |

(51) Int. Cl.

| A61K 49/04 | (2006.01) |
|---|---|
| A61K 49/00 | (2006.01) |
| A61K 51/04 | (2006.01) |
| A61K 49/10 | (2006.01) |
| A61B 5/055 | (2006.01) |
| G01R 33/56 | (2006.01) |
| A61B 6/03 | (2006.01) |

(52) U.S. Cl.
CPC .......... *A61B 6/501* (2013.01); *A61K 49/0002* (2013.01); *A61K 49/0438* (2013.01); *A61K 51/048* (2013.01); *A61B 5/055* (2013.01); *A61B 5/4082* (2013.01); *A61B 5/748* (2013.01); *A61B 6/037* (2013.01); *A61B 2576/026* (2013.01); *A61K 49/0004* (2013.01); *A61K 49/106* (2013.01); *G01R 33/5601* (2013.01)

(56) References Cited

U.S. PATENT DOCUMENTS

| 2012/0238865 A1 | 9/2012 | Han |
| 2013/0200900 A1 | 8/2013 | Buurman et al. |
| 2015/0254421 A1 | 9/2015 | Bateman et al. |
| 2015/0297160 A1 | 10/2015 | Orcutt et al. |
| 2016/0260216 A1 | 9/2016 | Wu et al. |
| 2016/0367166 A1 | 12/2016 | Piron et al. |

FOREIGN PATENT DOCUMENTS

| WO | WO-2011069283 A1 | 6/2011 |
| WO | WO-2012049584 A1 | 4/2012 |
| WO | WO-2014130777 A1 | 8/2014 |
| WO | WO-2016132176 A1 | 8/2016 |
| WO | WO-2017223092 A1 | 12/2017 |
| WO | WO-2018174721 A2 | 9/2018 |

OTHER PUBLICATIONS

Aspelund, A., et al., "A Dural Lymphatic Vascular System That Drains Brain Interstitial Fluid and Macromolecules," *The Journal of Experimental Medicine*, 212(7):991-999, Rockefeller University Press, United States, (2015).

Benveniste, H., et al., "The Glymphatic Pathway: Waste Removal from the CNS via Cerebrospinal Fluid Transport," *Neuroscientist*, 23(5):454-465, Sage Publications, United States, (Oct. 2017).

Eide, P.K., and Ringstad, G., "MRI With Intrathecal MRI Gadolinium Contrast Medium Administration: a Possible Method to Assess Glymphatic Function in Human Brain," *Acta Radiologica Open*, 4(11):1-5, Sage, England, (2015).

Hahn, G., et al., "Pharmacokinetics and Safety of Gadobutrol-enhanced Magnetic Resonance Imaging in Pediatric Patients," *Investigative Radiology*, 44(12):776-783, Lippincott Williams & Wilkins, United States, (2009).

Heit, J.J., and Wintermark, M., "Perfusion Computed Tomography for the Evaluation of Acute Ischemic Stroke: Strengths and Pitfalls," *Stroke*, 47(4):1153-1158, Lippincott Williams & Wilkins, United States, (Apr. 2016).

Hladky, S.B., and Barrand, M.A., "Mechanisms of Fluid Movement Into, Through and Out of the Brain: Evaluation of the Evidence," *Fluids and Barriers of the CNS*, 11:26, Biomed Central, England, (2014), 32 pages.

International Preliminary Report on Patentability for Application No. PCT/NO2018/050082, European Patent Office, HV Rijswijk, dated Jul. 24, 2019, 71 pages.

International Search Report and written opinion for International Application No. PCT/NO2018/050082, European Patent Office, HV Rijswijk, dated Nov. 7, 2018, 40 pages.

Invitation to Pay Additional Fees for International Searching Authority for Application No. PCT/NO2018/050082, European Patent Office, HV Rijswijk, dated Jul. 9, 2018, 23 pages.

Jost, G., et al., "Penetration and Distribution of Gadolinium-based Contrast Agents Into the Cerebrospinal Fluid in Healthy Rats: a Potential Pathway of Entry Into the Brain Tissue," *European Radiology*, 27(7):2877-2885, Springer International, Germany, (2017), published online Nov. 2016.

Koh, L., et al., "Integration of the Subarachnoid Space and Lymphatics: Is It Time to Embrace a New Concept of Cerebrospinal Fluid Absorption?," *Cerebrospinal Fluid Research*, 2:6, BioMed Central, England, (2005), 11 pages.

Louveau, A., et al., "Lymphatics in Neurological Disorders: A Neuro-Lympho-Vascular Component of Multiple Sclerosis and Alzheimer's Disease?," *Neuron*, 91(5):957-973, Cell Press, United States, (Sep. 2016).

Morris, A.W., et al., "Vascular Basement Membranes as Pathways for the Passage of Fluid Into and Out of the Brain," *Acta Neuropathologica*, 131(5):725-736, Springer Verlag, Germany, (2016), published online Mar. 2016.

Potter, G.M., et al., "Cerebral Perivascular Spaces Visible on Magnetic Resonance Imaging: Development of a Qualitative Rating Scale and its Observer Reliability," *Cerebrovascular Diseases*, 39(4):224-231, Karger, Switzerland, (2015).

Ramirez, J., et al., "Imaging the Perivascular Space as a Potential Biomarker of Neurovascular and Neurodegenerative Diseases," *Cellular and Molecular Neurobiology*, 36(2):289-299, Kluwer Academic/Plenum Publishers, United States, (2016), published online Mar. 2016.

Response to the PCT Written Opinion of the International Searching Authority for International Application No. PCT/NO2018/050082, European Patent Office, Munich, dated Jan. 25, 2019, 82 pages.

(56) References Cited

OTHER PUBLICATIONS

Response to the PCT Written Opinion of the International Searching Authority for International Application No. PCT/NO2018/050082, European Patent Office, Netherlands, dated May 20, 2019, 18 pages.
Ringstad, G., et al., "Glymphatic MRI in Idiopathic Normal Pressure Hydrocephalus," *Brain*, 140(10):2691-2705, Oxford University Press, England, (Aug. 2017).
Tarasoff-Conway, J.M., et al., "Clearance Systems in the Brain—Implications for Alzheimer Disease," *Nature Reviews Neurology*, 11(8):457-470, Nature Publishing Group, England, (2015).
Written Opinion of the International Preliminary Examining Authority for Application No. PCT/NO2018/050082, European Patent Office, HV Rijswijk, Apr. 25, 2019, 16 pages.
Zhelev, Z., et al., "Nitroxyl Radicals for Labeling of Conventional Therapeutics and Noninvasive Magnetic Resonance Imaging of Their Permeability for Blood-Brain Barrier: Relationship Between Structure, Blood Clearance, and MRI Signal Dynamic in the Brain," *Molecular Pharmaceutics*, 6(2):504-512, American Chemical Society, United States, (2009).

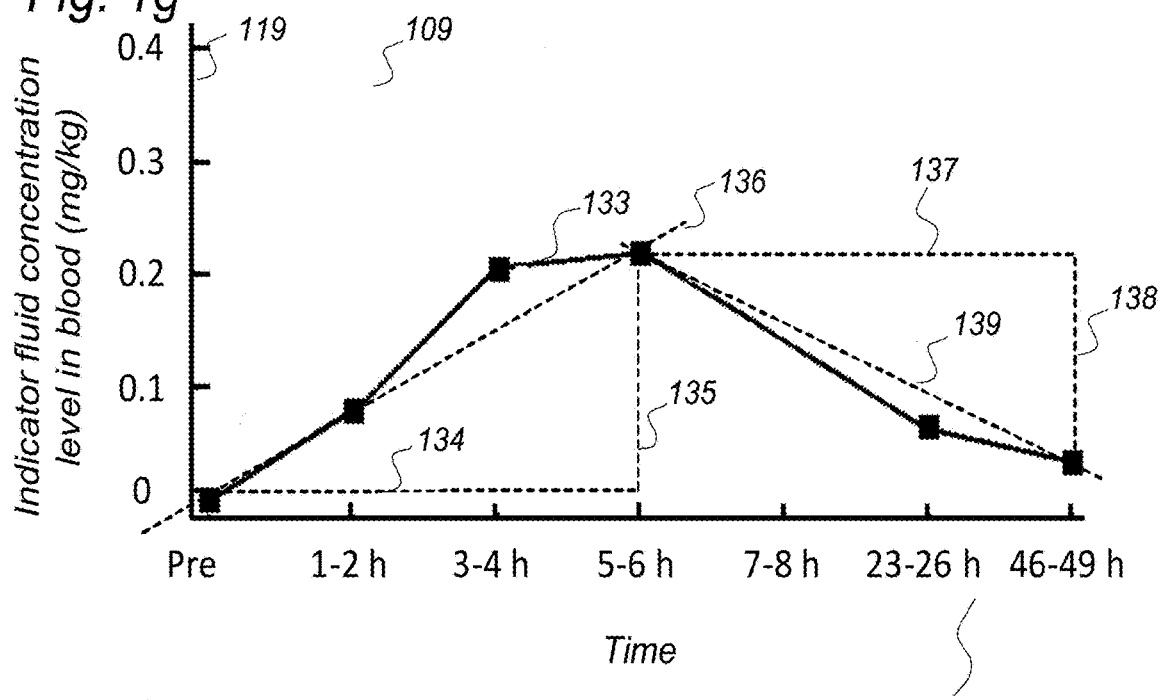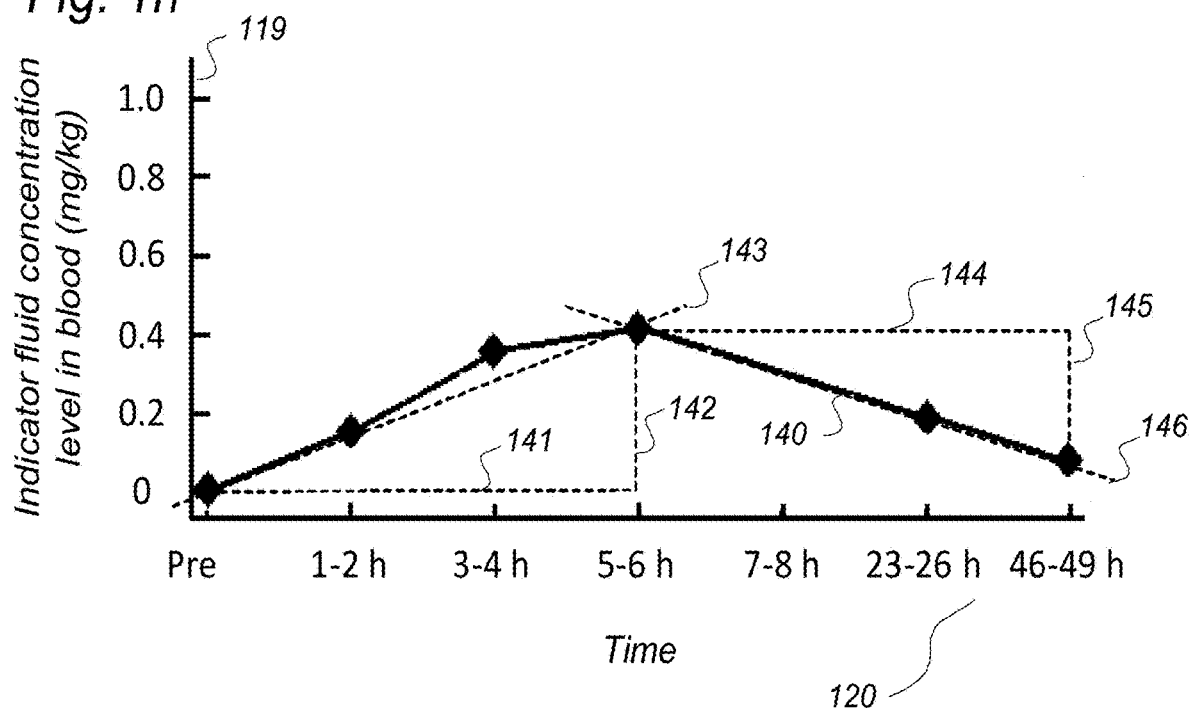

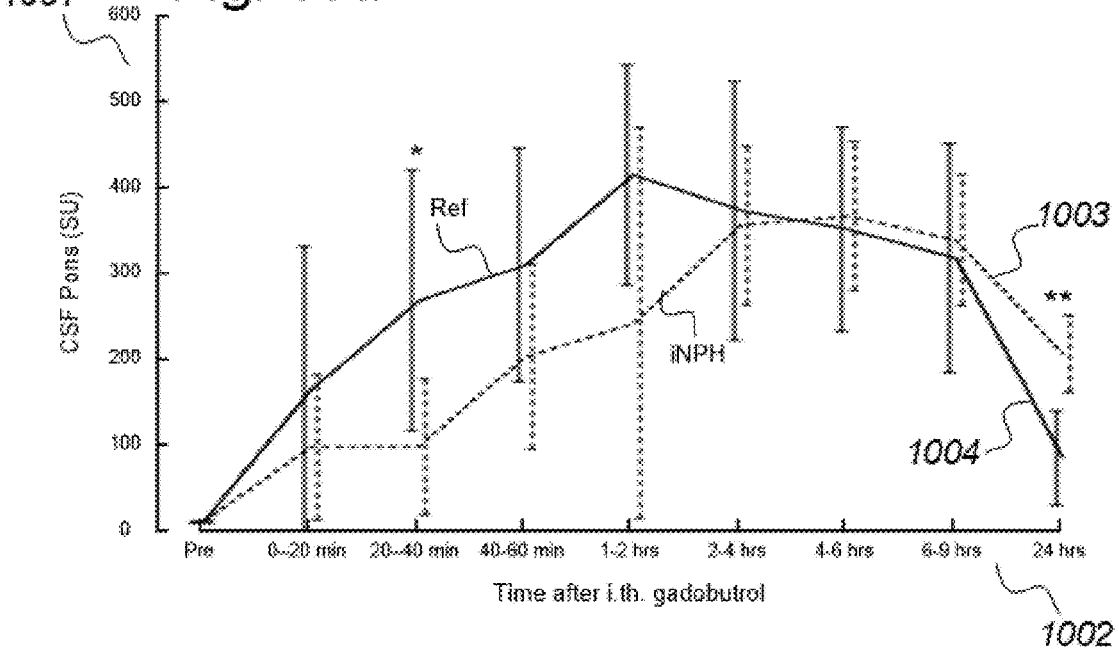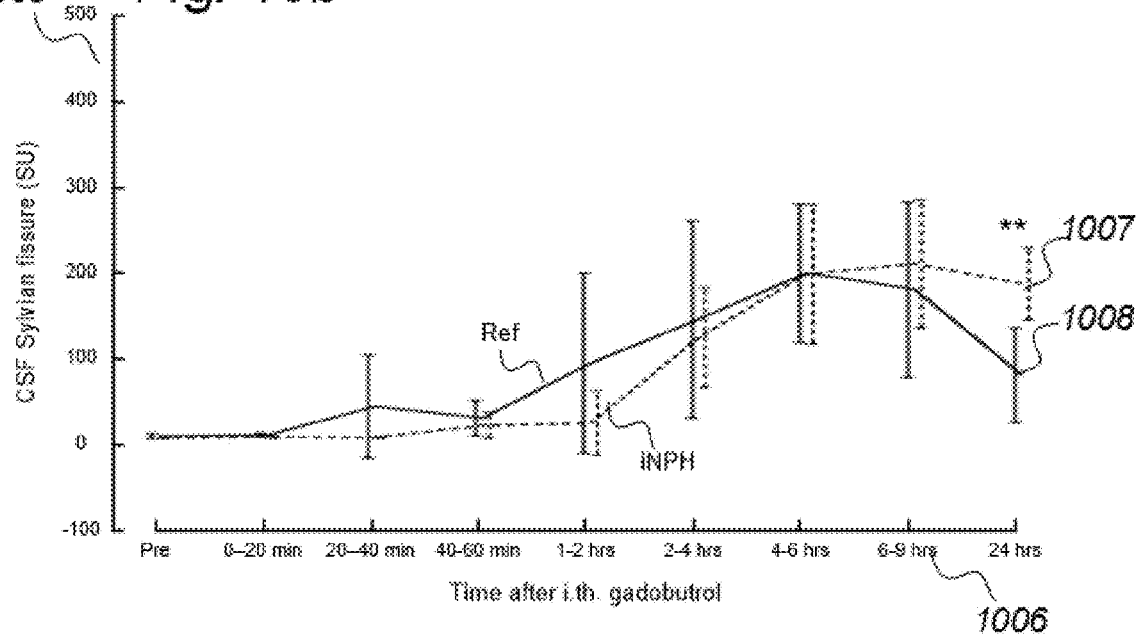

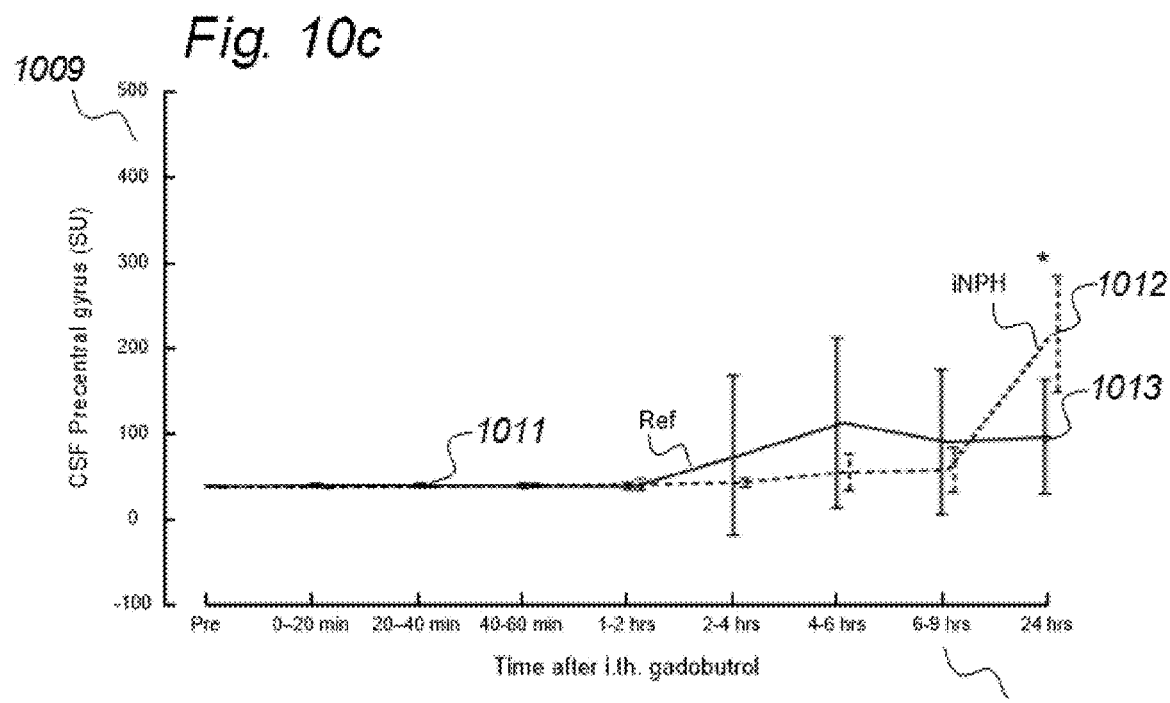
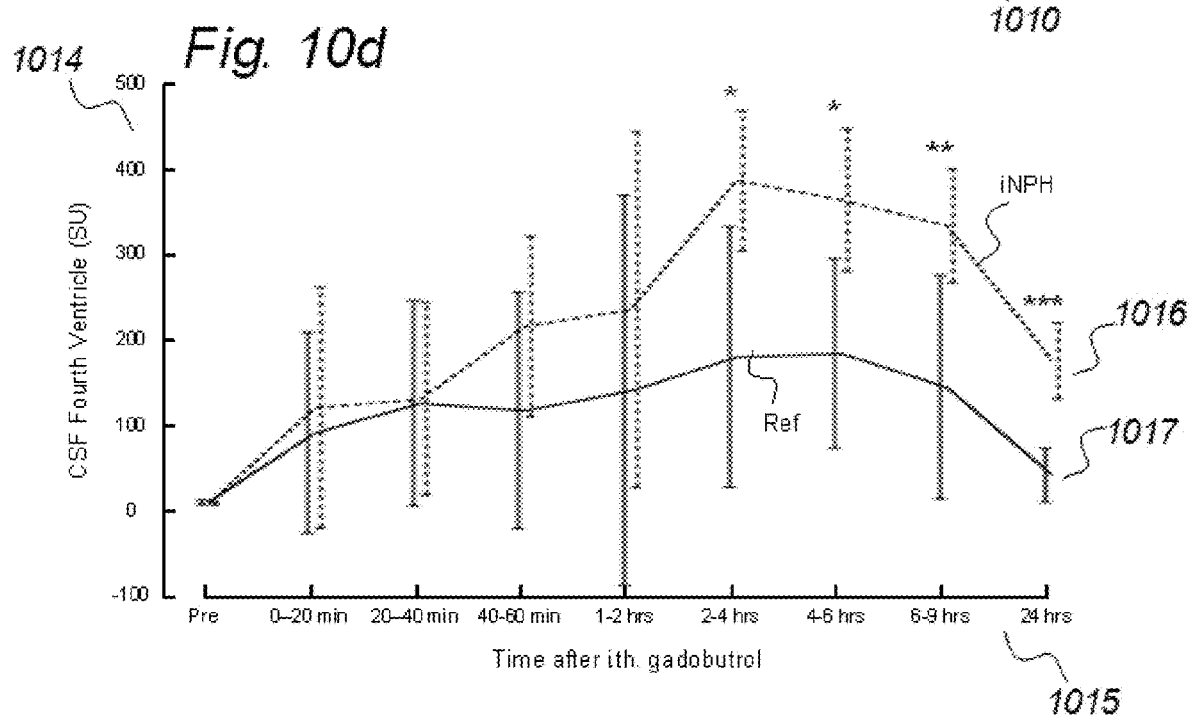

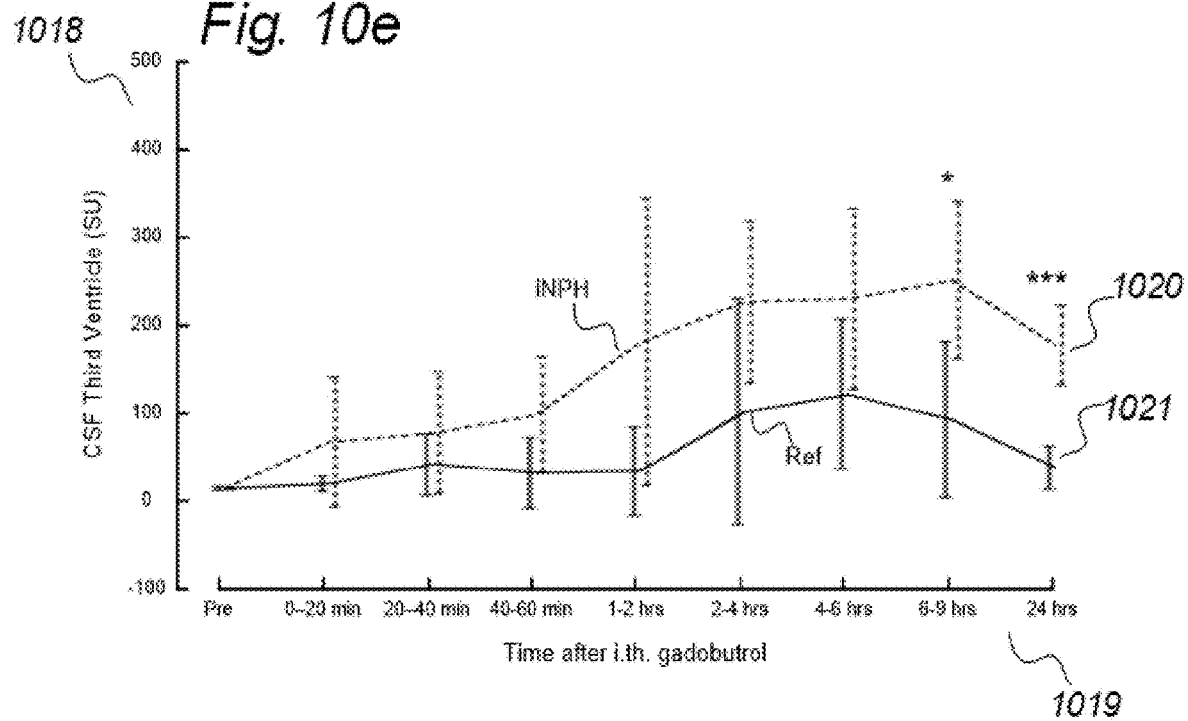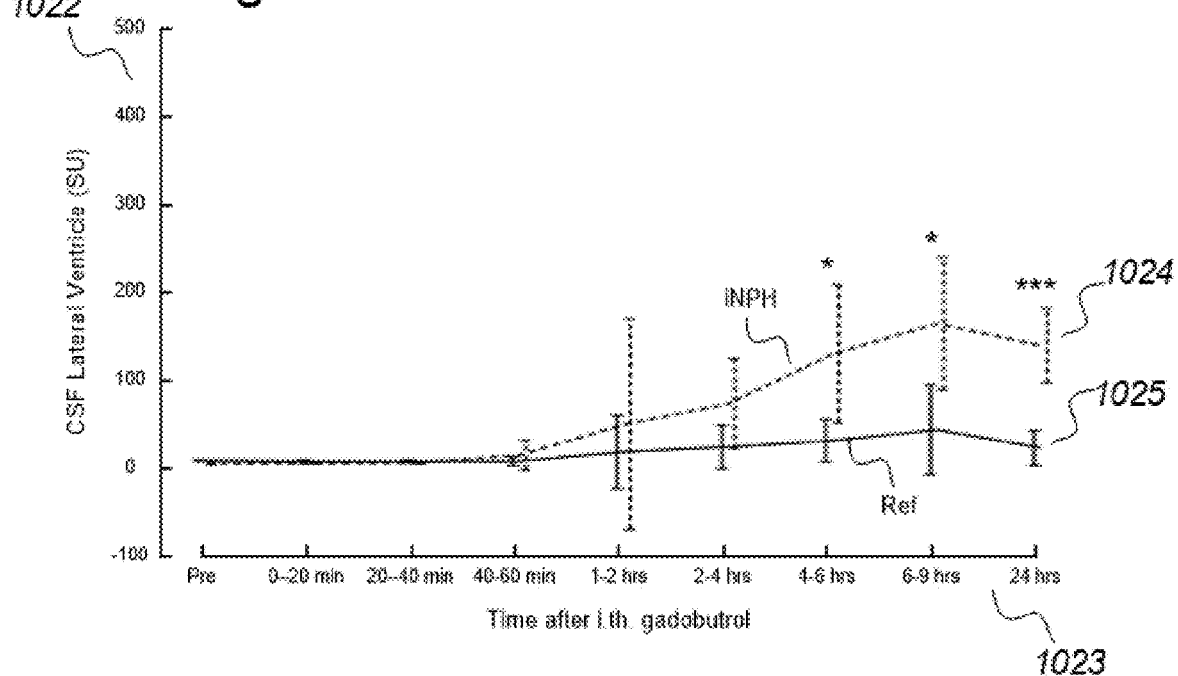

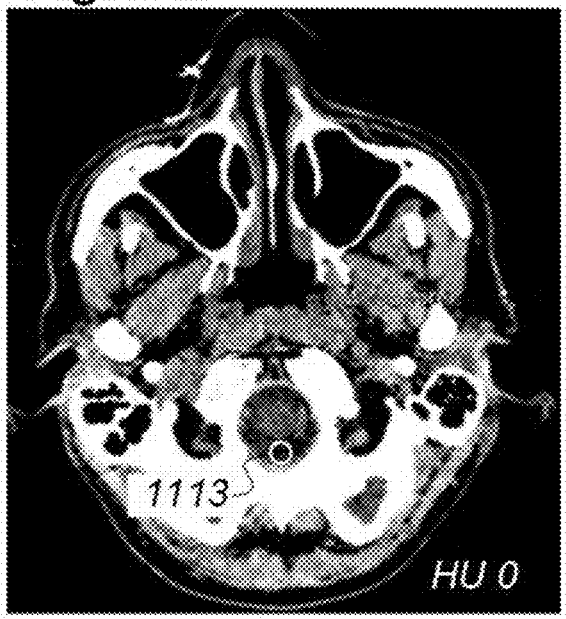
Fig. 11c — Pre — HU 0
Fig. 11d — After 2 hours — HU 31
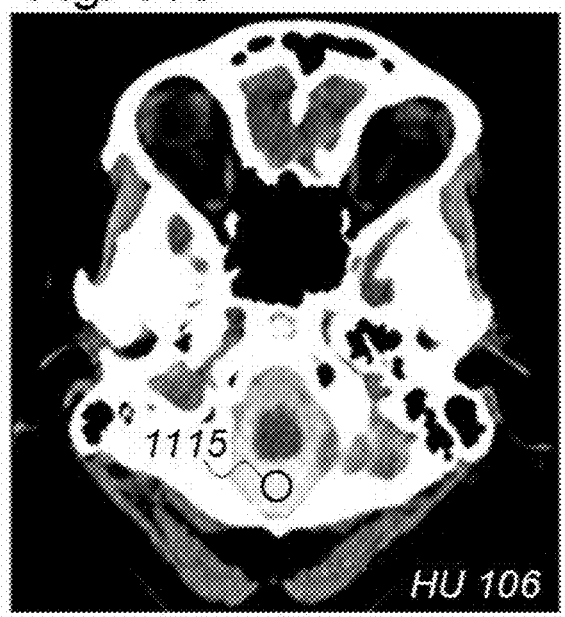
Fig. 11e — After 4 hours — HU 106
Fig. 11f — After 9 hours — HU 70

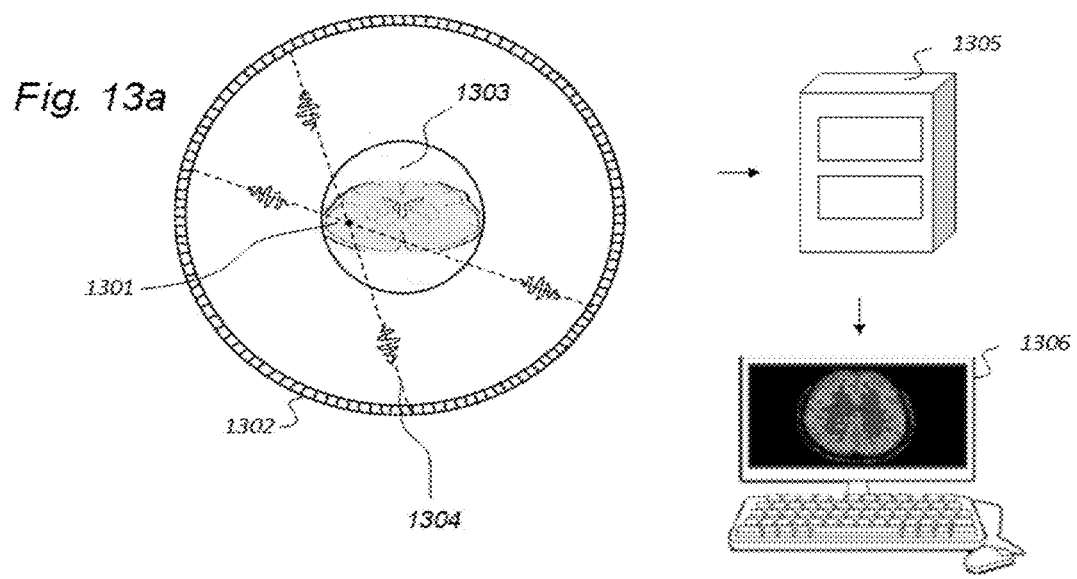
Fig. 13a
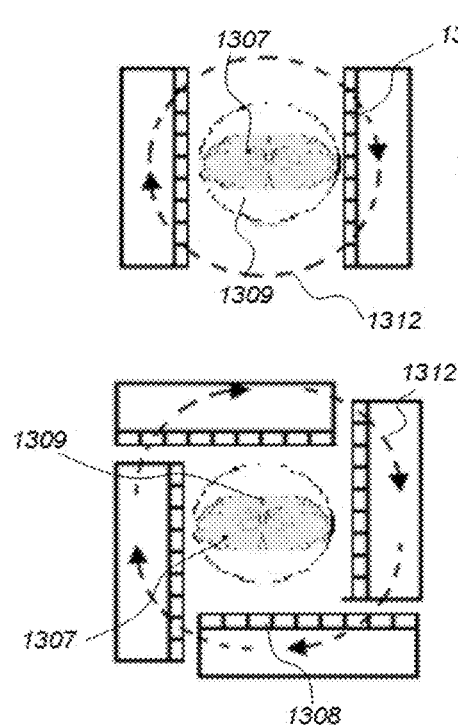
Fig. 13b
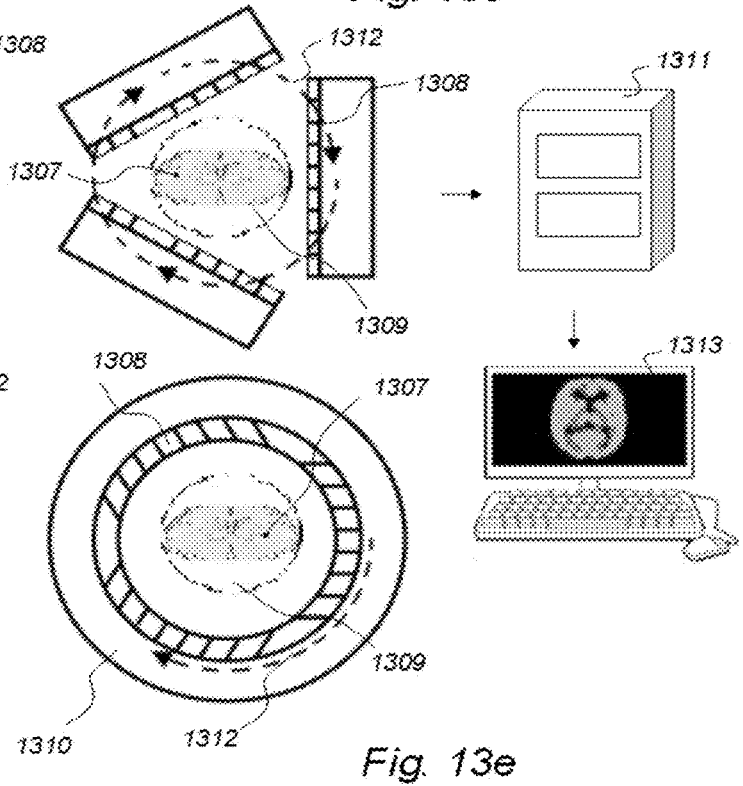
Fig. 13c
Fig. 13d
Fig. 13e

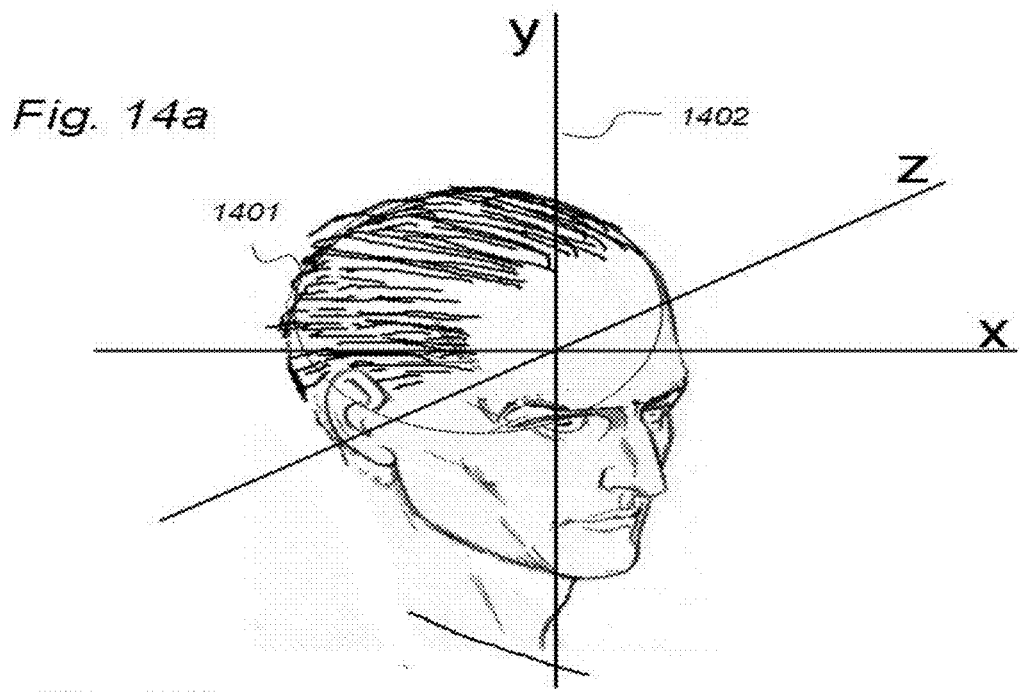
Fig. 14a
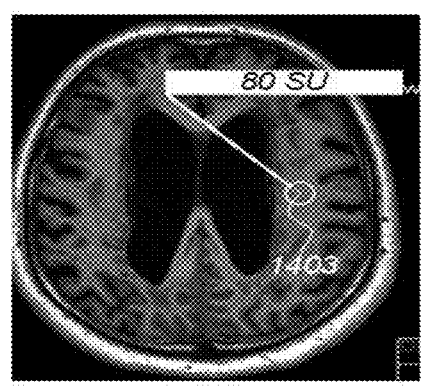
No gadobutrol
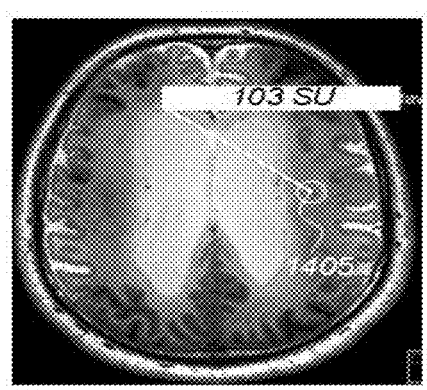
9 hrs after i.t.h. gadobutrol
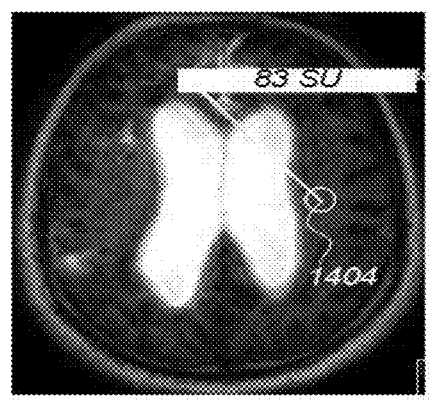
3 hr after i.t.h. gadobutrol
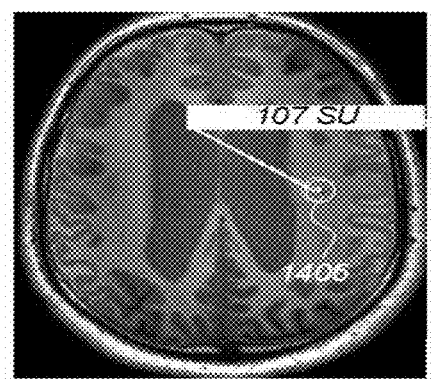
24 hrs after i.t.h. gadobutrol
Fig. 14b Time 1    Time 2    Time 1 + Time 2

Time 1    Time 2    Time 1 + Time 2

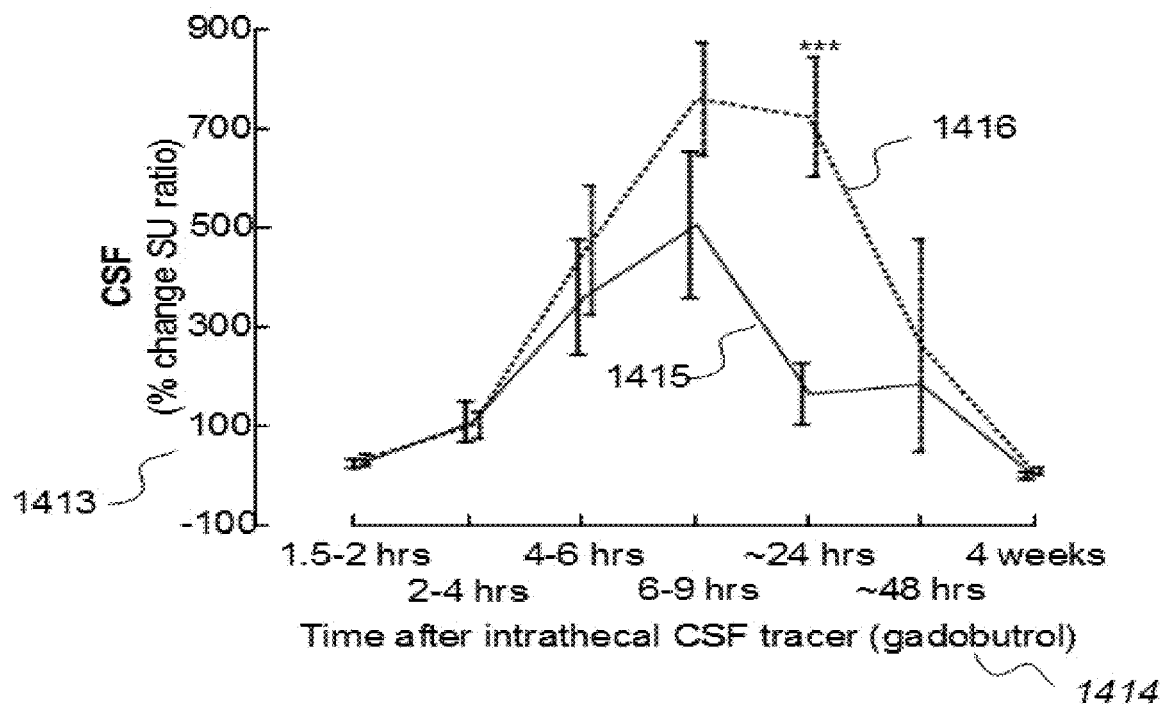
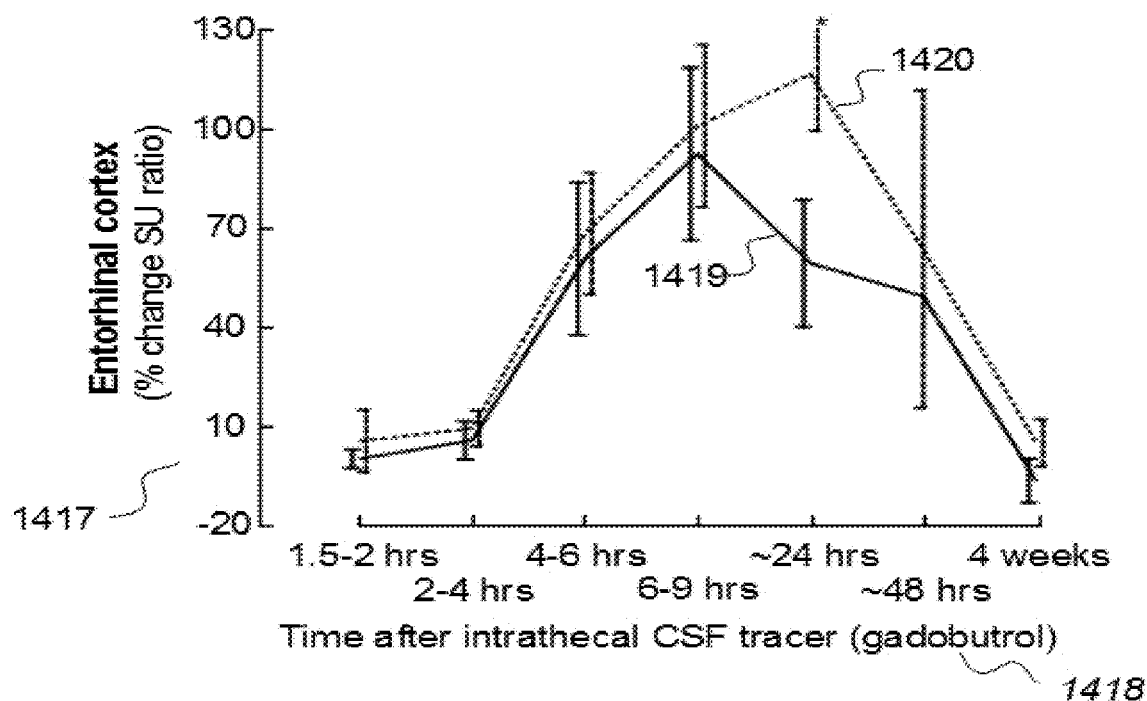

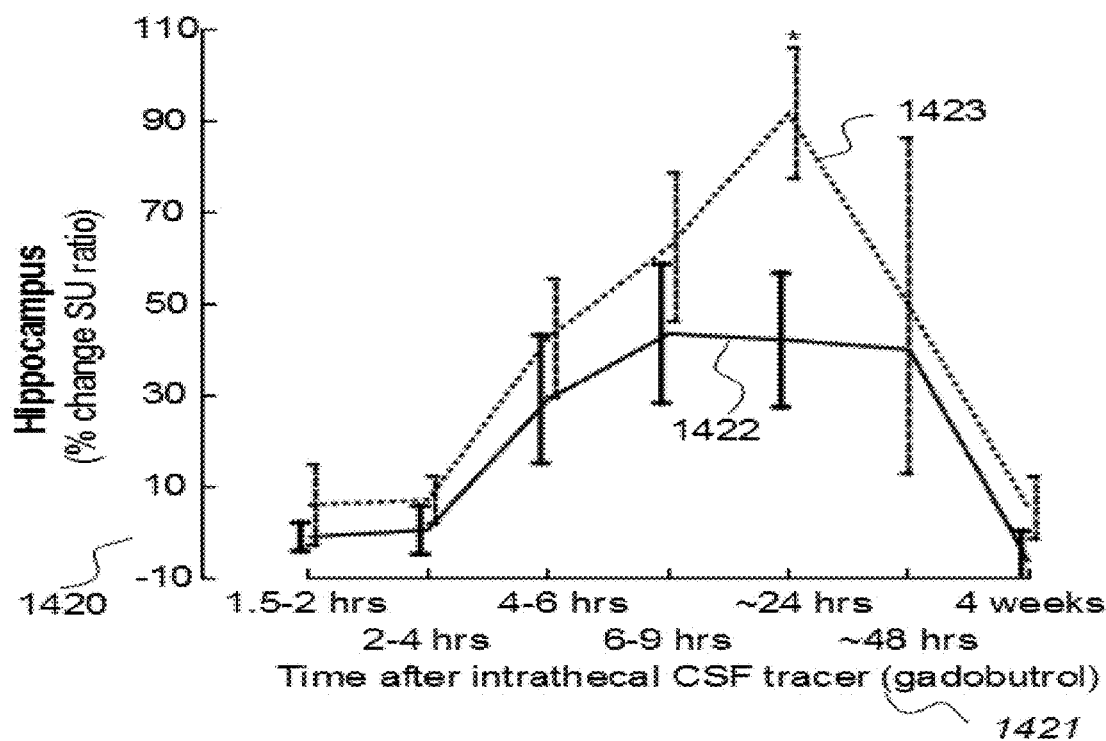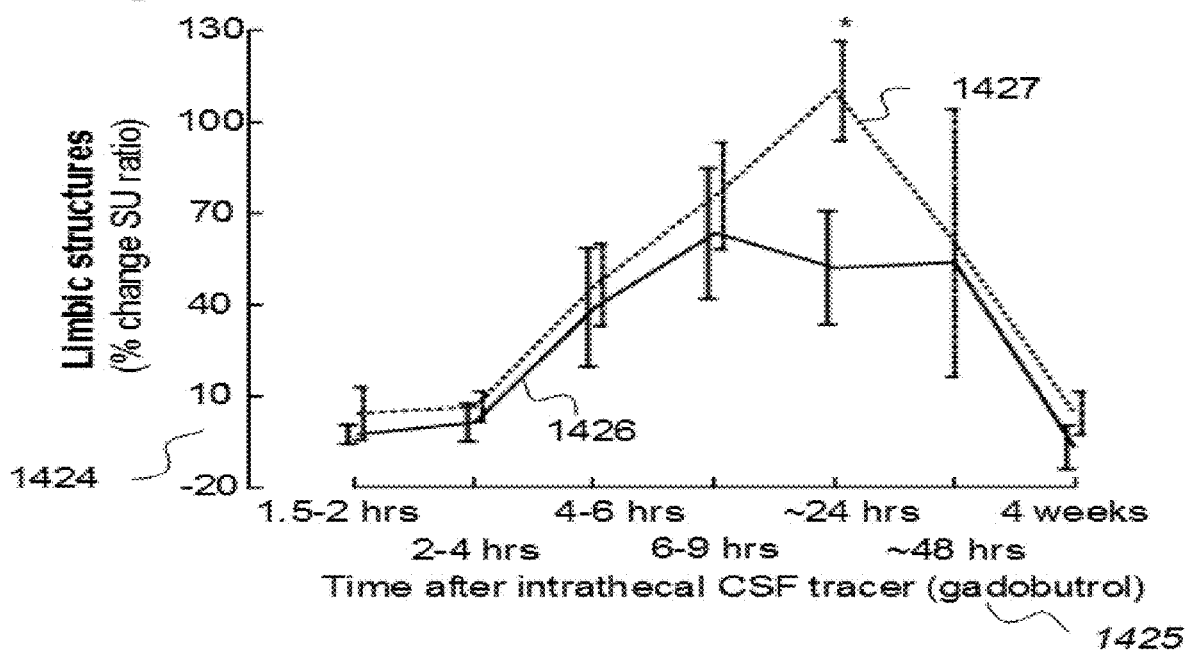

No gadobutrol 24 hours after i.t.h. gadobutrol

No gadobutrol 24 hours after i.t.h. gadobutrol

Image-series 1
(no contrast)

Image-series 2
(4 hours after i.t.h. contrast)

Image-series 2
(4 hours after i.t.h. contrast)

Image-series 3
(24 hours after i.t.h. contrast)

Image-series 4
(48 hours after i.t.h. contrast)

Image-series 3
(24 hours after i.th. Contrast)

T2

T1 (no gadobutrol)

T1 (24 hours after gadobutrol)

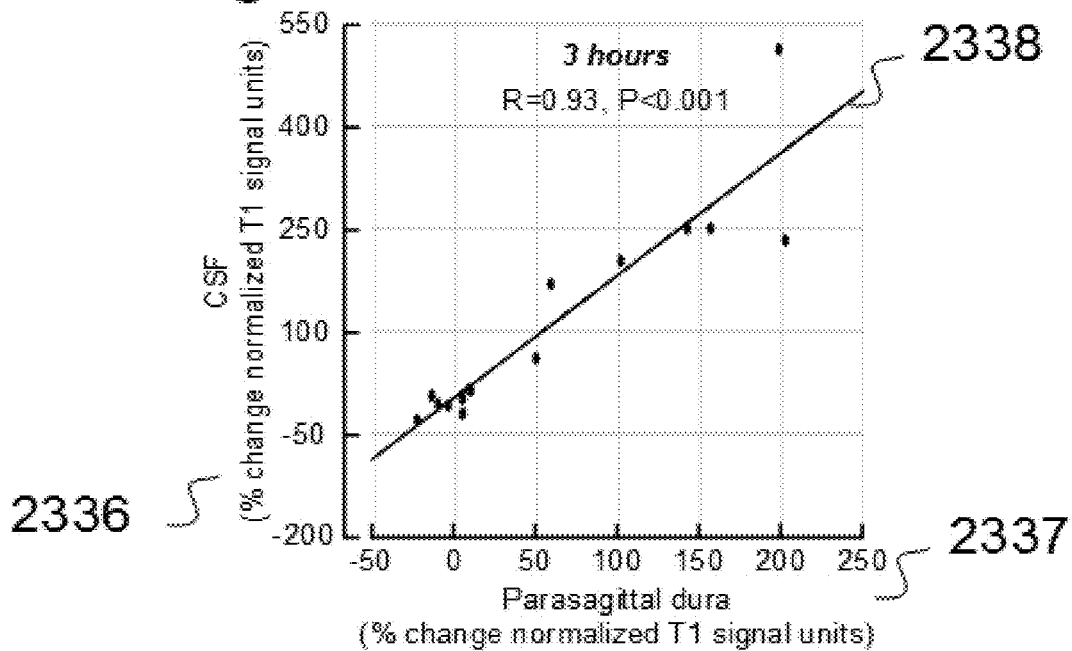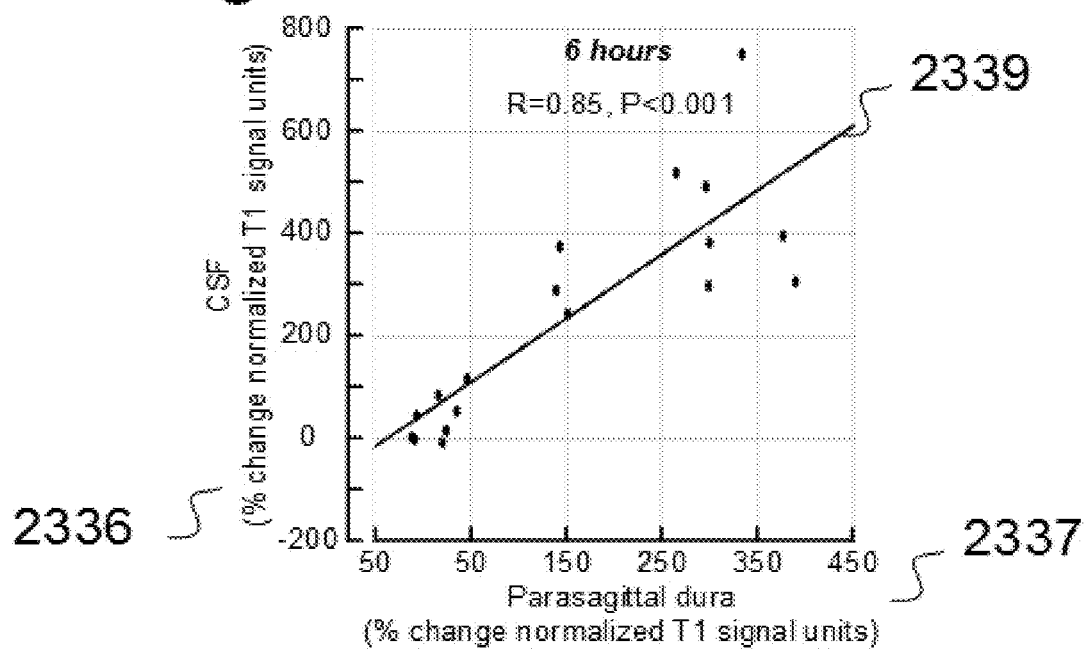

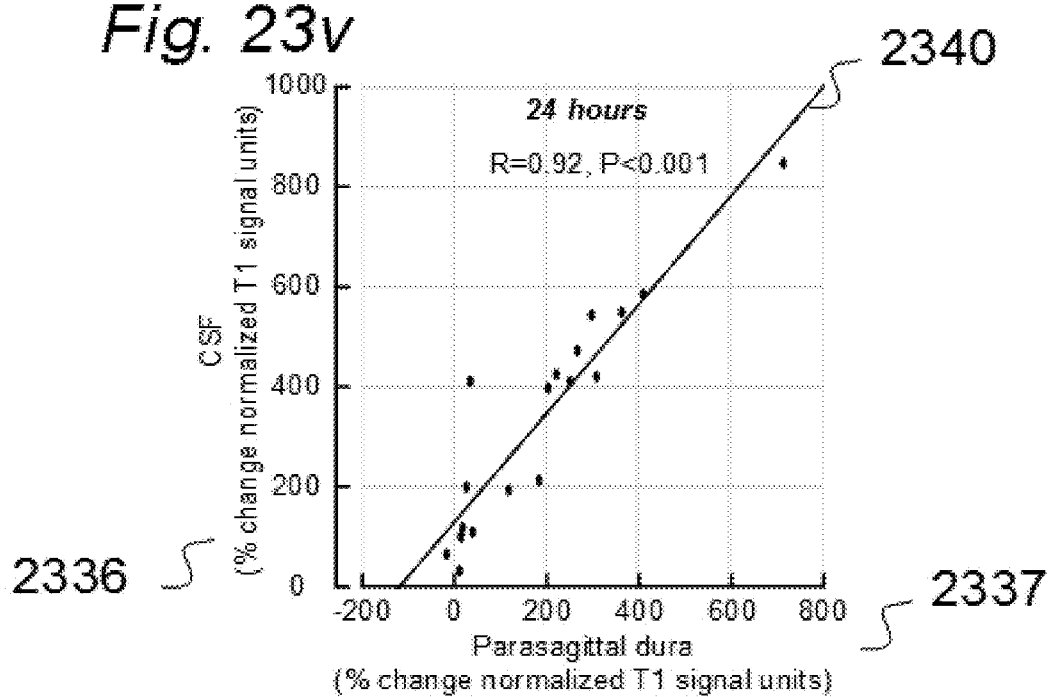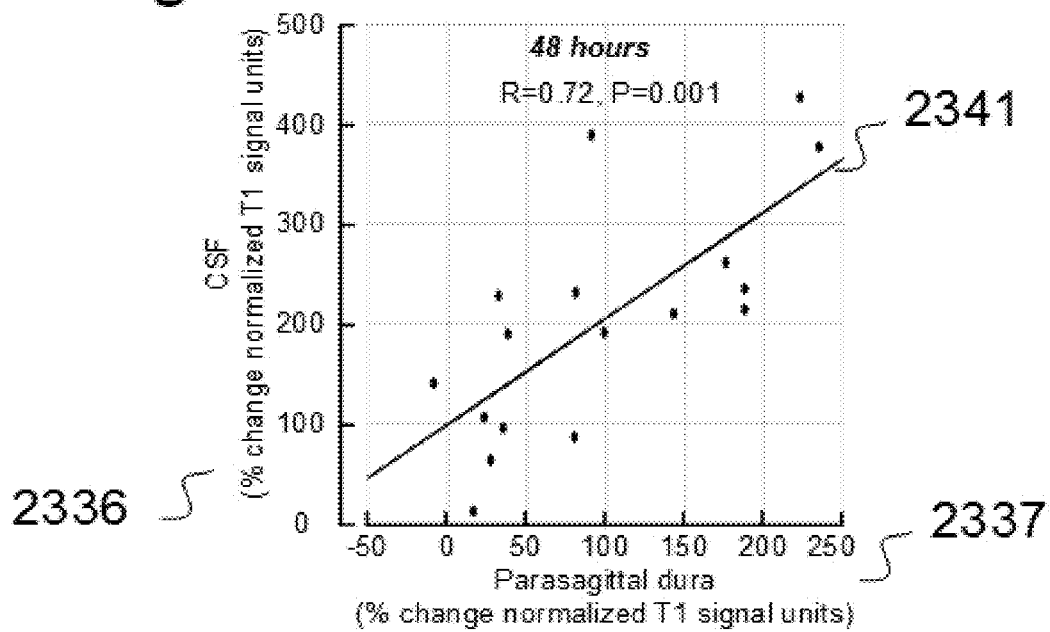

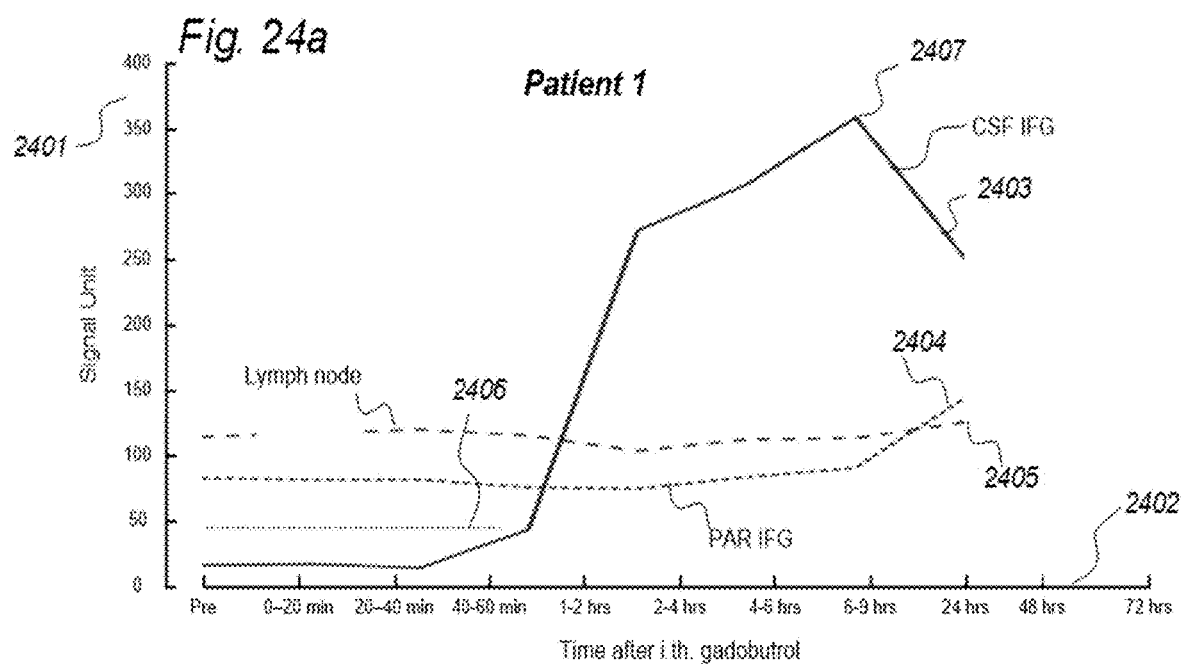
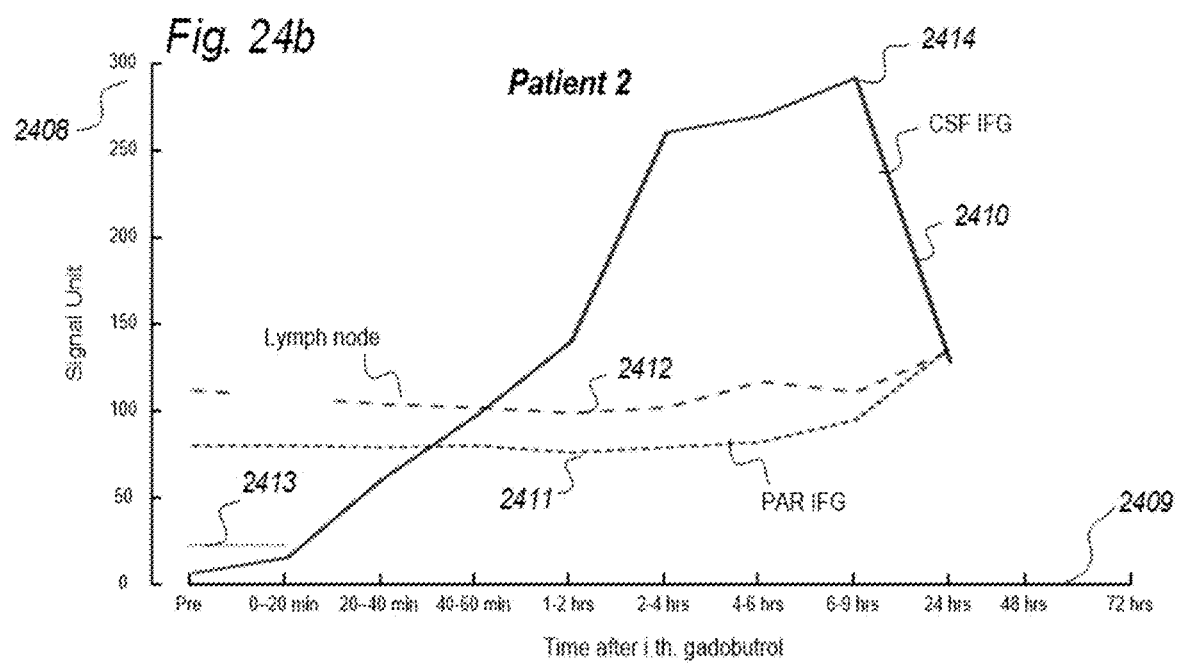

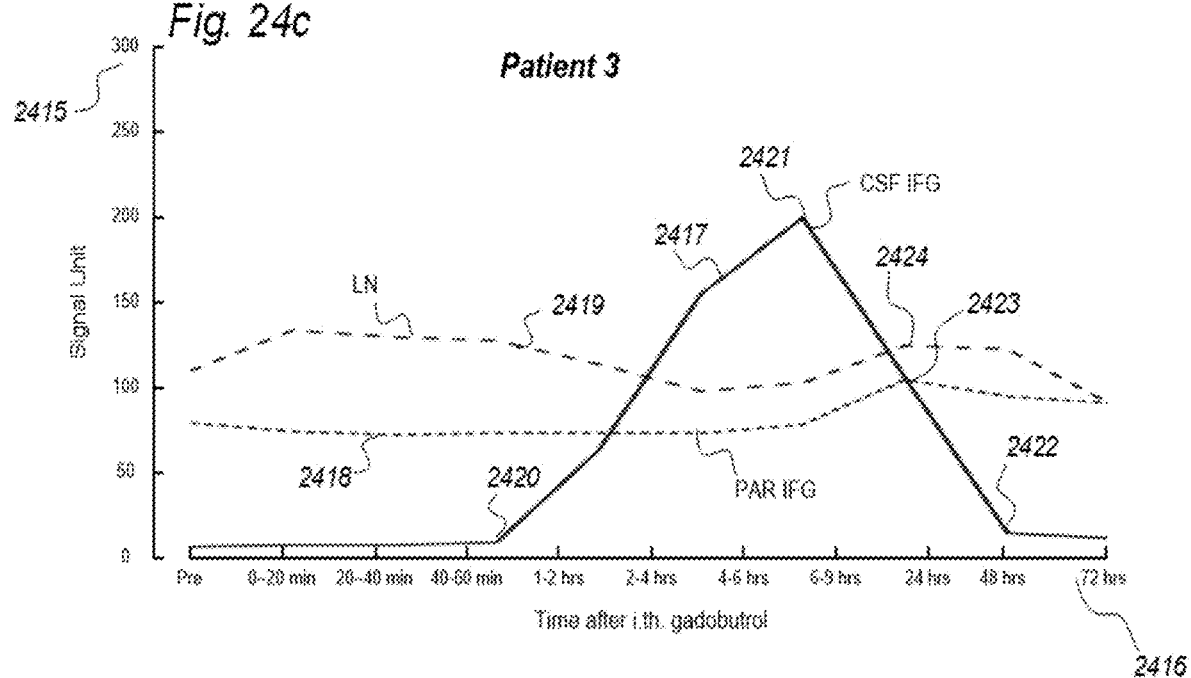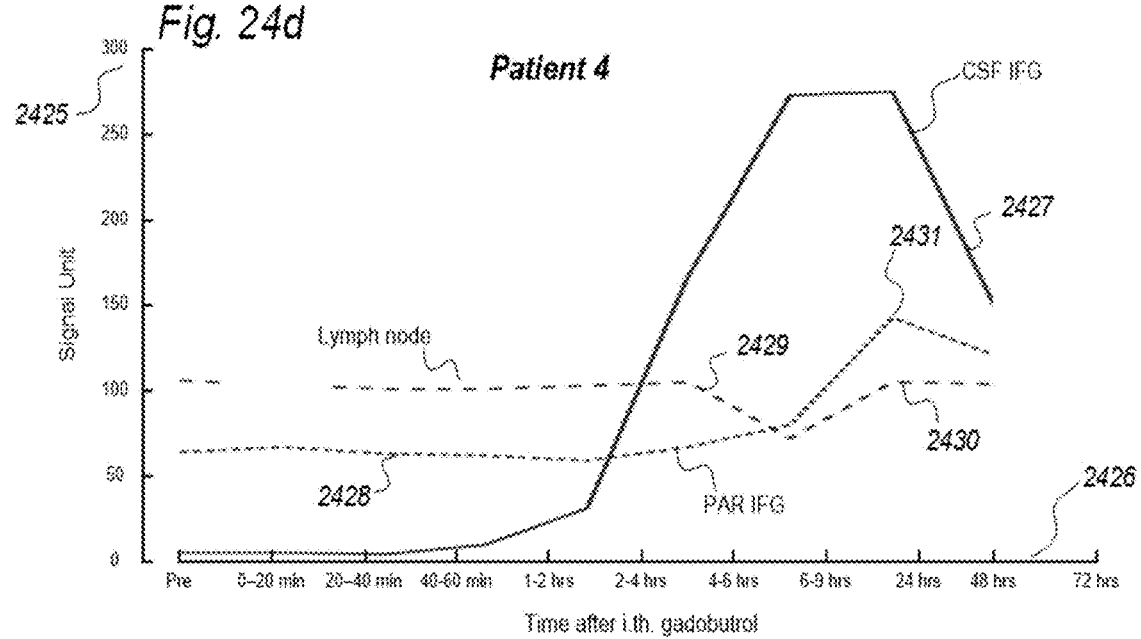

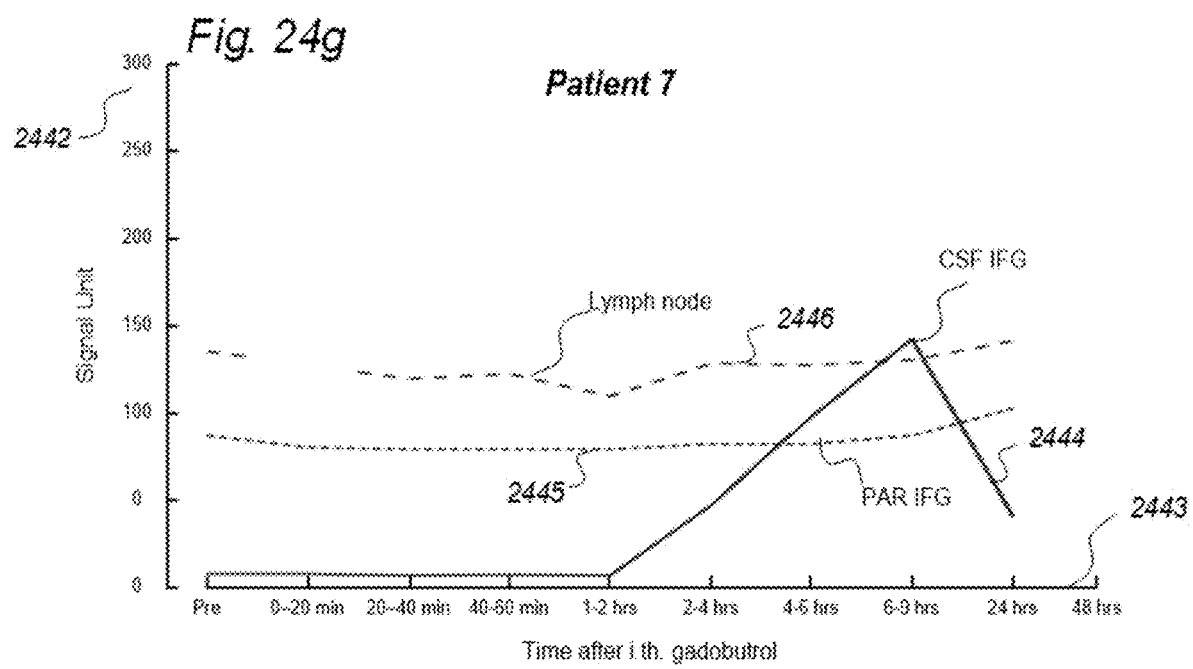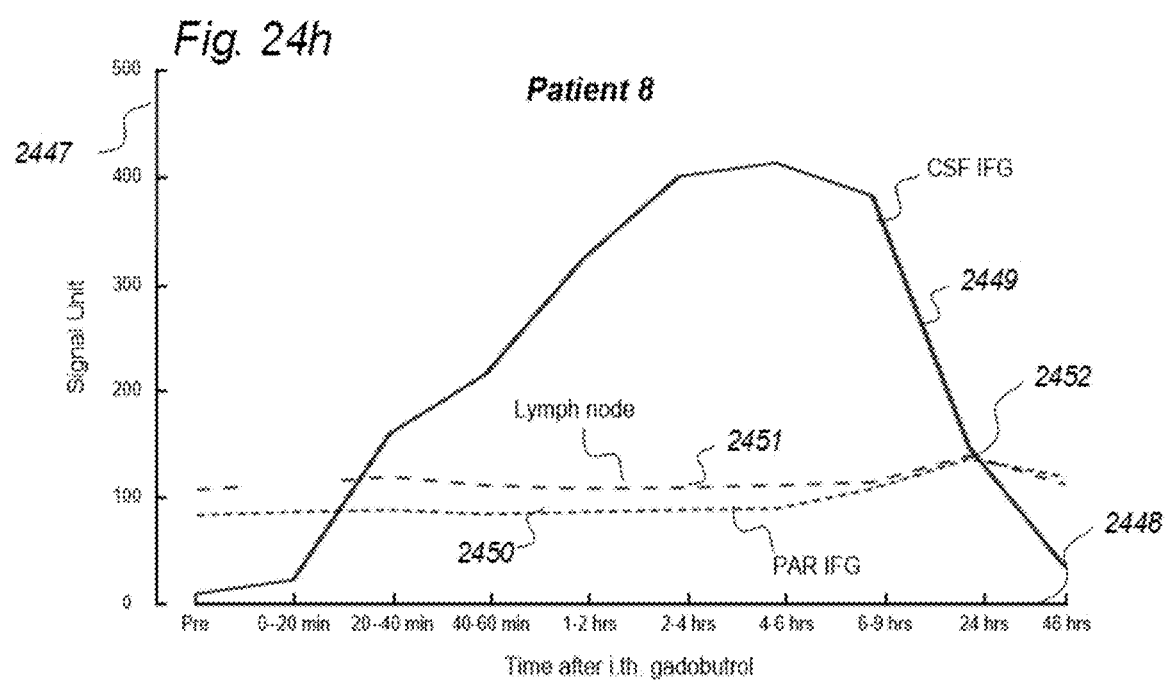

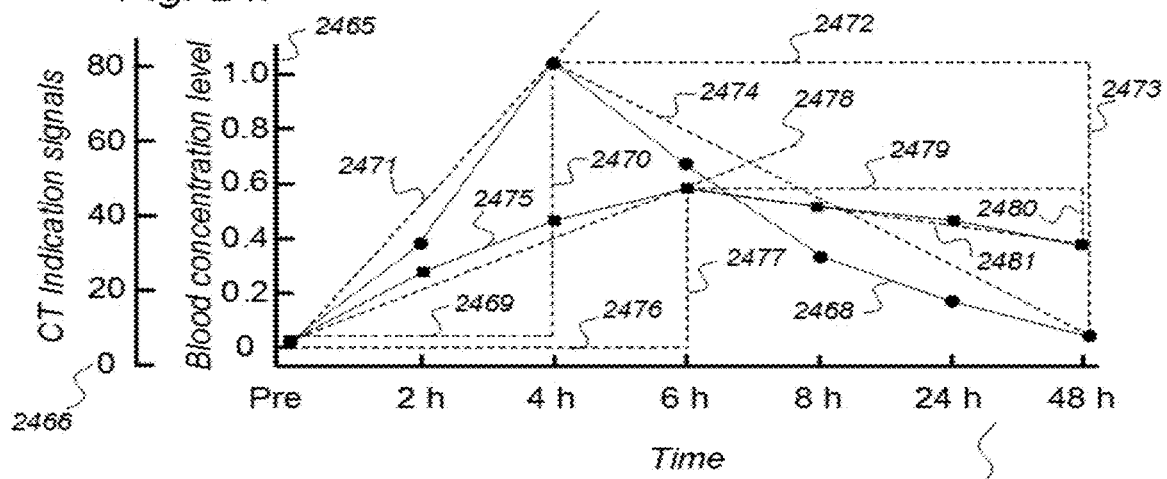
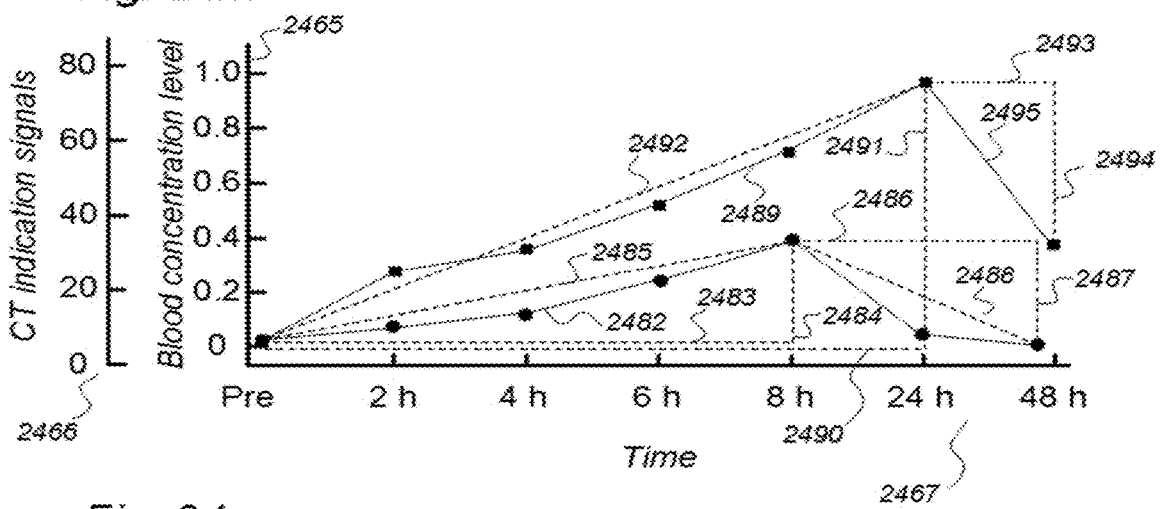
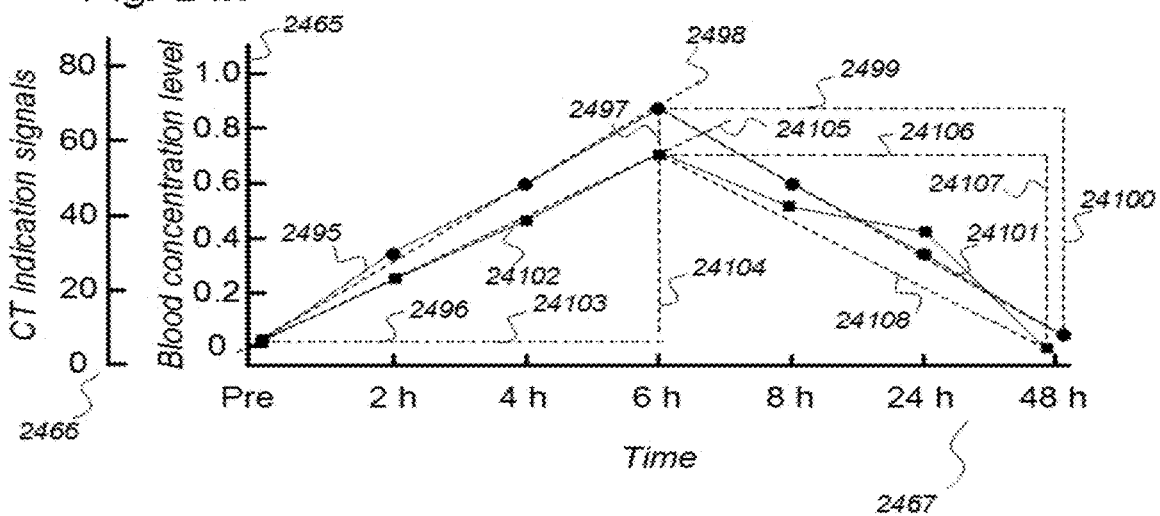

INDICATOR FLUIDS, SYSTEMS, AND METHODS FOR ASSESSING MOVEMENT OF SUBSTANCES WITHIN, TO OR FROM A CEREBROSPINAL FLUID, BRAIN OR SPINAL CORD COMPARTMENT OF A CRANIO-SPINAL CAVITY OF A HUMAN

BACKGROUND OF THE INVENTION

Field of the Invention

The present invention relates to various aspects of indicator fluids, systems, methods and devices for assessing movement of substances within, to or from a cerebrospinal fluid (CSF), brain or spinal cord compartment of a cranio-spinal cavity of a human.

More specifically, the present invention relates to indicator fluids, reference indicator fluid, and usage thereof, as well as systems and methods for assessing movement of substances within, to or from a cerebrospinal fluid, brain or spinal cord compartment of a cranio-spinal cavity of a human as defined in an introductory part of attached independent claims.

The three main elements of the cranio-spinal cavity are i) CSF compartment, ii) brain and spinal cord tissue compartment, and iii) vascular (blood) compartment. The central nervous system (CNS) consists of the brain and the spinal tissue cord, being confined within a cranio-spinal cavity, and residing within the CSF compartment. It has been disputed for decades how CSF and its constituents move within and from the cranio-spinal compartment. Neither has it been established how CSF communicates with the fluid within the brain and spinal cord tissue compartment. From a macro-anatomic perspective, the brain and spinal cord tissue compartment consists of the blood vessels (i.e. vascular space), cells with their processes (cellular space compartment), and the fluid residing between the cells and their processes, usually referred to as the interstitial fluid (ISF), and the fluid along the outside of the blood vessels, the so-called paravascular fluid. The notation extra-vascular space of the brain and spinal cord tissue compartment refers to the space outside the vessel walls and cell walls, and incorporates both the ISF and the paravascular fluid. One question that remains to be fully established is the molecules of various sizes are removed from the cranio-spinal cavity, particularly removal (clearance) of substances may be quantified.

The present invention includes several abbreviations; an overview of abbreviations used in this document is provided in Appendix A.

During normal brain metabolism, waste products are created that should be removed from the cranio-spinal cavity to prevent damage. Further, following brain injury, e.g. traumatic brain injury, stroke, neurodegenerative disease, CNS infection or inflammation, toxic waste products are created, which damage the brain. Therefore, the brain need to remove molecules that may be neuro-toxic. One example is the molecule amyloid beta (amyloid-$\beta$), which is in soluble form, but may deposit in the brain and cause formation of amyloid beta plaques. This compound seems to play an important role in the development of Alzheimer's dementia.

Over the last few years, the knowledge about clearance of waste solutes from the brain has increased. One important contribution includes a 2012 report from Iliff et al. in a Science Translational Medicine paper, about a brain-wide paravascular route for transport of water and solutes denoted as the glymphatic system. Experimental evidence from studies in rodents provided support to the hypothesis that CSF may flow along brain vessels residing within the brain tissue. With regard to the small vessels of the brain tissue compartment, the basement membrane and glia endfeet are one location for water transport between the vessel wall and ISF. Since this paravascular transport of water and solutes has similarities with the lymphatic system in other organs, it was denoted the glymphatic, or g-lymphatic system. The reason was that the system is dependent on water transport across glial (g) astrocytic foot processes. In this text, we prefer the term paravascular circulation, flow or transport to describe movement of molecular substances such as water and solutes along the vessels of the brain. Perivascular astrocytic end feet surround the wall of the small blood vessels, a wall which is created by endothelial cells and pericytes. Between the endothelial cells, certain proteins form tight junctions, creating a blood-brain-barrier (BBB). According to this model CSF and ISF mixes freely along the paravascular route. Regarding the concept of glymphatic circulation, this is still controversial. First, the current knowledge about paravascular transport of fluid and substances within the brain is based on experimental evidence from studies in animals only. Second, it is debated whether fluid is transported by diffusion, convection or a combination. The hypothesis about glymphatic circulation as described by Nedergaard et al. states that paravascular flow is convective, which may not to be correct. Fourth, it remains controversial how substances move along brain vessels and within the interstitial space of the brain. While some researchers argue that clearance of waste products is directed backwards along arteries towards the brain surface, the concept about glymphatic transport states that movement is directed inward along arteries, and outwards against the brain surface along veins. It is also unknown whether glymphatic transport of substances occurs within the deep portions of the brain. Presently, the available information derives from animals, primarily rodents, how humans behave in this respect remains unknown.

For decades it has been disputed whether the brain has a lymphatic system or not. In 2015, important contributions were provided by Louveau et al. and Aspelund et al., who described the existence of lymphatic vessels along the major dural sinuses of rodents. The dura mater is consisting of dense connective tissue enclosing the brain and spinal cord within the cranio-spinal cavity.

How the brain is able to remove toxic substances from the cranio-spinal cavity may be a fundamental pathogenic factor for various conditions and diseases in humans, such as individuals with Alzheimer's and dementia in general, brain tumor (e.g. astrocytoma), multiple sclerosis and inflammatory brain disease, stroke (brain infarction or bleeds), sleep disturbances, neurodegenerative disease, CSF circulation disorders, traumatic brain injury, neurometabolic diseases, glaucoma, chronic headache and migraine. Probably, the ability of the CNS to clear substances is affected by ageing, and dependent of sleep.

There are several reasons to why there is a lack of knowledge about the mechanisms behind movement of substances within, to and from the cranio-spinal cavity of the human brain. Concerning the present invention, we have identified at least seven important issues:

1) It has not been established how to measure and quantify capacity for clearance of substances from the cranio-spinal cavity of humans. We need tools to estimate the cranio-spinal cavity's ability to remove substances. The reason for this is lack of knowledge about movement of substances within, to and from a human cranio-spinal cavity.

2) We need tools to assess movement of substances within, to or from a CSF compartment of a cranio-spinal cavity in a human. It would be desirable to be able to assess the movement of substances within, to and from the CSF compartment.

3) There are no tools to assess movement of substances within, to or from a brain or spinal cord compartment of a cranio-spinal cavity in humans. The reason is a lack of knowledge of how substances move between the CSF, brain and spinal cord compartments in humans.

4) We need tools to assess movement of substances from a cranio-spinal cavity to extra-cranial organs, e.g. lymphatic pathways. Presently it is unclear how substances move from the cranio-spinal cavity to other organs or regions of the human body.

5) The brain and spinal cord compartments may be dichotomized into the vascular and extra-vascular compartments, which are strictly divided because of the BBB, not allowing for transport of most substances across the blood vessel wall. While contrast agents within the blood pool is utilized for contrast-enhanced imaging, no methods have been established to assess the dimensions of the extra-vascular compartment. This is an important aspect since many conditions and disease processes are confined to the extra-vascular space, and without necessarily disrupting the BBB. In this regard, imaging of the extra-vascular compartment would be advantageous.

6) Examples of disease processes that may be extensively located within the extra-vascular space are extravascular deposition of tumor cells, inflammatory cells, and even deposition of amyloid beta plaques. When the BBB is intact, these extra-vascular depositions may not be visualized by imaging techniques utilizing contrast agents or radioactive ligands that are confined to the blood. Currently, there are no methods for targeting extravascular CNS diseases with imaging incorporating use of tracer fluids of certain disease affinity. In this regard, assessment of the dimensions of the extra-vascular space would be useful.

7) Magnetic resonance imaging (MRI) has an important role in modern medicine, and might be a useful tool to quantify movement of substances within and from a cranio-spinal cavity in humans. However, one drawback is that variations between MRI machines and MR image sequences make it unreliable to compare image greyscale intensity signal units (SUs), both between time points in single individuals as well as between groups of individuals. There is a need for establishing standardized calibration of MRI SUs using MRI, for example establishing tools for standardization of MRI T1 SUs, which would render for quantification of MRI contrast agent concentration in biological tissue or fluid, preferably against a reference tissue or reference device.

Aiming at solving these issues, we have applied contrast agents and medical imaging when contrast agent is present in a human body. The present invention evolved from studies in humans. The present invention is related to indicator fluids, reference indicator fluid, and usage thereof, as well as systems and devices therein, and, methods for assessing movement of substances within, to and from a cranio-spinal cavity, including movement of substances to extra-cranial organs such as lymphatic pathways and kidneys. Notably, although the present invention claims typical secondary use of indicator fluids and their characteristics, a procedure of administering indicator fluid to a human body is not part of the invention. The invention provides tools by way of systems and methods to enable novel analyzing of movement of indicator fluid upon movement of the indicator fluid between locations of interest in a human body. The invention thus provides tools for analyzing movement of molecular substances within humans, but does not in any way provide for diagnosing of any disease.

Related Art

No methods have been established for determination of clearance function from the cranio-spinal cavity. One reason may be that there are yet no medical treatment strategies to modify removal of substances from the cranio-spinal cavity, making it less relevant at present. In comparison, assessment of renal clearance function may be done by measurement of glomerular filtration rate (GFR), utilizing intravenous contrast agents with known clearance rate in a healthy population. Clearance assessment of contrast agent may also be applied to some degree in medical imaging. Thus, by means of computed tomography (CT), adrenal adenomas located in the abdomen are assessed by means of CT contrast agent washout after having been injected intravenously. Further, positron emission tomography (PET) may be used to assess clearance of intravenously residing substances labeled with a radioactive nuclide, one example being distribution and clearance assessment of certain antibodies attached to $^{89}$Zirconium.

In rodents, the function of the paravascular or glymphatic system has been visualized by administering MRI contrast agent (Gadolinium-diethylenetriamine, Gd-diethylenetriaminepentaacetic acid; Gd-DTPA) to the cisterna magna (CSF space at the cranio-vertebral junction), and changes in image SUs have been followed over time. Comparably, in a human case, the increase in SUs following intrathecal administration of the MRI contrast agent gadobutrol suggested glymphatic circulation in humans, as well.

Various aspects of the glymphatic system are discussed in the international patent application WO 2014/130777 A1. It describes the use of MRI and measurements of SUs following intrathecal contrast administration, the measurements of SUs being done in various brain and CSF compartments over time, and the information being based on observations in rodents, primarily mice and rats. The present invention is based on novel observations in humans to quantify movement of substances from the cranio-spinal cavity, e.g. quantifying movement of molecules within the CSF compartment or quantifying dependencies between brain and CSF compartments with regard to molecular movement. Since distribution of contrast agents within a rodent brain is very fast and extensive, as well as substantially different from that in humans, novel aspects are provided by the present invention.

We have also considered the publications listed below:
Gallotti A, de Haen C, Smith A M, Eakins M N, Zodda J P. Devices for the standardization of signal intensity in magnetic resonance imaging. EP00793114 A1 (1997).
Bateman R, Patterson B W, Elbert D L. Methods of diagnosing amyloid pathologies using analysis of amyloid-beta enrichment kinetics. US 2015/0254421 A1
Wu T H, Yang Bit Lee J S, Guan Y X. System and method for quantitative analysis of nuclear medicine brain imaging. US 2016/0260216 A1.
Piron C, Stainsby J, Harris C. Systems and methods for measuring global glymphatic flow using magnetic resonance imaging. US 2016/0367166 A1.
Parsey R, Mikhno A, Mann J J. Voxel-based methods for assessing subjects using positron emission tomography. WO 2009/146388 A1.

Han H, Method for measuring physiological parameters in cerebral interstitial fluid and cerebral extracellular space. WO 2011/069283.

Buurman J, Karczmar G S, Mustafi D, Peng B, Ivancevic M K, Heisen M. MRI phantom with a plurality of compartments for T1 calibration. WO 2012/049584 A1.

Nedergaard M, Benveniste H, Deane R. Methods for evaluating brain-wide paravascular pathway for waste clearance function and methods for treating neurodegenerative disorders based thereon. WO 2014/130777 A1.

Bateman R, Patterson B W, Elbert D L. Methods of diagnosing amyloid pathologies using analysis of amyloid-beta enrichment kinetics. WO 2014/081851 A1.

Piron C, Stainsby J, Harris C. Systems and methods for measuring global glymphatic flow using magnetic resonance imaging. WO 2016/132176 A1.

Hahn G, Sorge I, Gruhn B, Glutig K., Hirsch W, Bhargava R, Fortner J, Born M, Schröder C, Ahlstrom H, Kaiser S, Moritz J D, Kunze C W, Shroff M, Stokland E, Trnkova Z J, Schultze-Mosgau M, Reif S, Bacher-Stier C, Mentzel H J.

Pharmacokinetics and safety of gadobutrol-enhanced magnetic resonance imaging in pediatric patients. Invest Radiol 2009; 44: 776-783.

Fide P K, Ringstad G. MRI with intrathecal MRI gadolinium contrast medium administration: A possible method to assess glymphatic function in human brain. Acta Radiologica Open 2015; 4 (11) 1-5.

Aspelund A, Antila S, Proulx S T, Karlsen T V, Karaman S, Detmar M, Wiig H, Antalo K. A dural lymphatic vascular system that drains brain interstitial fluid and macromolecules. J Exp. Med. 2015; 212 (7) 991-999.

Louveau A, Da Mesquita S, Kipnis J. Lymphatics in neurological disorders: A neuro-lympho-vascular component of multiple sclerosis and Alzheimer's disease. Neuron 2016; 91 (5) 957-973.

Morris A W J, Sharp M M G, Albargothy N J, Fernandes R, Hawkes C A, Verma. A, Weller R O, Carare R O. Vascular basement membranes as pathways for the passage of fluid into and out of the brain. Acta Neuropathol 2016; 131: 725-736.

Benveniste H, Lee H, Volkow N D. The glymphatic pathway: Waste removal from the CNS via cerebrospinal fluid transport. The neuroscientist 2017; 1-12.

The present invention provides multiple means, which are novel over prior art in several respects:

i) In a first aspect of the invention, means are disclosed for determining removal of a substance from the cranio-spinal cavity by determining blood and/or urine levels of said substance at different time points when an indicator fluid is present within a fluid cavity of a cranio-spinal cavity. This aspect is based on a concept that most of substances of a specific molecular weight (MW) within the CSF compartment is passing through the brain and via the lymphatic system before entering the blood circulation. Determining concentration level(s) of indicator fluid within blood and/or urine provides a measure of the capacity of the brain to remove substances with similar properties and of a certain MW.

ii) In a second aspect of the invention, means are disclosed for assessing movement of substances within, to and from a CSF compartment of a cranio-spinal cavity.

iii) In a third aspect of the invention, means are disclosed for determining quantitative relationships between clearance curves for different locations such as fluid and brain tissue compartments of a cranio-spinal cavity, extracranial tissue compartments, and extra-body compartments.

iv) in a fourth aspect of the invention, means are disclosed for assessing removal of substances from a cranio-spinal cavity to kidneys or extra-cranial lymphatic pathways.

v) In a fifth aspect of the invention, means are disclosed for novel visualization of the extra-vascular space of a brain and spinal cord tissue cavity. According to prior art, contrast-enhanced imaging of the cranio-spinal compartment utilizes administration of contrast agents routinely to the blood pool. Due to the BBB, the extra-vascular space is not visualized, except when dysfunction of the BBB causes leakage of contrast agent outside blood vessels. Therefore, visualization of the dimensional properties of the extra-vascular space is currently not performed in prior art techniques.

vi) In a sixth aspect of the invention, means are disclosed for quantifying movement of molecules connected to contrast agents for visualization by MRI. This aspect is intimately linked to the fifth aspect of visualization of the extra-vascular compartment.

vii) In a seventh aspect of the invention, means are disclosed for determining quantifiable measures/standardized measures of movement of defined MRI contrast agents.

Concerning medical imaging of metabolic activity, intravenous administration of radioactive ligands is most commonly used. Radioactivity is recorded by gamma camera imaging (GCI). Tracers with affinity to certain tissues and molecules, e.g. amyloid beta plaques, may be attached to the radioactive ligand. Due to the BBB, solely structures confined to the vascular system are visualized by this technique.

The present invention utilizes contrast agents for various medical imaging modalities, and utilizes anatomical characterization provided by different imaging modalities, namely one or more of CT, MRI, PET, single photon emission CT (SPECT), and scintigraphy. Even though said imaging modalities are well known from prior art, each modality is commented on for the sake of clarity.

The term CT is also known as computerized axial tomography (CAT) scanning, and refers to a computerized x-ray imaging procedure. It measures the attenuation of x-rays passing through the body. A feature distinguishing CT from conventional radiology is that the image is reconstructed from numerous measurements of attenuation coefficients.

MRI scanners create body images by applying strong magnetic fields, radio waves, and field gradients, based on the underlying science of nuclear magnetic resonance. Certain atomic nuclei can absorb and emit radio frequency energy when placed in an external magnetic field. Normally, protons, neutrons and electrons all spin around a central axis. In balanced nuclei, equal numbers of protons and neutrons within a nucleus will balance out and lead to a zero spin nucleus. On the contrary, an unbalanced nuclei, such as hydrogen, creates a small magnetic field, which is denoted a magnetic moment. Normally, these tiny magnetic moments oppose each other to generate a neutral magnetic field. However, the magnetic moments are affected by strong external magnetic fields, which is a prerequisite for MRI. Emission of a radiofrequency pulse against the precessing nuclei at a similar frequency (hence the term "resonance") causes the nuclei to shift to align in a different direction. Instead of the random precession caused by an external field, the nuclei will spin in harmony; they are "in phase". On this basis, a radio-frequency signal is generated that is detected by antennas (coils) nearby the anatomy under examination.

The image contrast may be weighted in order to reveal particular anatomical structures and pathological structures. Tissues return to their equilibrium state after excitation by the independent processes of T1 (spin-lattice) and T2 (spin-spin) relaxations. Hence, turning off the electromagnetic field causes the nuclei to return to their original precession around the external magnetic field, which involves two processes: The T1 relaxation time is a measure of how quickly the net magnetization vectors recover to their ground states along the direction of a MRI scanner's magnetic field (BO) after being unaligned by a radiofrequency (RF) pulse. A T1 weighted image has typically low echo and repetition times (TE and TR) to provide different signal on a grey scale from tissues with different T1 properties (image contrast). T2 relaxation is the loss of phase in nuclear precession in the transversal plane of the scanner's magnetic field BO after the effect of an RF pulse, and a T2 weighted image has typically long TR and TE. In the brain, T1- and T2 times differ between grey and white matter, and between normal and pathological tissue and provides for good image contrast when imaging the brain with MRI. Fat and methemoglobin (blood) are examples of biological tissue with short T1 times, while water has long T1 relaxation time. Gadolinium-based contrast agents used in MRI shorten the T1 time of water (and thereby increases signal from water in a T1 weighted image). The rotating, transverse components of net magnetization can induce electrical currents in a radiofrequency coil next to the patient. The coil picks up the signal and transmits it to a computer. The computer processes the data and an image is generated. A variety of other MRI sequences have also been developed, for example diffusion MRI, MRI angiography, fluid attenuated inversion recovery (FLAIR), and susceptibility weighted imaging (SWI).

A drawback with MRI is that recorded SUs are highly dependent on the MRI scanner and parameters of the image sequence. Therefore, absolute values of T1 weighted SU may not be measured quantitatively, making it difficult to directly compare T1 SUs between individuals and at different time points within an individual. Another approach is T1-mapping, which may provide for absolute values, but is time-consuming and has low image resolution, and is currently applied mostly for research purposes. Further, MRI machines may be calibrated by using a phantom that is placed within the scanner. However, phantoms are not used while performing scanning of patients, only for scanner calibration.

PET is based on the principle of positron annihilation by using radionuclides that decay through positive beta decay. Positrons generated by the decay combine with an electron and annihilate, releasing two photons with energies of 0.51 MeV in the process. The photons are released in opposite directions. The technique involves the injection of radionuclides, followed by detection of their activity with an imaging device, usually a gamma camera, i.e. a scintillating material attached to a photomultiplier tube. $^{18}$FDG (fluoro-2-deoxyglucose is the most commonly used radionuclide for PET scanning. This compound is metabolized within the cell initially but is unable to progress on to the citric acid cycle, and is also difficult for the cell to excrete. Therefore, cells that have a high glucose metabolism will concentrate $^{18}$FDG. $^{18}$FDG is manufactured in a cyclotron through proton bombardment of $^{18}$O ('heavy water'). This causes a proton to enter and a neutron to leave the nucleus, creating $^{18}$F (half-life <2 hours). Therefore, it must be brought to the PET scanner within hours to perform an adequate scan.

By means of gamma cameras, the technique of scintigraphy captures emitted radiation from internal radioisotopes (a radionuclide) to create 2D images. SPECT also uses gamma rays, though providing 3D information. To perform SPECT, a gamma-emitting radioisotope is given to the patient, usually intravenously into the bloodstream. The radioisotope may be a soluble dissolved ion, e.g. an isotope of gallium (III), but more commonly, the radioisotope is attached to a ligand (denoted radio ligand). Such a ligand may have affinity to certain types of tissues, allowing for concentration of the ligand to tissues wherein it has affinity. The combined radioisotope enables visualization by a gamma camera. Emissions from the radionuclide indicate amounts of blood flow in the capillaries of the imaged regions. Thereby, SPECT provides information about level of biological activity within regions of interest (ROIs) of the 3D region analyzed.

A convenient measure of tissue radiotracer is the standardized uptake value (SUV), which normalizes radioactivity concentration (Bq/mL) to injected radioactive dose and subject body weight.

BRIEF SUMMARY OF THE INVENTION

The present invention is disclosed in Aspects 1-7, which are shortly commented on in their consecutive order.

In Aspect 1 of the invention, we describe means for assessing removal (clearance) of substances from the cranio-spinal cavity. This aspect evolved from determining time-series of change in SUs when gadobutrol is present within CSF compartment, brain tissue compartment and extra-cranial lymph node (LN) compartment, and measurements of blood level concentrations of contrast agents. The underlying assumption is that substances within the CSF compartment of a certain MW, e.g. gadobutrol with MW 605 Da, are removed from the cranio-spinal cavity by paravascular transport and further via the lymphatic system. Hence, when a substance with a certain MW is present within a CSF compartment, single or repeated measurements of blood levels may be used to quantify the brain and spinal cord capacity of removing said substance. This concept differs substantially from prior concepts of how substances are removed from the cranio-spinal cavity, namely by non-lymphatic pathways, such as via arachnoid granulations and along nerve sheets. Based on our observations, we consider that a minor amount of molecular substances is removed from the cranio-spinal cavity via other routes than the brain and spinal cord tissue para-vascular route, and this minor part may be considered a constant. Blood-test and/or urine-test clearance assessment is created for several individuals and statistical measures are determined, e.g. 95% confidence intervals. Thereby, the blood-test-based clearance assessment of one individual may be compared with that of a cohort of individuals. Said first aspect of the invention incorporates one or more blood samples with determination of blood levels of a certain compound, and the information derived thereof. More specifically, said Aspect 1 incorporates four features.

A first feature of Aspect 1 discloses an indicator fluid comprising one or more of:
a CT contrast agent detectable by computed tomography (CT),
an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the selected indicator fluid is for use in a human to assist in assessing ability of a cranio-spinal cavity of the human, i.e. the brain or the spinal cord compartment, to remove molecular substances, wherein parameters of removal of molecular substances being a function of one or more of measured and analyzed level or change in level of indicator fluid concentration in urine or blood, removal of indicator fluid in urine or blood versus time, and indicator fluid half-time or radiation decay in urine or blood, and wherein the indicator fluid exhibits molecular properties suitable for movement from a cerebrospinal fluid compartment of said cranio-spinal cavity to allow levels or change in level of the indicator fluid in the urine or blood samples subsequently to be measured and analyzed once or at selectable time intervals to determine said parameters of removal.

A second feature of Aspect 1 discloses a system to assess ability of a cranio-spinal cavity of a human, i.e. the brain or the spinal cord compartment, to remove molecular substances therefrom, upon presence of an indicator fluid in movement from a cerebrospinal fluid compartment of said cranio-spinal cavity, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system comprising:

a) a sampling device being configured to sample and measure levels of said indicator fluid in blood or urine or radiation levels of the indicator fluid at selectable time intervals, b) an analyzer being configured to analyze amount of indicator fluid level in said blood or urine samples to determine parameters of removal of said indicator fluid from said cranio-spinal cavity, and c) an analyzer output to provide a presentation of said parameters of removal, said parameters of removal being at least one of:

level or change in level of indicator fluid concentration in blood or urine, coefficient of indicator fluid removal (clearance) versus time in blood or urine, indicator fluid half-time or nuclear radiation decay in blood or urine, and levels or change in levels of nuclear radiation acquisition from blood or urine, and said parameters of removal being indicative of ability of said cranio-spinal cavity, i.e. the brain or the spinal cord compartment, to remove said indicator fluid, and thereby being a function of ability of clearance of any waste solutes of molecular substances from the cerebrospinal fluid, brain or spinal cord compartment of said cranio-spinal cavity.

A third feature of Aspect 1 discloses a computer assisted method to assess ability of a cranio-spinal cavity of a human, i.e. the brain or the spinal cord compartment, to remove molecular substances therefrom, upon presence of an indicator fluid in movement from a cerebrospinal fluid compartment of said cranio-spinal cavity, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising:

a) measuring once or at selectable time intervals by means of detectors operatively linked to a computer a1) levels of said indicator fluid in blood or urine, or a2) levels of nuclear radiation from said indicator fluid in blood or urine, b) analyzing by means of the computer said levels of the indicator fluid to determine parameters of removal of said indicator fluid from said cranio-spinal cavity, and c) presenting said parameters of removal as delivered from a computer output, said parameters of removal being at least one of:

level or change in level of indicator fluid concentration in blood or urine, coefficient of contrast agent removal (clearance) versus time in blood or urine, indicator fluid half-time or nuclear radiation decay in blood or urine, and level or changes in level in blood or urine of nuclear radiation from indicator fluid, said presented parameters of removal being indicative of ability of said cranio-spinal cavity, i.e. a cerebrospinal fluid, brain or spinal cord compartment, to remove said indicator fluid therefrom.

A fourth feature of Aspect 1 discloses usage of an intrathecally injectable indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, to derive at a presentation of parameters of removal of said indicator fluid from a cranio-spinal cavity of a human, said parameters of removal being a function of ability of the cranio-spinal cavity to clear molecular waste solutes from the cerebrospinal fluid, brain or spinal cord compartment.

In Aspect 2 of the invention, we describe means for assessing movement of substances within, to and from a CSF compartment of a cranio-spinal cavity. This invention evolved from observations of contrast agent, e.g. gadobutrol, having been administered to a CSF compartment, followed by repeated standardized T1 MRI acquisitions to determine the change in SUs within selected ROIs. Using this approach, we found that movement of contrast agent was altered in some subjects, for example, it was directed into the ventricles. In addition, we found that the enhancement and clearance phases were changed in some individuals. Comparable observations have not been done previously. In this regard, animal studies with rodents have no relevance, as paravascular transport in rodents is much faster than in humans. Said second aspect of the invention includes novel methodology that may be incorporated in software. More specifically, said Aspect 2 incorporates three features.

A first feature of Aspect 2 discloses an indicator fluid comprising one or more of:

a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the indicator fluid is configured to assist in assessing movement of molecular substances from a cerebrospinal fluid compartment to a nearby brain or spinal cord compartment of a cranio-spinal cavity of a human, the indicator fluid to be movable along a movement path of said molecular substances, wherein upon movement of the indicator fluid from said cerebrospinal fluid compartment, indicator fluid indication signals being measurable at least once within regions of interest of said cerebrospinal fluid, brain or spinal cord compartment, measurements to be made of indication signals from the cerebrospinal fluid compartment or simultaneously both from the cerebrospinal fluid compartment and said brain or spinal cord compartment, and wherein enhancement phase parameters and/or parameters of removal of the indicator fluid from said cranio-spinal cavity being providable, said enhancement phase parameters and/or parameters of removal being based on at least one of change in indication signals, and being indicative of ability of said cranio-spinal cavity to remove molecular substances, said ability to remove molecular substances referring to clearance of waste solutes from the cerebrospinal fluid, brain or spinal cord compartment.

The notation indication signal has a broad meaning, and depends on imaging modality. CT refers to Hounsfield Units (HU), MRI refers to SU and PET, SPECT and scintigraphy refer to Standard Uptake Value (SUV). An indication signal is thus a measurable feature derived from an imaging modality, where the indication signal level may be influenced by presence of indicator fluid. The indicator fluid may be a CT or MRI contrast agent, or a radioactive ligand, and coupled with other molecules to render for certain properties within the cranio-spinal cavity.

A second feature of Aspect 2 discloses a system to assess movement of molecular substances from a cerebrospinal fluid compartment to a nearby brain or spinal cord compartment of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system comprising:

a) an apparatus configured for one of computed tomography (CT), magnetic resonance imaging (MRI), positron emission tomography (PET), single photon emission computed tomography (SPECT), and scintigraphy imaging, and related to the selected indicator fluid, b) a detector device and a sampling device configured to measure at least once indicator fluid indication signals from the cranio-spinal cavity as provided by use of said apparatus within regions of interest of said cerebrospinal fluid, brain or spinal cord compartment, the measuring to be made of indication signals from the cerebrospinal fluid compartment or simultaneously both from the cerebrospinal fluid compartment and said brain or spinal cord compartment, and c) an analyzer capable of determining any sampled and detected change in indication signals over time within selectable fluid compartments of said cranio-spinal cavity, said changes in indication signals being indicative of said movement of indicator fluid within, to or from said cerebrospinal fluid, brain or spinal cord compartment of said cranio-spinal cavity, and d) an analyzer output to provide a presentation of said changes in indication signals as enhancement phase parameters and/or parameters of removal of the indicator fluid as a function of ability of movement of molecular substances between individual cerebrospinal fluid compartments, e.g. cerebral ventricles within the cranio-spinal cavity, or removal of molecular substances via the cerebrospinal fluid, brain or spinal cord compartment from said cranio-spinal cavity, said ability of movement or removal of molecular substances referring to and being a function of clearance of waste solutes.

A third feature of Aspect 2 discloses a method aided by a computer to assess movement of molecular substances from a cerebrospinal fluid compartment to a nearby brain or spinal cord compartment of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising:

a) measuring at least once indicator fluid indication signals by use of a detector device and a sampling device linked to the computer and provided by use of one of: computed tomography (CT), magnetic resonance imaging (MRI), positron emission tomography (PET), single photon emission computed tomography SPECT), and scintigraphy, as related to a selected indicator fluid, within regions of interest of said cranio-spinal cavity said measuring to be made of indication signals from the cerebrospinal fluid compartment or simultaneously both from the cerebrospinal fluid compartment and said brain or spinal cord compartment, and b) determining by a determining section in the computer changes in indication signals over time within selectable regions of said cranio-spinal cavity, said change in indication signals being indicative of said ability of movement of indicator fluid within, to or from said regions of said cranio-spinal cavity.

c) presenting from an output of an analyzer section in the computer enhancement phase parameters and/or parameters of removal of the indicator fluid from said cranio-spinal cavity, said enhancement phase parameters and/or parameters of removal being based on at least one of said changes in indication signals, and being indicative of ability of said cranio-spinal cavity to remove molecular substances, the ability being a function of clearance of waste solutes from compartments of the cranio-spinal cavity.

In Aspect 3 of the invention, we describe means for assessing movement of substance within, to and from a brain and spinal cord tissue compartment, as related to movement of said substance within, to and from other compartments such as CSF compartment, extra-cranial LN compartment, and levels of substance within extra-body compartment. For this purpose, we examined repeated standardized T1 MRI acquisitions when a contrast agent was present within the CSF compartment. This included establishment of clearance curves for a set of pixels, defined by the selected ROIs. The clearance curves represent movement of indicator fluid within said selected pixels. A clearance curve is represented as change in indication signal, as for MRI is represented by the change in SUs when a MRI contrast agent having been administered to a CSF compartment. Further, relationships between the different clearance curves of one ROI may be expressed as a function of the clearance curves of another ROI. The invention gives no limitation of how many ROIs that may be related, though specific examples are presented. For example, by relating clearance curves of different ROIs, the invention may express a clearance curve of a brain tissue compartment as a function of another clearance curve within nearby CSF compartment. Alternatively, the clearance curve within one CSF compartment may be described as a function of a clearance curve of another CSF compartment. In another embodiment, the clearance curve of a brain tissue compartment may be expressed as a function of the clearance curve of an extra-cranial cavity (e.g. cervical LN). In still another embodiment, clearance curves of brain tissue, CSF, or LN compartments, may be expressed as a function of SUs of extra-body compartments. More specifically, said Aspect 3 incorporates two features.

A first feature of Aspect 3 discloses a system to assess movement of molecular substances within, to or from cerebrospinal fluid, brain or spinal cord compartments of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system comprising:

a) an apparatus configured for one of computed tomography (CT), magnetic resonance imaging (MRI), positron emission tomography (PET), single photon emission computed tomography (SPECT), and scintigraphy imaging, and related to the selected indicator fluid, b) a detector device and a sampling device to measure at least once indicator fluid indication signals provided by use of said apparatus within regions of interest of said cerebrospinal fluid, brain or spinal cord compartments c) an analyzer capable of determining c1) any sampled and detected change in indication signals over time within a selectable one of cerebrospinal fluid compartments of said cranio-spinal cavity, said changes in indication signals being indicative of said movement of indicator fluid within, to or from the selected cerebrospinal fluid compartment of said cranio-spinal cavity, and c2) any sampled and detected change in indication signals over time within a selectable brain or spinal cord compartment of said cranio-spinal cavity, said change in indication signals being indicative of movement of indicator fluid within, to or from the selected brain or spinal cord compartment of said cranio-spinal cavity, and d) an analyzer output to establish a presentation of said determination of said changes in indication signals within said regions of interest and indicative of enhancement phase parameters and/or parameters of removal of the indicator fluid being a function of ability and assessment of movement of molecular substances within, to or from the cerebrospinal fluid compartment, e.g. cerebral ventricles within the cranio-spinal cavity, or movement of molecular substances within, to or from the brain or the spinal cord compartment of said cranio-spinal cavity, said ability of a cranio-spinal cavity to remove molecular substances being a function of clearance of waste solutes from the cerebrospinal fluid, brain or spinal cord compartment.

A second feature of Aspect 3 discloses a computer aided method to assess movement of molecular substances within, to or from a cerebrospinal fluid, brain or spinal cord compartment of a cranio-spinal cavity of a human, with assistance from a selectable indicator fluid movable from a cerebrospinal fluid compartment along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising a) measuring at least once indicator fluid indication signals provided by use of a computer-linked detector device and a sampling device dedicated for one of computed tomography (CT), magnetic resonance imaging (MRI), positron emission tomography (PET), single photon emission computed tomography (SPECT), and scintigraphy, as related to said indicator fluid, within regions of interest of said brain or spinal cord compartment b) determining by means of a determining section in the computer:

b1) level or change in level of indication signals over time within a selectable one of cerebrospinal fluid compartments of said cranio-spinal cavity, e.g. cerebral ventricles within the cranio-spinal cavity, said change in indication signals being indicative of movement of indicator fluid within, to or from said selected cerebrospinal fluid compartment of said cranio-spinal cavity, and b2) level or change in level of indication signals over time within a selectable brain or spinal cord compartment of said cranio-spinal cavity, said change in indication signals being indicative of movement of indicator fluid within, to or from a brain or spinal cord compartment of said cranio-spinal cavity, and c) establishing, using an analyzer section in the computer, a presentation of said determination of change in indication signals within regions of interest of said brain or spinal cord compartment as a function of said determination of change in indication signals within regions of interest of said cerebrospinal fluid compartment of said cranio-spinal cavity, said function enabling said assessment of the ability of to move molecular substances within, to or from said cerebrospinal fluid, brain or spinal cord compartment of said cranio-spinal cavity, said ability of movement of molecular substances referring to clearance of waste solutes from the cerebrospinal fluid, brain or spinal cord compartment.

In Aspect 4 of the invention, means are provided for assessing movement of substances from a cranio-spinal compartment to kidneys or extra-cranial lymphatic pathways. This aspect of the invention evolved from repeated measurements of MRI T1 weighted sequences of equal parameter settings when a MRI contrast agent was present within CSF of a human. Measurements were done in CSF, brain and spinal cord compartments, as well as in cervical LNs. Based on the observations we made, we suggest that most of molecular substances are removed from the brain via the paravascular and lymphatic pathways. More specifically, said Aspect 4 incorporates three features.

A first feature of Aspect 4 discloses an indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the indicator fluid is of a type to assist in assessing movement of molecular substances from a cerebrospinal fluid, brain or spinal cord compartment of a cranio-spinal cavity to kidneys or lymphatic pathway regions, e.g. cervical lymph nodes, of a human, and the indicator fluid to be movable from a cerebrospinal fluid compartment along a movement path of said molecular substances, wherein indicator fluid indication signals being measurable at least once within regions of interest of said lymphatic pathways or kidneys, and wherein enhancement phase parameters and/or parameters of removal of the indicator fluid from said cranio-spinal cavity to kidneys or said lymphatic pathway regions being providable, said enhancement phase parameters and/or parameters of removal being based on changes in indication signals, and being indicative of ability of said cranio-spinal cavity, i.e. the cerebrospinal fluid, brain or spinal cord compartment, to remove molecular substances from the cranio-spinal cavity to the lymphatic pathways or the kidneys.

A second feature of Aspect 4 discloses a system to assess movement of molecular substances from a cerebrospinal fluid, brain or spinal cord compartment of a cranio-spinal cavity to kidneys or lymphatic pathway regions, e.g. cervical lymph nodes, of a human, when an indicator fluid is to be movable from a cerebrospinal fluid compartment along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system comprising:

a) an apparatus configured for one of: computed tomography (CT), magnetic resonance imaging (MRI), positron emission tomography (PET), single photon emission computed tomography (SPECT), and scintigraphy imaging, and related to properties of the indicator fluid, b) a detector device and a sampling device to measure at least once indicator fluid indication signals provided by use of said indicator fluid and said apparatus within regions of interest of kidneys or one or more lymphatic pathway regions, c) an analyzer capable of determining any sampled and detected change in indication signals over time within said kidneys or said one or more lymphatic pathway regions, said changes in indication signals being indicative of ability of the cranio-spinal cavity to remove indicator fluid and inherently molecular substances from said cranio-spinal cavity to kidneys or lymphatic pathway regions, and d) an analyzer output to establish a presentation of said determination of said changes in indication signals as a function of ability and assessment of removal of molecular substances from said cranio-spinal cavity to kidneys or lymphatic pathway regions, and said function being indicative of the ability of removal of molecular substances referring to removal of waste solutes.

A third feature of Aspect 4 discloses a computer aided method to assess movement of molecular substances from a cerebrospinal fluid, brain or spinal cord compartment of a cranio-spinal cavity to kidneys or lymphatic pathway regions, e.g. cervical lymph nodes, of a human, when an indicator fluid is movable from a cerebrospinal fluid compartment of the cranio-spinal cavity along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising:

a) measuring at least once indicator fluid indication signals provided through use of a detector device and a sampling device linked to the computer and used with an indicator fluid imaging apparatus within regions of interest of the kidneys or one or more lymphatic pathway regions, b) determining, using a determining section in the computer, change in indication signals over time within the kidneys or said one or more lymphatic pathway regions, said change in indication signals being indicative of ability of the cranio-spinal cavity to move indicator fluid to kidneys or cervical lymph nodes, and c) providing, using an output from an analyzer section in the computer, a presentation of said determination of said changes in indication signals as a function of ability of removal of molecular substances from said cranio-spinal cavity to kidneys or lymphatic pathway regions, said function being indicative of the ability of removal of molecular substances referring to removal of waste solutes.

In Aspect 5 of the invention, means are provided for assessing the dimensional properties of extra-vascular space of a brain and spinal cord tissue compartment. This method incorporates one or more imaging acquisitions to visualize the total extra-vascular space of brain and spinal cord tissue when an indicator fluid is present outside the intact BBB. More specifically, said Aspect 5 incorporates three features.

A first feature of Aspect 5 discloses an indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the indicator fluid is of a type to be movable, in a mode a) selectively from a cerebrospinal fluid compartment of a cranio-spinal cavity and intravenously of a human, or in a mode b) from a cerebrospinal fluid compartment of the cranio-spinal cavity of a human, to assist in assessing dimensional properties of extra-vascular space of a brain or spinal cord compartment of a cranio-spinal cavity of the human, wherein indicator fluid indication signals being measurable at least once within regions of interest of said brain or spinal cord compartment of the cranio-spinal cavity, and either wherein in indicator fluid mode a) said dimensional properties of the extra-vascular space of said brain or spinal cord compartment is a function of a determined difference in indicator fluid indication signals of similar regions of interest, or wherein in indicator fluid mode b) said dimensional properties of the extra-vascular space of said brain or spinal cord compartment is a function of determined indicator fluid indication signals of regions of interest.

A second feature of Aspect 5 discloses a system to assist in assessing dimensional properties of extra-vascular space of a brain or spinal cord compartment of a cranio-spinal cavity of a human, upon an indicator fluid being in movement in the body of the human, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system comprising:

an apparatus configured for imaging by one of computed tomography (CT), magnetic resonance imaging (MRI), positron emission tomography (PET), single photon emission computed tomography (SPECT), and scintigraphy imaging, a detector device and a sampling device to measure indicator fluid indication signals within regions of interest as indicator fluid flows from a cerebrospinal fluid compartment of the cranio-spinal cavity, to a1) measure at least once indication signals through use of imaging acquisition of brain or spinal cord compartment, and an analyzer capable of assessing any sampled and detected indication signals, said analyzer being configured:

a2) to determine, based on said imaging acquisition, value of level of indication signal or value of change in level of indication signals over time within said brain or spinal cord compartment of said cranio-spinal cavity, and to assess said dimensional properties of said extra-vascular space of said brain or spinal cord compartment as a function of indication signals of regions of interest as determined by feature a2), and an analyzer output to provide an extra-vascular enhanced visual presentation of assessed dimensional properties of said extra-vascular space of said brain or spinal cord compartment.

The detector device and sampling device are in addition configured to:

b1) measure at least once indicator fluid indication signals through use of imaging acquisition of brain or spinal cord compartment as indicator fluid flows intravenously, wherein the analyzer in addition are configured to:

b2) determine, based on said imaging acquisition, value of change in indication signals over time within said brain or spinal cord compartment of said cranio-spinal cavity, and assess said dimensional properties of said extra-vascular space of said brain or spinal cord compartment as a function of difference in indication signals of similar regions of interest as determined by features b2) and a2), and wherein the analyzer output in addition is configured to provide an extra-vascular enhanced visual presentation of dimensional properties of said extra-vascular space of said brain or spinal cord compartment based on such a difference in indication signals.

A third feature of Aspect 5 discloses a computer aided method to assist in assessing dimensional properties of extra-vascular space of a brain or spinal cord compartment of a cranio-spinal cavity of a human, upon an indicator fluid being in movement in the body of the human, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising:

a1) measuring at least once, using a detector device and a sampling device linked to the computer, indicator fluid indication signals through use of imaging acquisition of brain or spinal cord compartment upon indicator fluid flow movement from a cerebrospinal compartment of said cranio-spinal cavity and a2) determining, by use of a determining section in the computer, based on said imaging acquisition, value of indication signal level or change in value of indication signal levels over time within said brain or spinal cord compartment of said cranio-spinal cavity, the measuring of indication signals in feature a1) being provided by a selected one of CT, MRI, PET, SPECT, and scintigraphy imaging, assessing, by use of an analyzer section in the computer, said dimensional properties of extra-vascular space of said brain or spinal cord compartment as a function of indication signal of regions of interest as determined by said feature a2), and providing from an analyzer output an extra-vascular enhanced visual presentation of assessed dimensional properties of said extra-vascular space of said brain or spinal cord compartment.

The method further comprises:

b1) measuring at least once, using a detector device and a sampling device linked to the computer indicator fluid indication signals through use of imaging acquisition of brain or spinal cord compartment, upon said indicator fluid having an intravenous flow movement, and b2) determining, by use of a determining section in the computer, based on said imaging acquisition, value of indication signal level or change in value of indication signal levels over time within said brain or spinal cord compartment of said cranio-spinal cavity, said feature b1) and b2) being provided by one of CT, MRI, PET, SPECT, and scintigraphy imaging, assessing, by use of an analyzer section in the computer, said dimensional properties of extra-vascular space of said brain or spinal cord compartment as a function of difference in indication signals of regions of interest as determined by features a2) and b2), and providing from an analyzer output an extra-vascular enhanced visual presentation of assessed dimensional properties of said extra-vascular space of said brain or spinal cord compartment based on features a2) and b2).

In Aspect 6 of the invention, means are provided for assessing movement of substances within, to and from a cranio-spinal cavity, when a substance such as a contrast agent is a carrier of another compound and being present within the CSF, for example after having been injected to the CSF at the lumbar level. For example, changes in SUs caused by presence of a MRI contrast agent within CSF may be coupled with attaching ligands to the MRI contrast agent. Thereby, a variety of clinical conditions may be studied such as paravascular and extracellular spread of tumor cells, inflammation, and the extent of amyloid-β plaque deposits. The invention represents no limitation to which other molecules that may be attached. We suggest molecules with affinity to tumor cells, inflammatory cells and amyloid-β plaque deposits. This may be used to quantify to which extent the extra-vascular space is invaded by neoplastic disease, inflammatory cells, or amyloid-β plaque deposits, respectively. Hence, the fourth, fifth and sixth aspects of the invention may conveniently be combined. More specifically, said Aspect 6 incorporates one feature.

A first and sole feature of Aspect 6 discloses an indicator fluid for use in a human, the indicator fluid comprising a contrast agent being one or more of:
- a computed tomography (CT) contrast agent selected from one of iohexol, iodixanol, iomeprol, ioversol and iobitridol,
- an magnetic resonance imaging (MRI) contrast agent being one of gadobutrol, gadoteric acid, and a dendrimer based macromolecular magnetic resonance imaging contrast agent of size sufficiently high to be retained outside the blood-brain-barrier,
- a radioactive ligand suitable for positron emission tomography (PET), single photon emission computed tomography (SPECT) or scintigraphy, and
- a substance exhibiting recognized pharmacokinetic properties, for a selected and related one of: CT, MRI, PET, SPECT, and scintigraphy, wherein the indicator fluid is of a type to be movable from a cerebrospinal compartment of a cranio-spinal cavity of the human and thus when present in a human body to contribute to one of:
  assessing ability of a cranio-spinal cavity of the human to remove molecular substances therefrom, and levels of the indicator fluid to be measured subsequently once or at selectable time intervals in blood or urine of the human,
  assessing movement of molecular substances within, to or from a cerebrospinal fluid, brain or spinal cord compartment of a cranio-spinal cavity of the human, and
  assessing movement of molecular substances from a cranio-spinal cavity to lymphatic pathways, e.g. cervical or neck lymph nodes, or kidneys of a human,
  or
wherein the indicator fluid is of a type to be movable intravenously as well as from a cerebrospinal compartment of a cranio-spinal cavity of the human, and thus when present in the human body to contribute to:
  assessing dimensional properties of extra-vascular space of a brain or spinal cord compartment of a cranio-spinal cavity of a human.

In Aspect 7 of the invention, a reference indicator fluid is provided for standardization of MRI acquisitions. An extracorporal device allows for determining absolute values of changes in SUs, e.g. for T1 signals. The device consists of a device containing different concentrations of a selectable MRI contrast agent. Thereby, SUs of e.g. T1 3D acquisitions may be related to this extra-body device. The device may be connected to the head or neck MRI coil. One advantage is establishment of accurate comparisons between repeated MRI acquisitions within individuals and between individuals using different MRI scanners and different MRI sequence parameters, e.g. T1 sequences. Using this device, changes in SUs within e.g. CSF compartment or brain tissue compartment may be expressed as function of SUs retrieved from said extra-body standardization device. Even though related art phantom devices (phantoms) are presently in use for MRI scanner calibration, we consider the present aspect and its four defined features to be novel and inventive, in particular when applied together with any selected other aspect of the invention, and/or as an inherent part of imaging humans. More specifically, said Aspect 7 incorporates four features.

A first and sole feature of Aspect 7 discloses a reference indicator fluid, configured to be used with a standardization device having at least one reference indicator fluid housing locatable on an exterior surface of a human body, to standardize values of detected signal units measurable through use of imaging of human body regions of interest by use of magnetic resonance imaging (MRI) and in interaction with a matching indicator fluid to be in flow movement inside a human, the reference indicator fluid providing for MRI signal unit values measured through use of MRI imaging of said human and based on said indicator fluid in flow movement inside the human to be standardized through a calibration against reference values of signal units measured from the reference indicator fluid, wherein the reference indicator fluid is MRI compatible and being a contrast agent of a type of said matching indicator fluid and selected from one of: gadobutrol, gadoteric acid, and a dendrimer based macromolecular magnetic resonance imaging contrast agent of molecular size sufficiently large to be retained outside a blood-brain-barrier of the human body.

The concept of allowing for two or more containers with an MRI contrast agent inside each container in different, but preset concentrations, allows for estimating the change in SUs being a function of change in contrast agent concentration. This operation allows for extracting parameters, such as a constant, which can be applied to assess contrast agent concentration in a fluid cavity and/or body tissue quantitatively, or semi-quantitatively.

Said respective features of the seven aspects of the invention detailed above and their further embodiments appear from respective sets of attached patent claims, and will now be further described with reference to the attached drawings.

BRIEF DESCRIPTION OF THE DRAWINGS

FIG. 1a-h illustrate the concept of determining the ability of a cranio-spinal cavity to remove substances when an indicator fluid moves from a CSF compartment and subsequently measure levels of indicator fluid in blood and/or urine. Measurements of concentrations in blood of an indicator fluid being administered to CSF is shown for a group of individuals (e), and for three individuals (f-h).

FIG. 10a-f illustrate trend plots of changes in SUs of the T1 signal within various CSF compartments of two groups of patients, namely idiopathic normal pressure hydrocephalus (iNPH) and reference (Ref; i.e. control) individuals, wherein indication signals are measured using MRI.

FIGS. 11a-g provide a schematic overview of two techniques for medical imaging, namely the techniques of CT (a) and MRI (b) scanning, including measurements of Hounsfield units by CT (c-f) and establishment of clearance curves based on trend plots of Hounsfield units (g).

FIG. 13a-e provide a schematic overview of two techniques for medical imaging, namely the techniques of PET and SPECT scanning.

FIG. 14a-h illustrate the incorporation of an anatomical coordinate system, repeated measurements from the same ROIs over time, the process of alignment of images, and how changes in signal unit ratios within selected segmented brain regions may be plotted over time.

DETAILED DESCRIPTION OF PREFERRED EMBODIMENTS

Figure 1A:
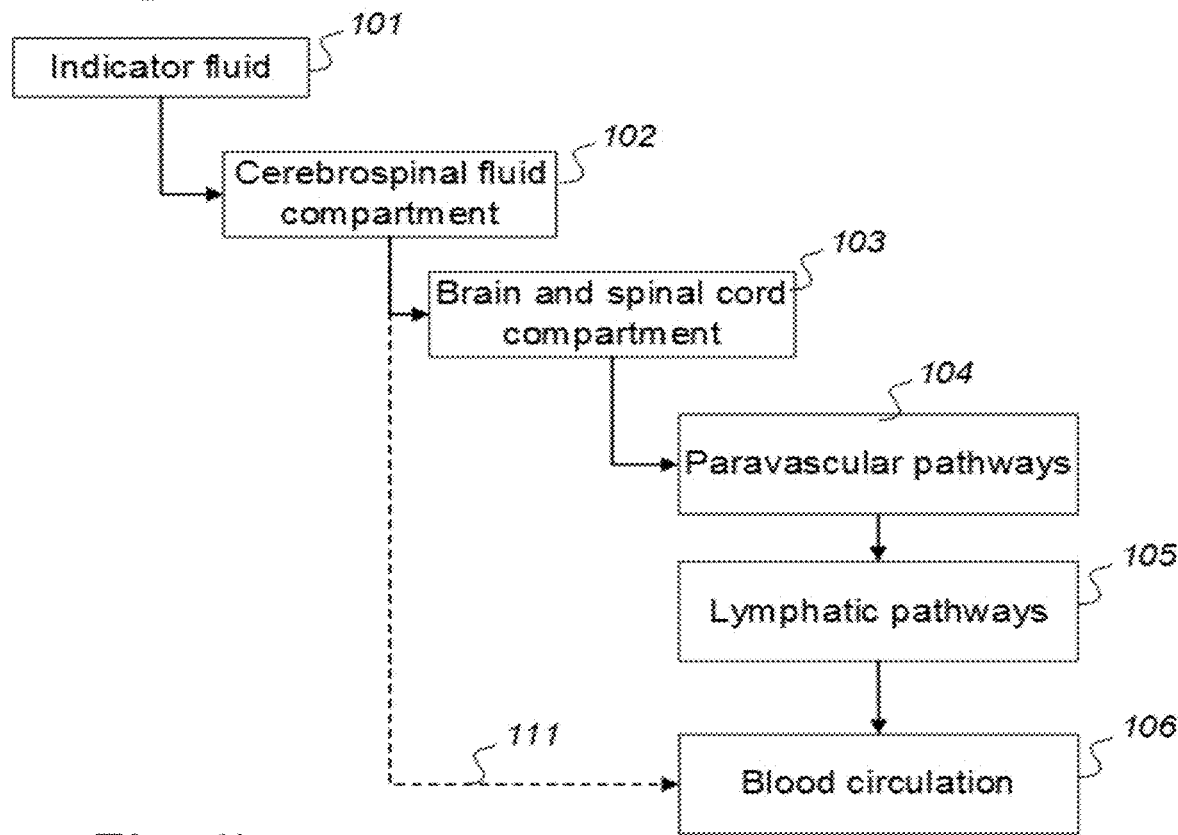

As mentioned above, the invention incorporates seven aspects with respective features and respective supplementary embodiments, and which are now to be described in consecutive order, with reference to the drawings.

In the following, Aspect 1 of the invention is described. This aspect provides means (indicator fluid, system, a computer-assisted method and indicator fluid usage) for assessing the ability of the cranio-spinal cavity, i.e. CSF compartment and brain and spinal cord compartments, to remove molecular substances (molecules, proteins, peptides, etc.). Normal brain metabolism, ageing as well as brain injury or various diseases may cause formation of substances that may damage the brain if not removed properly. Examples of two macromolecules are amyloid-β and the tau-protein, which both are toxic to the brain when deposited as plaques and neurofibrillary tangles, respectively. The amyloid-β peptide in soluble form may aggregate and form plaques within the brain, and has a role in the pathogenesis of Alzheimer's disease. The tau-protein is another protein that may be formed after injury, and may also be seen in Alzheimer's. Presently, there are no tools for assessing removal (or clearance) of substances from the human brain since it remains unclear how substances are removed from the brain. The reason is that it has not been established how substances are removed from the brain. Development of such new helpful means is expected to have large impact on our understanding of neurological diseases.

In this context, the term "molecular substance" has a wide meaning. It may be small molecules [e.g. water ($H_2O$) molecule, MW 18 gr/mole (=18 Dalton, Da)], macromolecules (e.g. the contrast agents gadobutrol (Gadovist™; MW 605 Da) and iohexol (Omnipaque™, MW 821 Da), peptides (e.g. amyloid-β protein fragment 1-42, MW 4,514 Da), proteins (e.g. Tau-protein, MW 55-62 kDa), and antibodies (e.g. immunoglobulin G, MW 150 kDa). Obviously, the movement of a molecular substance within, to or from compartments within the cranio-spinal cavity depends on the size of the substance.

Regarding possible indicator fluids for assessing ability of a craniospinal cavity to remove molecular substances, the indicator fluid should preferably not pass the BBB, and not interact with other molecules or with cellular metabolism, and be of a defined size. In addition, it should be completely removed from the cranio-spinal cavity. The invention does not restrict which kind of indicator fluids that may be used.

When an indicator fluid (e.g. contrast agent) having been administered to a CSF compartment, this substance with suitable molecular size will, like other substances with similar properties, enter paravascular spaces along the outside of vessels penetrating through the surface of the brain and spinal cord. The BBB will prevent the substance from leaking into the blood circulation when this is one of the known features of the substance. From the paravascular space, the substance will pass through the brain or spinal cord extra-vascular space, from where it is removed to lymphatic pathways and further to the blood circulation, and eventually secreted through kidneys to urine. This process is further illustrated in FIG. 1a. An indicator fluid 101 is administrable to a CSF compartment 102, e.g. by spinal puncture at the lumbar level. Based on our experimental studies, evidence was obtained that indicator fluid 101 escapes from the cranio-spinal cavity by entering the brain and/or spinal cord tissues 103, following the paravacsular pathways 104 and via the lymphatic vessels along the veins (dural sinuses), which leads to the extracranial lymphatic pathways 105 including lymph nodes. The indicator fluid passes to the blood circulation 106 and to exit the body via kidneys and urine. As illustrated in FIG. 1b, the function of this pathway may be tested by examining the concentration of the indicator fluid in blood or urine 107, once or at selectable time points 108. Hence, the amount of indicator fluid 101 entering the blood circulation 106 may be assessed by obtaining blood and/or urine samples of the substance. If blood or urine level concentrations 107 are measured at different time points 108, a graphical presentation 109 of repeated blood and/or urine measurements 110 may be obtained, which provides for determination of blood and/or urine concentrations 107 of indicator fluid 101. This curve provides information about clearance of indicator fluid 101 from the cranio-spinal cavity.

Some indicator fluid 101 present within the cerebrospinal compartment 102 may also escape the craniospinal compartment through non-lymphatic pathways 111. Experimental evidence from prior art suggests that in animals, molecular substances may leave the craniospinal cavity via non-lymphatic pathways such as along nerve sheets. Drainage via non-lymphatic pathways may have a different time course. Moreover, knowledge from animal studies may not necessarily be translated to humans.

An important discovery by the inventors was that the MRI contrast agent gadobutrol 101, when present within the CSF compartment 102, caused peak increase of T1 weighted MRI signal units (SUs) at the same time within the brain and spinal cord parenchyma 103 and the cervical lymph nodes 105. Peak enhancement in T1 SUs occurred when gadobutrol had been present within CSF for 24 hours, even though peak enhancement within CSF compartment 102 occurred when gadobutrol had been present in CSF for a few hours. From this, we assumed that non-lymphatic drainage 111 of contrast agent (indicator fluid) 101 from the CSF compartment 102 occurred early after indicator fluid 101 reached the CSF compartment 102, while contrast agent 101 distributing within the brain and spinal cord compartment 103 and paravascular pathways 104 escaped the cranio-spinal cavity via lymphatic pathways 105 later. Hence, different time course of removal of indicator fluid allows for measuring function of different removal pathways.

Figure 1B:
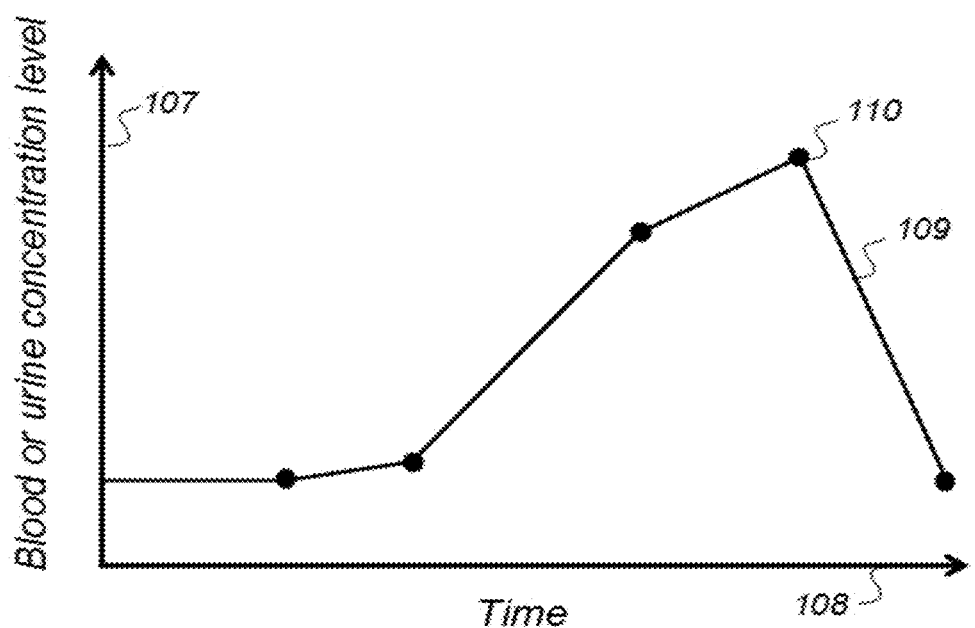
Figure 1C:
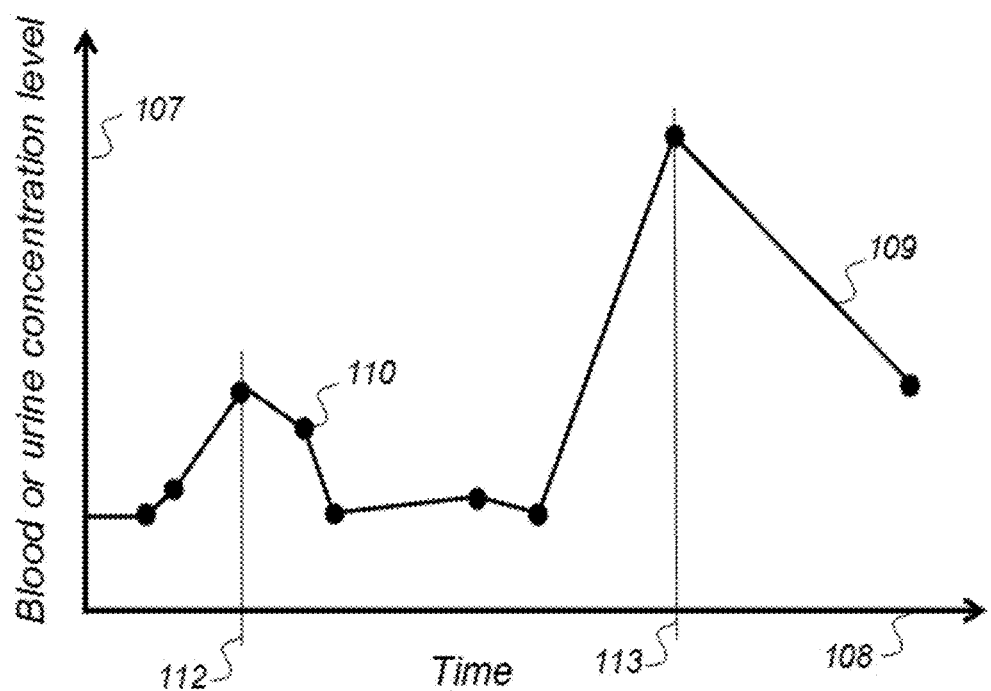

This latter aspect is further illustrated in FIG. 1c. Repeated blood and/or urine samples measurements 110 is plotted in a plot with blood or urine concentrations on the y-axis 107 and time on the x-axis 108. Repeated measurements 110 are plotted in a curve 109. The graphical curve 109 shows two peaks 112, 113, illustrating peak concentration for non-lymphatic removal of indicator fluid 112, and a later peak of lymphatic removal of indicator fluid 113. Thus, FIG. 1c illustrates how timing of different peak concentrations within blood and/or urine may be applied to differentiate various types of drainage. For example, an early peak 112 caused by CSF leakage may contaminate results. Further documentation that indicator fluid escapes the cranio-spinal cavity via lymphatic pathways is given regarding description for Aspect 4.

Notably, the graphical presentations in FIGS. 1b and 1c do not represent a restriction how graphical presentation may look. The curves of indicator fluid removal may have different profiles, not least depending on type of indicator fluid 101 used.

Figure 1D:
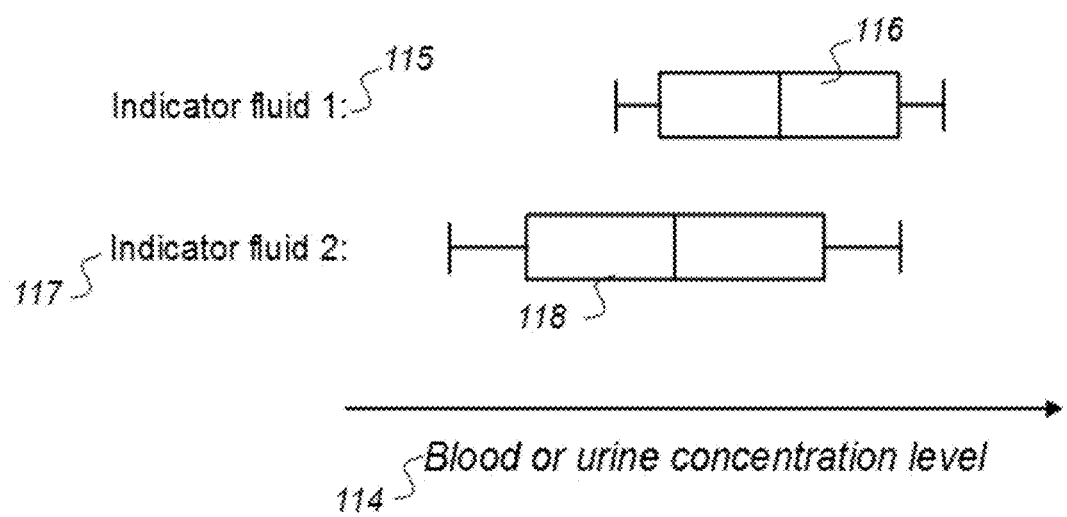

Measuring blood and/or urine concentrations from a cohort of individuals, for example at a defined time 112, 113, allows for establishing reference values of concentrations 114. This aspect is further illustrated in FIG. 1d. For Indicator fluid 1 115, reference values are presented as a box plot with median, $25^{th}$ and $75^{th}$ percentiles, respectively, and ranges 116. For Indicator fluid 2 117, different reference values are found, here illustrated by a box plot with median, $25^{th}$ and $75^{th}$ percentiles, respectively, and ranges 118. Reference values may be determined for the individual indicator fluids, and for various cohorts of humans such as different age groups.

In test studies, the inventors measured concentrations of the indicator fluid gadobutrol in blood at different time points after indicator fluid was present in CSF. Notably, the method by which gadobutrol is measured is not part of the invention. In FIG. 1e-h are provided examples of measurements of gadobutrol (indicator fluid) concentrations in blood. On the y-axis is shown the indicator fluid concentration level 119 in blood (i.e. concentration of gadobutrol measured in units mg/kg), and on x-axis the time 120 elapsed from gadobutrol was present within the CSF. The concentration level of gadobutrol was measured after different time points 120, including after 1-2 hours, 3-4 hours, 5-6 hours, 7-8 hours, 23-26 hours, and 46-49 hours, for different individuals.

Figure 1E:
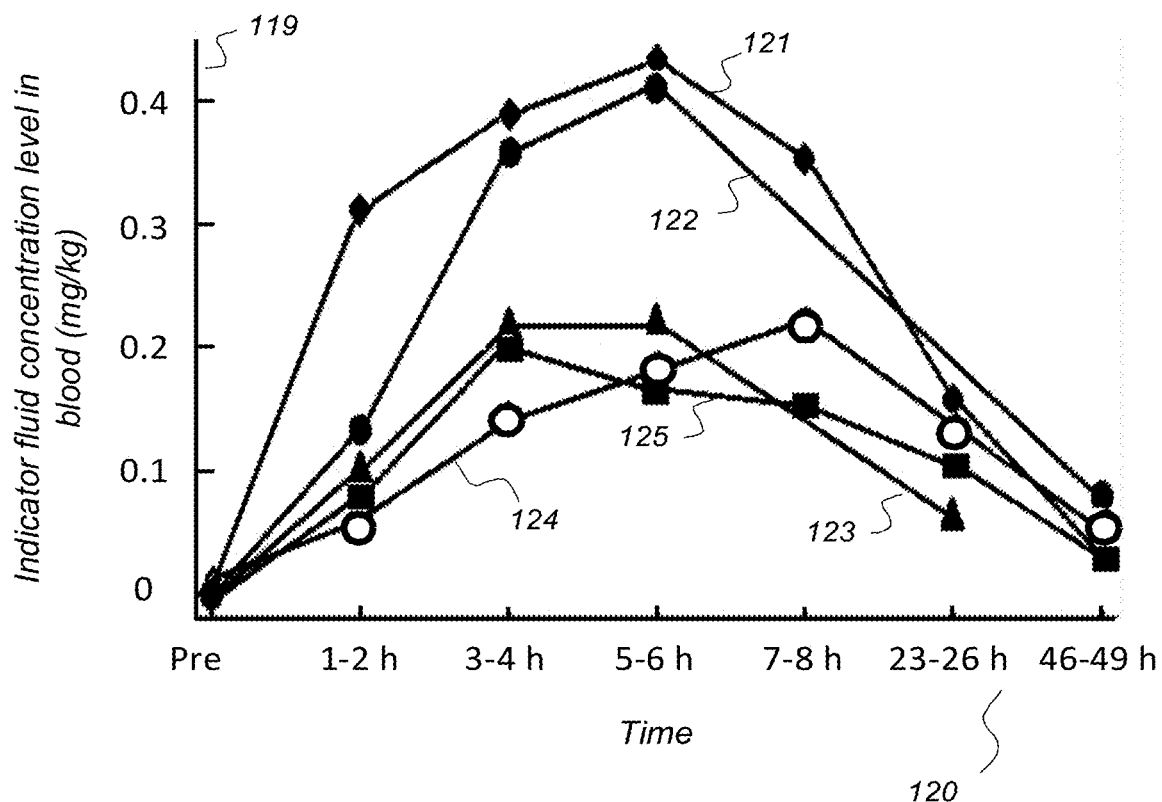

With reference to FIG. 1e, trend plots of average values of gadobutrol concentrations in blood (mg/kg) are shown for individuals with intracranial hypotension 121 (symbol ♦; n=4), idiopathic intracranial hypertension 122 (symbol ●; n=1), idiopathic normal pressure hydrocephalus 123 (symbol ▲; n=1), cerebral cyst 124 (symbol O; n=4), and arachnoid cyst 125 (symbol ■; n=4). The letter n refers to number of individuals within each group. Hence, the trend plots in FIG. 1e are based on blood concentration measurements from 14 individuals with different kinds of clinical conditions, and the trend plots reveal the time course of appearance of gadobutrol in blood. Half-time of gadobutrol in blood is about 1.8 hours. It should be noted that the amount and time course of appearance of gadobutrol in blood differs for the various groups of individuals, related to the fact that the ability to remove substances from the cranio-spinal compartment varies between individuals. While individuals with hypotension (symbol ♦; n=4) show a rapid rise in blood concentration level of indicator fluid 121, a slower increase in blood concentration level 123 was seen in the case with idiopathic normal pressure hydrocephalus (symbol ▲; n=1). Moreover, the time course suggests a maximum concentration after 5-6 hours for the trend plots 121, 122, 123, while after 3-4 hours for trend plot 125 and after 7-8 hours for trend plot 124. It should also be noted that after 23-26 hours, the indicator fluid concentration level 123 in blood was lowest for the individual with idiopathic normal pressure hydrocephalus. This condition is a dementia disease, and the low indicator fluid concentration in blood might be related to impaired ability to remove molecular substances from the cranio-spinal compartment. Regarding time 120 for measurement of indicator fluid concentration or level 119 in blood, there is no limitation concerning the present invention. It will be appreciated that measurement of indicator fluid concentration level could equally apply to concentration level in urine. Further, in FIG. 1e, the indicator fluid used was gadobutrol. The time periods indicated in FIG. 1e have shown preferable time points according to the inventor's experience. The concentrations may be determined after 24 or 48 hours or after any time point within 72 hours after the indicator fluid is present in CSF.

Indicator fluid concentration levels in blood or urine may be measured at selectable time points after indicator fluid was present in CSF. It is also possible to measure indicator fluid concentration at only time point, for example only after 23-26 hours. In this situation, the indicator fluid concentration of one individual should preferably be compared with the indicator fluid concentration of a group of individuals, for example a group of reference individuals. For example, if concentration level of indicator fluid in blood or urine is measured only once 23-26 hours after indicator fluid being present in CSF, changed concentration level may be indicative of impaired ability to remove molecular substances from the craniospinal cavity.

Figure 1F:
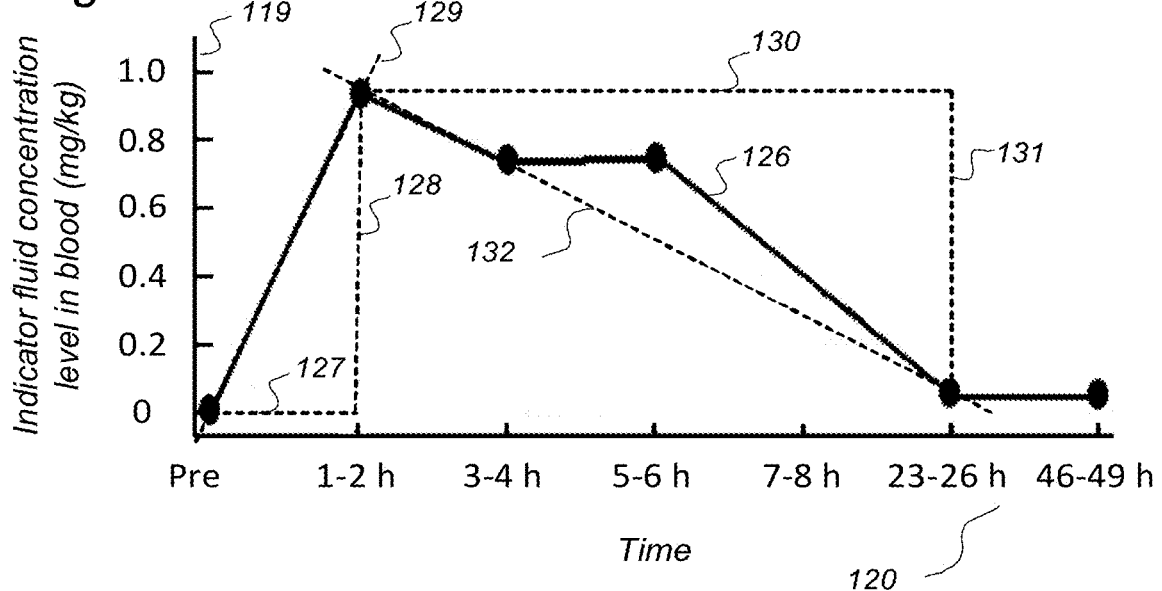

In FIG. 1f-h, the inventors provide some examples of measurements of indicator fluid (the MRI contrast agent gadobutrol) concentration level in blood at different time points after indicator fluid being present in CSF in three separate individuals. It should be noted that the invention gives no limitation regarding the method by which the blood concentration is measured. There is neither any limitation how often measurements may be done, or at which time points.

FIG. 1f shows the trend plot 126 of blood concentration level 119 of gadobutrol over time 120 after gadobutrol was present in CSF. Different parameters are indicated, namely time 127 to maximum concentration in blood, maximum level 128 of gadobutrol in blood, the coefficient 129 between maximum level and time to maximum concentration. Moreover, it is indicated the time 130 from maximum level to minimum level, the decline 131 in level, and the coefficient 132 between level and time from maximum to minimum. In addition, the blood concentration at each individual time point represents a separate variable. For this individual, it should be noted that the maximum level in blood occurred rapidly after indicator fluid (gadobutrol) was present in CSF, and a rather high concentration was present for the subsequent hours, as revealed in the trend plot 126. This could be related to the fact that the individual presented abnormal leakage of CSF from cranio-spinal compartment due to a rupture of the dura that surrounds the CSF spaces.

FIG. 1g shows the trend plot 133 of concentration level 119 of gadobutrol in blood over time 120 after being present in CSF of an individual with the dementia subtype normal pressure hydrocephalus. As compared with the individual presented in FIG. 1f, time 134 to maximum level in blood was longer, and the maximum level 135 in blood was lower, providing a lower coefficient 136 between level and time for maximum blood concentration. The time 137 from maximum level to minimum level, the decline 138 in level, and the coefficient 139 between level and time from maximum to minimum, are all indicated. As compared with the individual presented in FIG. 1f, the blood concentration values in FIG. 1g were lower at all time points, which is indicative of reduced ability to remove molecular substances from the craniospinal cavity.

In FIG. 1h is presented the trend plot 140 of concentration level 119 of gadobutrol (i.e. indicator fluid) in blood over time 120 after being present in CSF of an individual with idiopathic intracranial hypertension, which is a clinical condition with increased intracranial pressure of unknown cause. The time 141 to maximum level in blood was comparable to that seen in FIG. 1g, while the maximum level 142 in blood was between that seen in FIG. if and FIG. 1g. The coefficient 143 between level and time for maximum blood concentration is also indicated. In FIG. 1h is also presented the time 144 from maximum level to minimum level, the decline 145 in level, and the coefficient 146 between level and time from maximum to minimum. Compared with the blood concentrations presented in FIG. 1g, this individual had better ability to remove indicator fluid from craniospinal compartment.

The individual blood concentration levels presented in FIGS. 1f, 1g, and 1h and the average values for groups of individuals presented in FIG. 1e are examples of measurements in some individuals and are included for the purpose of illustration of the invention. These examples do, however, not represent a limitation of the invention. Regarding determination of reference values 116, 117 of different indicator fluids, reference values may be determined for a number of variables such as blood or urine concentration at any time point after indicator fluid being present in CSF, maximum level independent of time point, coefficient 129, 136, 143 between level and time for maximum concentration, or coefficient 132, 139, 146 between maximum decline and time to lowest level. Repeated measurements of blood or urine concentrations may be difficult, and single measurements after given time points might be preferable. Reference values may be based on such single measurements.

Blood or urine concentrations levels of indicator fluid may be related to other variables such as gender, age, body mass index. The ability to remove molecular substances from the craniospinal compartment to blood and urine probably heavily relies on physiological variables like these.

A first feature of Aspect 1 concerns an indicator fluid. A schematic view of the various characteristics is provided in FIG. 2. More specifically, this first feature relates to indicator fluid 201 comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. The selected indicator fluid 201 is for use in a human to assist in assessing ability of a cranio-spinal cavity of the human, i.e. the brain or the spinal cord compartment, to remove molecular substances 202. Parameters of removal 203 molecular substances 203 are a function of one or more of measured and analyzed level or change in level of indicator fluid concentration in urine or blood 204, removal of indicator fluid in urine or blood versus time, and indicator fluid half-time or radiation decay in urine or blood, and wherein the indicator fluid 201 exhibits molecular properties suitable for movement from a cerebrospinal fluid compartment of said cranio-spinal cavity to allow levels or change in level of the indicator fluid in the urine or blood samples 205 subsequently to be measured and analyzed once or at selectable time intervals 204 to determine said parameters of removal 203.

The indicator fluid 201 may be of a type being detectable by one or more of CT, MRI, PET, SPECT, and scintigraphy. Hence, the indicator fluid 201 may be a CT contrast agent, an MRI contrast agent, or a substance exhibiting recognized pharmacokinetic properties. Further, the indicator fluid 201 may be one of the CT contrast agents iohexol, iodixanol, iomeprol, ioversol, and iobitridol, or one of the MRI contrast agent gadobutrol or gadoteric acid. Gadolinium-diethylenetriamine (Gd-DTPA) is one of other MRI contrast agents that may be used (non-macrocyclic type contrast agents); however, non-macrocyclic contrast agents are less preferable than gadobutrol and gadoteric acid since they are considered chemically less stable in biological tissue. Moreover, the indicator fluid 201 can be a dendrimer based macromolecular MRI contrast agent of size sufficiently high to be retained outside the BBB, or a substance exhibiting resembling pharmacokinetic properties.

In addition, the indicator fluid 201 may be a radioactive ligand suitable for PET, SPECT or scintigraphy tied to or chelated with a CT or MRI contrast agent substance or a substance exhibiting recognized pharmacokinetic properties, and wherein the radioactive ligand is selectable tracer material from one or more of: $^{89}$Zirconium, $^{99m}$Tc-DTPA and $^{111}$In-DTPA. The indicator fluid 201 may contain a radioactive ligand, which is chelated with one or more of: large-molecule biotechnology based products, antibodies, monoclonal antibodies, recombinant proteins, and antisense or gene therapeutics means.

In another embodiment, the indicator fluid 201 may be a ligand with at least partial property of making a bond to tumor cells or inflammation cells or amyloid beta plaques.

The parameters of removal 203 are indicative of ability of the cranio-spinal cavity to remove substances 202 and refer to clearance of waste solutes from the CSF compartment or the brain or the spinal cord compartment. The clearance curve 109 depends on various factors such as the weight and size of the substance. Hence, the clearance curve 109 may differ depending on the substance used. Preferably, the indicator fluid 201 is configured to be deliverable to said CSF compartment by spinal puncture and intrathecal injection. The injection part itself is not part of the invention, as the invention comes to play after an indicator fluid having been administered to a human.

Some important features of the applicable indication fluids 201 should be noted. An indication fluid 201 should be non-BBB-penetrant, stable in brain tissue and preferably osmotically neutral, or near-neutral. Passive transfer across the BBB is promoted by low MW (<500 Da), small cross-sectional area (<80 Å$^2$), low hydrogen bonding capacity and lack of formal charge. The possible substances should preferably not have any of these traits, and should not be lipophilic. Nor should it be substrate for brain efflux transporters at the BBB, and therefore not be a substrate for a variety of transport proteins that work to extrude compounds from the brain. We used gadobutrol, which is an MRI contrast agent with MW 605 Da although iohexol (Omnipaque™; MW 821 Da) or the iso-osmolal iodixanol (Visipaque™; MW 1550 Da) could be used as they are commonly used CT contrast agents. Iohexol has already application for measurement of renal clearance following intravenous administration. Alternatively, when iohexol is present within the CSF compartment, one or repeated blood level measurements of iohexol may be applied for assessing cerebral clearance. It would also be possible to measure iohexol or iodixanol in urine as they do not degrade from blood to urine, and are neither excreted via other pathways, and the excretion rate to urine is predictable when kidney function is normal. According to prior art, the CSF compartment is assessable via the intrathecal route, or via cisterna magna or the cerebral ventricles. The CT contrast agents are from prior art approved for intrathecal use to enhance CSF (CT myelography, CT cisternography). The current invention described here utilizes secondary use of contrast agents or radioisotopes as indicator fluids to assess metabolic clearance function of the cranio-spinal cavity.

The half-life of a radiotracer should preferably exceed 24 hours. In this regard, it should be noted that all large-molecule products of biotechnology, such as monoclonal antibodies (mAbs), recombinant proteins, antisense, or gene therapeutics, do not cross the BBB. Regarding radioligands, one radionuclide that may be used as biomarker of paravascular clearance is $^{89}$Zirconium (half-life 78.4 hours). $^{89}$Zirconium may be chelated with monoclonal antibodies. Conjugation and radiolabeling of monoclonal antibodies with $^{89}$Zirconium for PET imaging using the bifunctional chelate p-isothiocyanatobenzyl-desferrioxamine. Other radioligands that may be used are $^{99m}$Tc-DTPA or $^{111}$In-DTPA.

Table 1 provides an overview of currently used contrast agents intended for use with CT and MRI, and radioactive ligands intended for use with PET, SPECT and scintigraphy. The table also shows manufacturers. These are possible indicator fluids 201 according to the invention.

refers to clearance of waste solutes from the CSF compartment 102 or the brain or the spinal cord compartment 103. The clearance curve 109 depends on various factors such as the weight and size of the indicator fluid. Examples of parameters of removal 203 include:

level or change in level of indicator fluid concentration within blood and/or urine 204, coefficient of contrast agent removal (clearance) versus time, indicator fluid half-time, (or half-life for radioactive substances), and level or changes in level of nuclear radiation from indicator fluid.

Figure 3:
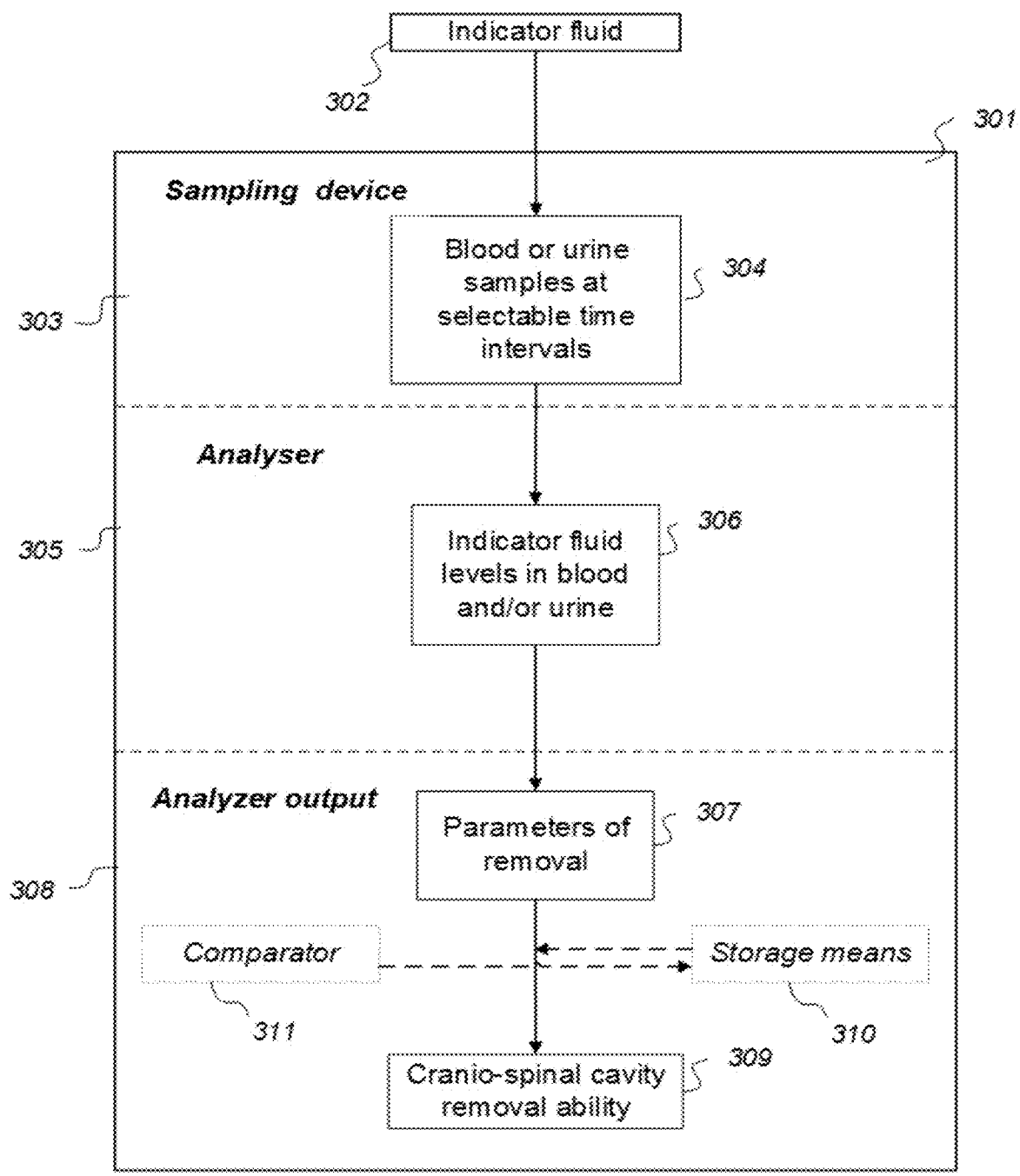
FIG. 3 illustrates both a system for assessing ability of a cranio-spinal cavity of a human to remove substances therefrom, and usage of an intrathecally injectable indicator fluid to assess ability of a cranio-spinal cavity of a human to clear waste solutes therefrom.

A second feature of Aspect 1 concerns a system to assess ability of a cranio-spinal cavity of a human, i.e. the brain or the spinal cord compartment, to remove molecular substances therefrom, upon presence of an indicator fluid in movement from a cerebrospinal fluid compartment of said cranio-spinal cavity. This aspect is illustrated in FIG. 3. The system 301 comprises an indicator fluid 302 comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the system 301 comprising:

a) a sampling device 303 being configured to sample and measure levels of said indicator fluid in blood or urine or radiation levels of the indicator fluid at selectable time intervals 304, b) an analyzer 305 being configured to analyze amount of indicator fluid level 306 in said blood or urine samples 304

TABLE 1

CT and MM contrast agents and radioactive ligands, which may serve as indicator fluids 201.

| Generic name | Brand name | MW (Da; g/mol) | Pharmaceutical company | Primary usage |
|---|---|---|---|---|
| Iohexol | Omnipaque® | 821 | GE Healthcare | CT/radiography |
| Iodixanol | Visipaque® | 1,550 | GE Healthcare | CT/radiography |
| Iomeprol | Iomeron® | 777 | Bracco Imaging | CT/radiography |
| Ioversol | Optiray® | 807 | Blue Ridge Xray/Guerbet | CT/radiography |
| Iobitridol | Xenetix® | 835 | Guerbet | CT/radiography |
| Gadobutrol | Gadovist®/Gadavist® | 605 | Bayer | MRI |
| Gadoteric acid | Dotarem® | 559 | Guerbet | MRI |
| $^{89}$Zirconium | $^{89}$Zirconium | 753* | PerkinElmer Inc/Cyclotron$^{VU}$ | Immuno-PET |
| $^{99m}$Tc-DTPA | | 487 | CheMall Corporation | Radionuclide |
| $^{111}$In-DTPA | | 545 | GE Healthcare | Radionuclide |

*when conjugated with the monoclonal antibody Df-Bz-NCS.
MW: Molecular weight.

Other CT and MRI contrast agents may also be used. The indicator fluid 201 may also be a CT or a MRI contrast agent coupled with one or more of: large-molecule biotechnology based products, antibodies, monoclonal antibodies, recombinant proteins, and antisense or gene therapeutics means. Gadolinium-diethylenetriamine (Gd-DTPA) is another MRI contrast agent that may be used; however, this contrast agent is less preferable than gadobutrol and gadoteric acid since it is chemically less stable. Therefore, it is not listed in Table 1.

The parameters of removal 203 are indicative of ability of the cranio-spinal cavity to remove indicator fluids 202, and to determine parameters of removal 307 of said indicator fluid from said cranio-spinal cavity, and c) an analyzer output 308 to provide a presentation of said parameters of removal 307, said parameters of removal 307 being at least one of:

level or change in level of indicator fluid concentration in blood or urine 306, coefficient of indicator fluid removal (clearance) versus time in blood or urine, indicator fluid half-time or nuclear radiation decay in blood or urine, and levels or change in levels of nuclear radiation acquisition from blood or urine, and said parameters of removal 307 being indicative of ability of said cranio-spinal cavity, i.e. the brain or the spinal cord compartment, to remove said indicator fluid 309, and thereby being a function of ability of clearance of any waste solutes of molecular substances from the cerebrospinal fluid, brain or spinal cord compartment of said cranio-spinal cavity.

The indicator fluid 302 of the system may be of a type being detectable by CT, MRI, PET, SPECT, and scintigraphy. Furthermore, indicator fluid 302 of the system 301 may contain a CT contrast agent, or an MRI contrast agent, or be a substance exhibiting recognized pharmacokinetic properties. The CT contrast agent may be iohexol, iodixanol, iomeprol, ioversol, and iobitridol, and the MRI contrast agent may be gadobutrol or gadoteric acid, see Table 1. Other CT and MRI contrast agents may also be used. For example, gadolinium-diethylenetriamine (Gd-DTPA) is another MRI contrast agent that might be used; however, it is less preferable than gadobutrol and gadoteric acid since it is considered chemically less stable in biological tissue.

The indicator fluid 302 may also be a CT or an MRI contrast agent coupled with one or more of: large-molecule biotechnology based products, antibodies, monoclonal antibodies, recombinant proteins, and antisense or gene therapeutics means. Moreover, the indicator fluid 302 can be a dendrimer based macromolecular MRI contrast agent of size sufficiently high to be retained outside the BBB, or a substance exhibiting resembling pharmacokinetic properties.

The indicator fluid 302 of the system 301 may as well be a radioactive ligand suitable for PET, SPECT or scintigraphy imaging tied to or chelated with a CT or MRI contrast agent substance or a substance exhibiting recognized pharmacokinetic properties. The radioactive ligand may be a selectable tracer material from one of: $^{89}$Zirconium, $^{99m}$Tc-DTPA, and $^{111}$In-DTPA. Further, the indicator fluid 302 may contain a radioactive ligand which is chelated with one or more of: large-molecule biotechnology based products, antibodies, monoclonal antibodies, recombinant proteins, and antisense or gene therapeutics means. The ligand may have a property of making a bond to tumor cells or inflammation cells or amyloid beta plaques.

The indicator fluid 302 of the system 301 may be deliverable to a CSF compartment of the cranio-spinal cavity by spinal puncture and intrathecal injection, or via intracisternal or intraventricular routes. The indicator fluid administration step itself is not part of the invention as the invention comes to play when an indicator fluid is present within a CSF compartment.

In one embodiment of the system 301, storage means 310 are provided to store parameters of removal 307, which are determined for a cohort of human individuals, and wherein a comparator 311 is provided to compare parameters of removal 307 obtained from at least one individual human against said stored parameters of removal 307 of said cohort of humans.

The levels of any substances measured in human blood or urine 306 will vary. Using information provided by storage means 310 and comparator 311, the clearance-curve derived parameters of removal 109 may be established for groups of individuals. For example, the inter-individual variance may be characterized by 95% confidence intervals (CI). Thereby, individual measurements may be compared against a cohort. Preferably, statistical presentations of clearance curves should be created from a large cohort of individuals, and preferably be categorized according to such as: Age, health state (healthy or chronic disease), presence of co-morbidity, presence of certain diseases (e.g. Alzheimer's, hydrocephalus, intracranial hypertension etc.), duration of disease, and other factors. Each clearance curve 109 must be defined by the substance used, volume and concentration of said substance 107, and the time for blood samples 108.

The first aspect of the invention may be applied to assess removal of substances from the cranio-spinal cavity via lymphatic pathways to blood (FIG. 1a). Brain clearance of substances may be affected by a wide range of circumstances such as sleep disturbances, headache, neurodegenerative disease, neuro-inflammatory disease, abnormal intracranial pressure (ICP), and following acute brain injuries such as traumatic brain injury, stroke and brain infection.

Figure 4:
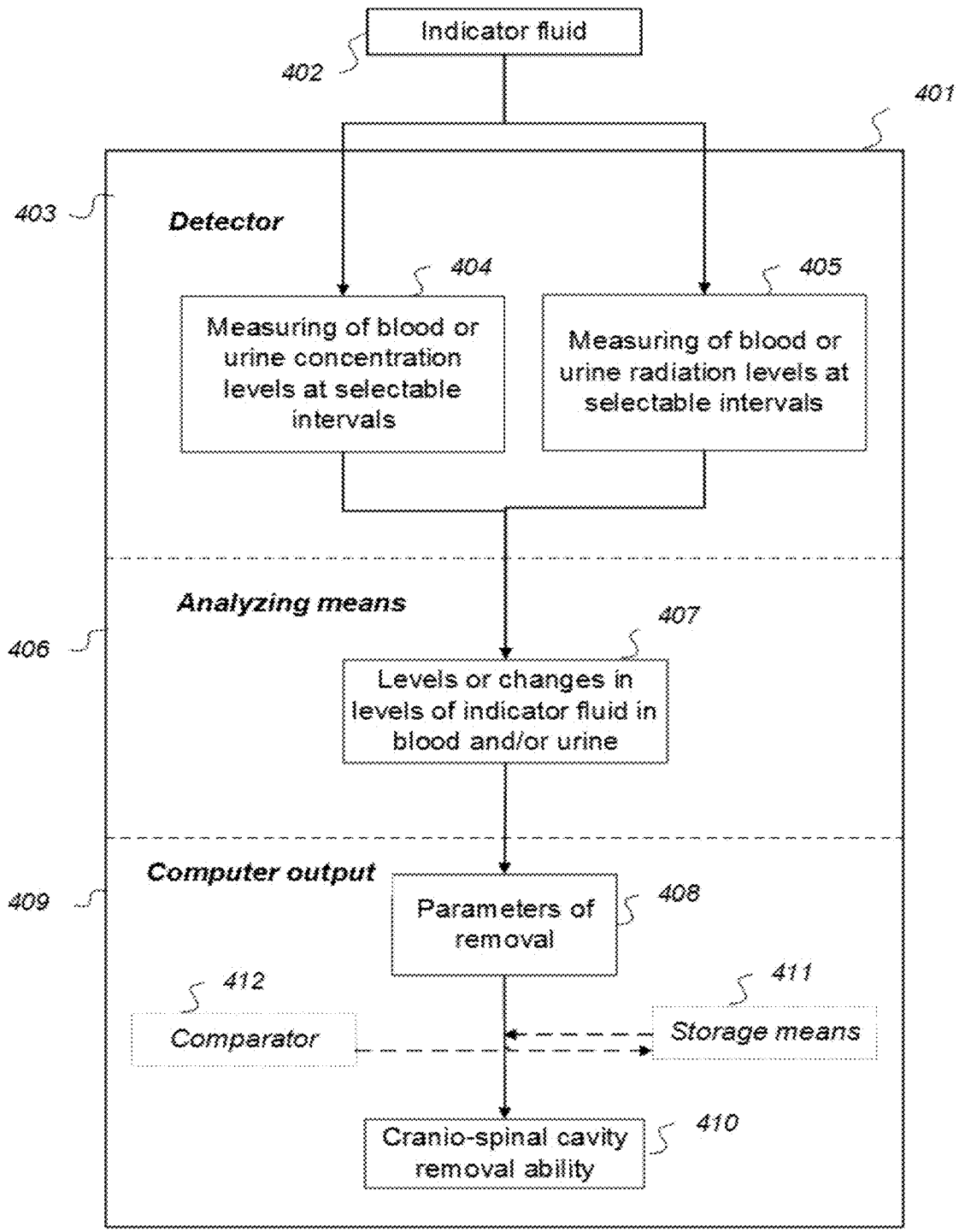
FIG. 4 illustrates a computer-assisted method for assessing ability of a cranio-spinal cavity of a human to remove substances therefrom.

In a third feature of Aspect 1, a computer-assisted method is disclosed, see FIG. 4. More specifically, the third feature relates to: A computer assisted method 401 to assess ability of a cranio-spinal cavity of a human, i.e. the brain or the spinal cord compartment, to remove molecular substances therefrom, upon presence of an indicator fluid 402 in movement from a cerebrospinal fluid compartment of said cranio-spinal cavity. The indicator fluid 402 is comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, the method comprising:

a) measuring once or at selectable time intervals by means of detectors 403 operatively linked to a computer a1) levels of said indicator fluid in blood or urine 404, or a2) levels of nuclear radiation from said indicator fluid in blood or urine 405, b) analyzing by means of the computer 406 said levels of the indicator fluid 407 to determine parameters of removal 408 of said indicator fluid 402 from said cranio-spinal cavity, and c) presenting said parameters of removal 408 as delivered from a computer output 409, said parameters of removal 408 being at least one of:

level or change in level of indicator fluid concentration in blood or urine 407, coefficient of contrast agent removal (clearance) versus time in blood or urine, indicator fluid half-time or nuclear radiation decay in blood or urine, and level or changes in level in blood or urine of nuclear radiation from indicator fluid, said presented parameters of removal 408 being indicative of ability of said cranio-spinal cavity, i.e. a cerebrospinal fluid, brain or spinal cord compartment, to remove said indicator fluid therefrom 410.

The presented parameters of removal 408 are indicative of the ability of the cranio-spinal cavity, i.e. the brain or spinal cord compartment, to remove the indicator fluid therefrom 410. The ability of a cranio-spinal cavity to remove substances 410 refers to clearance of waste solutes from the CSF compartment or the brain or spinal cord compartment.

A selectable indicator fluid 402 may be administrable to a CSF compartment via spinal puncture and intrathecal injection, or via the intracisternal or intraventricular routes, though the administration step itself is not part of the invention.

The method may utilize an indicator fluid 402 that is detectable by one or more of: CT, MRI, PET, SPECT, and scintigraphy. The indicator fluid 402 may contain a CT contrast agent, or an MRI contrast agent, or being a substance exhibiting recognized pharmacokinetic properties. Further, the CT contrast agent may be one of: iohexol, iodixanol, iomeprol, ioversol, and iobitridol, and the MRI contrast agent may be gadobutrol or gadoteric acid. Other CT and MRI contrast agents may also be used. The indicator fluid 402 may also be a CT or an MRI contrast agent coupled with one or more of: large-molecule biotechnology based products, antibodies, monoclonal antibodies, recombinant proteins, and antisense or gene therapeutics means. Moreover, the indicator fluid 402 may be a dendrimer based macromolecular MRI contrast agent of size sufficiently high to be retained outside the BBB, or a substance exhibiting resembling pharmacokinetic properties.

The method may as well utilize an indicator fluid 402 being composed of a radioactive ligand suitable for PET, SPECT or scintigraphy tied to or chelated with a CT or MRI contrast agent substance or being a carrier substance with recognized pharmacokinetic properties. Further, the indicator fluid 402 may contain a radioactive ligand, which is chelated with at least one of: large-molecule biotechnology based products, antibodies, monoclonal antibodies, recombinant proteins, and antisense or gene therapeutics means. The radioactive ligand may be a selectable tracer material being one of: $^{89}$Zirconium, $^{99m}$TC-DTPA, and $^{111}$In-DTPA. According to the method, said ligand may at least have partial property of making a bond to tumor cells or inflammation cells or amyloid beta plaques.

Concerning one embodiment of the invention, parameters of removal 408 are determined for a cohort of human individuals and stored in a computer storage means 411, which allows parameters of removal 408 associated with one human individual to be compared 412 with said stored parameters of removal.

In a fourth feature of Aspect 1 is disclosed usage of an intrathecally injectable indicator fluid 201, 302, 402 comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, to derive at a presentation of parameters of removal 203, 307, 408 of said indicator fluid from a cranio-spinal cavity of a human, said parameters of removal 203, 307, 408 being a function of ability of the cranio-spinal cavity to clear molecular waste solutes from the cerebrospinal fluid, brain or spinal cord compartment 202, 309, 410.

The main elements of said usage are illustrated in FIG. 3. An indicator fluid 302 is administrable to a CSF compartment. The administration step itself is not part of the invention. When an indicator fluid is present within CSF, measurements of concentration level or radiation level within blood and/or urine 306 allows determination of parameters or removal 307, which are indicative of the ability of the cranio-spinal cavity to remove substances therefrom 309.

The usage of an indicator fluid 302 may imply that the indicator fluid 302 is of a type being detectable by one or more of: CT, MRI, PET, SPECT, and scintigraphy. Accordingly, the indicator fluid 302 may contain a CT contrast agent, or a MRI contrast agent, or a substance exhibiting recognized pharmacokinetic properties. The CT contrast agent may be a selected one of: iohexol, iodixanol, iomeprol, ioversol, and iobitridol, or a MRI contrast agent of either gadobutrol or gadoteric acid. Other CT and MRI contrast agents may also be used. The indicator fluid 302 may also be a CT or an MRI contrast agent coupled with one or more of: large-molecule biotechnology based products, antibodies, monoclonal antibodies, recombinant proteins, and antisense or gene therapeutics means. Moreover, the indicator fluid can be a dendrimer based macromolecular MRI contrast agent of size sufficiently high to be retained outside the BBB, or a substance exhibiting resembling pharmacokinetic properties.

The indicator fluid 302 may also be a radioactive ligand suitable for PET, SPECT or scintigraphy imaging tied to or chelated with a contrast agent substance or a substance exhibiting recognized pharmacokinetic properties. The radioactive ligand may be a selectable tracer material from at least one of: $^{89}$Zirconium, $^{99m}$Tc-DTPA and $^{111}$In-DTPA. In another embodiment, the indicator fluid 302 may contain a radioactive ligand, which is chelated with at least one of: large-molecule biotechnology based products, antibodies, monoclonal antibodies, recombinant proteins, and antisense or gene therapeutics means. Said ligand may have at least partial property of making a bond to tumor cells or inflammation cells or amyloid beta plaques.

The inventive steps presented in the various features of Aspect 1 evolved from a series of studies in humans. We performed repeated MRI acquisitions with standardized T1 weighted sequences with a MRI contrast agent gadobutrol and CT contrast agent iodixanol present within the CSF compartment, including imaging of the cranio-spinal compartments and the cervical LNs. In these studies, gadobutrol and iodixanol served as examples of indicator fluids 302. These observations are described in more detail under Aspect 4 of this invention. In short, after gadobutrol having been administered intrathecal, the increase in MRI SUs within brain tissue and cervical LNs occurred at similar time. Our experimental studies provided evidence that substances/indicator fluids (e.g. gadobutrol and iodixanol) 101 within the CSF compartment 102 leave the human craniospinal cavity by passing through the paravascular spaces 104 of the brain or spinal cord compartment 103 and further through the lymphatic pathways 105, including cervical LNs, and finally to the blood circulation 106.

Our observations imply that substances (molecules, proteins, peptides etc.) of a certain size 101 within the CSF compartment 102 is removed by passage through the CNS tissue 103 via the paravascular pathways, via the lymphatic vessels of the veins and dural sinuses of the cranio-spinal cavity, and eventually drained unto the extra-cranial lymphatic pathways and LNs 105, and then to the blood circulation 106. From the blood, many substances are typically cleared via the renal system and out of the body via the urine. An indicator fluid 101 may be present within the CSF compartment of the cranio-spinal cavity 102, for example after having been delivered via the lumbar or ventricular routes. As illustrated in FIG. 1b, a selectable number of blood samples, typically venous blood, are obtained at regular intervals or at a single time point 109. Urine samples at different time points may also be obtained if the indicator fluid passes unaltered to the urine from the blood. For example, blood samples are obtained after 1, 6, 24 and 48 hours, though this represents no limitation. The blood sample values are plotted against time and when several samples are obtained, a clearance curve 109 may be created. This is illustrated in FIG. 1b. The clearance curve 109 of one individual may be characterized by the change in plasma concentration, the clearance time and the clearance coefficient. Various modifications of the equation may be done. A single blood or urine sample value may be compared with an established reference interval.

While this invention presumes that the most of waste solutes are cleared via the paravascular routes of the brain and further to dural lymphatic vessels, the invention does not exclude the opportunity for clearance via other routes 111 such as perineural routes (e.g. along optic and ophthalmic nerves) or through the cribriform plate and nasal lymphatics. The proportion drained via non-lymphatic pathways 111 may be determined as a constant, and partly by its different time course. In this regard, it is important to note that the mechanisms of removal of substances from the brain depend on the substance in question. For example, the removal of water ($H_2O$ molecule) with MW 18 Da may be different from removal of iohexol or gadobutrol with much higher MWs.

In the following, Aspect 2 of the invention is commented on, which incorporates means (indicator fluid, system and computer-aided method) to assess movement of substances within, to or from a CSF, brain or spinal cord compartment of a cranio-spinal cavity of a human.

Figure 5:
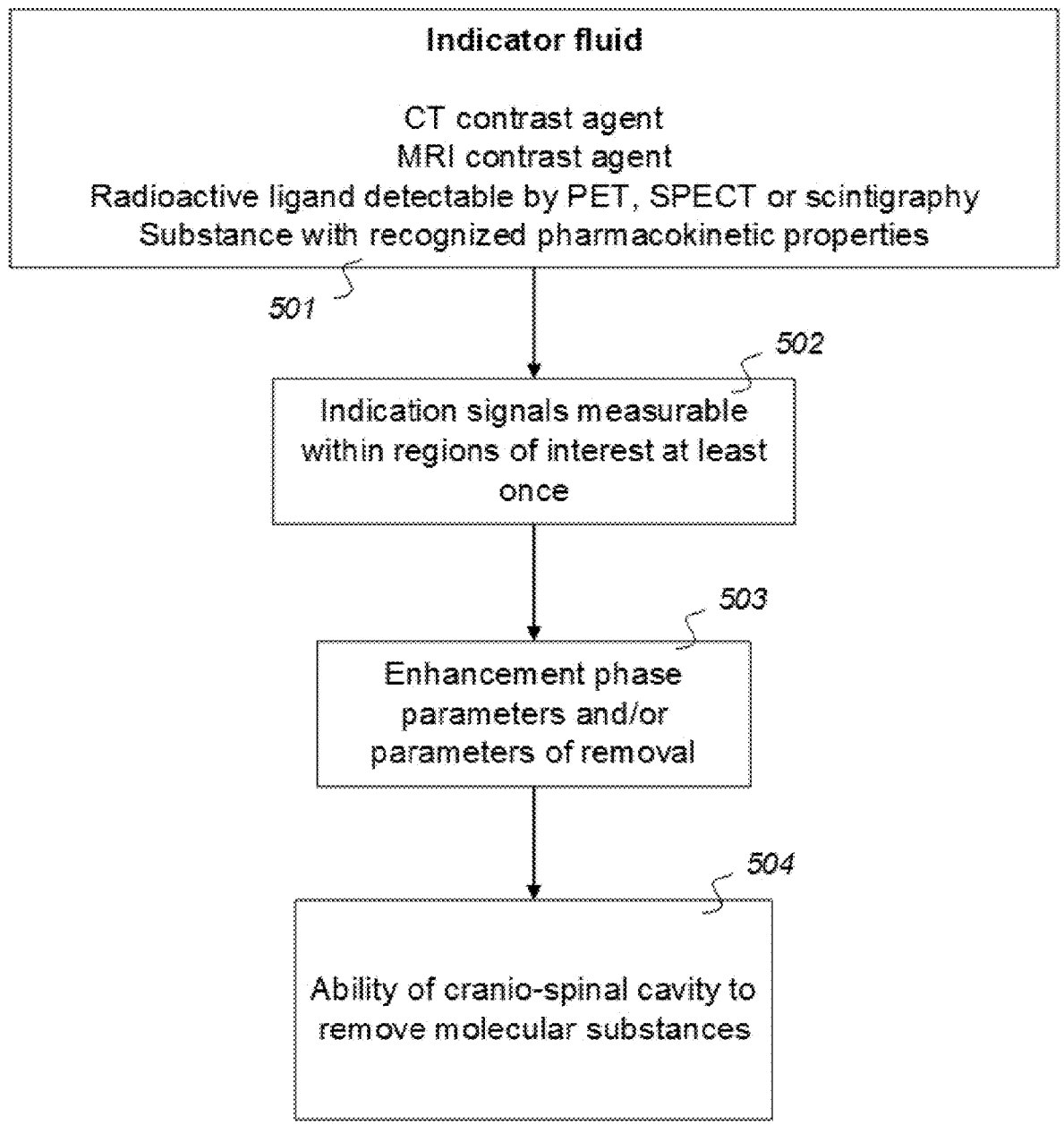
FIG. 5 illustrates usage of an indicator fluid to assess movement of substances within, to or from a CSF, brain or spinal cord compartment of a cranio-spinal cavity of a human.

In a first feature of Aspect 2 an indicator fluid is disclosed. More specifically, and as illustrated in FIG. 5, said first feature relates to: An indicator fluid 501 comprising one or more of:

a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. The indicator fluid 501 is configured to assist in assessing movement of molecular substances from a cerebrospinal fluid compartment to a nearby brain or spinal cord compartment of a cranio-spinal cavity of a human. Moreover, the indicator fluid 501 to be movable along a movement path of said molecular substances, wherein upon movement of the indicator fluid 501 from said cerebrospinal fluid compartment, indicator fluid indication signals being measurable at least once within regions of interest of said cerebrospinal fluid, brain or spinal cord compartment 502, measurements to be made of indication signals from the cerebrospinal fluid compartment or simultaneously both from the cerebrospinal fluid compartment and said brain or spinal cord compartment 502, and wherein enhancement phase parameters and/or parameters of removal of the indicator fluid 503 from said cranio-spinal cavity being providable, said enhancement phase parameters and/or parameters of removal 503 being based on at least one of change in indication signals, and being indicative of ability of said cranio-spinal cavity to remove molecular substances 504, said ability to remove molecular substances referring to clearance of waste solutes from the cerebrospinal fluid, brain or spinal cord compartment.

In this context, the term "molecular substance" has a wide meaning. It may be small molecules [e.g. water ($H_2O$) molecule, MW 18 gr/mole (=18 Da)], macromolecules (e.g. the contrast agents gadobutrol (Gadovist™; MW 605 Da) and iohexol (Omnipaque™, MW 821 Da), peptides (e.g. amyloid-β protein fragment 1-42, MW 4 514 Da), proteins (e.g. Tau-protein, MW 55-62 000 Da), and antibodies (e.g. immunoglobulin G, MW 150 kDa). Obviously, the movement of a substance within, to or from a cranio-spinal cavity depends on the size of the substance.

The notation "indication signal" has a broad meaning, and depends on imaging modality. CT refers to Hounsfield Units (HU), MRI refers to SUs and PET, SPECT and scintigraphy refer to Standard Uptake Value (SUV). The present invention is primarily based on MRI studies; then the indication signals refer to MRI SUs.

Concerning regions of interest (ROIs), a selectable number of ROIs containing image voxels of which the MRI indication signals (i.e. SUs) or radioactive radiation imaging indication signals (i.e. SUV) can be measured. An indication signal is thus a measurable feature derived from an imaging modality, where the indication signal level may be influenced by presence of indicator fluid. Most importantly, indication signals may be measured both in the presence or absence of indicator fluid. In other words, the presence of an indicator fluid is not a requirement for measuring indication signals.

The movement of the indicator fluid 501 within, to or from a CSF compartment may be a function of ability of a) movement of substances between individual CSF compartments, e.g. cerebral ventricles within the cranio-spinal cavity, or b) removal of substances via the brain or spinal cord compartment from said cranio-spinal cavity 504. In this regard, the indicator fluid 501 may be a CT contrast agent, or an MRI contrast agent, or a substance exhibiting recognized pharmacokinetic properties. Examples of indicator fluids 501 are given in Table 1. The CT contrast agent may be a selected one of: iohexol, iodixanol, iomeprol, ioversol, and iobitridol, and the MRI contrast agent may be gadobutrol or gadoteric acid. Furthermore, the indicator fluid 501 may be a radioactive ligand suitable for PET, SPECT or scintigraphy tied to or chelated with a CT or MRI contrast agent substance or a substance exhibiting recognized pharmacokinetic properties. The radioactive ligand may be a selectable tracer material from at least one of: $^{89}$Zirconium, $^{99m}$Tc-DTPA, and $^{111}$In-DTPA. In another embodiment, the indicator fluid 501 may contain a radioactive ligand, which is chelated with material being at least one of: large-molecule biotechnology based products, antibodies, monoclonal antibodies, recombinant proteins, and antisense or gene therapeutics means. Various modifications are possible. Hence, the indicator fluid 501 may be constructed so that the material is chelated with a radioactive ligand having at least a partial property of making a bond to tumor cells or inflammation cells or amyloid beta plaques.

The indicator fluid 501 may also be a CT or an MRI contrast agent coupled with one or more of: large-molecule biotechnology based products, antibodies, monoclonal antibodies, recombinant proteins, and antisense or gene therapeutics means. Moreover, the indicator fluid can be a dendrimer based macromolecular MRI contrast agent of size sufficiently high to be retained outside the BBB, or a substance exhibiting resembling pharmacokinetic properties. The indicator fluid 501 may be configured to be administrable to a CSF compartment by spinal puncture and intrathecal injection, or via the intracisternal or intraventricular routes.

In a second feature of Aspect 2 a system is disclosed. More specifically, this second feature relates to a system to assess movement of molecular substances from a cerebrospinal fluid compartment to a nearby brain or spinal cord compartment of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. The system is further illustrated in FIG. 6. The system 601 comprises:

a) an apparatus 602 configured for one of computed tomography (CT), magnetic resonance imaging (MRI), positron emission tomography (PET), single photon emission computed tomography (SPECT), and scintigraphy imaging, and related to the selected indicator fluid 603, b) a detector device 604 and a sampling device 605 configured to measure at least once indicator fluid indication signals 606 from the cranio-spinal cavity as provided by use of said apparatus 602 within regions of interest of said cerebrospinal fluid, brain or spinal cord compartment, the measuring to be made of indication signals from the cerebrospinal fluid compartment or simultaneously both from the cerebrospinal fluid compartment and said brain or spinal cord compartment 607, and c) an analyzer 608 capable of determining any sampled and detected change in indication signals 609 over time within selectable fluid compartments of said cranio-spinal cavity, said changes in indication signals being indicative of said movement of indicator fluid within, to or from said cerebrospinal fluid, brain or spinal cord compartment of said cranio-spinal cavity, and d) an analyzer output 610 to provide a presentation of said changes in indication signals 609 as enhancement phase parameters and/or parameters of removal of the indicator fluid 611 as a function of ability of movement of molecular substances between individual cerebrospinal fluid compartments, e.g. cerebral ventricles within the cranio-spinal cavity, or removal of molecular substances via the cerebrospinal fluid, brain or spinal cord compartment from said cranio-spinal cavity 612, said ability of movement or removal of molecular substances 612 referring to and being a function of clearance of waste solutes.

For this system, the ROIs are related to a selectable number of ROIs containing image voxels of which the MRI indication signals 606, 607 or radioactive radiation imaging indication signals 606, 607 can be measured. Image acquisition may be MRI incorporating T1 weighted sequences with standardized acquisition parameters being at least echo and repetition time, flip angle, matrix, and field of view. Other imaging parameters may also be standardized to maximize T1 SU reproducibility.

The indicator fluid 603 of the system 601 may be a CT contrast agent, or a MRI contrast agent, or a substance exhibiting recognized pharmacokinetic properties. The CT contrast agent may be a selected one of: iohexol, iodixanol, iomeprol, ioversol, and iobitridol, and the MRI contrast agent either gadobutrol or gadoteric acid. The indicator fluid 603 may as well be a radioactive ligand suitable for PET, SPECT or scintigraphy imaging tied to or chelated with a contrast agent substance or a substance exhibiting recognized pharmacokinetic properties. Furthermore, the radioactive ligand may be a selectable tracer material from at least one of: $^{89}$Zirconium, $^{99m}$Tc-DTPA, and $^{111}$In-DTPA. In another embodiment, the indicator fluid 603 contains a radioactive ligand which is chelated with a material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques. The indicator fluid 603 may also be a CT or an MRI contrast agent coupled with one or more of: large-molecule biotechnology based products, antibodies, monoclonal antibodies, recombinant proteins, and antisense or gene therapeutics means. The indicator fluid 603 may be administrable to a CSF compartment by spinal puncture and intrathecal injection.

The system 601 allows for comparisons between individuals and a cohort of individuals. For this purpose, the system has a transfer device 613 capable of transferring ROI from the imaging acquisition to an anatomical coordinate system 614; the anatomical coordinate system is configured to enable segmentation of selectable anatomic regions. Further, the system has a comparator 615 enabling a comparison of change in indication signals over time between indication signal changes in a single human individual and changes in multiple ones of human individuals, using a database of multiple human individuals 616. A comparator output 617 is configured to provide a presentation of any deviation in movement of substances in as measured and acquired from a single human individual compared to average movement of substances in multiple ones of human individuals. Thereby, the system 601 allows for comparisons of clearance curves derived from selectable ROIs with clearance curves derived from comparable ROIs from a cohort of humans, by means of said anatomical coordinate system.

In one embodiment, the system is cooperative with an MRI SU standardization device (see Aspect 7) to cause indication signals being SUs to be standardized SUs, where the standardization device comprises an extra-body device containing at least one reference indicator fluid of specific concentration 618. At least one reference indicator fluid 618 is located within one or more containers to be located externally of the body of the human, and the containers may also be filled with other dedicated material; standardized SUs allow for measurement of absolute values of indicator fluid within the ROI of a human individual. Changes in standardized SUs over time may be presented as a graphically drawn curve illustrating clearance of indicator fluid within a selectable ROI. The dedicated material may be a dummy material having liquid properties, e.g. viscosity or molecular property, of standard cranio-spinal cavity liquid or having semi-solid material properties. e.g. density or molecular property, of standard properties of standard brain tissue. This particular embodiment is described in detail for Aspect 7 of the invention. Some characteristics of a clearance curve of indicator fluid are illustrated in FIG. 7. Notably, the clearance illustrating curve is representative for Aspect 2-7 of the present invention.

Figure 7A:
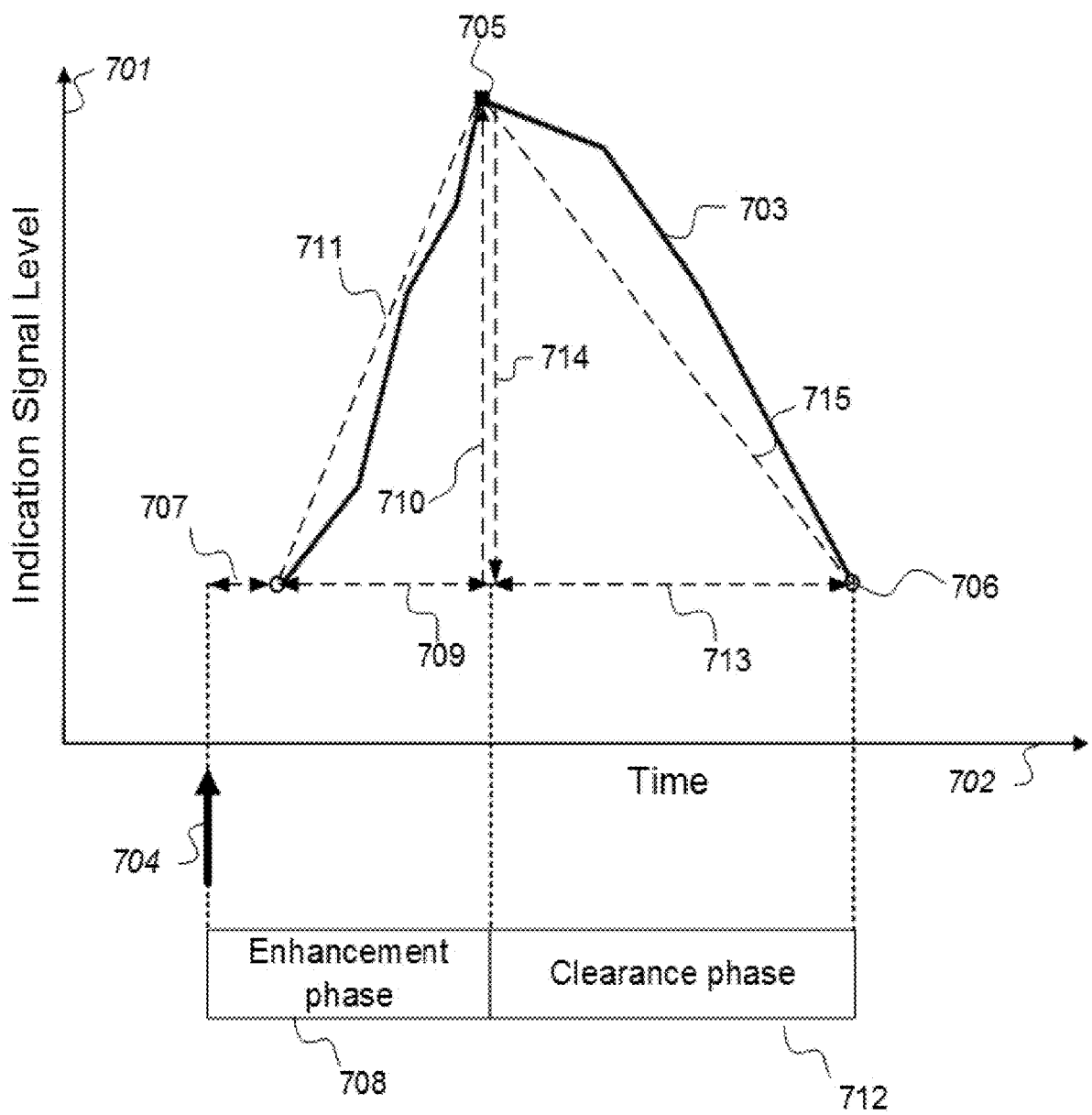
FIG. 7a-e provide a schematic illustration of a graphic curve illustrating clearance, providing for enhancement phase parameters and parameters of removal related to clearance of substances, and illustrates the process of measuring signal units within regions of interest, including determination of signal unit ratios.

In FIG. 7a the change in indication signals 701 are plotted over time 702, providing for a graphically drawn curve 703, which illustrates clearance of indicator fluid. When an indicator fluid 704 is present within the CSF, the indication signals typically increase, reach a maximum 705, and then declines to a minimum 706. The time 707 from indicator fluid having been injected until first measurement of indication signal may depend on site of injection; there is inter-individual variation. When the indicator fluid is administered to the spinal compartment by intrathecal administration, we denote this the spinal transit time 707. Hence, the clearance illustrating curve 703 describes the time-dependent changes in indication signals, and may provide for at least one of the following parameters:

a) enhancement phase 708 with attributes selectable from: time to peak (TTP) 709, time to first enhancement 707, maximum increase of indication signals 710 and enhancement coefficient 711, and b) clearance (or removal) phase 712 with attributes selectable from: clearance time 713, maximum reduction of indication signals 714, clearance coefficient 715, area under the clearance illustrating curve, and indicator fluid half-time.

Figure 7B:
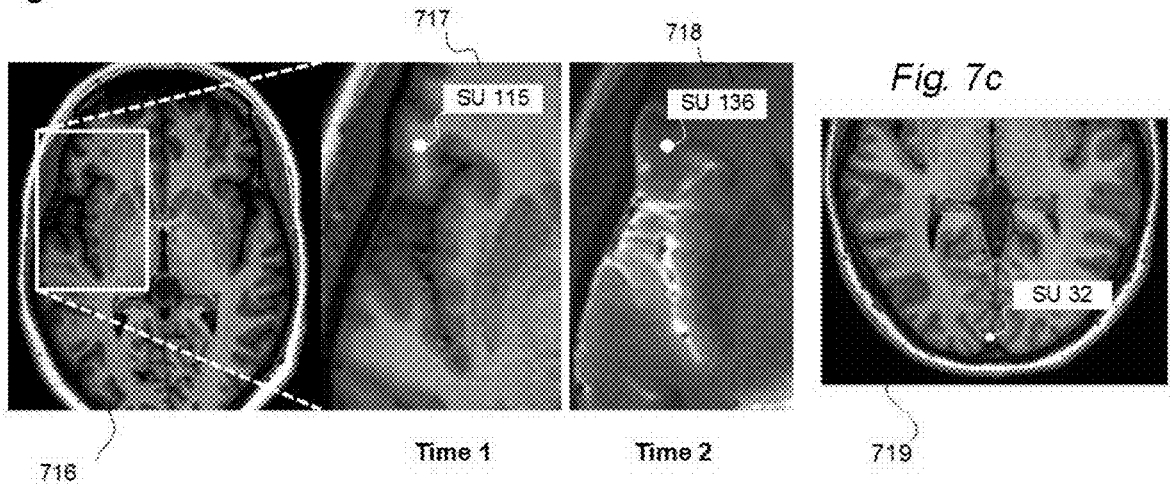
Figure 7C:
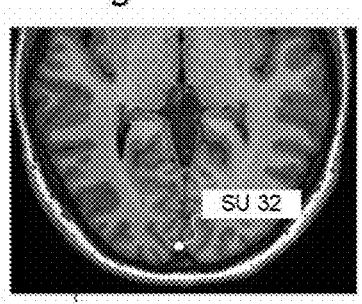

The invention allows for different presentations of indication signals 701. When measuring indication signals 701 as MRI T1 signal units (SUs), the grey-scale may differ slightly between repeated MRI acquisitions even though the MRI protocol is strictly standardized. To correct for this methodological issue, the inventors have also used determination of indication signal unit ratios. The strategy used by the inventors is shortly described. Indication signal ratios may also be referred to as normalized indication signals, or normalized T1 SUs, when T1 weighted MRI is used. One illustrative example is presented in FIG. 1b-d, but this approach does not represent a limitation with the invention. FIG. 7b shows an axial multiplanar reformatted T1 weighted MR image 716, zooming in on the Sylvian fissure area of the brain. A T1 weighted image at Time 1 717 and Time 2 718 is shown, illustrating measurement of indication signals as signals units (SU) within inferior frontal gyms at Time 1 (SU=115) 717 and Time 2 (SU 136) 718. A reference region of interest was selected within the lumen of superior sagittal sinus of the same MRI acquisitions 716, which is illustrated in FIG. 7c. The measured T1 SU was 32 at both Time 1 and Time 2 719. The normalized T1 SU within the inferior frontal gyms was 3.59 (=115/32) at Time 1 717 and 4.25 (=136/32) at Time 2 718. Accordingly, the normalized T1 SU (signal unit ratio) had increased 18.4% from Time 1 to Time 2.

Figure 7D:
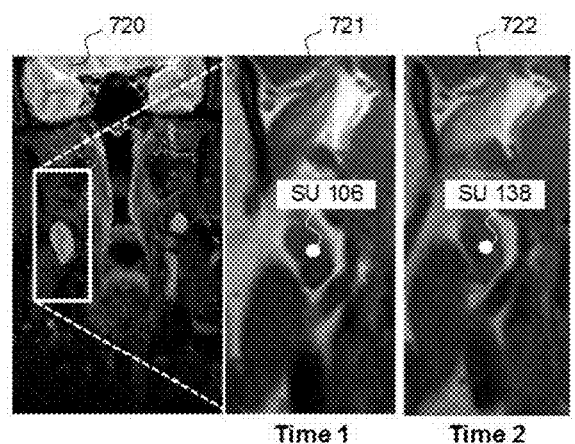
Figure 7E:
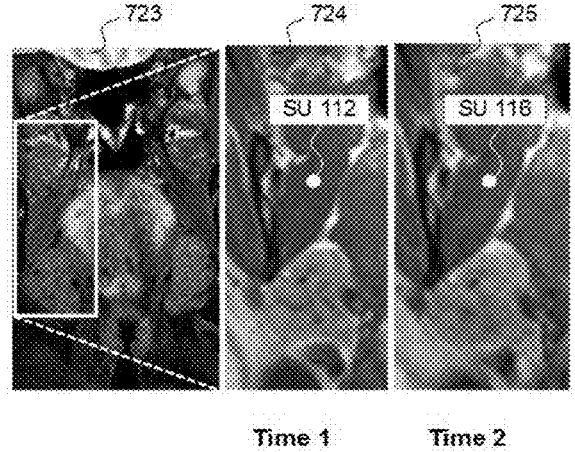

A similar approach as illustrated in FIG. 7b-c may be applied to other regions. This is illustrated by neck MRI in FIGS. 7d and 7e. In FIG. 7d is shown a cervical lymph node on a coronal T2 weighted MRI 720, and T1 weighted neck MRI zooming in on a cervical lymph node at Time 1 721 and Time 2 722. The indication signals were measured as signals units (SU) within the cervical lymph node at Time 1 (SU=106) 721 and at Time 2 (SU 138) 722. For neck MRIs, the medial pterygoid muscle was used as reference tissue, as illustrated in FIG. 7e. For identification of the medial pterygoid muscle a T2 weighted MRI was used 723. T1 weighted MR images are shown at Time 1 724 and Time 2 725. The measured Signal unit (SU) was 112 at Time 1 724 and 116 at Time 2 725. Accordingly, the normalized T1 SU within the cervical lymph node was 0.95 (=106/112) at Time 1 721, 724 and 1.19 (=138/116) at Time 2 722, 725. Accordingly, the normalized T1 SU (signal unit ratio) had increased about 25% from Time 1 to Time 2.

In this present invention, we provide several examples of clearance illustrating curves in individuals and in groups of individuals. The examples are retrieved from MRI studies wherein indication signals refer to MRI SUs, and indicator fluid refers to gadobutrol, which was present within the CSF after having been administered via the intrathecal route. For the included individuals, establishment of a clearance illustrating curve required repeated MRI acquisitions, and repeated assessments of the same ROIs. The MRI acquisitions were standardized as much as possible. One challenge is that this process requires MR image alignment to compare the same pixels or ROI. Comparison of the same pixels may be a difficult since it is dependent of image alignment.

The third feature of Aspect 2 discloses a method aided by a computer to assess movement of molecular substances from a cerebrospinal fluid compartment to a nearby brain or spinal cord compartment of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. The computer aided method is further illustrated in FIG. 8. The method using a computer 801 comprises:

a) measuring at least once indicator fluid indication signals 802 by use of a detector device 803 and a sampling device 804 linked to the computer 801 and provided by use of one of: computed tomography (CT), magnetic resonance imaging (MRI), positron emission tomography (PET), single photon emission computed tomography SPECT), and scintigraphy 805, as related to a selected indicator fluid 806, within regions of interest of said cranio-spinal cavity, said measuring to be made of indication signals from the cerebrospinal fluid compartment or simultaneously both from the cerebrospinal fluid compartment and said brain or spinal cord compartment 807, and b) determining by a determining section 808 in the computer 801 changes in indication signals 809 over time within selectable regions of said cranio-spinal cavity, said change in indication signals being indicative of said ability of movement of indicator fluid within, to or from said regions of said cranio-spinal cavity.

c) presenting from an output of an analyzer section 810 in the computer enhancement phase parameters and/or parameters of removal 811 of the indicator fluid 806 from said cranio-spinal cavity, said enhancement phase parameters and/or parameters of removal 811 being based on at least one of said changes in indication signals 809, and being indicative of ability of said cranio-spinal cavity to remove molecular substances 812, the ability being a function of clearance of waste solutes from compartments of the cranio-spinal cavity.

According to the method using the computer 801, MRI 805 acquisition incorporates T1 weighted sequences with standardized imaging parameters being at least echo and repetition time, flip angle, matrix, and field of view. Other imaging parameters may also be standardized to maximize T1 SU reproducibility. Preferably, but not necessarily, the same MRI scanner is used for consecutive scans to ensure reproducibility of T1 SU measurements.

The indicator fluid 806 within, to or from a CSF compartment is a function of ability of a) movement of substances between individual CSF compartments, or b) removal of substances via the brain or the spinal cord compartment from said cranio-spinal cavity 812.

For this method, the indicator fluid 806 may contain a CT contrast agent, or a MRI contrast agent, or a substance exhibiting recognized pharmacokinetic properties. The CT contrast agent is a selected one of: iohexol, iodixanol, iomeprol, ioversol, and iobitridol, and the MRI contrast agent may be either gadobutrol or gadoteric acid. The indicator fluid 806 may be a radioactive ligand suitable for PET, SPECT or scintigraphy imaging tied to or chelated with a contrast agent substance or a substance exhibiting recognized pharmacokinetic properties. The radioactive ligand may be selectable tracer material from at least one of: $^{89}$Zirconium, $^{99m}$Tc-DTPA, and $^{111}$In-DTPA. Further, the indicator fluid 806 may contain a radioactive ligand, which is chelated with material being at least one of: large-molecule biotechnology based products, antibodies, monoclonal antibodies, recombinant proteins, and antisense or gene therapeutics means. The ligand may have at least a partial property of making a bond to tumor cells or inflammation cells or amyloid beta plaques. The indicator fluid 806 may also be a CT or an MRI contrast agent coupled with one or more of: large-molecule biotechnology based products, antibodies, monoclonal antibodies, recombinant proteins, and antisense or gene therapeutics means. Moreover, the indicator fluid can be a dendrimer based macromolecular MRI contrast agent of size sufficiently high to be retained outside the BBB, or a substance exhibiting resembling pharmacokinetic properties. Further, the indicator fluid 806 may be administrable to a CSF compartment by spinal puncture and intrathecal injection.

The method described in the third feature of Aspect 2 may be applied onto multiple ones of human individuals to determine indication signals through use of said imaging within selectable ROIs to determine indicator fluid 806 induced changes in indication signals 809 over time. The ROIs of said imaging acquisition may be transferred by transfer section 813 to an anatomical coordinate system 814, which is configured to enable segmentation of selectable anatomic regions. A comparison of said change in indication signals over time is made between indication signal changes in a single human individual and changes in said multiple ones of human individuals using a comparator section 815. By using a database of multiple human individuals 816, a comparator output 817 section presents deviations in movement of substances as measured and imaged from a single human individual compared to average movement of substances in said multiple ones of human individuals.

According to the method using the computer 801, the indication signals 802 may be MRI SUs, which may be made into standardized SUs through use of a standardization device (see Aspect 7) comprising an extra-body device containing at least one reference indicator fluid 818 of specific concentrations. At least one reference indicator fluid is located within one or more containers to be located externally of the body of the human, and filled with dedicated material. The standardized SUs allow for measurement of absolute values of indicator fluid within the ROI of a human individual. Said dedicated material may be a dummy material having liquid properties, e.g. viscosity or molecular property, resembling standard cranio-spinal cavity liquid or having semi-solid material properties, e.g. density or molecular property, resembling standard properties of standard brain tissue.

This third aspect of the invention may be used to quantify abnormal movement of substances confined to CSF compartments, either movement of substances within or from a CSF compartment. Several conditions are associated with CSF disturbances, such as hydrocephalus and dementia. Said third aspect of the invention may be applied to quantify type of abnormal CSF movement.

The different features of Aspect 2 are based on novel in-vivo observations in humans. The inventive steps of the invention have previously not been addressed in animal studies probably since it does not represent an issue in animals. In the following paragraphs, these novel observations in humans are commented on in more detail. In these studies, the MRI contrast agent gadobutrol served as indicator fluid and MRI SUs were indication signals. MRI T1 weighted signal units were measured when gadobutrol was present within CSF after having been administered to the CSF compartment, and were compared with MR images having identical sequence parameter settings and with no gadobutrol present in CSF. Change in SU is a measure of contrast agent enrichment and hence movement of contrast agent within the cranio-spinal cavity. With a MW of 605 Da, gadobutrol is a rather large molecule in comparison to the MW of water ($H_2O$) molecule, which is 18 Da. Clearance of gadobutrol is then indicative of clearance of other substances with similar properties.

According to prior art, animal studies (Nedergaard M, Iliff J, Benveniste H, Deane R. Methods for evaluating brain-wide paravascular pathway for waste clearance function and methods for treating neurodegenerative disorders based thereon. WO 2014/130777 A1) and one human case report (Eide P K, Ringstad G. MRI with intrathecal MRI gadolinium contrast medium administration: A possible method to assess glymphatic function in human brain. Acta Radiologica Open 2015; 4 (11) 1-5) did not measure contrast enrichment within the brain compartment as related to contrast enrichment within the CSF compartment. This aspect appeared not to be of importance in animals since contrast enrichment within brain tissue of animals occurred very suddenly. Therefore, previous studies have not examined how changes in indication signals within ROIs of brain or spinal cord compartment depend on changes in indication signals within the CSF compartment. Since the present invention relates to humans, this is an important inventive step.

We explored both movement of the contrast agent within, to, and from the cranio-spinal cavity, including CSF, brain and spinal cord compartment, and from the cranio-spinal cavity to extra-cranial LNs. With gadobutrol present within CSF, blood level concentrations of contrast agents were determined at various time point. The repeated MRI acquisitions made it possible to create clearance curves for one or more pixels, defined by ROIs. ROIs were placed within CSF compartments, brain and spinal cord tissue compartments, and extracranial LN tissue compartments. By means of MRI, we could create graphic curves illustrating clearance of substances (clearance illustrating curves) for defined ROIs built up of a defied number of pixels for each individual. For details of said clearance curves, see FIG. 7. The establishment of clearance curves was dependent on repeated MRI acquisitions over a long period.

Figure 9A:
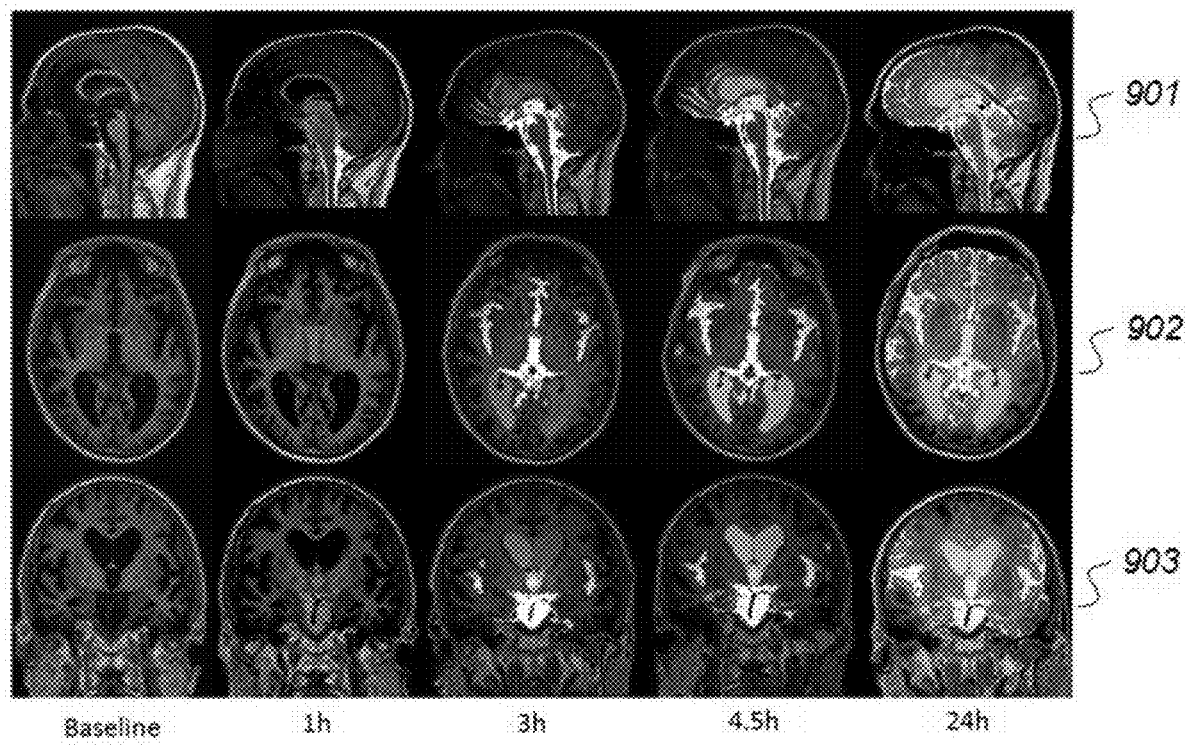
FIG. 9a-b illustrate repeated T1-weighted MRI of two individuals, respectively, where images in each column are retrieved from the same image acquisition; T1 weighted images were obtained without any MRI contrast agent present within CSF ("Baseline"), and also with MRI contrast agent (gadobutrol) present within CSF (1 hour, 3 hours, 4.5 hours and 24 hours after intrathecal gadobutrol). The enrichment of contrast agent in CSF and brain tissue is shown as enhancement of T1 SUs (increased SUs are presented with whiter tones at the greyscale).
Figure 9B:
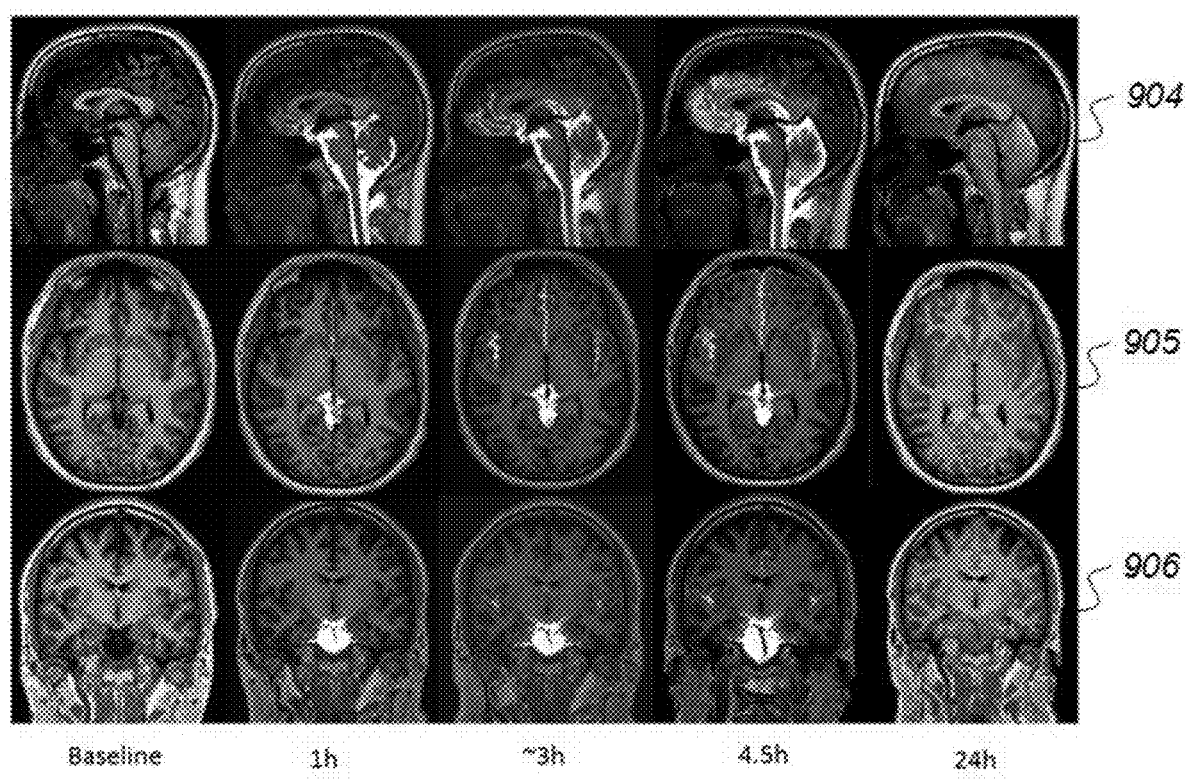

FIG. 9a and FIG. 9b show the repeated MRI images of two individuals, where FIG. 9a is a patient with enlarged brain ventricles (hydrocephalus), and FIG. 9b is a reference patient with normal ventricles. The images of the upper array are sagittally oriented, in the middle array images are of axial orientation, and in the lower array images are coronally oriented. All image planes presented in each column represent reformations of the same T1 weighted volume MRI acquisition. Hence, each column shows T1 weighted images that were obtained at different time points, i.e. no gadobutrol present, and after intrathecal gadobutrol had been present for 1 hour, 3 hours, 4.5 hours and 24 hours, respectively. The movement of contrast agent is shown as change in T1 SUs, where enrichment of contrast agent yields a brighter signal at the image greyscale. It should be noted that this may be visually analyzed. Most markedly, the movement of contrast agent is very different between the two individuals; the temporal course of change in SU differs between the two individuals.

In patient A with iNPH (FIG. 9a) contrast agent moves rapidly towards the ventricular system, which may be visually seen as contrast enrichment within the ventricles over the period 1 h, 3 h, 4.5 h and 24 h. The upper array of images is sagittally oriented 901, the middle array is of axial orientation 902, and the lower array of images are coronally oriented MRI 903. This observation illustrates how the method may be used for quantification of CSF flow direction. Either using T1 maps or the extra-body device (Aspect 7 of present invention), the quantities of contrast agent may be determined. For example, the amount of contrast agent moving into the ventricles may be quantified. Further, the amount of contrast agent moving towards other regions, e.g. precentral gyms, may be quantified. By use of fixed sequence parameters at all imaging time points, semi-quantitative measurements may be made, and may e.g. be given as percentage change in SUs.

In patient B, not with iNPH (FIG. 9a), there was no flow into the ventricles, which could be visually inspected at sagittal 904, axial 905 and coronal 906 MRI at the time points 1 hour, 3 hours, 4.5 hours and 24 hours after intrathecal gadobutrol. The two patients, A and B, illustrate how movement of contrast agent movement is different between individuals and that measurements of MRI SUs may be used to quantify CSF flow and hence movement of substances within a CSF compartment.

Using MRI SUs, we created clearance illustrating curves, see FIG. 7, for the individual patients as well as for groups of individuals. Tables 2-4 illustrate various examples of parameter values of the clearance illustrating curves.

Figure 2:
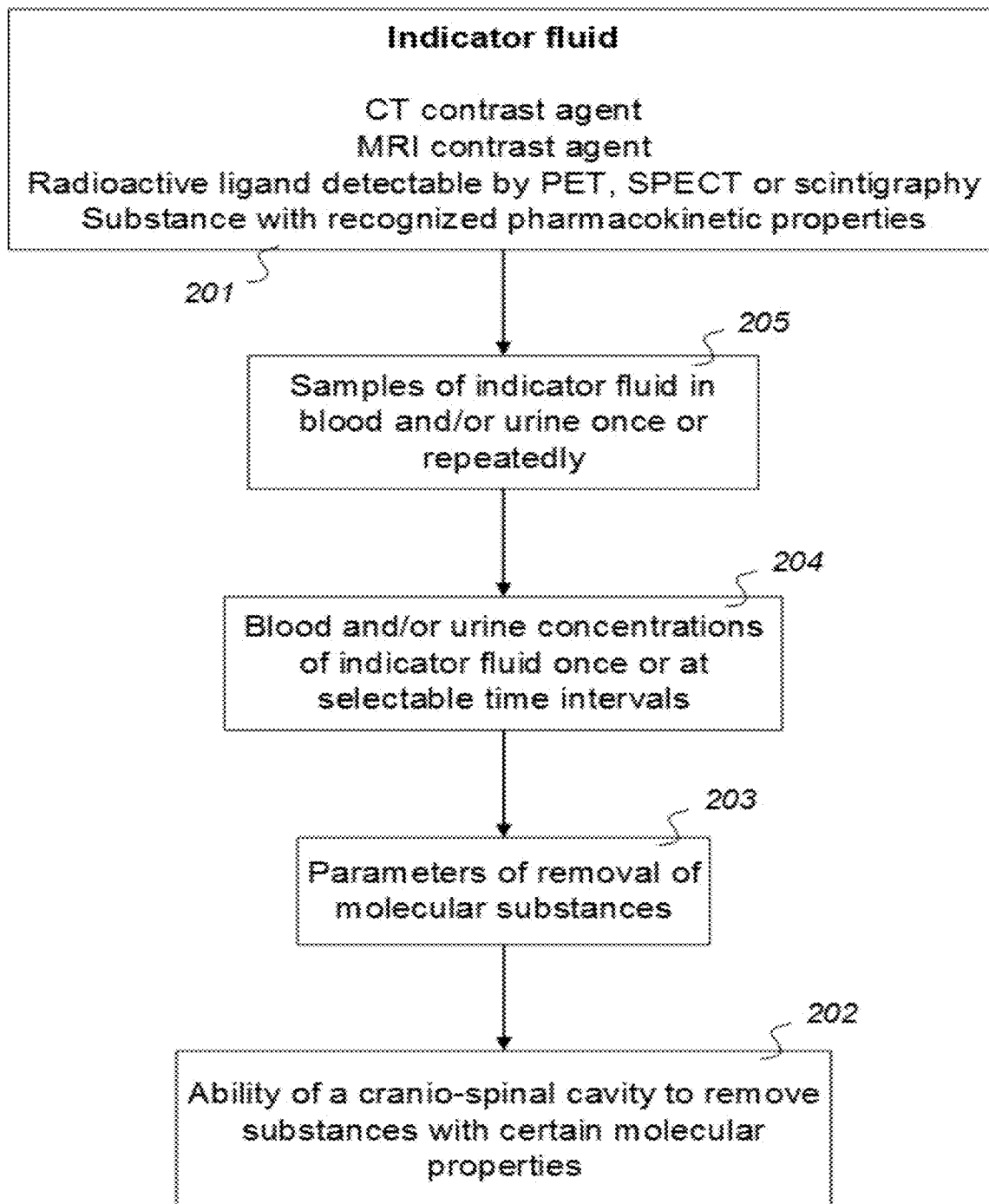
FIG. 2 illustrates usage of an indicator fluid suitable for use in a human for assessing ability of a cranio-spinal cavity of the human to remove substances, utilizing measurements of concentration levels in blood and/or urine.

Table 2, as discussed with FIG. 2, illustrates how maximum increase in SUs varies between individuals and patient groups. Tables 3 and 4 compare such clearance curve parameters from two patient groups, namely iNPH and reference (i.e. control) patients, illustrating inter-individual differences and differences between patient groups. These patient groups represent no limitation of the invention as it may be used in various patient groups such as Alzheimer's and dementia in general, brain tumor (e.g. astrocytoma), multiple sclerosis and inflammatory brain disease, stroke (brain infarction or bleeds), sleep disturbances, neurodegenerative disease, CSF circulation disorders, traumatic brain injury, neurometabolic diseases, glaucoma, chronic headache and migraine, and in assessment of ageing in general.

TABLE 2

For 15 + 8 patients are shown SU of T1 signal in brain tissue without gadobutrol having been administered intrathecal (Pre) and the maximum increase in SU after gadubutrol having been administered intrathecal.

| | | Pons | | Thalamus | | Frontal horn | | Inferior frontal gyrus (IFG) | | Precentral gyrus Max | |
|---|---|---|---|---|---|---|---|---|---|---|---|
| PatID | Diagn. | Pre | Max Increase | Pre | Max Increse | Pre | Max Increase | Pre | Max Increase | Pre | Increase |
| 1 | iNPH | 9 | 12 (12%) | 88 | 21 (24%) | 62 | 88 (141%) | 80 | 41 (52%) | 86 | 19 (22%) |
| 2 | iNPH | 97 | 16 (16%) | 90 | 15 (16%) | 45 | 80 (178%) | 82 | 82 (100%) | 78 | 22 (28%) |
| 3 | iNPH | 100 | 17 (17%) | 91 | 16 (18%) | 88 | 13 (15%) | 85 | 70 (83%) | 87 | 28 (32%) |
| 4 | iNPH | 102 | 24 (24%) | 93 | 23 (24%) | 51 | 103 (204%) | 82 | 56 (68%) | 89 | 7 (8%) |
| 5 | iNPH | 95 | 15 (16%) | 83 | 9 (11%) | 86 | 35 (40%) | 82 | 32 (38%) | 87 | 7 (7%) |
| 6 | iNPH | 89 | 21 (24%) | 80 | 14 (17%) | 48 | 76 (159%) | 81 | 51 (63%) | 81 | 2 (2%) |
| 7 | iNPH | 98 | 14 (14%) | 90 | 25 (28%) | 70 | 92 (131%) | 78 | 74 (95%) | 82 | 18 (22%) |
| 8 | iNPH | 100 | 4 (4%) | 93 | 4 (4%) | 51 | 50 (98%) | 89 | 21 (23%) | 85 | 5 (5%) |
| 9 | iNPH | 92 | 9 (10%) | 80 | 9 (11%) | 83 | 2 (2%) | 77 | 24 (31%) | 80 | 8 (10%) |
| 10 | iNPH | 92 | 9 (10%) | 82 | 10 (12%) | 39 | 49 (126%) | 78 | 36 (46%) | 66 | 2 (3%) |
| 11 | iNPH | 102 | 18 (18%) | 89 | 19 (21%) | 48 | 53 (110%) | 87 | 59 (68%) | 83 | 6 (7%) |
| 12 | iNPH | 96 | 3 (3%) | 83 | 7 (8%) | 59 | 42 (70%) | 78 | 10 (12%) | 76 | 4 (5%) |
| 13 | iNPH | 91 | 2 (2%) | 81 | 2 (2%) | 51 | 8 (15%) | 80 | −1 (−1%) | 88 | 6 (7%) |
| 14 | iNPH | 97 | 6 (6%) | 85 | 12 (14%) | 86 | 19 (22%) | 90 | 10 (11%) | 86 | 3 (4%) |
| 15 | iNPH | 102 | 4 (4%) | 92 | 12 (13%) | 88 | 21 (23%) | 88 | 25 (28%) | 87 | 2 (2%) |
| 1 | REF | 96 | 20 (21%) | 90 | 23 (26%) | 61 | 23 (37%) | 86 | 68 (80%) | 87 | 10 (12%) |
| 2 | REF | 100 | 5 (5%) | 97 | 4 (4%) | 97 | 7 (7%) | 93 | 5 (5%) | 91 | 1 (1%) |
| 3 | REF | 107 | 3 (3%) | 103 | 3 (2%) | 103 | 4 (3%) | 91 | 24 (27%) | 94 | 8 (9%) |
| 4 | REF | 105 | 5 (5%) | 94 | 2 (2%) | 96 | 4 (4%) | 91 | 13 (14%) | 86 | 2 (2%) |
| 5 | REF | 100 | 9 (9%) | 95 | 13 (13%) | 100 | 3 (3%) | 91 | 23 (25%) | 88 | 6 (7%) |
| 6 | REF | 103 | 7 (7%) | 98 | 13 (13%) | 104 | 9 (8%) | 88 | 37 (41%) | 83 | 34 (41%) |
| 7 | REF | 93 | 9 (10%) | 83 | 8 (9%) | 82 | 17 (21%) | 84 | 18 (21%) | 83 | 3 (4%) |
| 8 | REF | 105 | 1 (1%) | 91 | 8 (9%) | 110 | −1 (0%) | 92 | 4 (4%) | 87 | −2 (−2%) |

REF = Reference. Max increase in SU given as numerical change (pentage change in arenthesis). Bold font for individuals with ≥10% increase in SUs after gadobutrol.

TABLE 3

Information about the enhancement phase for different ROIs within CSF and venous spaces and brain tissue.

| | Enhancement phase | | | | | | | |
|---|---|---|---|---|---|---|---|---|
| | Baseline (SU) | | Max increase (SU) | | Time to peak (min) | | Enhancement coefficient (SU/min) | |
| | iNPH | Reference | iNPH | Reference | iNPH | Reference | iNPH | Reference |
| CSF space | | | | | | | | |
| Foramen Magnum | 10.3 + 3.4 | 8.9 + 2.6 | 398.3 ± 108.0 | 426.0 ± 123.0 | 174.5 ± 94.2 | 129.4 ± 156.7 | 5.9 ± 12.2 | 17.7 ± 24.5 |
| Sylvian fissure | 7.0 + 1.6 | 8.6 + 3.6 | 226.2 ± 100.2 | 204.2 ± 104.4 | 689.0 ± 536.3$^a$ | 258.6 ± 114.8 | 0.57 ± 0.41 | 0.9 ± 0.7 |

TABLE 3-continued

Information about the enhancement phase for different ROIs within CSF and venous spaces and brain tissue.

| | Enhancement phase | | | | | | | |
|---|---|---|---|---|---|---|---|---|
| | Baseline (SU) | | Max increase (SU) | | Time to peak (min) | | Enhancement coefficient (SU/min) | |
| | iNPH | Reference | iNPH | Reference | iNPH | Reference | iNPH | Reference |
| Pons | 10.2 + 3.7 | 9.5 + 1.3 | 378.2 ± 133.0 | 388.5 ± 121.7 | 230.9 ± 98.4 | 159.8 ± 148.9 | 2.4 ± 2.3 | 10.8 ± 18.2 |
| 4$^{th}$ Ventricle | 11.3 + 3.1 | 12.6 + 3.0 | 386.5 ± 138.2$^a$ | 236.0 ± 142.9 | 286.7 ± 322.9 | 123.4 ± 98.1 | 5.6 ± 14.5 | 6.3 ± 14.0 |
| 3$^{rd}$ Ventricle | 14.4 ± 2.6 | 14.5 + 2.8 | 243.6 ± 136.9$^a$ | 115.1 ± 103.8 | 615.3 ± 587.5 | 253.8 ± 133.2 | 1.4 ± 1.7 | 0.4 ± 0.4 |
| Lateral Ventricle | 6.0 + 1.2$^c$ | 9.4 + 1.5 | 168.5 ± 99.8$^b$ | 42.5 ± 51.9 | 843.4 ± 560.2 | 402.6 ± 446.1 | 0.41 ± 0.39 | 0.13 ± 0.16 |
| Precentral sulcus | 7.6 + 1.6 | 8.1 + 1.2 | 131.1 ± 94.1 | 87.8 ± 99.3 | 1254.7 ± 483.8$^b$ | 475.0 ± 601.9 | 0.10 ± 0.06 | 0.29 ± 0.39 |
| Central venous space | | | | | | | | |
| Sagittal sinus/confluence | 34.9 + 7.2 | 32.3 + 7.6 | 8.1 ± 8.0 | 7.4 ± 9.6 | 350.2 ± 457.3 | 524.4 ± 591.3 | 0.16 ± 0.25 | 0.41 ± 0.85 |
| Brain parenchyma | | | | | | | | |
| Inferior frontal gyrus (IFG) | 82.5 + 4.3$^b$ | 89.5 + 3.2 | 39.1 ± 25.3 | 23.8 ± 20.9 | 1358.0 ± 313.4 | 1421.3 ± 53.1 | 0.03 ± 0.02 | 0.02 ± 0.02 |
| Pons | 96.8 + 4.2$^a$ | 101.1 + 4.8 | 11.6 ± 7.0 | 7.4 ± 5.8 | 1090.0 ± 602.3 | 929.4 ± 676.9 | 0.03 ± 0.08 | 0.08 ± 0.17 |
| Thalamus | 86.7 + 4.8$^b$ | 93.9 + 6.0 | 13.0 ± 6.8 | 9.0 ± 7.1 | 1261.7 ± 462.6 | 1288.4 ± 386.3 | 0.01 ± 0.02 | 0.01 ± 0.01 |
| Frontal horn | 63.9 + 18.4$^b$ | 94.1 + 15.7 | 48.5 ± 32.8$^b$ | 7.9 ± 7.9 | 1349.3 ± 350.9 | 1109.8 ± 585.6 | 0.04 ± 0.02 | 0.05 ± 0.12 |
| Precentral gyrus | 82.7 + 6.0 | 87.4 + 3.7 | 9.0 ± 8.3 | 7.8 ± 11.2 | 900.0 ± 686.4 | 742.8 ± 727.9 | 0.04 ± 0.06 | 0.03 ± 0.03 |

Significant differences between iNPH and reference groups were determined by independent samples t-test: $^a$P < 0.05, $^b$P < 0.01, $^c$P < 0.001.

TABLE 4

Information about the clearance phase for different regions of interest within CSF and venous spaces.

| | Clearance phase | | | | | |
|---|---|---|---|---|---|---|
| | Clearance time (min) | | Max reduction (SU) | | Clearance coefficient (SU/min) | |
| | iNPH | Reference | iNPH | Reference | iNPH | Reference |
| CSF space | | | | | | |
| Foramen Magnum | 1264.3 ± 116.1 | 1294.4 ± 154.5 | −206.7 ± 90.8$^b$ | −358.1 ± 117.7 | −0.16 ± 0.07$^b$ | −0.28 ± 0.08 |
| Sylvian fissure | 1123.7 ± 41.1 | 1162.6 ± 78.1 | −68.0 ± 51.2$^a$ | −133.0 ± 68.4 | −0.06 ± 0.05$^a$ | −0.12 ± 0.06 |
| Pons | 1207.9 ± 114.8 | 1261.5 ± 137.0 | −177.9 ± 95.5$^b$ | −313.3 ± 105.3 | −0.15 ± 0.08$^b$ | −0.25 ± 0.08 |
| 4$^{th}$ Ventricle | 1234.6 ± 109.1 | 1287.6 ± 105.9 | −231.6 ± 128.1 | −232.6 ± 103.7 | −0.19 ± 0.1 | −0.18 ± 0.08 |
| 3$^{rd}$ Ventricle | 1234.3 ± 116.2 | 1135.3 ± 74.2 | −114.4 ± 76.8 | −103.7 ± 83.9 | −0.10 ± 0.07 | −0.09 ± 0.08 |
| Lateral Ventricle | 1115.1 ± 46.3 | 1098.0 ± 12.5 | −57.3 ± 48.9 | −72.3 ± 11.9 | −0.05 ± 0.04 | −0.07 ± 0.01 |
| Central venous space | | | | | | |
| Sagittal sinus/confluence | 1287.4 ± 150.9 | 1247.3 ± 175.9 | −12.1 ± 6.7 | −9.5 ± 3.9 | −0.01 ± 0.006 | −0.008 ± 0.003 |

Significant differences between iNPH and reference groups were determined by independent samples t-test: $^a$P < 0.05, $^b$P < 0.01, $^c$P < 0.001.

The method may be used to quantify clearance from the CSF compartment per se. As shown in FIG. 10a-f clearance from the CSF compartment differs between groups of individuals, and the clearance curves differ widely depending on which ROIs that are analyzed. For all different locations within CSF compartments, CSF clearance was delayed in patients with iNPH-dementia. FIG. 10a-f show clearance curves for two cohorts of individuals, the first group with tentative iNPH, a sub-type of dementia, and the other group with presumptive normal CSF circulation. The time plots illustrate delayed enhancement and clearance in iNPH. For FIG. 10a, the ROI is within CSF nearby pons, and the change in SUs 1001 are plotted against time 1002, the changes in SUs for the groups of iNPH patients 1003 and reference individuals 1004 are presented as average with 95% confidence intervals. Within the iNPH cohort, the enhancement phase is delayed while at 24 hours clearance is delayed in this group. As shown in FIG. 10b, plotting SUs within the CSF 1005 of the Sylvian fissure against time 1006, showed delayed clearance of gadobutrol after 24 hours for the iNPH cohort 1007 as compared to the reference individuals 1008. When the ROIs were placed in the CSF of the precentral gyms (FIG. 10c), plotting changes in SUs 1009 against time 1010, time to first enhancement 1011 was longer. The shape of the clearance curve at group level differed substantially as compared with CSF nearby pons (FIG. 10a), and within Sylvian fissure (FIG. 10b). Further, clearance was delayed in iNPH 1012 as compared with reference 1013 individuals. As already commented on, FIG. 9a showed rapid distribution of contrast agent into the ventricles in an iNPH patient, while this was not seen in a reference patient (FIG. 9b). This aspect is further illustrated in FIG. 10d, plotting change in SUs within the fourth ventricle 1014 against time 1015, which revealed that change in SUs for iNPH was more profound and delayed in iNPH 1016 than reference 1017. This same effect was seen in two other ventricles, namely the third ventricle (FIG. 10e) and the lateral ventricle (FIG. 10f). With regard to the third ventricle (FIG. 10e), plotting SUs 1018 against time 1019, showed stronger contrast enrichment in iNPH 1020 than reference 1021 individuals. Further, concerning the lateral ventricles (FIG. 10f, plotting SUs 1022 against time 1012 showed contrast enrichment in iNPH patients 1024 but not in reference 1025 individuals. Taken together, these experimental studies examining changes in SUs within various ROIs of the CSF compartment illustrate the applicability of the features of Aspect 2.

Even though several of the inventive steps described in Aspect 2 were derived from MRI, the technique of MRI represents no limitation to the present invention. The present invention is applicable in five different medical imaging modalities, namely CT, MRI, PET, SPECT and scintigraphy. Various aspects of these image modalities are shortly commented on in the following paragraphs.

Figure 11A:
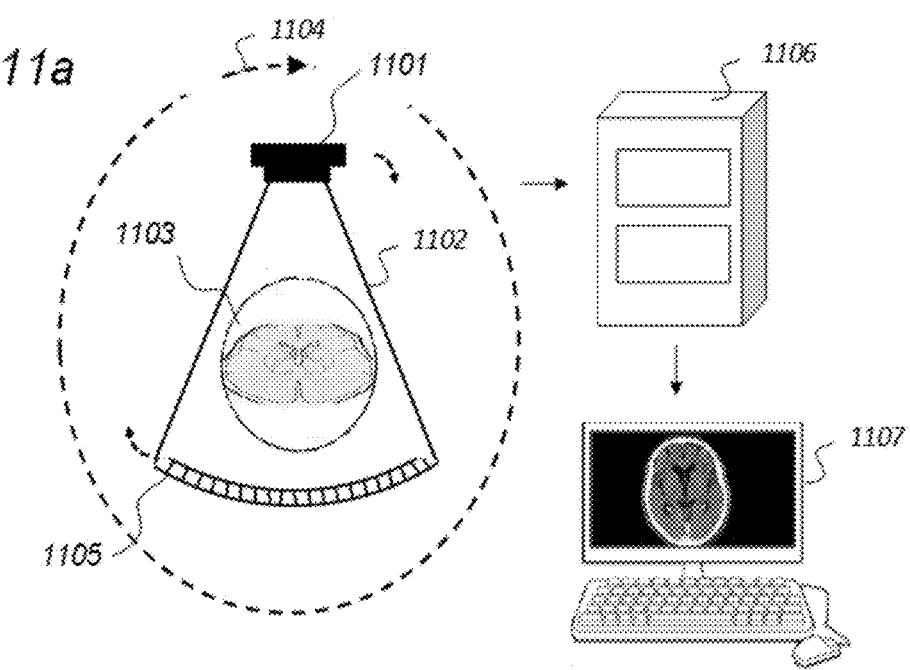

The technique of CT is illustrated in FIG. 11a. Regarding CT, from the emitter of x-rays 1101, a narrow beam of x-rays 1102 is aimed at region of a patient, e.g. head and brain 1103, and being quickly rotated 1104 around the object. Hence, CT uses multiple fan beams of kilo voltage (kV) photons that pass through the desired object, e.g. head and brain 1103. On the opposite side of the volume is a dosimeter 1105, which measures the amount of ionizing radiation reaching it, allowing for determination of attenuation of the individual beams passing through the object volume. Each part of the volume may be considered a voxel, which is a 3D pixel with width, height and depth. Each beam from the emitter will pass through numerous voxels wherein the attenuation of the beam passing through the volume represents the sum of attenuations in each voxel. The density of the tissue passed by the X-ray beam is determined from the attenuation coefficient. Using a computer 1106 for image reconstruction, complex mathematical algorithms are applied for simultaneous equation with more than several hundred variables based on the attenuation information from each beam. A 3D image of e.g. the brain is created from the digital gathering of the successive slices collected by the computer, and presented on a monitor 1107. The image by the CT scanner is a digital image and consists of a square matrix of elements (pixels), each of which represents a voxel (volume element) of the tissue of the patient. Currently, a typical CT image is composed of 512 rows, each of 512 pixels, i.e., a square matrix of 512×512=262,144 pixels (one for each voxel). In the process of the image, the value of attenuated coefficient for each voxel corresponding to these pixels needs to be calculated. Once the attenuation for each voxel is determined, the computer system assigns a Hounsfield Unit (HU) to each part of the volume. Hounsfield Units range from −1000 (air), to 0 (water), to +1000 (compact bone). Fat is about −60 to −120 HU.

Figure 11B:
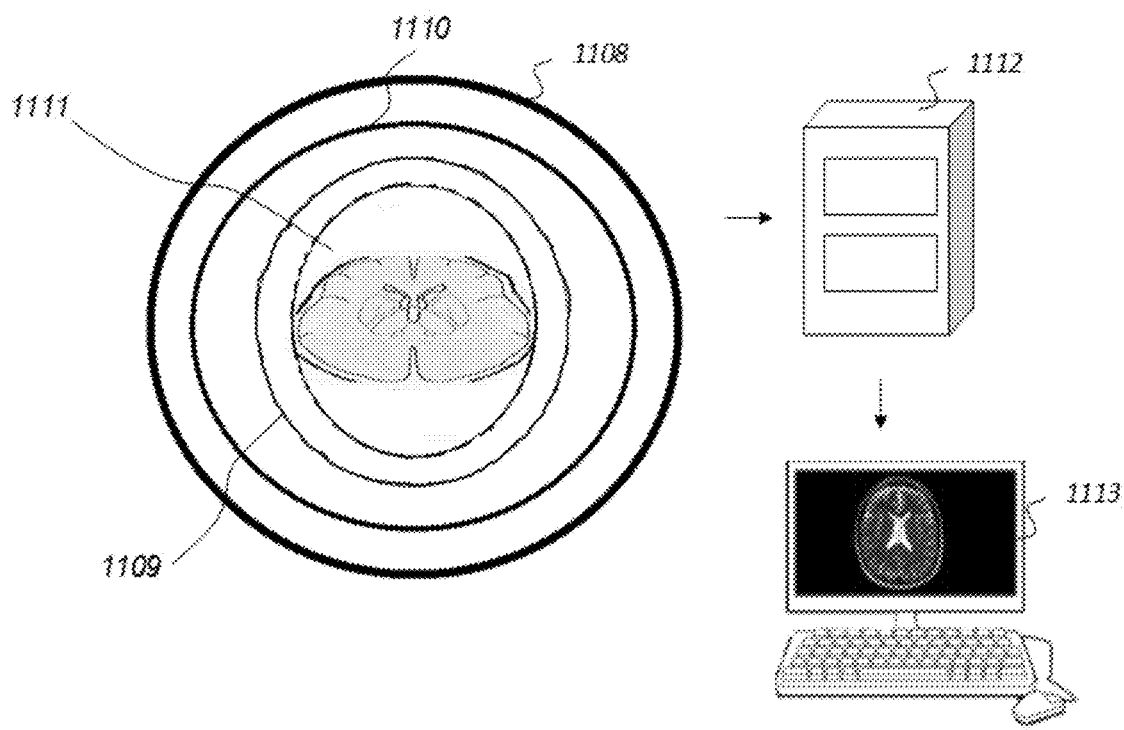

A schematic overview of the technique of MRI scanning is provided in FIG. 11b. MRI scanners create body images by applying strong magnetic fields 1108, radio waves 1109, and field gradients 1110. Hydrogen atoms are abundant in living organisms, particularly in water and fat. Therefore, particularly water and fat are imaged by MRI. The radio wave pulses 1109 excite the nuclear spin energy transition, and the magnetic field gradients 1110 renders for localization of the signal in space. It then becomes possible to generate different image contrasts to differentiate tissues by varying the parameters of the pulse sequences 1109, since the hydrogen atoms of the different tissues have different relaxation properties. Accordingly, MRI incorporates a strong magnetic field 1108 to a human object such as head and brain 1111; the magnetic field 1108 is usually 1.5-3 Tesla (T), but stronger fields are also in use, especially for animal studies. A coil picks up the MRI signal that is induced and emitted from the patient and transmits it to a computer 1112. The computer processes the data and an image is generated, which can be presented on a monitor screen 1113.

Figure 11G:
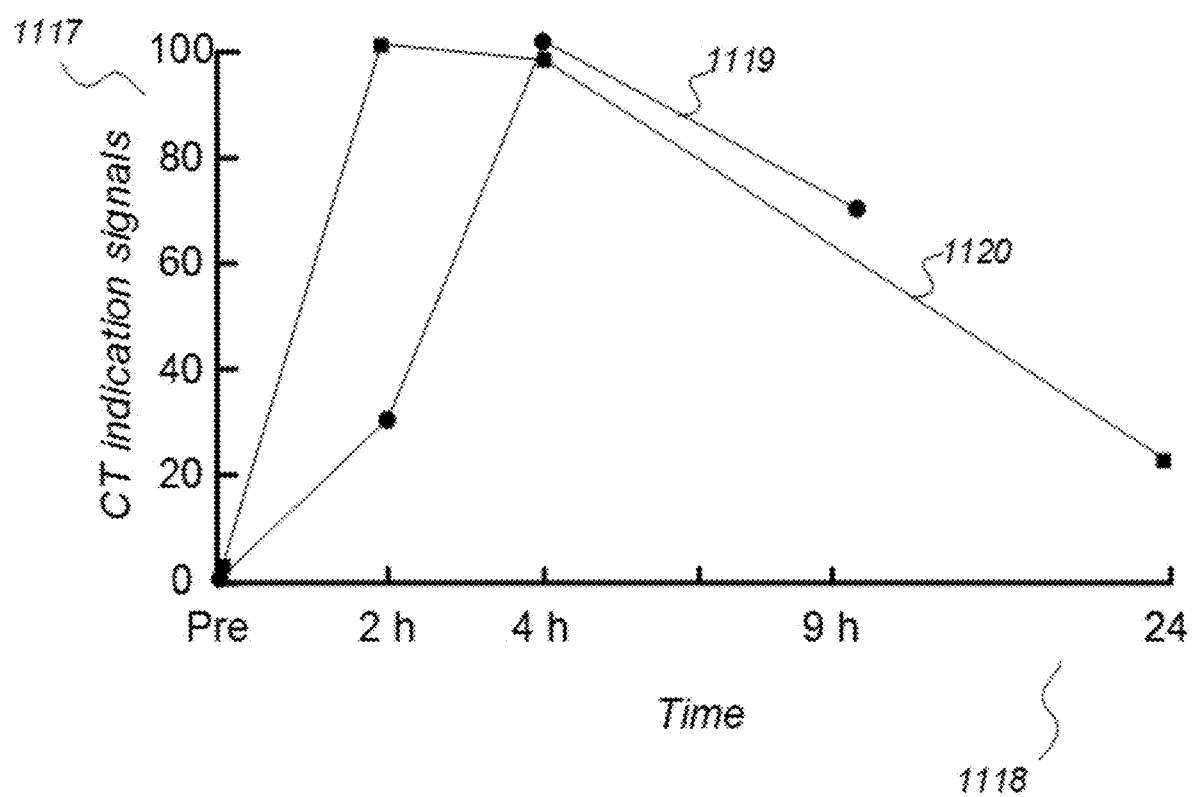

In FIG. 10a-f are presented plots of indication signals measured using MRI. In FIGS. 11c-g, it is illustrated that indication signals may as well be measured using CT. For illustration, measurement of Hounsfield units (HU) in CSF of cisterna magna is included. FIGS. 11c-f show axial CT images with ROI placed in CSF of cisterna magna, showing change in HU from before indicator fluid is present in CSF 1113 (Pre), after 2 hours 1114, 4 hours 1115, and 9 hours 1116. The values of HU measured within each ROI were HU 0 at Pre 1113, HU 31 at 2 hours 1114, HU 106 at 4 hours 1115, and HU 70 at 9 hours 1116. In FIG. 11g is shown the level of CT indication signal (expressed in HU) at they axis 1117 and the time 1118 from indicator fluid being present in CSF to measurement of CT indication signal. The trend plot of CT indication signal 1119 for the measurements presented in FIG. 11c-f is presented, as well as trend plot 1120 of average values of indication signals measured from a group of 4 individuals.

Figure 12A:
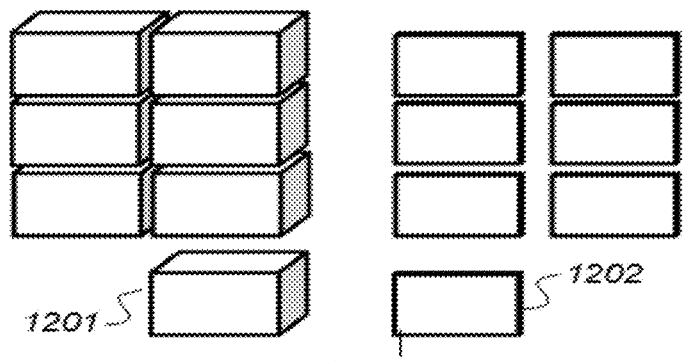
FIG. 12a-c illustrate the differences between voxels and pixels, alignment of images, and the establishment and comparison of clearance illustrating curves from a selectable number of pixels.
Figure 12B:
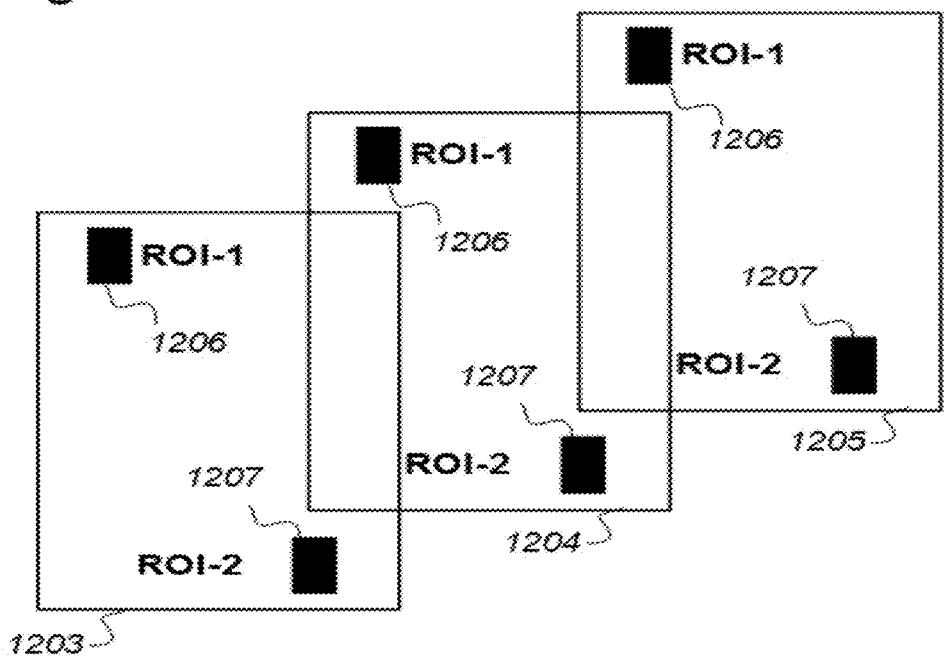
Figure 12C:
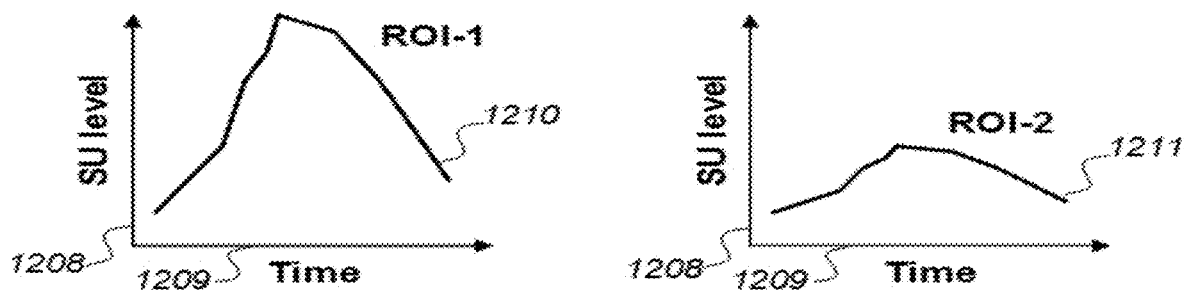

FIG. 12a-c further illustrates the differences between voxels and pixels, which was somewhat commented on regarding CT. Alignment of images depends on alignment of image volumes. The voxels 1201 from T1 weighted volume acquisitions (3D) are isometric or near isometric (FIG. 12a), and may be averaged into 2D pixels 1202 and values presented on a grey scale. While this process cannot be done perfectly, this methodological limitation does not represent any major limitation to the present invention. Each ROI includes several pixels 1202, which reduces the impact of this limitation. When imaging the brain, it is mathematically divided into volume elements (voxels), the signal within each voxel are averaged and turned into a number, representing a certain level on a grey scale. It is these numbers that are used to create a picture consisting of pixels.

One example is provided. 256×256×1 voxels are created of a slice of an object and turned into the picture elements (pixels), which reflect the content of the volume elements (voxels). The 256×256 picture elements are called the image matrix (consisting of a grid of x rows and y columns). Such an image matrix is characterized by the number of pixels in the x- and y-directions. They are defined by the steepness of the x-gradient (the frequency-encoding gradient) and the number of phase-encoding steps in the y-gradient, which combined represent the field-of-view (FOV). Usually in MRI, FOV is at least 256×256. If the matrix is the whole head with an edge length of 25.6 cm and a matrix size of 256×256 is used, then a single pixel represents 1 mm. Conversely, if the FOV is smaller (e.g., 12.8 cm) and the same matrix size is used, the spatial resolution is 0.5 mm. It should be noted that voxel and pixel sizes influence spatial resolution and thus signal-to-noise ratio. All anatomical structures within one voxel add to its averaged signal intensity in the final image. Hence, if the voxel has a large volume, it can contain many different structures and tissue types. In the final image pixel, they will be indistinguishable. If the voxel can be kept smaller, fewer structures will be represented by one single pixel, and therefore image spatial resolution will be better. It is differentiated between isotropic and anisotropic reconstructions; while isotropic reconstructions use cubes, in anisotropic methods, one side is longer than the two others. Even though they may look the same in the image plane, the content and thus the calculated number for the gray level representation in the pixel can be different. Different slice thickness can lead to isotropic or anisotropic volume elements and different signal intensities. Blurry aspects of these images may be caused by the averaging of different structures, and referred to as a partial volume effect. The smaller the pixel size, the better the suppression of partial volume effects. However, the bigger the voxel size, the better will be the signal (and signal-to-noise ratio). In general, the signal-to-noise ratio is the determining factor for the final voxel-versus-pixel size. Hence, increasing the matrix size from 128×128 to 256×256, but keeping field-of-view, slice thickness and imaging constant, will reduce the signal-to-noise ratio by a factor of 4. Therefore, the signal-to-noise ratio must be high enough to provide for proper resolution.

Even though perfect match of ROIs of repeated images may be difficult to obtain, the second aspect of the invention is facilitated by that image acquisition parameters at repeated MRI acquisitions are kept fixed and thus standardized. One example of such a standardized MRI sequence is a sagittal 3D T1 weighted volume scan with imaging parameters of repetition time=5.1 ms, echo time=2.3 ms, Flip angle=8 degrees, Field of view=256×256 cm, and matrix=256×256 pixels (reconstructed 512×512). Further, to make best possible alignments of pixels, methods for alignment of repeated MRI acquisitions need to be implemented. Methods for alignment of repeated MRI images belong to prior art. Aids to improve alignment may incorporate landmark locations such as the cranial vault, pineal gland, and ventricular system.

According to the present invention, clearance curves (see FIG. 7), indicative of movement of substances, are determined for a selectable number of pixels. Such a selected number of pixels are defined within ROI. FIG. 12b illustrates that for repeated MR images, here illustrated by Image 1 1203, Image 2 1204, and Image 3 1205, similar ROIs may be compared between the repeated images. Hence, the same ROI (ROI-1) 1206 was compared for Image 1 1203, Image 2 1204 and Image 3 1205. Similarly, the same ROI (ROI-2) 1207 was compared for Image 1 1203, Image 2 1204 and Image 3 1205. The number or size of ROIs represents no limitation as a selectable number of ROIs may be used. Finally, for each ROI a clearance curve is created (FIG. 12c), by plotting change in SUs 1208 against time 1209, making it possible to compare the clearance illustrating curve of ROI-1 1210 and ROI-2 1211. The shape of the clearance curve will depend on the location studied, here illustrated by clearance curves for ROI-1 1210 and ROI-2 1211. Clearance may also be defined by percentage SU change between given time points.

Several aspects of the present invention utilize repeated MRI acquisitions with comparison of the same regions over time. The present inventive methods could suitably be implemented in software, wherein the present method may be incorporated. This process of combining repeated MRI acquisitions is referred to as aligning (or co-registering) of MRI acquisition volumes. Concerning the present invention, this is needed to be able to record change in SUs within the same pixels or area of the scanner coordinate system. The methodology to align MRI acquisition volumes from different scanning sessions is known from prior art. The file format required for aligning images represents no limitation. One file format previously used is neuroimaging informatics technology initiative (niftii) file format. The type of image processing algorithm for refined alignment represents no limitation to the present invention. However, the aim is as an exact alignment of brain volumes as possible, specified according to each individual voxel. This is required for at a later stage to compare similar pixels of the repeated scanning. For alignment, the present invention applies T1 weighted images derived from scans with similar image sequence settings in order to be reproducible for alignment and comparison of SUs between time points and subjects. Other MRI sequences may as well be used. While automated alignment is preferable, manual alignment may as well be optimal.

Image segmentation is a common procedure in MRI brain analysis, referring to the process of measuring and visualizing specific brain anatomical structures, which may be used to analyze brain changes, and regions with pathology. One example referred to in this invention is the segmentation of the entorhinal cortex, which plays an important role in the early development of Alzheimer's disease and dementia in general. For the present invention, segmentation of selectable anatomical regions is relevant, depending on the problem to be explored. The methods (e.g. incorporated in software) and wherein the invention is incorporated, includes automatic methodology for anatomical segmentation.

One computerized imaging technique, PET, images radioactive substances that may be bound to other molecules. The technique of PET scanning is illustrated in FIG. 13a. For example, the isotope or radio ligand 1301 may be bound to glucose, which is taken up by tissue with increased metabolic demand (inflammation, tumors). The PET methods are the most widespread molecular imaging techniques. In the same way, various molecules might be attached to MRI contrast agents for molecular imaging. PET applies positron annihilation by using radionuclides 1301. The technique involves the injection of radionuclides 1301, followed by detection of their activity with an imaging device 1302, usually a gamma camera. The patient, e.g. patients head 1303, is placed within a circle of detectors 1302. These are capable of measuring both the attenuation of the annihilation photons as well as the time taken for photons to reach opposite sets of detectors 1304. The image acquisition is based on the external detection 1302 in coincidence of the emitted gamma-rays. A valid annihilation event requires a coincidence within 12 nanoseconds between two detectors on opposite sides of the scanner. For accepted coincidences, lines of response connecting the coincidence detectors are drawn through the object and used in the image reconstruction. Any scanner requires that the radioisotope 1301, in the field of view, does not redistribute during the scan. Image reconstruction requires a computer 1305 that present the image reconstruction on the monitor 1306. Presently, PET imaging combined with CT or MRI (denoted co-registration) providing the combination of anatomic and metabolic information.

SPECT uses gamma rays and provides 3D information. The SPECT imaging technique is further shown schematically in FIG. 13b. A gamma-emitting radioisotope 1307 is given to the patient, usually by intravenous injection into the bloodstream. The combined radioisotope enables visualization by a gamma camera 1308. The head and brain 1309 of an individual is placed within the machine. Different designs of SPECT may be used. Using a dual-head system (FIG. 13b), the acquisition time is half that for a single-head camera, and reduced by a factor of 3 with a 3-head system (FIG. 13c). The use of four heads (FIG. 13d) allow for large-FOV cameras to image the brain. As shown in FIG. 13e, a ring/helmet detector 1310 makes it possible to rotate only the collimator inside the crystal and shielding. Independent of the number of heads used, a computer 1311 is used applying a tomographic reconstruction algorithm to the multiple projections to provide for 3D data sets. The gamma camera is rotated around the object 1312, e.g. head/brain 1309, and projections are acquired at defined points, typically every 3-6 degrees. Often, a full 360-degree rotation is used to obtain an optimal reconstruction. The output may be shown on the monitor 1313 as slices like those created from the other tomographic techniques, including CT, MRI and PET. Both SPECT and PET apply GCI to detect gamma rays emitted by radioactive tracer material. However, while SPECT measures directly the gamma radiation emitted by radioactive tracers, PET tracers emit positrons that annihilate with electrons up to a few millimeters away, causing two gamma photons to be emitted in opposite directions, and being detected by the PET scanner "coincident" in time. This latter provides more radiation event localization information and, higher spatial resolution images than SPECT. SPECT imaging has about 1 cm resolution. In most cases, the use of PET is preferred over SPECT since higher spatial resolution images can be obtained and images can be analyzed quantitatively more accurately with PET.

Figure 8:
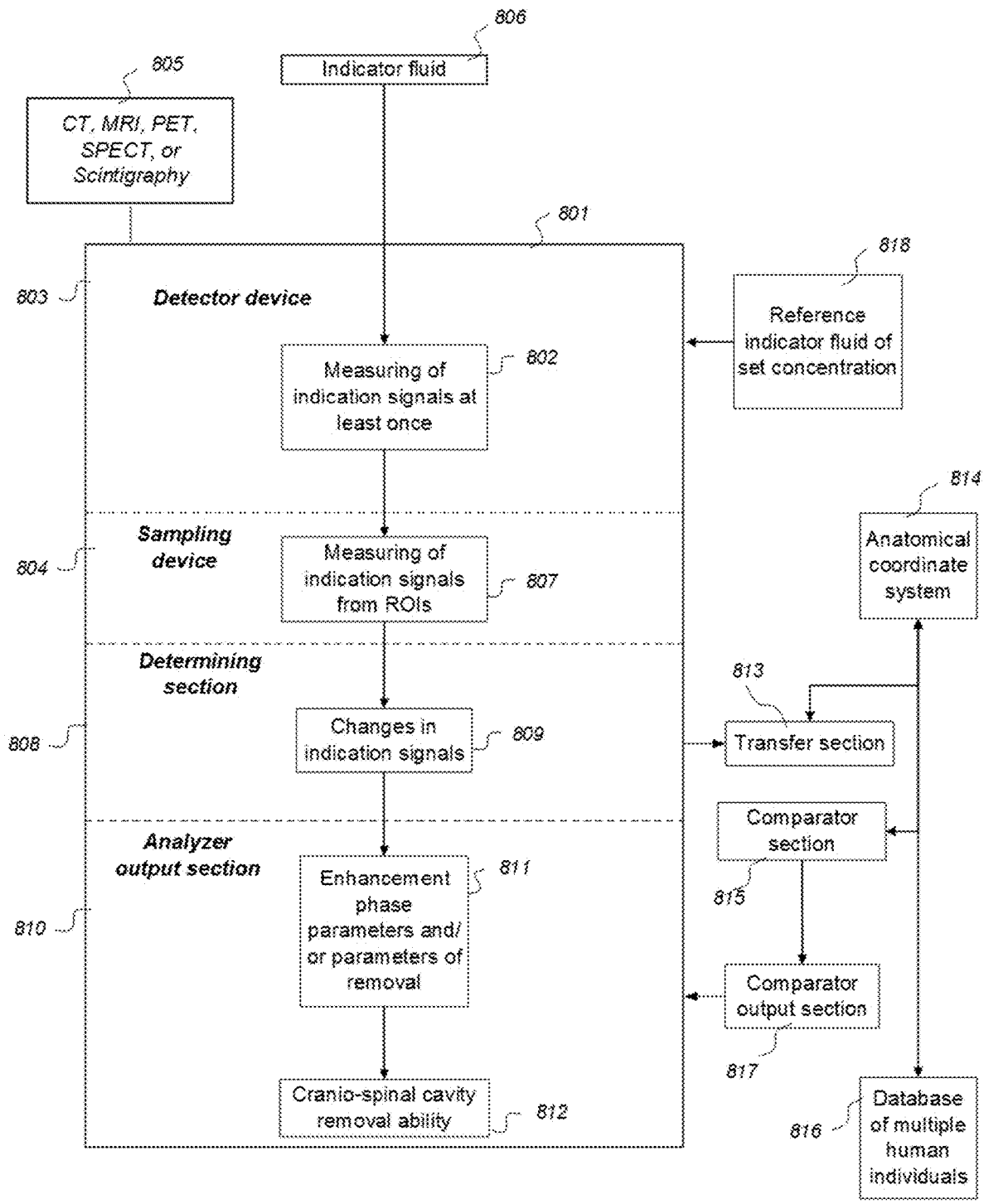
FIG. 8 illustrates a computer-aided method to assess movement of substances within, to or from a CSF, brain or spinal cord compartment of a cranio-spinal cavity of a human.

Both the system and computer-aided method features of Aspect 2 relate to the method of comparing individuals against a cohort. As illustrated in FIG. 14a, this embodiment incorporates the use of an anatomical coordinate system 614 (FIG. 6), 814 (FIG. 8). The present invention is neither limited to the type of anatomical coordinate system nor to the specific methods of image transfer 613 (FIG. 6), 813 (FIG. 8). According to prior art and current clinical use, three systems are most commonly used in imaging applications, i.e. the world, anatomical (also called patient coordinate system) and image coordinate systems. Thus, prior art technology enables transfer of images into anatomical coordinate systems. For example, MATLAB may be used to map Slicer RAS coordinates to voxel space of a nifti image. Hence, the images imported into a coordinate system should meet certain requirements: The image specifications should meet certain requirements (e.g. type of MRI image type, repetition time, echo time, flip angle, FOV, matrix etc.), and adjustment according to SUs of extra-body device (second aspect of the invention). Therefore, to get permission to import data from one patient, the repeated MRI acquisitions should meet requirements regarding MRI settings and use of extra-body device. This is because a dataset from many individuals based on a variety of MRI examination protocols have less value. For the sake of clarity, an anatomical coordinate system makes it possible to describe every region (or ROI) within the cranial cavity 1401 according to the x, y, and z coordinates 1402. For the present invention, a ROI within the brain may be characterized according to the anatomical coordinate system 1402, enabling comparisons between individuals. This is further exemplified in FIG. 14b.

The same ROI is identified on T1 weighted MRI with standardized settings with no gadobutrol present, and after intrathecal gadobutrol had been present for 3 hours, 9 hours, and 24 hours. At the various time points, the average indication signals within the ROIs were 80 SU 1403, 83 SU 1404, 103 SU 1405 and 107 SU 1406 (FIG. 14b). Utilizing an anatomical coordinate system, this enhancement in SUs within one individual could be compared with a cohort of individuals. The application of a coordinate system is beneficial for comparison of the same ROIs.

Figure 14C:
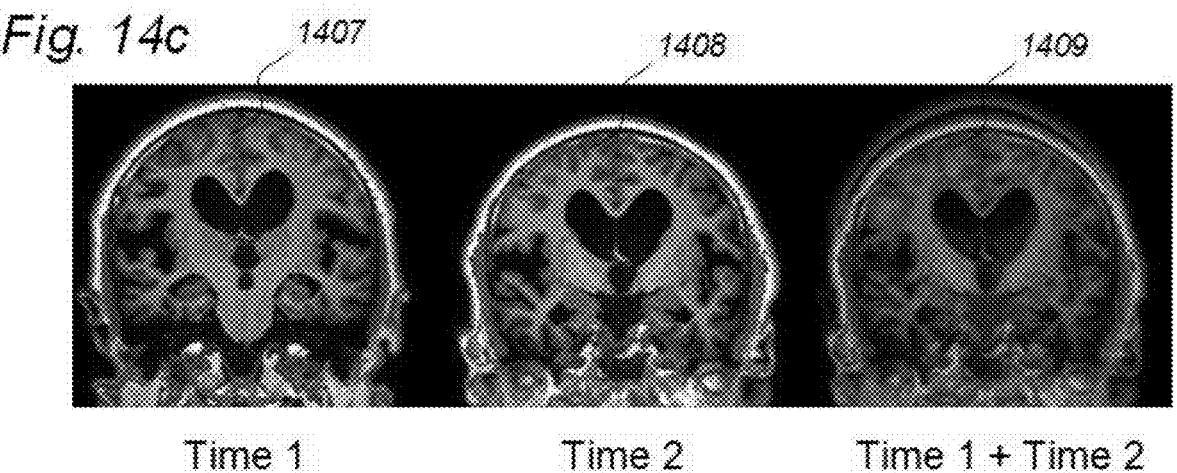
Figure 14D:
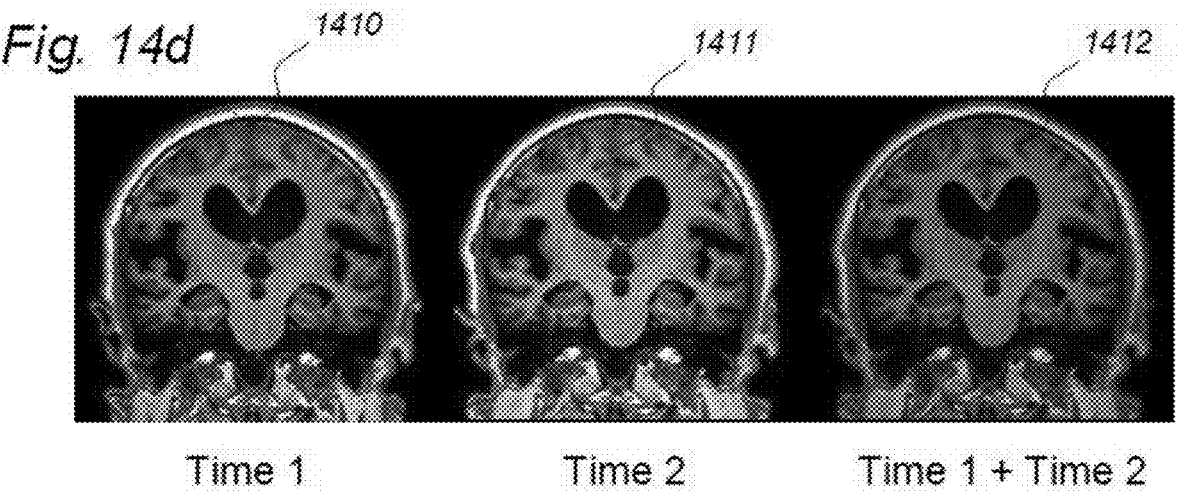

The alignment of longitudinal data is illustrated in FIG. 14c-d. When repeated MRIs are obtained proper alignment is necessary for use of segmentation tools. Otherwise, it is not possible to examine how signals within defined regions of interest change over time. FIG. 14c shows a coronal T1 weighted MRI at Time 1 1407 and Time 2 1408, and the co-registered MRIs 1409. The co-registered MRI 1409 show no good co-registration. In FIG. 14d is shown coronal T1 MRIs at Time 1 1410 and Time 2 1411, including co-registered MRIs 1412. In this latter case proper alignment is obtained. Methodology for alignment is established from prior art, as is methodology for segmentation of MRI acquisitions. The inventors have used the FreeSurfer software (version 6.0) (http://surfer.nmr.mgh.harvard.edu/) for segmentation and parcellation, and to measure how an indicator fluid present within CSF (the MRI contrast agent gadobutrol) changed the T1 SU. In this case, the MRI contrast agent was used as CSF tracer. The FreeSurfer software utilizes automated Talairach transformation 1402, and allows for segmentation of a wide range of brain regions, including the subcortical white matter and deep gray matter volumetric structures (including hippocampus, amygdala, caudate, putamen, ventricles).

Using prior art methodology for alignment and segmentation, changes in indication signals over time may be determined. This is further illustrated in Table 5. The results are from 8 individuals who underwent MRI for tentative idiopathic intracranial hypotension due to CSF leakage. A CSF leakage was identified in 3/8 individuals. Otherwise the individuals were healthy. Table 5 presents the percentage change in normalized T1 signals, i.e. indication signal ratios, over time, as compared to T1 weighted MRI without CSF tracer present. Table 5 shows percentage change in normalized T1 SUs within various brain regions that were segmented using FreeSurfer: Cerebral cortex (grey matter), cerebral white matter, basal ganglia, thalamus, limbic structures (hippocampus, amygdala, nucleus accumbens and entorhinal cortex), cerebellar cortex, and cerebellar white matter. The MRI signal increase was significant at all main locations (Table 5). The determination of signal unit ratios was described with reference to FIG. 7.

For clarity, one typical MRI protocol used by the inventors is shortly commented on, though this represents no limitation with the invention. Repeated T1-weighted MRI scans of the intracranial compartment (and neck region for imaging of cervical lymph nodes), either in the presence or absence of the MRI contrast agent gadobutrol (0.5 ml of 1.0 mmol/ml; Gadovist®, Bayer Pharma AG, GE) delivered to the CSF compartment. MRI scans were acquired on a 3 Tesla Philips Ingenia MRI scanner (Philips Medical systems, Best, The Netherlands). The inventors used a dedicated imaging protocol for each region, that was applied to all time points. The following parameters for 3D T1 w imaging of the intracranial compartment were used: repetition time (TR) =5.1 ms (set to minimum), echo time (TE)=2.3 ms (set to minimum), flip angle=8 degrees, field of view=256×256 cm, and matrix=256×256 pixels (reconstructed 512×512). Total 184 over-contiguous slices with 1 mm thickness were sampled and automatically reconstructed to 368 slices and a thickness of 0.5 mm. Each image acquisition lasted 6 minutes and 29 seconds. An automated anatomy recognition protocol based on landmark detection in MRI data (Smart-Exam™, Philips Medical Systems, Best, The Netherlands) was applied at every time point to secure consistency and reproducibility of the MRI studies. Neck images were obtained in an anatomical standardized coronal plane, using T1 weighted turbo spin echo (TSE) DIXON with the following main image sequence parameters: TR=560 ms, TE=14 ms, flip angle=90 degrees, field of view 250×198 mm, voxel size=1×1×3 mm reconstructed to 0.58×0.58×3 mm³, gap 0.3 mm, number of slices=30. For detection of neck lymph nodes, we obtained coronal T2 weighted TSE DIXON with TR=ranged 2500-3500 (actual 2500), TE=80 ms, flip angle=90 degrees, field of view 250×200 mm, resolution 0.6×0.79×3 mm³ reconstructed to 0.58×0.58×3 mm³, gap 0.3 mm, number of slices=30. Moreover, to ensure same position on the coronal slices between scan times a screen dump showing the placement of the first coronal images was saved and used as a reference for subsequent planning by the radiographer. In general, the center slice was placed at the anterior superior part of the 4$^{th}$ cervical vertebra. As indicator fluid, the inventors gained most experience by doing assessments after 0.5 ml of 1.0 mmol/ml gadobutrol (Gadovist™, Bayer Pharma AG, Berlin, Germany) having been administered intrathecal.

viduals 1420. Peak for reference subjects occurred after 6-9 hours while after 24 hours for the dementia population. Further, segmentation of hippocampus using FreeSurfer (FIG. 14g), and determination of percentage change in signal unit ratios 1420 versus time 1421, revealed that trend plot of percentage change of signal unit ratios in reference subjects 1422 peaked after 6-9 hours 1422, while after 24 hours for the dementia cohort 1423. Considering limbic structures using FreeSurfer (FIG. 14h), and determination of percentage change in signal unit ratios 1424 versus time 1425 also showed peak CSF tracer enhancement in references subjects 1426 after 6-9 hours while percentage change in signal unit ratios reach maximum after 24 hours in the dementia cohort 1427. The markedly increased CSF tracer enrichment in dementia cohort within the CSF 1416, entorhinal cortex 1420, hippocampus 1423 and limbic structures 1427 point at hampered removal of CSF tracer from the respective regions.

Figure 15:
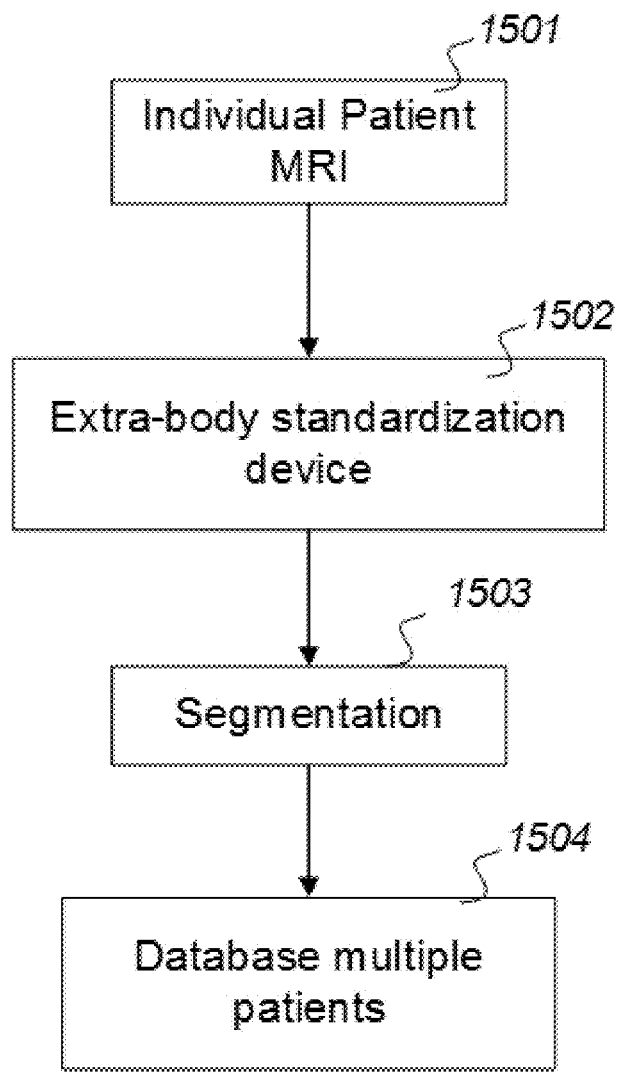
FIG. 15 illustrates the incorporation of a database cooperating with an extra-body standardization device.
Figure 16A:
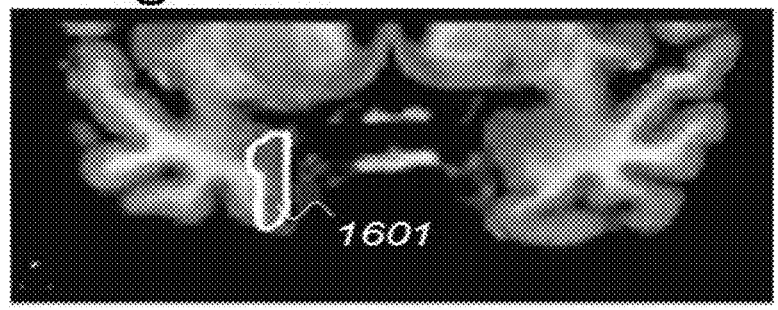
FIG. 16a-h illustrate one example of segmentation of areas of cortical grey matter in the medial temporal lobe, including the entorhinal cortex (a-d). Repeated measurements of SUs (i.e. indication signals) in ROIs segmented according to the entorhinal cortex with gadobutrol (i.e. indicator fluid) present within the CSF (e-h). The entorhinal cortex is used as an illustration since this area is of relevance for cognitive function and Alzheimer's disease. It consists of six layers. Repeated MRI images (e-h) may be segmented for the entorhinal cortex.
Figure 16B:
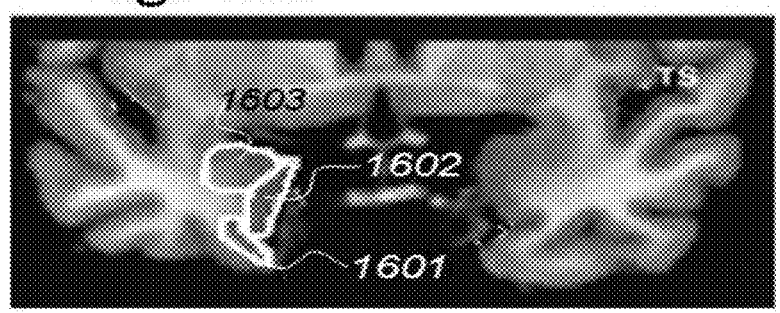
Figure 16C:
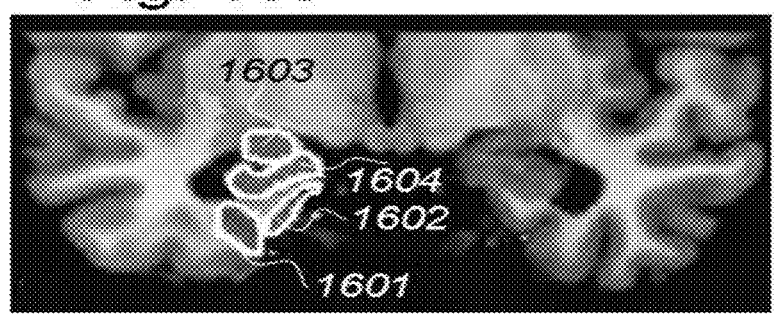
Figure 16D:
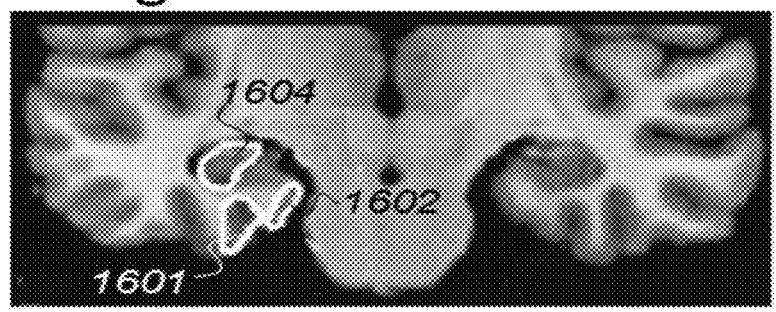
Figure 16E:
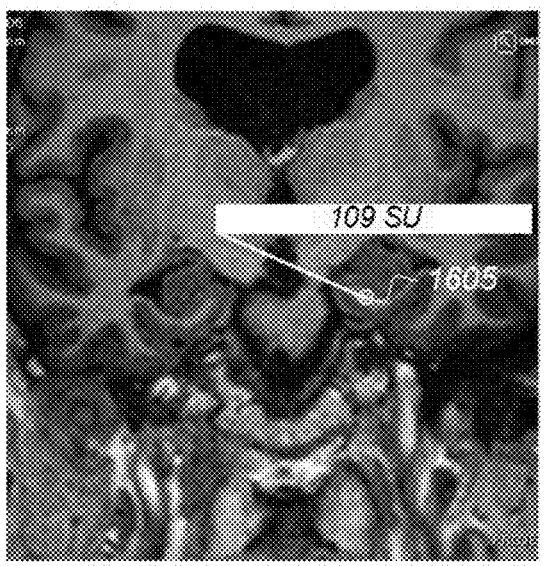
Figure 16F:
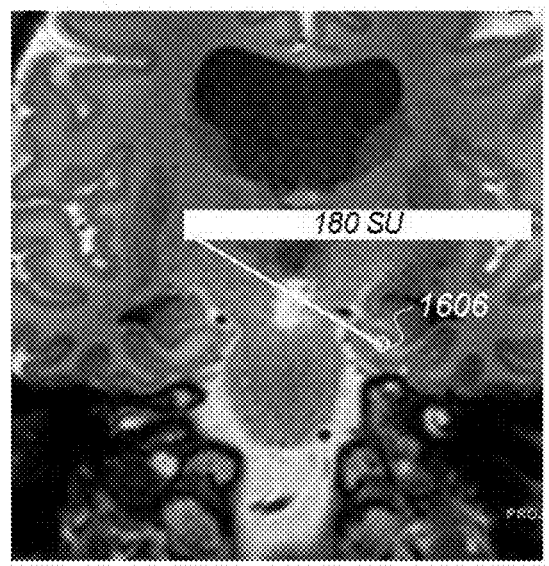
Figure 16G:
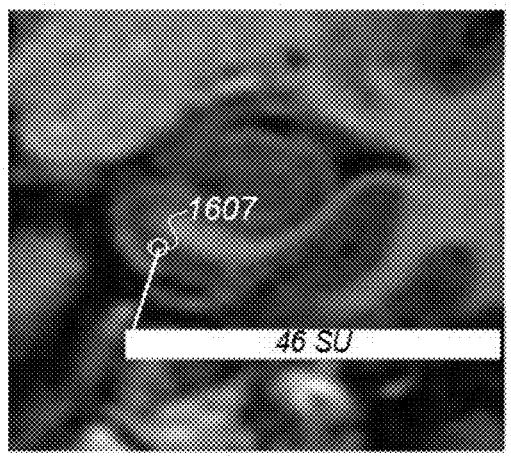
Figure 16H:
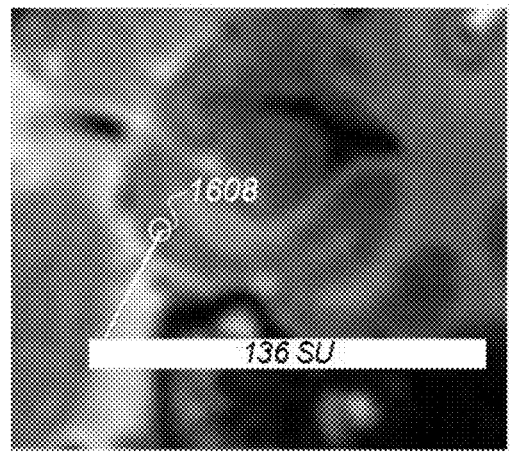

As illustrated in FIG. 15, the MRI scanning in humans 1501 may apply a standardization device 1502 together with an anatomical coordinate system 1402. This aspect is further detailed in Aspect 7. An extra-body standardization device 1502 (see Aspect 7) is used for standardization of MRI SUs. Segmentation 1503 of selectable regions may be done to examine defined regions. Thereby, a database 1504 may be created based on standardized SUs. The trend plots shown in FIG. 14e-h refer to brain regions segmented using Free-

TABLE 5

Percentage change in signal unit ratios after intrathecal gadobutrol had been moving from CSF in humans.

| Anatomical region | Time after intrathecal gadobutrol | | | | |
|---|---|---|---|---|---|
| [FreeSurfer] | 1.5-2 hours | 2-4 hours | 4-6 hours | 6-9 hours | 24 hours |
| CSF [24] | 16 ± 20 | 101 ± 116 | 354 ± 309 | 500 ± 421 | 157 ± 164 |
| Cerebral cortex (grey matter) [1000-1035 (left) + 2000-2035 (right)] | −3 ± 7 | −1 ± 15 | 26 ± 44 | 44 ± 50 | 52 ± 54 |
| Cerebral white matter [2, 41] | −3 ± 9 | −1 ± 18 | 26 ± 40 | 34 ± 46 | 27 ± 33 |
| Basal ganglia [11, 12, 13, 50, 51, 52] | −3 ± 8 | −6 ± 14 | 1 ± 25 | −4 ± 14 | 4 ± 18 |
| Thalamus [10, 49] | −2 ± 8 | −4 ± 15 | 5 ± 26 | 2 ± 18 | 11 ± 21 |
| Hippocampus, amygdala, accumbens, entorhinal [17, 18, 26, 53, 54, 58, 1006, 2006] | −2 ± 7 | −1 ± 15 | 28 ± 38 | 43 ± 43 | 42 ± 39 |
| Cerebellar cortex [8, 47] | 6 ± 6 | 12 ± 27 | 45 ± 58 | 67 ± 80 | 53 ± 47 |
| Cerebellar white matter [7, 46] | 1 ± 9 | −3 ± 14 | 3 ± 23 | 2 ± 19 | 15 ± 23 |

Continuous variables given as mean ± standard deviation.

FIG. 14e-h shows trend plots of changes in signal unit ratios over time in two cohorts of individuals. The inventors determined percentage change in signal units when indicator fluid was present in the CSF compartment, as compared to a point of time without any indicator fluid within the CSF compartment. Four different regions were examined, segmented using FreeSurfer, namely CSF (FIG. 14e), entorhinal cortex (FIG. 14f), hippocampus (FIG. 14g) and Limbic structures (FIG. 14h). The two cohorts of individuals included reference subjects who were close to healthy and a population with a subtype of dementia. For the CSF compartment (FIG. 14e) is shown percentage change in signal unit ratios 1413 versus time 1414, including trend plots for reference subjects 1415 and individuals with dementia 1416. The trend plots 1415, 1416 were significantly different, with peak indicator fluid enhancement after 6-9 hours. Regarding the entorhinal cortex (FIG. 14f), a plot of percentage change in signal unit ratios 1417 versus time 1418 revealed different trend plots for reference subjects 1419 and dementia indi- Surfer, namely the CSF (FIG. 14e), entorhinal cortex (FIG. 14f), hippocampus (FIG. 14g) and limbic structures (FIG. 14h).

To further illustrate this aspect, segmentation of the parahippocampal region, including the entorhinal cortex is given as an example, and illustrated in FIG. 16. The entorhinal cortex is used as an illustration since this area is of relevance for Alzheimer's disease. The entorhinal cortex consists of six layers. FIG. 16a-d shows segmentation of the parahippocampal region, illustrating the perirhinal cortex 1601, entorhinal cortex 1602, amygdala 1603, and hippocampus 1604. Using an anatomical coordinate system, for example using FreeSurfer, comparisons of ROIs within such an anatomical region becomes more feasible. These areas of the brain have vital impact on memory functions. Further, FIG. 16e-h shows change in SUs when gadobutrol was present within CSF, i.e. repeated MRI images segmented with ROIs placed within (g and h) and subcortical to (e and f) the entorhinal cortex. Thus, repeated MRI images with a ROI within the subcortical area of entorhinal cortex 109 SU 1605 without gadobutrol (FIG. 16*e*) and 180 SU 1606 when intrathecal gadobutrol had been present for 24 hours (FIG. 16*f*). Further, more detailed inspection of entorhinal cortex revealed 46 SU 1607 without gadobutrol (FIG. 16*g*) and 136 SU 1608 after intrathecal gadobutrol had been present for 24 hours (FIG. 16*h*). The differences in average of SUs depend on the size of the ROI. By transferring T1 3D images to an anatomical coordinate system 1402, images from numerous individuals may be added to the coordinate system. Information within the coordinate system may be segmented, e.g. for the entorhinal cortex. Thereby, the details of information may be increased, such as identifying changes within defined layers of entorhinal cortex and towards hippocampus.

Transfer of images to an anatomical coordinate system may be done using dedicated software. In an Aspect 7 of the invention, we propose several means to allow for standardization of MRI images, which will improve comparisons between MRI scanners and creating big datasets. Another option is the determination of signal unit ratios, as described for FIG. 7*b-e* and FIG. 14*d-h*. To create a database of MRI images (see 616 in FIG. 6; 816 in FIG. 8; and 1504 in FIG. 15), the extra-body device described as Aspect 7 of the invention, and used for standardization of SUs, is of great advantage and will be beneficial to obtain improved measurement quality. The standardization device allows for comparisons of absolute SU values between individuals and within an individual at different time points. In this embodiment of the invention, we propose to record observations within a 3D coordinate system of the human brain. One example of such a coordinate system is the Talairach coordinates, wherein the brain 1401 is characterized within a coordinate system according to the x, y, and z axes 1402. Hence, alignment of repeated MRI images (see FIG. 14*b*) may be interfaced with Talairach coordinates, which can be done across subjects. For this purpose, subsequent MRI image volumes are aligned in each individual, and the movement of molecules (indicator fluid such as contrast agents) is determined in tissue versus fluid compartment. Transformation to the Talairach coordinates may be aided by specific anatomical landmarks, such as anterior commissure, posterior commissure, pineal gland etc. It should be noted that other coordinate systems than that of Talairach are available.

Import of MRI images into a coordinate system may be web-based. Hence, the user may upload the dataset anonymously on a web-based platform. Thereby, users from many countries may participate to create data from a large cohort of individuals, i.e. "big data". Information from many individuals may be categorized according to age, gender, diagnosis, co-morbidity etc. Such a categorization may be important for many diagnoses. Examples of categories include: Alzheimer's and dementia in general, brain tumor (e.g. astrocytoma), multiple sclerosis and inflammatory brain disease, stroke (brain infarction or bleeds), sleep disturbances, neurodegenerative disease, CSF circulation disorders, traumatic brain injury, neurometabolic diseases, glaucoma, chronic headache and migraine, and in assessment of ageing in general. For example, changes in clearance of substances and water may be compared between Alzheimer's patients and other individuals, and categorized between patients having sleep disturbances or not.

The implementation of a methodology using coordinate system has several functions:

1) Opportunity to add information from one individual into a coordinate system consisting of data from individuals with a variety of diagnoses and clinical situations. Using coordinate systems such as that of Talairach; information from numerous individuals is gathered to create "big data".

2) Opportunity to compare observations from one individual patient with that of a big patient cohort. This can be done using the web-based platform. The "web" here refers to the World Wide Web (internee), but may also constitute a cluster of co-operating centers at a smaller scale.

Figure 17:
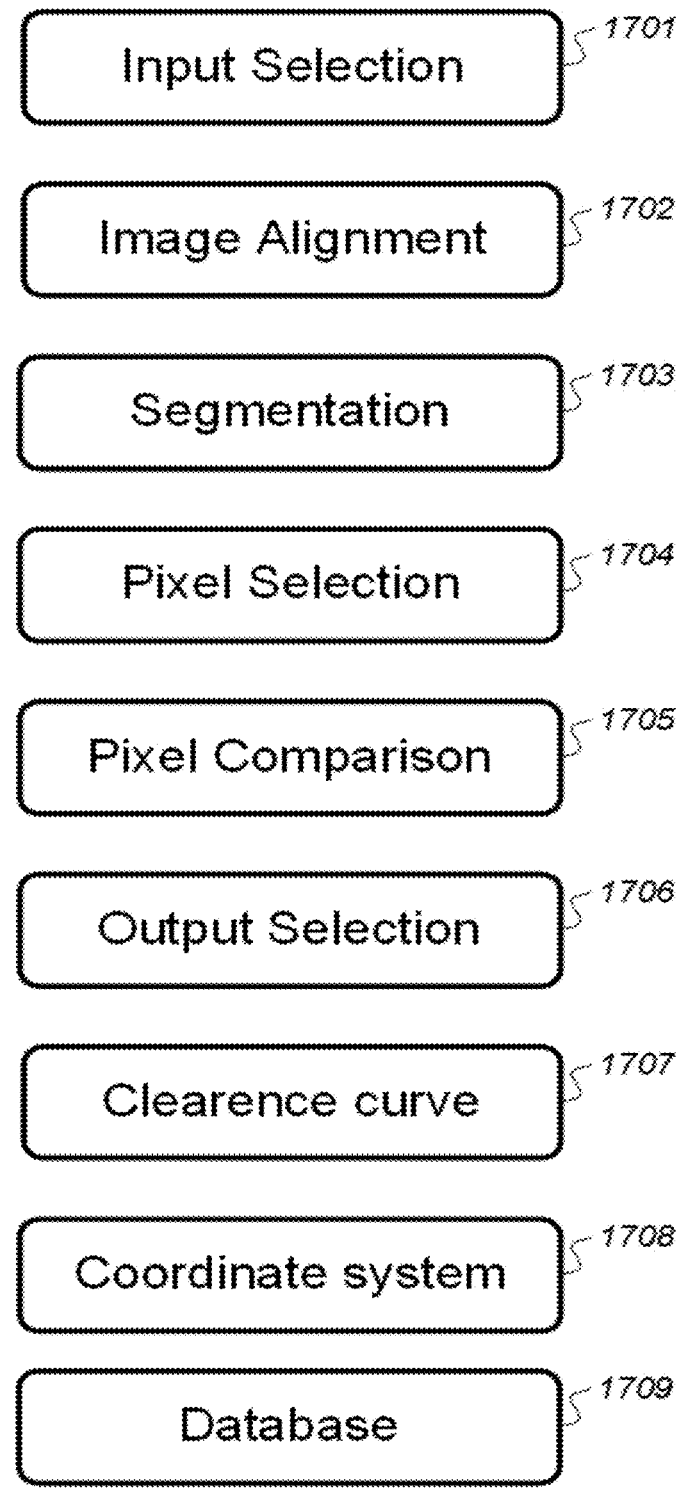
FIG. 17 illustrates some main elements incorporated in software used for post-processing of images.

The system and computer-aided method of Aspect 2 may be implemented in a software for post-processing of images. Some main elements are highlighted in FIG. 17. Software may incorporate various input selections 1701, methods for image alignment 1702, segmentation of selected anatomical regions 1703 (exemplified by segmentation of entorhinal cortex; FIG. 16), selection of ROIs containing a set of pixels 1704 for automatic determination of clearance curves, which ROIs (and pixels) to compare 1705, and output selection 1706, e.g. which clearance curves 1707 that should be expressed as a function of another. Interaction with an anatomical coordinate system 1708 is possible. The software may be used for post-processing of MRI acquisitions. One kind of use implies that the user defines which ROIs that shall be included in analysis, and defines which MRI acquisitions that shall be used. The software automatically calculates clearance curves, time series, and relationships between different ROIs. Moreover, results from individual subjects may be related to results from a cohort of patients using the database 1709 information. It should be noted that these elements of software are not exclusive for Aspect 2, but are common for all Aspects 2-7 of the present invention. The examples of elements given in FIG. 17 represent no limitation concerning implementation of the invention in software. The software may be fully integrated as an add-on program in a picture archiving and communication system (PACS), which is a commonly used technology to archive and present radiological images. Alternatively, the software is used on a separate work station. In addition to the elements presented in FIG. 17, some other elements of software may be noted:

The user may select type of study and input variables such as disease, age, gender.

Software should be able to read the most commonly used file formats.

Software should include methods for aligning repeated MRI images, segmentation of selected anatomical regions, selection of pixels for automatic determination of clearance curves, which ROIs to compare, and which clearance curves that should be expressed as a function of another.

Software should have both manual and automatic options for selection of locations to be analyzed. It should be possible to manually select ROIs. The program also should incorporate methodology for automatic segmentation of particular regions. For example, cervical LNs may be detected automatically using T2-weighted images, where LNs typically have higher SU than surrounding soft tissue. Optional areas for segmentation of contents within the cranial cavity include ventricular system, periventricular frontal horn, entorhinal cortex, frontal inferior gyms, Sylvian fissure, cervical LNs, though these areas represent no limitation. The ROIs and number of pixels can be selected, including the ROIs to be compared.

Software should have options for calibration of MRI acquisition, e.g. T1 weighted images, which allows for comparison of repeated MRI acquisitions within individuals and comparison of different individuals. This functionality is connected to the extra-body device used for estimation of absolute values of changes in SUs, further described as the fifth aspect of the invention. The ability to quantify in absolute terms alterations in SUs is a valuable functionality.

Software should incorporate the methods of the present invention, as further detailed in systems and methods embodiments of Aspects 2-7 of the present invention. Thereby, automatic analysis provides for computation of clearance curves of selectable number of pixels, determination of relationships between pixels of various locations (CSF compartment, brain compartment, extracranial tissue compartment and extra-body compartment). Various kinds of statistical analyses and presentations are available.

Software includes visualizations of clearance curves. Using colors, regions within the cranio-spinal cavity and the extra-cranial compartments may be highlighted according to clearance time or other attributes of clearance curves.

Software should have file export options. Results of applying the inventive method can be exported to a coordinate system to gather results from many individuals. This aspect is described in more detail for aspect eight of the present invention. Moreover, software should incorporate database(s) for saving results of analyses. Results from individuals can be compared with results from a larger cohort.

In one embodiment of the invention, the user makes all selection on the first image series and the automated software computes automatically all ROIs, clearance curves and relationships between clearance curves. Further, clearance curves as a function of the others are also determined automatically.

The types of output selection may be determined by the user. Clearance curves may be determined. Visualization using colors may be created.

The present functionalities of software represent no limitation to the invention as various modifications are possible.

In the following, Aspect 3 of the invention is described, namely solutions (system, computer-aided method) to assess movement of substances within, to or from a CSF compartment, a brain or spinal cord compartment, of a cranio-spinal cavity of a human.

Figure 6:
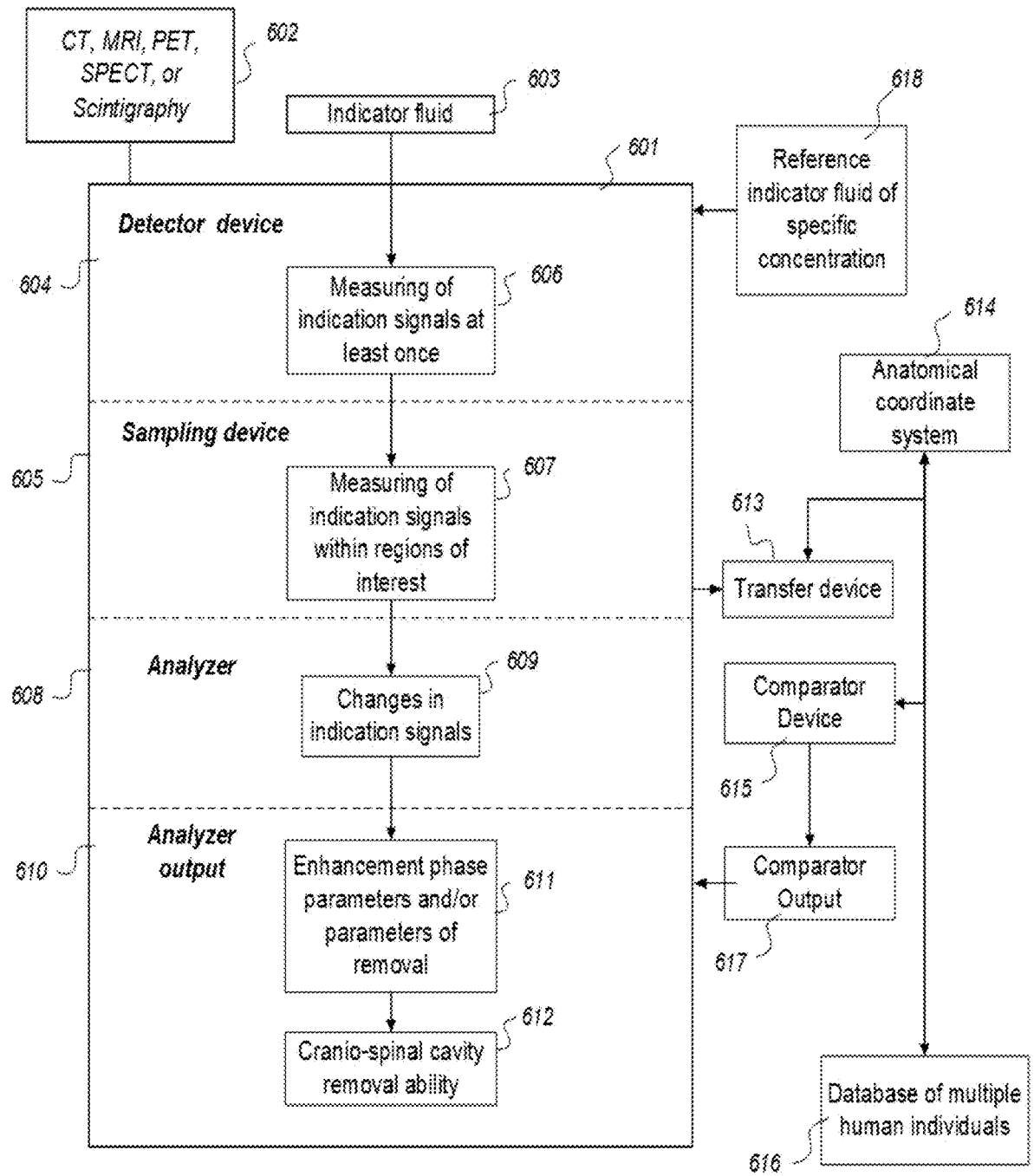
FIG. 6 illustrates a system to assess movement of substances within, to or from a CSF, brain or spinal cord compartment of a cranio-spinal cavity of a human.

A first feature of Aspect 3 discloses a system to assess movement of molecular substances within, to or from cerebrospinal fluid, brain or spinal cord compartments of a cranio-spinal cavity of a human, with assistance from a selectable indicator fluid movable along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, Various elements of the system are illustrated in FIG. 6. The system 601 comprising:

a) an apparatus 602 configured for one of computed tomography (CT), magnetic resonance imaging (MRI), positron emission tomography (PET), single photon emission computed tomography (SPECT), and scintigraphy imaging, and related to the selected indicator fluid 603, b) a detector device 604 and a sampling device 605 to measure at least once indicator fluid indication signals 606 provided by use of said apparatus 602 within regions of interest of said cerebrospinal fluid, brain or spinal cord compartments 607, c) an analyzer 608 capable of determining c1) any sampled and detected change in indication signals 609 over time within a selectable one of cerebrospinal fluid compartments of said cranio-spinal cavity, said changes in indication signals 609 being indicative of said movement of indicator fluid within, to or from the selected cerebrospinal fluid compartment of said cranio-spinal cavity, and c2) any sampled and detected change in indication signals over time within a selectable brain or spinal cord compartment of said cranio-spinal cavity, said change in indication signals being indicative of movement of indicator fluid within, to or from the selected brain or spinal cord compartment of said cranio-spinal cavity, and d) an analyzer output 610 to establish a presentation of said determination of said changes in indication signals within said regions of interest and indicative of enhancement phase parameters and/or parameters of removal 611 of the indicator fluid 603 being a function of ability and assessment of movement of molecular substances within, to or from the cerebrospinal fluid compartment, e.g. cerebral ventricles within the cranio-spinal cavity, or movement of molecular substances within, to or from the brain or the spinal cord compartment of said craniospinal cavity, said ability of a cranio-spinal cavity to remove 612 molecular substances being a function of clearance of waste solutes from the cerebrospinal fluid, brain or spinal cord compartment.

The notation indication signal 606, 607, and 609 has a broad meaning, and depends on imaging modality. CT refers to Hounsfield Units (HU), MRI refers to SU and PET, SPECT and scintigraphy refer to Standard Uptake Value (SUV). An indication signal 606, 607, and 609 is thus a measurable feature derived from an imaging modality 602, where the indication signal level may be influenced by presence of indicator fluid 603. Indication signals may also be measured in the absence of indicator fluid, as presence of indicator fluid within the body is no precondition for measurement of indication signals.

The ROIs are related to a selectable number of MRI acquisitions or radioactive radiation imaging acquisitions.

MRI may incorporate T1 weighted sequences with standardized acquisition parameters being at least echo and repetition time, flip angle, matrix, and field of view. Further, all parameters essential for a T1 weighted image should be standardized as far as possible to enable for the highest reproducibility of T1 SU, both between different time points in single human subjects, but also between subjects, and between different MRI scanners. Other MRI sequences that may show useful are T1-mapping, susceptibility weighted imaging, and FLAIR.

Concerning the indicator fluid 603 used by the system, it may contain a CT contrast agent, or a MRI contrast agent, or a substance exhibiting recognized pharmacokinetic properties. The CT contrast agent may be a selected one of: iohexol, iodixanol, iomeprol, ioversol, and iobitridol, and the MRI contrast agent may be either gadobutrol or gadoteric acid. Moreover, the indicator fluid can be a dendrimer based macromolecular MRI contrast agent of size sufficiently high to be retained outside the BBB, or a substance exhibiting resembling pharmacokinetic properties.

The indicator fluid 603 may as well be a radioactive ligand suitable for PET, SPECT or scintigraphy imaging tied to or chelated with being a contrast agent substance or a substance exhibiting recognized pharmacokinetic properties. Further, the radioactive ligand may be a selectable tracer material from at least one of: $^{89}$Zirconium, $^{99m}$TC-DTPA, and $^{111}$In-DTPA. The indicator fluid may contain a radioactive ligand, which is chelated with material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques. The indicator fluid 603 may also be a CT or an MRI contrast agent coupled with one or more of: large-molecule biotechnology based products, antibodies, monoclonal antibodies, recombinant proteins, and antisense or gene therapeutics means. Further, the indicator fluid 603 may be configured to be delivered to the CSF compartment by spinal puncture and intrathecal injection.

The analyzer 608 is capable of determining c1) any sampled and detected change in indication signals over time within a selectable one of cerebrospinal fluid compartments of said cranio-spinal cavity, said changes in indication signals being indicative of said movement of indicator fluid within, to or from the selected cerebrospinal fluid compartment of said cranio-spinal cavity, and c2) any sampled and detected change in indication signals over time within a selectable brain or spinal cord compartment of said cranio-spinal cavity, said change in indication signals being indicative of movement of indicator fluid within, to or from the selected brain or spinal cord compartment of said cranio-spinal cavity. Features c1) and c2) may originate from a simultaneous operation, or features c1) and c2) originate from operations spaced in time.

The system 601 may be used for comparison of individuals against a cohort. For this purpose, the system 601 may have a transfer device 613 capable of transferring said ROIs of said imaging acquisition to an anatomical coordinate system 614, the anatomical coordinate system 614 being configured to enable segmentation of selectable anatomic regions. The system 601 may as well have a comparator device 615 enabling a comparison of said change in indication signals over time between indication signal changes in a single human individual and changes in said multiple ones of human individuals, using a database 616. A comparator output 617 is configured to provide a presentation of any deviation in movement of substances in as measured and imaged from a single human individual compared to average movement of substances in said multiple ones of human individuals.

The system may be cooperative with an MRI SU standardization device (see Aspect 7) to cause said indication signals being SUs to be standardized SUs, said standardization device comprising an extra-body device containing at least one reference indicator fluid of specific concentration 618. At least one reference indicator fluid 618 is located within one or more containers to be located externally of the body of the human, and the containers being also filled with dedicated material. The standardized SUs allow for measurement of absolute concentrations or quantitative measures of indicator fluid within the ROI of a human individual. Changes in standardized SUs over time may refer to a graphically drawn curve, see FIG. 7, illustrating clearance of indicator fluid within a selectable ROI. In this regard, clearance curves of one or more selectable ROI may be compared with clearance curves of comparable ROI from a cohort of humans, by means of said anatomical coordinate system. Said dedicated material may be a dummy material having liquid properties, e.g. viscosity or molecular property, resembling standard cranio-spinal cavity liquid or having semi-solid material properties, e.g. density or molecular property, resembling standard properties of standard brain tissue.

A second feature of Aspect 3 discloses computer aided method to assess movement of molecular substances within, to or from a cerebrospinal fluid, brain or spinal cord compartment of a cranio-spinal cavity of a human, with assistance from a selectable indicator fluid movable from a cerebrospinal fluid compartment along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. FIG. 8 illustrates some elements of the computer-aided method 801, which comprises:

a) measuring at least once indicator fluid indication signals 802 provided by use of a computer-linked detector device 803 and a sampling device 804 dedicated for one of computed tomography (CT), magnetic resonance imaging (MRI), positron emission tomography (PET), single photon emission computed tomography (SPECT), and scintigraphy 805, as related to said indicator fluid 806, within regions of interest of said brain or spinal cord compartment 807 b) determining by means of a determining section 808 in the computer 801:

b1) level or change in level of indication signals 809 over time within a selectable one of cerebrospinal fluid compartments of said cranio-spinal cavity, e.g. cerebral ventricles within the cranio-spinal cavity, said change in indication signals 809 being indicative of movement of indicator fluid within, to or from said selected cerebrospinal fluid compartment of said cranio-spinal cavity, and b2) level or change in level of indication signals 809 over time within a selectable brain or spinal cord compartment of said cranio-spinal cavity, said change in indication signals being indicative of movement of indicator fluid within, to or from a brain or spinal cord compartment of said cranio-spinal cavity, and c) establishing, using an analyzer section 810 in the computer 801, a presentation of said determination of change in indication signals 809 within regions of interest of said brain or spinal cord compartment as a function of said determination of change in indication signals within regions of interest of said cerebrospinal fluid compartment of said cranio-spinal cavity, said function enabling said assessment of the ability of to move molecular substances within, to or from said cerebrospinal fluid, brain or spinal cord compartment of said cranio-spinal cavity, said ability of movement of molecular substances referring to clearance of waste solutes from the cerebrospinal fluid, brain or spinal cord compartment 812.

The ROIs may refer to a selectable MRI acquisition, and the MRI acquisition may incorporate T1 weighted sequences with selectable and standardized imaging parameters being at least echo and repetition time, flip angle, matrix, and field of view.

According to this method 801, the movement of indicator fluid 806 within, to or from a brain or spinal cord compartment is a function of ability of a) movement of substances within a brain or spinal cord compartment, or b) removal of substances via the brain or spinal cord compartment away from said cranio-spinal cavity 812.

The indication signals 802, 807, 809 may be MRI SUs, which can be normalized or standardized relative to a reference being an extra-body device, which allows for quantification or measurement of absolute values of indicator fluid within a CSF compartment of a cranio-spinal cavity of a human. By use of fixed sequence parameters at all imaging time points, semi-quantitative measurements may also be carried out, and may e.g. be given as percentage change in SUs.

The change in indication signals 809 over time may refer to a graphically drawn curve, see FIG. 7, illustrating indicator fluid clearance or enhancement and being indicative of clearance of indicator fluid from a brain or spinal cord compartment within a selectable region of the brain or spinal cord compartment. The curve may be representative of parameters being one or both of a) enhancement phase 811 with attributes selectable from: TTP, maximum increase of indication signals, and enhancement coefficient, and b) clearance phase 811 with attributes selectable from: decline time, maximum decrease of indication signals, clearance coefficient, and parameter area being present under said curve.

The indicator fluid 806 may contain a CT contrast agent, or a MRI contrast agent, or a substance exhibiting recognized pharmacokinetic properties. The CT contrast agent may be a selected one of: iohexol, iodixanol, iomeprol, ioversol, and iobitridol, and a MRI contrast agent either gadobutrol or gadoteric acid. Moreover, the indicator fluid 806 can be a dendrimer based macromolecular MRI contrast agent of size sufficiently high to be retained outside the BBB, or a substance exhibiting resembling pharmacokinetic properties. The indicator fluid 806 may be a radioactive ligand suitable for PET, SPECT or scintigraphy imaging tied to or chelated with a contrast agent substance or a substance exhibiting recognized pharmacokinetic properties. The radioactive ligand may be selectable tracer material from at least one of: $^{89}$Zirconium, $^{99m}$Tc-DTPA, and $^{111}$In-DTPA. In another embodiment, the indicator fluid 806 may contain a radioactive ligand, which is chelated with material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques. The indicator fluid 806 may also be a CT or an MRI contrast agent coupled with one or more of: large-molecule biotechnology based products, antibodies, monoclonal antibodies, recombinant proteins, and antisense or gene therapeutics means. Independent on type, the indicator fluid 806 may be deliverable to a CSF compartment by spinal puncture and intrathecal injection.

The method according to the second feature of Aspect 3 can be applied onto multiple ones of human individuals to determine indication signals 802, 807, 809 through use of said imaging within ROIs to determine changes in indication signals over time within said ROI upon the presence of indicator fluid 806. The ROIs of said imaging acquisition are transferred by transfer mean 813 to an anatomical coordinate system 814, the anatomical coordinate system being configured to enable segmentation of selectable anatomic regions. A comparison 815 of said change in indication signals over time is made between indication signal changes in a single human individual and changes in said multiple ones of human individuals by means of database 816 information, and a presentation by comparator output means 817 may be provided of any deviation in movement of substances as measured and imaged from a single human individual compared to average movement of substances in said multiple ones of human individuals.

The notation indication signal 802, 807, and 809 has a broad meaning, and depends on imaging modality 805. CT refers to Hounsfield Units (HU), MRI refers to SU and PET, SPECT and scintigraphy refer to Standard Uptake Value (SUV). An indication signal 802, 807, and 809 is thus a measurable feature derived from an imaging modality 805, where the indication signal level 809 may be influenced by presence of indicator fluid. Indication signals 802, 807, and 809 may be measured independent of presence or absence of indicator fluid.

In MRI, the indication signals 802, 807, and 809 are MRI SUs, which are made into standardized MRI SUs through use of a standardization device may comprise an extra-body device containing at least one reference indicator fluid of specific concentrations, wherein said at least one reference indicator fluid 818 is located within one or more containers to be located externally of the body of the human, and may also be filled with dedicated material, and wherein standardized SUs allow for measurement of absolute values of indicator fluid within the ROI of a human individual. The dedicated material may be a dummy material having liquid properties, e.g. viscosity or molecular property, resembling standard cranio-spinal cavity liquid or having semi-solid material properties, e.g. density or molecular property, resembling standard properties of standard brain tissue.

The changes in standardized SUs over time may refer to a curve of clearance of indicator fluid within a selectable ROI, see FIG. 7. These curves of clearance of a selectable ROI are compared with curves of clearance of comparable ROI from a cohort of humans, by means of said anatomical coordinate system.

The features of Aspect 3 allow for determining relationships between changes in MRI SUs of different locations, for example CSF compartment versus brain tissue compartment, CSF compartment versus extra-cranial tissue compartment (e.g. LN), brain tissue compartment versus extra-cranial tissue compartment (e.g. LN), or between compartments within or outside cranio-spinal-compartment and extra-body compartments.

The cranio-spinal cavity consists of three major parts, brain and spinal cord tissue (referred to as brain and spinal cord compartments), blood (referred to as intra-vascular or preferably vascular space), and CSF. The CSF is referred to as CSF compartment. It should be noted that the term ISF includes the paravascular fluid along vessels within the brain tissue. Hence, when determining changes in SU within some pixels as a function of changes in SUs of other pixels, attention is paid to movement of substances (water and molecules) within the brain tissue compartment. The importance of this aspect is high-lighted by denoting the present MRI sequence CSF enhanced MRI, which requires presence of a MRI contrast agent within the cranio-spinal cavity. The contrast agent may be administrable to the CSF compartment by intrathecal (injection to the spinal cavity), intracisternal or intraventricular (requires an implanted drain). The type of contrast agent represents no limitation, but should preferably be of low MW; the invention allows for various contrast agents with various MWs. Table 1 presented in Aspect 1 of the invention, provides an overview of contrast agents that may serve as indicator fluids. Concerning MRI, one example is gadobutrol (Gadovist®/Gadavist®).

The third aspect of the invention is as well based on novel observations in humans. In the following, we refer observations from repeated MRI acquisitions done when a MRI contrast agent, gadobutrol, was present within the CSF compartment. FIG. 14*b* illustrates change in SUs within brain tissue when gadobutrol having been administered intrathecal. Contrast enrichment within brain tissue was revealed by average of SUs (i.e. indication signal change) 80 SU 1403 in absence of gadobutrol, and when gadobutrol having been administered intrathecal 83 SUs 1404 at 3 hours, 103 SUs at 9 hours 1405, and 107 SUs at 24 hours 1406. The change in SUs increase within the brain tissue compartment is indicative of paravascular and extracellular movement of gadobutrol within the human brain. Notably, the change in SU differs markedly between individuals and patients with different conditions regarding movement of contrast agent within the CSF compartment, as illustrated in FIGS. 9*a-b* and 10*a-f*. Similarly, the change in SUs within the brain tissue compartment varies considerably between individuals.

Figure 18A:
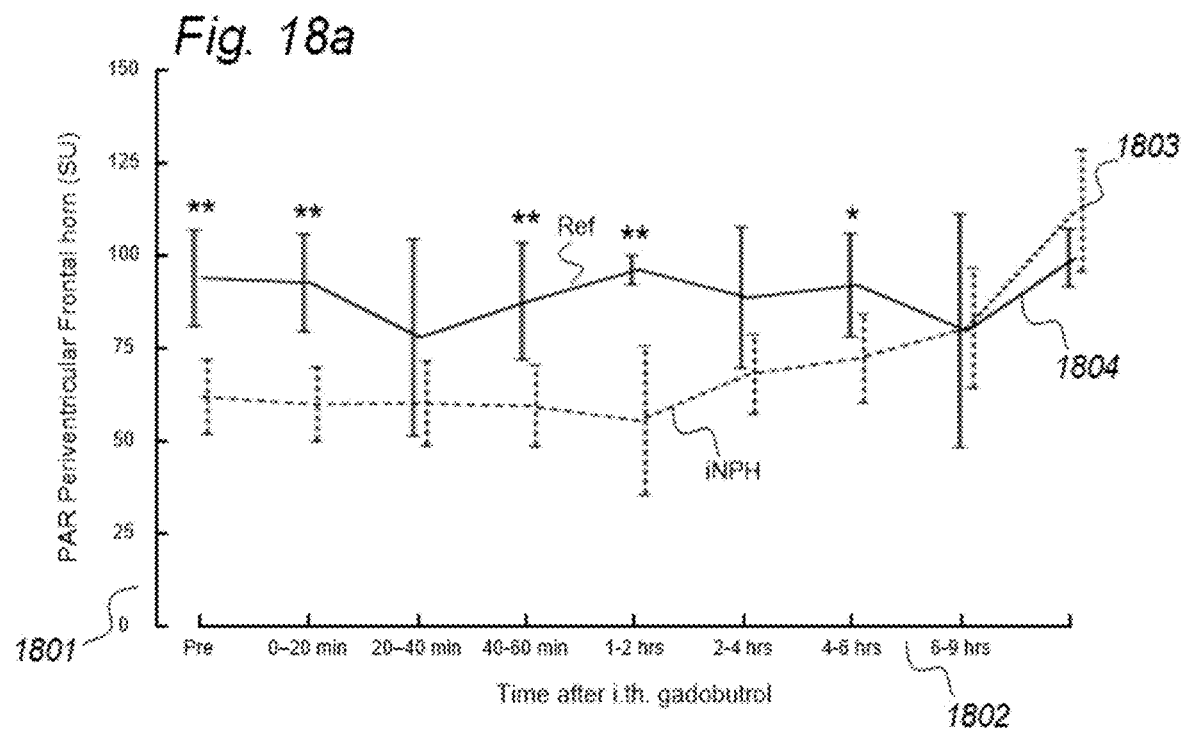
FIG. 18a-18b show trend plots of changes in SUs within two brain tissue compartments of two patient cohorts, namely idiopathic normal pressure hydrocephalus (iNPH) and reference (Ref; i.e. control) individuals.
Figure 18B:
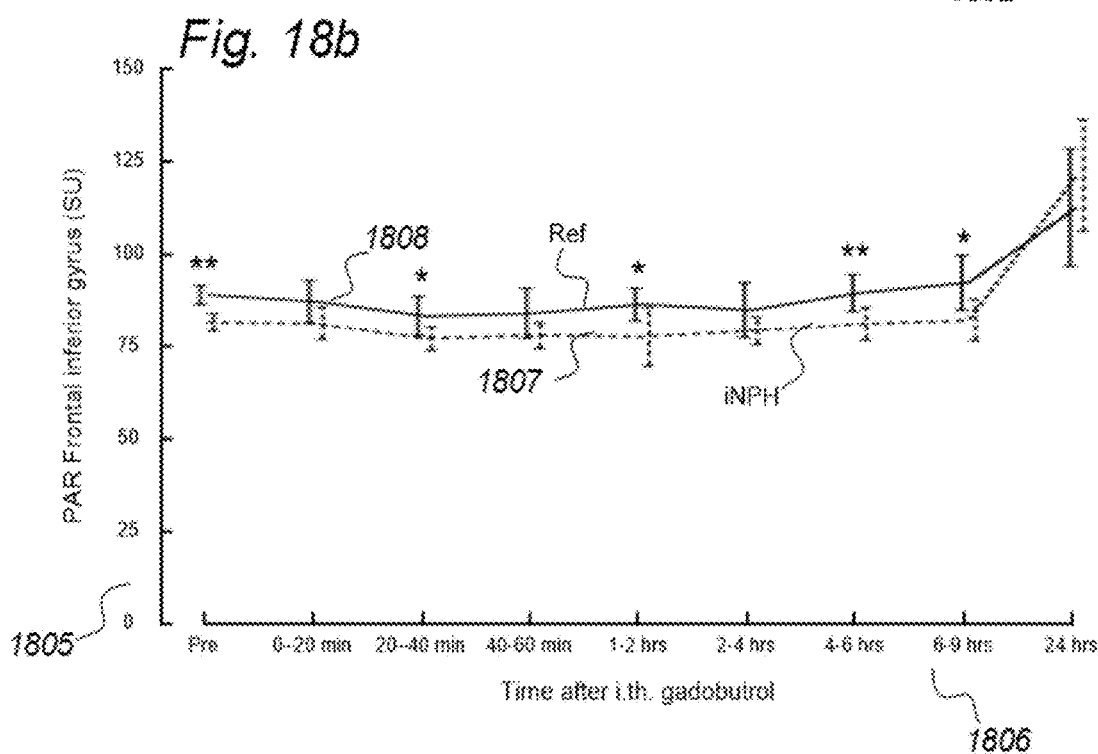

Aspect 3 is further illustrated in FIG. 18*a-b*, showing trend plots of changes in SU (i.e. T1 weighted image greytone level) within two brain tissue compartments of two patient cohorts, namely iNPH and reference (control). FIG. 18*a* shows changes in SUs within brain tissue of periventricular frontal horn 1801 against time 1802, showing that trend plots of average of SUs (variation is 95% CI) for iNPH groups 1803 and reference patients 1804 are different, with iNPH showing stronger increase in SUs than reference patients. Further, FIG. 18*b* shows change in SUs within brain tissue of inferior frontal gyrus (IFG) 1805 against time 1806. The plots of average of SUs for iNPH groups 1807 and reference patients 1808 are different, with iNPH showing stronger increase in SUs than reference patients at 24 hours-time point. The trend plots illustrate several aspects. First, the movement of contrast varies greatly depending on the location, i.e. the selected ROIs. Second, at the group level, clearance curve varies between the two groups. For example, within the periventricular frontal horn, the increase of SUs is delayed in iNPH versus reference (i.e. control).

It has previously not been shown in humans that the brain-wide distribution depends on the availability of contrast within the CSF, and the temporal aspects for contrast agent distribution in humans have previously not been elaborated. There are substantial differences between the paravascular transport mechanisms in animals and humans. Most importantly, the knowledge retrieved from animal experiments cannot be simply transferred to humans.

CSF enhanced MRI in patients reveals that contrast availability in CSF spaces is a critical factor for transport to the brain. Therefore, determining change in SUs within brain tissue as a function of contrast agent availability in adjacent CSF space is useful in humans. Observations in humans suggest that the availability of contrast agent within CSF is critical for transport of contrast agent within the brain tissue. The penetration of contrast agents to the brain tissue appears to heavily depend on location with respect to the proximity of nearby large arteries in the CSF compartment. Thus, the arterial pulsations seem to be vital for transport of contrast agents to the tissue, presumably because the penetrating arteries are the leading pathway of the paravascular-interstitial route (glymphatic pathway) for transport of water and solutes.

Figure 19A:
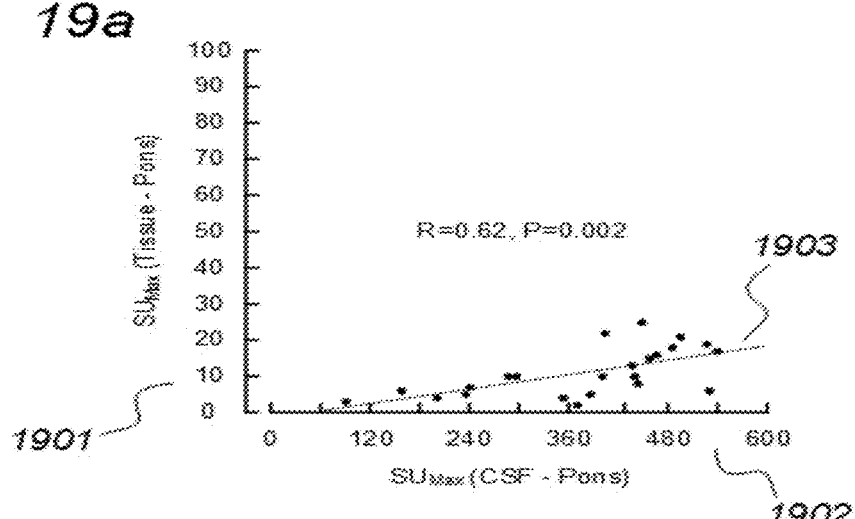
FIG. 19a-e show correlation plots between the maximum change in MRI SU's for selected ROIs within the CSF compartment and nearby brain tissue compartment, demonstrating that the change in indication signals within the brain tissue depends on the presence of indicator fluid within nearby CSF.

Therefore, one inventive step is to define movement of substances within brain tissue as a function of level of the substance in nearby CSF compartment. This aspect is further illustrated in FIG. 19*a-e*. Using T1 weighted MRI; maximum increase in SUs within ROIs of CSF spaces and ROIs of nearby brain tissue was compared; the individual correlation plots are commented on in more detail:

FIG. 19*a* shows highly significant correlation between maximum increase in SUs within brain tissue of pons 1901 and maximum increase in SUs within CSF nearby pons 1902, with highly significant fit line 1903 and Pearson correlation (R=0.62; P=0.002).

Figure 19B:
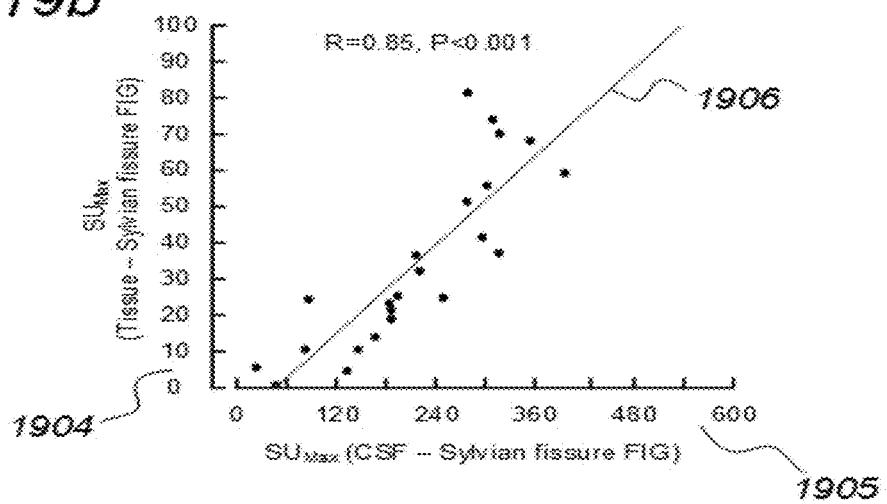

FIG. 19*b* shows highly significant correlation between maximum increase in SUs within brain tissue of inferior frontal gyrus (IFG) 1904 and maximum increase in SUs within nearby CSF of Sylvian fissure 1905, with highly significant fit line 1906 and Pearson correlation (R=0.85; P<0.001).

Figure 19C:
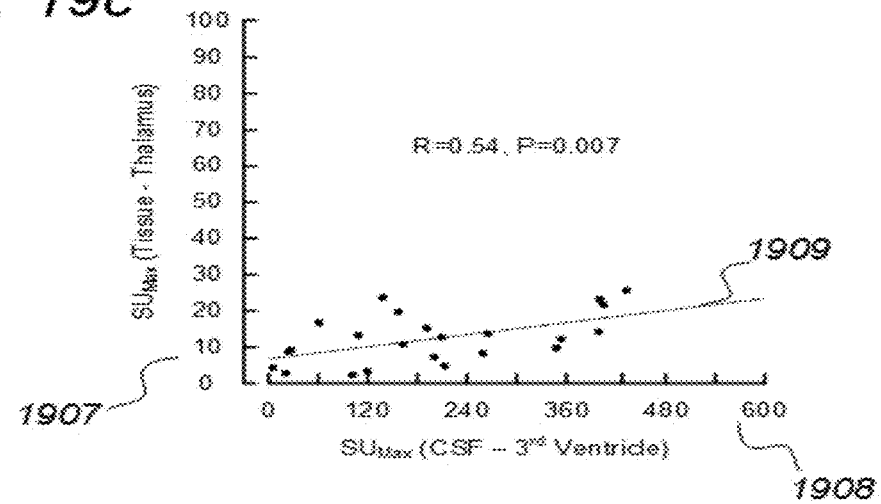

FIG. 19*c* shows highly significant correlation between maximum increase in SUs within brain tissue of thalamus 1907 and maximum increase in SUs within nearby CSF of third ventricle 1908, with highly significant fit line 1909 and Pearson correlation (R=0.54; P=0.007).

Figure 19D:
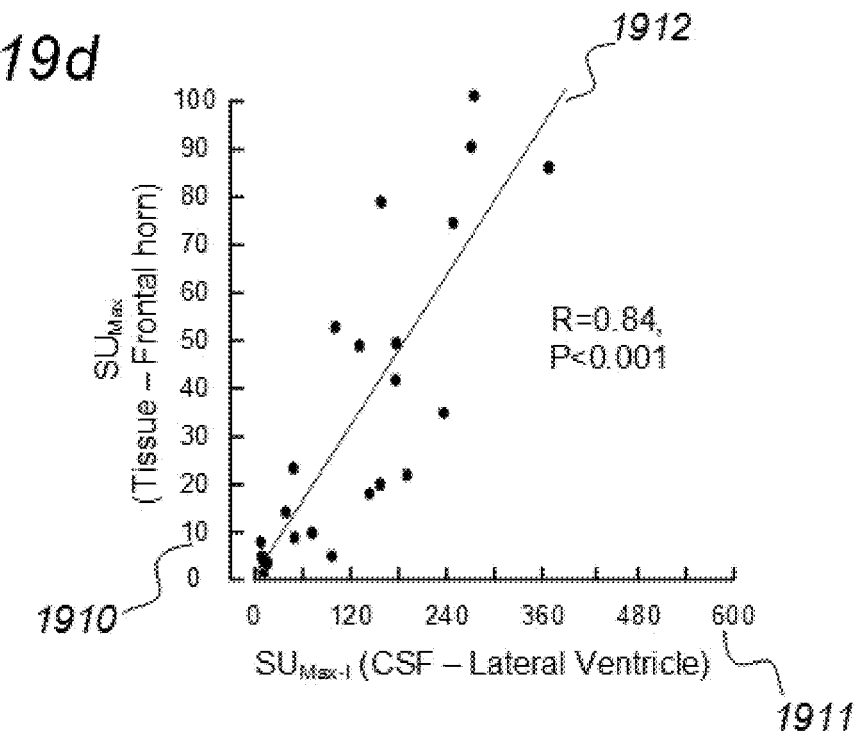

FIG. 19*d* shows highly significant correlation between maximum increase in SUs within brain tissue of periventricular frontal horn 1910 and maximum increase in SUs within nearby CSF of third ventricle 1911, with highly significant fit line 1912 and Pearson correlation (R=0.84; P<0.001).

Figure 19E:
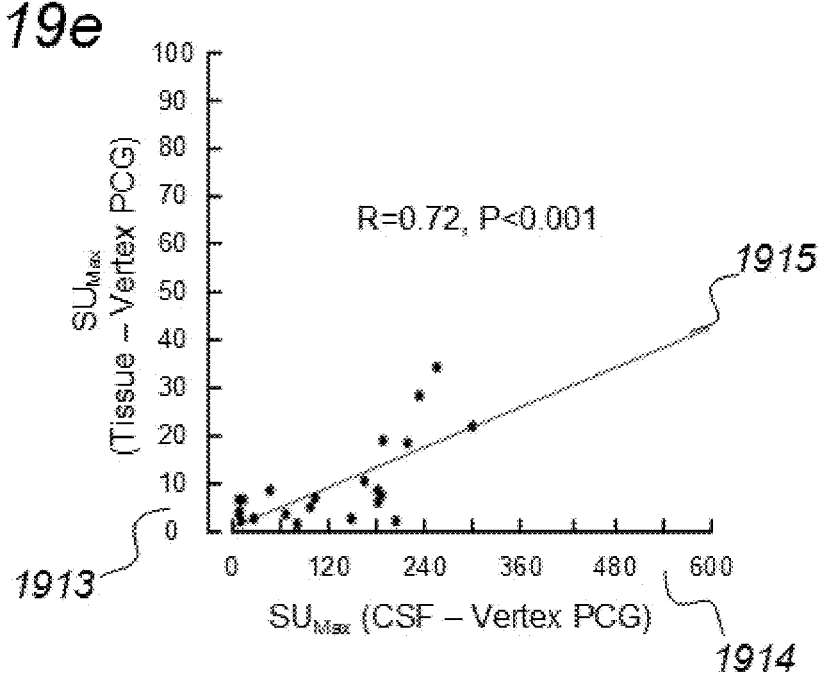

FIG. 19*e* shows highly significant correlation between maximum increase in SUs within brain tissue of precentral gyrus 1913 and maximum increase in SUs within nearby CSF of precentral sulcus 1914, with highly significant fit line 1915 and Pearson correlation (R=0.72; P<0.001).

Taken together, FIG. 19*a-e* reveals a highly significant association between availability of contrast agent within CSF and contrast enrichment within nearby brain tissue. The most significant association between change in SU within CSF and brain tissue compartments was in Sylvian fissure were the large arterial vessels are located. We interpret our observations that the paravascular transport of contrast agent (i.e. indicator fluid) depends on the amount of contrast agent in nearby CSF. Our observations therefore suggest that the changes in SUs within the brain should be evaluated according to the availability of contrast agent within the CSF compartment. Therefore, the movement of contrast agents within the brain tissue compartment (shown as increase of SUs) is a function of the availability of contrast agent within the nearby CSF compartment. The paravascular and extracellular transport of substances (water and other molecules and in this situation with MRI contrast agent as indicator fluid) is from the outside of the brain and along the arterial blood vessels into the brain, and out of the brain along venous blood vessels and lymphatic vessels. Based on this observation, we propose to determine change in SU within one compartment as a function of change in SU within another compartment. In this regard, a selectable number of different ROIs may be compared.

The inventive method therefore determines changes in SUs over time for a selectable number of pixels, whether within a cranio-spinal cavity, outside a cranio-spinal cavity, or outside a body cavity. According to Aspect 3 of the invention, changes in SUs within one set of ROIs are determined as a function of changes in SUs within another set of ROIs, each ROI being determined by a set of pixels. In other words, a clearance illustrating curve may be determined for each individual patient within a set of ROIs, and said clearance curve may be expressed as a function of another simultaneous clearance curve from another set of ROIs. As described in FIG. 7, one clearance curve determines changes in SUs when a contrast agent was present within the CSF compartment. An inventive step includes determination of relationships between changes in SUs of different locations, and the determination of relationships between changes in SUs within a cranio-spinal cavity and another extra-cranial compartment, and also extra-body compartment (device).

Clearance curves between selectable ROIs may be determined as a function of another in several ways. Some examples are provided:

Relating the parameters of the respective clearance illustrating curves by determining dividends, subtractions, or by determining formula-based relationships. Example: Determination of ratios between enhancement coefficients. There is no limitation as to the number of mathematical functions to be used or which parameters to compare.

Incorporate thresholds for which changes in SU within CSF compartment after contrast that are required for estimation of change in SU within brain tissue to be valid. For example, one requirement might be to determine change in brain tissue SU only when change in nearby CSF compartment is above certain levels, e.g. change ≥10%.

In the following paragraphs, several comparisons of clearance illustrating curves between different ROIs (i.e. clearance curve for ROI-1 versus clearance curve for ROI-2) are presented. This is done to illustrate the context in which Aspect 3 is applicable. Notably, the number, size and location of ROIs to be compared is selectable. Further, there is no limitation as to the number of possible combinations. The following examples are only for the purpose to illustrate.

Figure 20A:
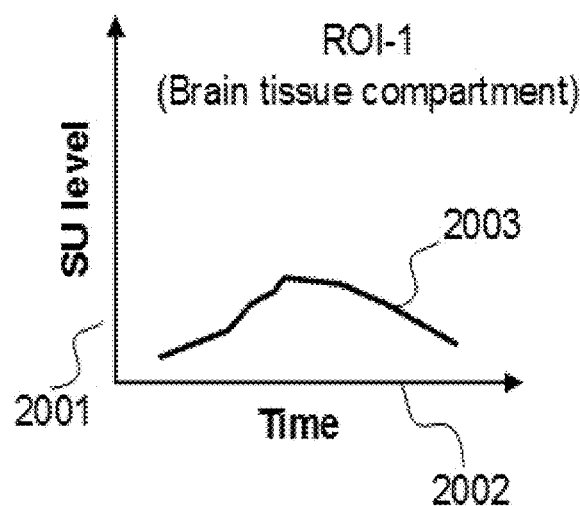
FIG. 20a-20d illustrate four examples of comparing different SU-based clearance illustrating curves from different ROIs (ROI-1 versus ROI-2).

FIG. 20a demonstrates changes in SUs 2001 against time 2002 and the clearance illustrating curve 2003 within a ROI of a brain tissue compartment (ROI-1), and changes in SUs 2004 against time 2005 and the clearance illustrating curve 2006 within a ROI of a CSF compartment (ROI-2). Based on these simultaneous clearance curves 2003 and 2006, changes in SUs within brain tissue compartment may be expressed as a function of change in SU within nearby CSF compartment. This is an inventive step to more precisely determine movement of substances within the paravascular pathways of brain tissue regions. Example: Determine change in indication signal (e.g. SUs) within entorhinal cortex as a function of change in SU in nearby CSF space with indicator fluid (e.g. contrast agent) being in movement to, within or from the CSF compartment.

Figure 20B:
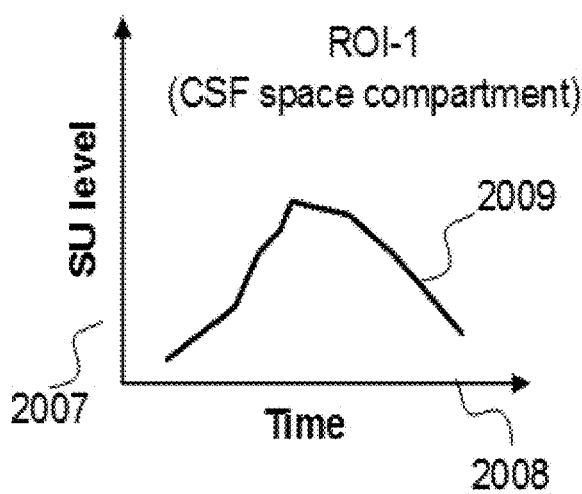

FIG. 20b demonstrates changes in SUs 2007 against time 2008 and the clearance illustrating curve 2009 within a ROI of a CSF compartment (ROI-1), and changes in SUs 2010 against time 2011 and the clearance illustrating curve 2012 within a ROI of another CSF compartment (ROI-2). Based on these simultaneous clearance curves 2009 and 2012, changes in SUs within one CSF compartment may be expressed as a function of changes in SUs within another CSF compartment. This is an inventive step to describe movement of substances within the CSF spaces. Example: Describe change in indication signal (e.g. SUs) between cerebral ventricles and between extra-cerebral and ventricular CSF compartments after indicator fluid having been administered intrathecal.

Figure 20C:
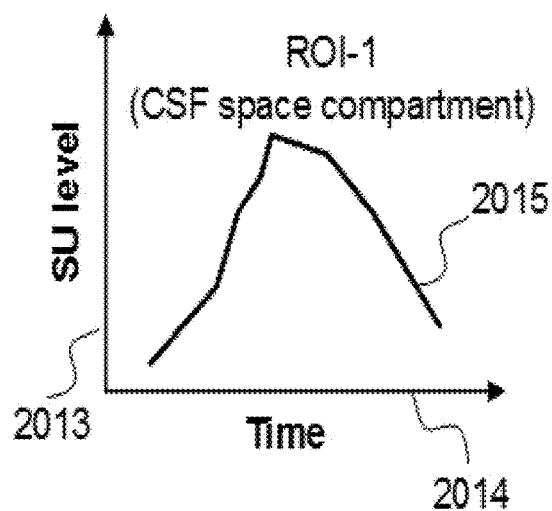

FIG. 20c demonstrates changes in SUs 2013 against time 2014 and the clearance illustrating curve 2015 within a ROI of a CSF compartment (ROI-1), and changes in SUs 2016 against time 2017 and the clearance illustrating curve 2018 within a ROI of an extra-cranial compartment (ROI-2). Based on these simultaneous clearance curves 2015 and 2018, change in SU within a CSF compartment may be expressed as a function of change in SU within an extra-cranial compartment and vice versa. This is an inventive step to determine rate of removal (i.e. clearance) from a CSF space of a cranial cavity to an extra-cranial compartment. Example: Describe change in indication signal (e.g. SUs) as a function of changes in SUs within a selected cervical LN when an indicator fluid having been administered intrathecal.

Figure 20D:
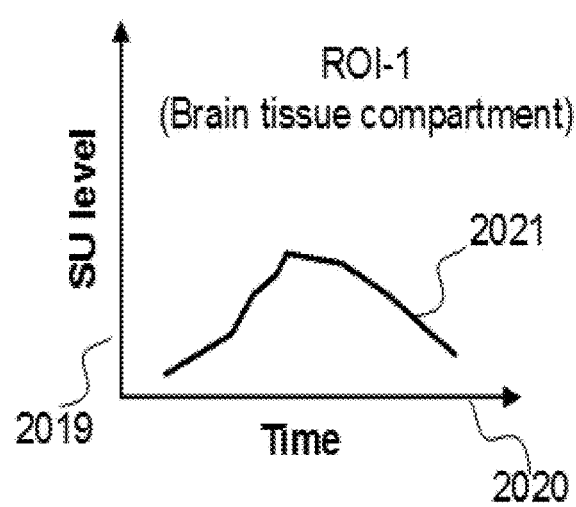

FIG. 20d demonstrates changes in SUs 2019 against time 2020 and the clearance illustrating curve 2021 within a ROI of a brain tissue compartment (ROI-1), and changes in SUs 2022 against time 2023 and the clearance illustrating curve 2024 within a ROI of an extra-cranial compartment (ROI-2). Based on these simultaneous clearance curves 2021 and 2024, change in SU within a brain tissue compartment may be expressed as a function of change in SU within an extra-cranial compartment and vice versa. This is an inventive step to determine rate of removal (i.e. clearance) from a brain tissue compartment of a cranial cavity to an extra-cranial compartment. Example: Determine change in SU within brain tissue of entorhinal cortex as a function of change in SU within a selected cervical LN.

Figure 21A:
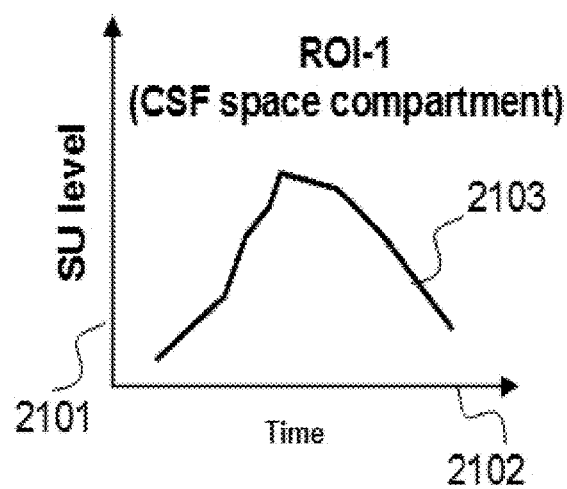
FIG. 21a-21d illustrate four examples of comparing SU-based clearance illustrating curves from different ROIs (ROI-1) against SUs measured from another source.

A wide range of comparisons between different ROIs is possible. Further examples are provided in FIG. 21. FIG. 21a demonstrates changes in SUs 2101 against time 2102 and the clearance illustrating curve 2103 within a ROI of a CSF compartment (ROI-1), and SUs 2104 against time 2105 and the SU-curve 2106 from an extra-body device (ROI-2). Based on these simultaneous measurements of change in SU, the changes in SUs within the CSF compartment may be expressed as a function of the SU measurements from the extra-body device. This is an inventive step to semi-quantify changes in SUs within a CSF space of a cranial cavity as a function of SUs from an extra-body device. Example: Determine change in SU within cisterna magna as a function of change in SU within an extra body device to quantify changes in MRI contrast agent concentrations when using MRI. One alternative method is the use of T1 maps. Other MRI sequences responsive to MRI contrast agents may also be applied, e.g. SWI, FLAIR and T2*, although these represent no limitation.

Figure 21B:
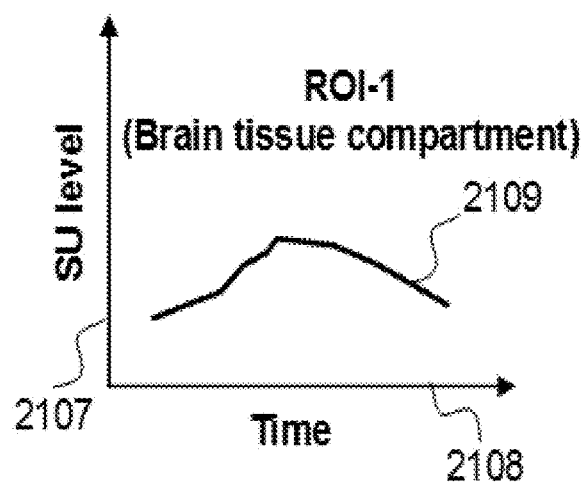

FIG. 21b demonstrates changes in SUs 2107 against time 2108 and the clearance illustrating curve 2109 within a ROI of a brain tissue compartment (ROI-1), and SUs 2110 against time 2111 and the SU-curve 2112 from an extra-body device (ROI-2). Based on these simultaneous measurements of change in SU, the change in SUs within the brain tissue compartment may be expressed as a function of the SU measurements from the extra-body device. This is an inventive step to quantify changes in contrast agent concentration within a brain tissue of a cranial cavity as a function of SUs from an extra-body device. Example: Determine change in SU within entorhinal cortex as a function of change in SU within an extra-body device to quantify changes in contrast agent concentration when using MRI. One alternative method is the use of T1 maps.

Figure 21C:
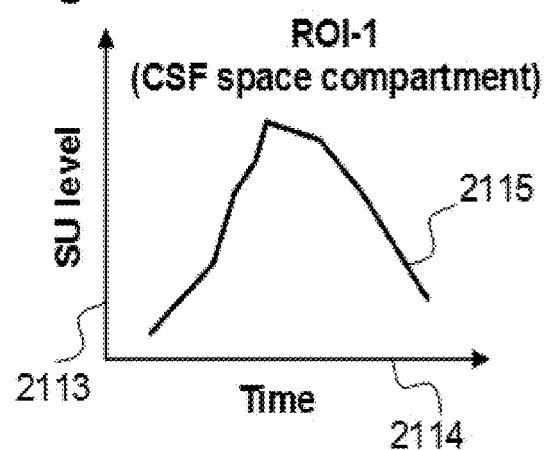

FIG. 21c demonstrates changes in SUs 2113 against time 2114 and the clearance illustrating curve 2115 within a ROI of a CSF space compartment (ROI-1), and changes in SUs 2116 against time 2117 and the clearance illustrating curve 2118 within a ROI of a blood vessel compartment (ROI-2). Based on these simultaneous clearance curves 2115 and 2118, change in SU within a CSF compartment may be expressed as a function of change in SU within a blood vessel compartment, which also may be coupled with determination of contrast agent concentration within blood. This is an inventive step to determine passage of contrast agent to the blood circulation. Example: Determine change in SU within cisterna magna as a function of change in SU within the superior sagittal sinus, and at the same time obtain blood samples to quantify contrast agent concentration.

Figure 21D:
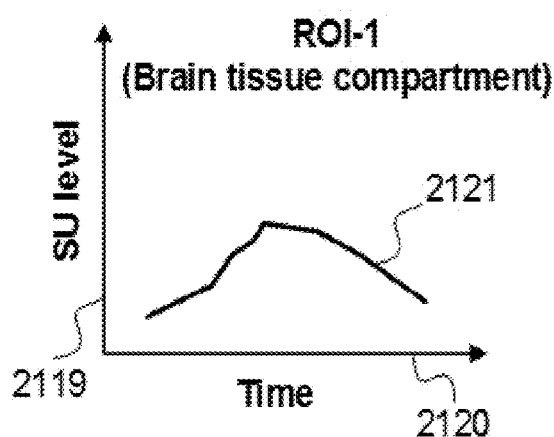
Figure 22A:
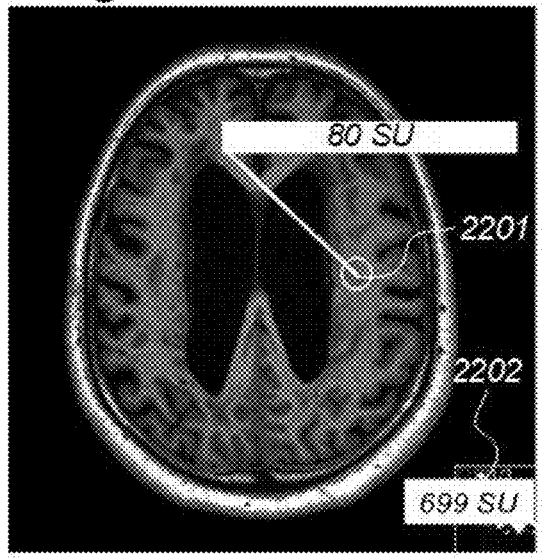
FIG. 22a-f illustrates CSF contrast agent enhancement at multiple time points. Reconstructed images from T1-weighted MRI at baseline (a) (no contrast agent present within CSF) and with contrast agent present within CSF (b-f) demonstrating contrast enhancement of deep white matter (a-b and d and f) and LN (c and e). SUs increase within the brain tissue compartment is indicative of paravascular and extracellular movement of water and other molecules within the human brain.
Figure 22B:
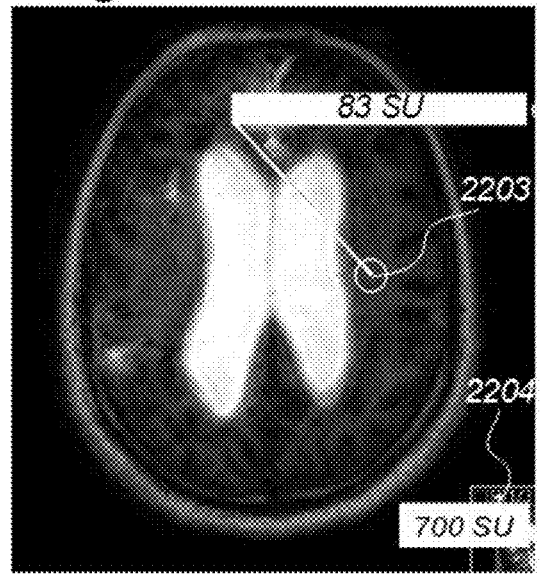
Figure 22C:
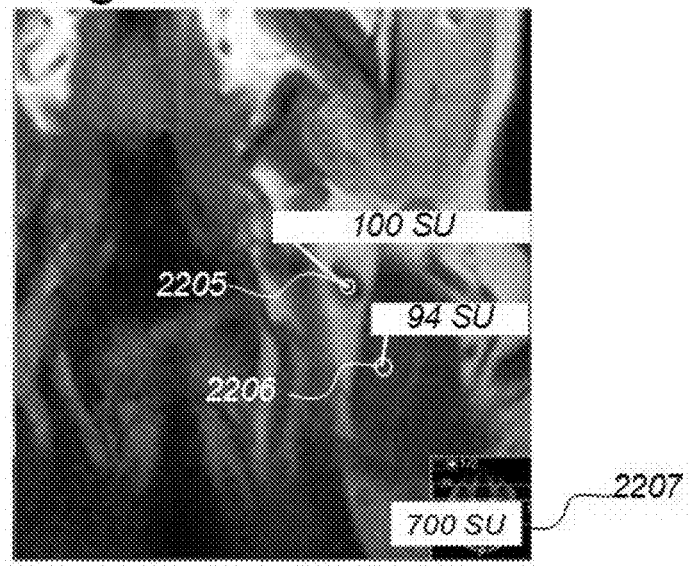
Figure 22D:
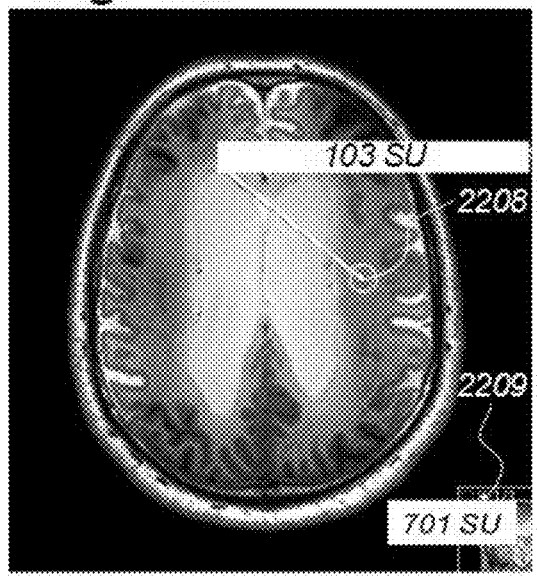
Figure 22F:
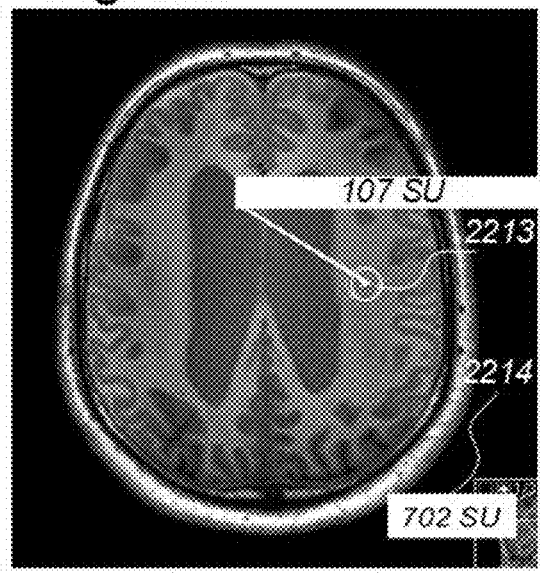
Figure 22E:
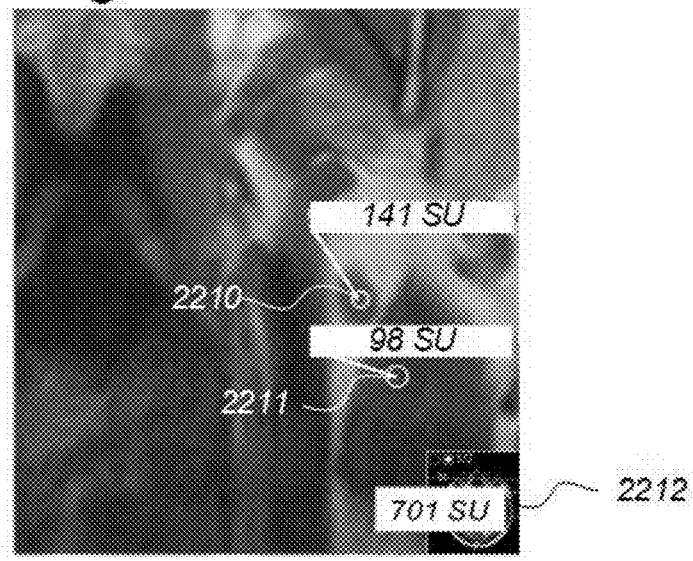

FIG. 21d demonstrates changes in SUs 2119 against time 2120 and the clearance illustrating curve 2121 within a ROI of a brain tissue compartment (ROI-1), and changes in SUs 2122 against time 2123 and the clearance illustrating curve 2124 within a ROI of a blood vessel compartment (ROI-2). Based on these simultaneous clearance curves 2121 and 2124, change in SU within a brain tissue compartment may be expressed as a function of change in SU within a blood vessel compartment, which also may be coupled with determination of contrast agent concentration within blood. This is an inventive step to determine passage of contrast agent to the blood circulation. Example: Determine change in SU within entorhinal cortex as a function of change in SU within the superior sagittal sinus, and at the same time obtain blood samples for quantification of contrast agent concentration.

Both the ROI-1 and ROI-2 presented in FIG. 20a-d and FIG. 21 a-d include a selectable number of pixels, i.e. the size of the ROI is selectable. The change in SU per one or more pixels (i.e. number of pixels defining the ROI) defines the clearance curve including its various attributes. A clearance curve may be created for every pixel, or being averaged for a set of pixels. The latter is most convenient when ROIs are defined manually, while defining clearance illustrating curves for a smaller number of pixels require an automatic procedure, incorporating post-processing software. Thereby, change in SU for a smaller number of pixels may be related more precisely to brain topography. The present invention does not define the number of pixels most suitable for defining ROIs as the most suitable number of pixels may depend on region, and is selectable.

In this context, measurement of SUs of a T1 weighted signal is used as a measure of the movement of substances. Hence, the movement of substances not passing the BBB is measured as change in SUs. As already commented on, the SUs are points along a grey scale set by the MRI scanner. Presence of a contrast agent within a cranio-spinal cavity alters the SU, the change is dependent on enrichment of contrast. The changes in SUs may be determined as absolute or relative changes in MRI greyscale SUs with standardized MRI sequence settings.

The changes in SUs seen when a contrast agent having been administered to a cranio-spinal cavity may be determined by different means and from different parameters derived from indication signals, for example as absolute values or as percentage change. It may also be visualized in different ways. Regarding the site of measurement within the cranial cavity, this represents no limitation. In human subjects, we have measured changes in SUs within a variety of CSF compartments (e.g. cisterna magna, prepontine cisternal space, Sylvian fissure, central sulcus, $4^{th}$, $3^{rd}$ and lateral ventricles). Within the brain tissue, we have measured changes in SUs within the spinal cord, brainstem, thalamus, IFG, precentral gyms. Within the blood vessels we have measured changes in SUs within the superior sagittal sinus. The site of measurement represents no limitation. Even though MRI SUs are exemplifying indication signals, it should be noted that the other image modalities CT, PET, SPECT and scintigraphy may as well be used for establishing indication signals when an indicator fluid is present.

In another aspect of the invention, change of SU in CSF compartment is related to proximity of large arteries at the brain surface. Arteries are clearly identified on T1-weighted 3D images. The change in SU along these arteries provides evidence for the importance of pulsations for propagation of water within the SAS.

The system 601 and computer assisted method 801 of Aspect 3 may be implemented as an automatic procedure. Preferably, it may be implemented in software for post-processing of MRI acquisitions. Another option is implementation as embedded software. For example, the present invention may be incorporated in a fully automated method, namely comprehensive CSF-enhanced MRI with pixel-by-pixel estimation of the T1 image signal over time. Components of automated software components are further illustrated in FIG. 17. The software elements described in FIG. 17 are applicable for all seven aspects of the present invention.

While the computer aided method 801 has here been described in most detail for MRI, this represents no limitation, and indication signals from other imaging modalities (CT, PET, SPECT, scintigraphy) may be utilized as well.

In the following, attention is given to Aspect 4 of the invention, which incorporates means (indicator fluid, system and computer-aided method) to assess movement of substances from a cranio-spinal cavity to kidneys or lymphatic pathway regions, e.g. cervical LNs, of a human.

In a first feature of Aspect 4 is disclosed an indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the indicator fluid is of a type to assist in assessing movement of molecular substances from a cerebrospinal fluid, brain or spinal cord compartment of a cranio-spinal cavity to kidneys or lymphatic pathway regions, e.g. cervical lymph nodes, of a human. Various aspects of the indicator fluid are given in FIG. 5. The indicator fluid 501 is movable from a cerebrospinal fluid compartment along a movement path of said molecular substances, wherein indicator fluid indication signals 502 are measurable at least once within regions of interest of said lymphatic pathways or kidneys, and wherein enhancement phase parameters and/or parameters of removal 503 of the indicator fluid 501 from said cranio-spinal cavity to kidneys or said lymphatic pathway regions being providable, said enhancement phase parameters and/or parameters of removal 503 being based on changes in indication signals 502, and being indicative of ability of said cranio-spinal cavity, i.e. the cerebrospinal fluid, brain or spinal cord compartment, to remove molecular substances from the cranio-spinal cavity to the lymphatic pathways or the kidneys 504.

The indicator fluid 501 may be administrable to the CSF compartment by spinal puncture and intrathecal injection 502, or via the intracisternal or intraventricular routes. The indicator fluid 501 may contain a CT contrast agent, or an MRI contrast agent, or a substance exhibiting recognized pharmacokinetic properties. The CT contrast agent may be a selected one of: iohexol, iodixanol, iomeprol, ioversol, and iobitridol, and the MRI contrast agent either gadobutrol or gadoteric acid.

The indicator fluid 501 may as well be a radioactive ligand suitable for PET, SPECT or scintigraphy imaging tied to or chelated with being a contrast agent substance or a substance exhibiting recognized pharmacokinetic properties. In this regard, the radioactive ligand may be selectable tracer material from at least one of: $^{89}$Zirconium, $^{99m}$Tc-DTPA, and $^{111}$In-DTPA. Further, the indicator fluid 501 may contain a radioactive ligand which is chelated with material selectable from one or more of: large-molecule biotechnology based products, antibodies, monoclonal antibodies, recombinant proteins, and antisense or gene therapeutics means. The material may be chelated with said ligand has at least a partial property of making a bond to tumor cells or inflammation cells or amyloid beta plaques. The indicator fluid 501 may also be a CT or an MRI contrast agent coupled with one or more of: large-molecule biotechnology based products, antibodies, monoclonal antibodies, recombinant proteins, and antisense or gene therapeutics means. Moreover, the indicator fluid 501 can be a dendrimer based macromolecular MRI contrast agent of size sufficiently high to be retained outside the BBB, or a substance exhibiting resembling pharmacokinetic properties.

The notation indication signal 502 has a broad meaning, and depends on imaging modality. CT refers to Hounsfield Units (HU), MRI refers to SU and PET, SPECT and scintigraphy refer to Standard Uptake Value (SUV). An indication signal 502 is thus a measurable feature derived from an imaging modality, where the indication signal level may be influenced by presence of indicator fluid. Indication signals 502 may be measured both on the presence and absence of indicator fluid.

When the indicator fluid 501 is applied in conjunction with MRI, the indication signals 502 are MRI SUs, which may be made into standardized SUs through use of a standardization device, which comprises an extra-body device containing at least one reference indicator fluid of specific concentrations. Said at least one reference indicator fluid is located within one or more containers to be located externally of the body of the human, and may also be filled with dedicated material. Standardized SUs allow for measurement of absolute values of indicator fluid within the ROI of a human individual.

A second feature of Aspect 4 discloses a system to assess movement of molecular substances from a cerebrospinal fluid, brain or spinal cord compartment of a cranio-spinal cavity to kidneys or lymphatic pathway regions, e.g. cervical lymph nodes, of a human, when an indicator fluid is to be movable from a cerebrospinal fluid compartment along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. Some elements are shown in FIG. 6. The system 601 comprises:

a) an apparatus 602 configured for one of: computed tomography (CT), magnetic resonance imaging (MRI), positron emission tomography (PET), single photon emission computed tomography (SPECT), and scintigraphy imaging, and related to properties of the indicator fluid 603, b) a detector device 604 and a sampling device 605 to measure at least once indicator fluid indication signals 606 provided by use of said indicator fluid 603 and said apparatus 602 within regions of interest of kidneys or one or more lymphatic pathway regions 607, c) an analyzer 608 capable of determining any sampled and detected change in indication signals 609 over time within said kidneys or said one or more lymphatic pathway regions, said changes in indication signals 609 being indicative of ability of the crania-spinal cavity to remove indicator fluid and inherently molecular substances from said craniospinal cavity to kidneys or lymphatic pathway regions, and d) an analyzer output 610 to establish a presentation of said determination of said changes in indication signals as a function of ability and assessment of removal of molecular substances from said cranio-spinal cavity to kidneys or lymphatic pathway regions 611, and said function being indicative of the ability of removal of molecular substances 612 referring to removal of waste solutes.

The detector device 604 and analyzer 608 may be configured to enable one or more cervical LNs to be identified through use of high-sensitive imaging acquisition sequences, and wherein LNs are incorporated for determination of indication signals.

According to this system 601, a ROI may be related to a selectable region of a MRI acquisition or radioactive radiation imaging acquisition. MRI incorporates T1 weighted sequences with standardized imaging parameters being at least echo and repetition time, flip angle, matrix, and field of view. Further, all parameters essential for a T1 weighted image should be standardized as far as possible to enable for the highest reproducibility of T1 SU, both between different time points in single human subjects, but also between subjects, and between different MRI scanners. Other MRI sequences that may show useful are T1-mapping, susceptibility weighted imaging, and FLAIR, but these represent no limitation.

The change in indication signals 609 over time provided by the system 601 may refer to a graphically drawn curve illustrating enhancement of indicator fluid as a function of time related to clearance of indicator fluid within a selectable region of a lymphatic pathway 611, e.g. a cervical or neck region LN. Further details about a clearance illustrating curve 703 are provided in FIG. 7; the curve incorporates parameters being one or more of:

a) enhancement phase 708 with attributes selectable from: TTP 709, maximum increase of indication signals 710, and enhancement coefficient 711, and b) clearance phase 712 with attributes selectable from: decline time 713, maximum decrease of indication signals 714, clearance coefficient 715, and area being present under said curve.

The notation indication signal 606, 607, and 609 has a broad meaning, and depends on imaging modality. CT refers to Hounsfield Units (HU), MRI refers to SU and PET, SPECT and scintigraphy refer to Standard Uptake Value (SUV). An indication signal 606, 607, and 609 is thus a measurable feature derived from an imaging modality 602, where the indication signal level may be influenced by presence of indicator fluid 603. Indication signals 606, 607, and 609 may be measured both in the presence and absence of indicator fluid.

The indicator fluid 603 used by the system may contain a CT contrast agent, or a magnetic MRI contrast agent, or a substance exhibiting recognized pharmacokinetic properties. The CT contrast agent may be a selected one of: iohexol, iodixanol, iomeprol, ioversol, and iobitridol, and the MRI contrast agent may be either gadobutrol or gadoteric acid. Moreover, the indicator fluid 603 can be a dendrimer based macromolecular MRI contrast agent of size sufficiently high to be retained outside the BBB, or a substance exhibiting resembling pharmacokinetic properties.

The indicator fluid 603 may as well be a radioactive ligand suitable for PET, SPECT or scintigraphy imaging tied to or chelated with being a contrast agent substance or a substance exhibiting recognized pharmacokinetic properties. For example, the radioactive ligand may be a selectable tracer material from at least one of: $^{89}$Zirconium, $^{99m}$Tc-DTPA, and $^{111}$In-DTPA. Further, the indicator fluid 603 may contain a radioactive ligand which is chelated with material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques.

The indicator fluid 603 may also be a CT or an MRI contrast agent coupled with one or more of: large-molecule biotechnology based products, antibodies, monoclonal antibodies, recombinant proteins, and antisense or gene therapeutics means.

The indicator fluid 603 may be configured to be delivered to said cranio-spinal cavity by spinal puncture and intrathecal injection. The administration part itself is not part of the invention.

The system 601 may be used for comparisons of individual cases against a cohort.

For this purpose, the system has a transfer device 613 capable of transferring said ROI of said imaging acquisition to an anatomical coordinate system 614, which is configured to enable segmentation of selectable anatomic regions. The system 601 has a comparator device 615 enabling a comparison of said change in indication signals over time between indication signal changes in a single human individual and changes in said multiple ones of human individuals using a database 616. Further, a comparator output 615 is configured to provide a presentation of any deviation in movement of substances as measured and imaged from a single human individual compared to average movement of substances in said multiple ones of human individuals 616.

The system 601 may be cooperative with an MRI SU standardization device to cause said indication signals being SUs to be standardized SUs (see Aspect 7). The standardization device may comprise an extra-body device containing at least one reference indicator fluid of specific concentration 618, and wherein said at least one reference indicator fluid 618 is located within one or more containers to be located externally of the body of the human, and the containers may also be filled with dedicated material, and wherein standardized SUs allow for measurement of absolute values of indicator fluid within the ROI of a human individual.

According to this system 601, changes in standardized SUs over time refer to a graphic curve illustrating clearance of indicator fluid within a selectable ROI. Clearance curves of selectable ROI are compared with clearance curves of comparable ROI from a cohort of humans, by means of said anatomical coordinate system 614. The dedicated material may be a dummy material having liquid properties, e.g. viscosity or molecular property, resembling standard cranio-spinal cavity liquid, or having semi-solid material properties, e.g. density or molecular property, resembling standard properties of standard brain tissue.

A third feature of Aspect 4 describes a computer aided method to assess movement of molecular substances from a cerebrospinal fluid, brain or spinal cord compartment of a cranio-spinal cavity to kidneys or lymphatic pathway regions, e.g. cervical lymph nodes, of a human, when an indicator fluid is movable from a cerebrospinal fluid compartment of the cranio-spinal cavity along a movement path of said molecular substances, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties. FIG. 8 provides an illustration of some main elements. The computer aided method 801 comprises:

a) measuring at least once indicator fluid indication signals 802 provided through use of a detector device 803 and a sampling device 804 linked to the computer 801 and used with an indicator fluid 806 imaging apparatus 805 within regions of interest of the kidneys or one or more lymphatic pathway regions 807, b) determining, using a determining section 808 in the computer 801, change in indication signals 809 over time within the kidneys or said one or more lymphatic pathway regions, said change in indication signals 809 being indicative of ability of the cranio-spinal cavity to move indicator fluid to kidneys or cervical lymph nodes, and c) providing, using an output from an analyzer section 810 in the computer 801, a presentation 811 of said determination of said changes in indication signals 809 as a function of ability of removal of molecular substances from said cranio-spinal cavity to kidneys or lymphatic pathway regions 812, said function being indicative of the ability of removal of molecular substances 812 referring to removal of waste solutes.

According to this computer aided method 801, one or more LNs in said lymphatic pathways are to be identified through use of high-sensitive imaging sequences, and wherein LNs are incorporated for determination of indication signals 802, 807, 809.

The ROIs 807 may refer to a selectable number of ROIs containing image voxels of which the MRI indication signals or radioactive radiation imaging indication signals can be measured. MRI acquisition incorporates T1 weighted sequences with standardized imaging parameters being at least echo and repetition time, flip angle, matrix, and field of view. Other MRI sequences responsive to MRI contrast agents may also be applied, e.g. SWI, FLAIR and T2*, although these represent no limitation.

For this method, the change in indication signals 809 may be illustrated by a graphically drawn curve illustrating clearance of indicator fluid from the cranio-spinal cavity to said kidneys or said one or more lymphatic pathway regions. A schematic illustration of such a clearance illustrating curve is provided in FIG. 7. The clearance illustrating curve 703 provides for parameters of clearance, which may be selectable from such as:

a) enhancement phase 708 with attributes selectable from one or more of: TTP 709, maximum increase of indication signals 710, and enhancement coefficient 711, and b) clearance phase 712 with attributes selectable from one or more of: decline time 713, maximum decrease of indication signals 714, clearance coefficient 715, and parameter area being present under said curve.

There are, however, no limitations to which parameters that could be extracted from the clearance curve (FIG. 7), or to other methods for post-processing of information derived from levels, or change of levels, in indication signals.

The notation indication signal 802, 807, and 809 has a broad meaning, and depends on imaging modality. CT refers to Hounsfield Units (HU), MRI refers to SU and PET, SPECT and scintigraphy refer to Standard Uptake Value (SUV). An indication signal 802, 807, and 809 is thus a measurable feature derived from an imaging modality, where the indication signal level may be influenced by presence of indicator fluid 806. Indication signals 802, 807, and 809 may be measured both in the presence and absence of indicator fluid.

The indicator fluid 806 may contain a CT contrast agent, or a MRI contrast agent, or a substance exhibiting recognized pharmacokinetic properties. The CT contrast agent may be a selected one of: iohexol, iodixanol, iomeprol, ioversol, and iobitridol, and the MRI contrast agent may be either gadobutrol or gadoteric acid. Moreover, the indicator fluid 806 can be a dendrimer based macromolecular MRI contrast agent of size sufficiently high to be retained outside the BBB, or a substance exhibiting resembling pharmacokinetic properties.

The indicator fluid 806 may as well be a radioactive ligand suitable for PET, SPECT or scintigraphy imaging tied to or chelated with being a contrast agent substance or a substance exhibiting recognized pharmacokinetic properties. In this regard, the radioactive ligand may be selectable tracer material from at least one of: $^{89}$Zirconium, $^{99m}$Tc-DTPA, and $^{111}$In-DTPA. Further, the indicator fluid 806 may contain a radioactive ligand, which is chelated with material selected from one or more of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques.

The indicator fluid 806 may also be a CT or an MRI contrast agent coupled with one or more of: large-molecule biotechnology based products, antibodies, monoclonal antibodies, recombinant proteins, and antisense or gene therapeutics means.

The indicator fluid 806 may be configured to be delivered to said cranio-spinal cavity by spinal puncture and intrathecal injection, though the injection part itself is not part of the invention.

The method may be used for comparisons between individuals against a cohort. In this context, the method 801 is applied onto multiple ones of human individuals to determine indication signals 802, 807, 809 through use of said imaging within ROIs in the presence of indicator fluid 806 to determine changes in indication signals over time within said ROI. The ROIs of said imaging acquisition are transferred by transfer means 813 to an anatomical coordinate system 814, which is configured to enable segmentation of selectable anatomic regions, wherein comparator means 815 enables comparison of said change in indication signals over time between indication signal changes in a single human individual and changes in said multiple ones of human individuals, using database 816 information. A comparator output 817 section may provide for a presentation of any deviation in movement of substances as measured and imaged from a single human individual compared to average movement of substances in said multiple ones of human individuals 816.

When the computer aided method 801 is applied in conjunction with MRI, the indication signals 802, 807, 809 are MRI SUs, which are made into standardized SUs through use of a standardization device comprising an extra-body device containing at least one reference indicator fluid of specific concentrations 818. Said at least one reference indicator fluid 818 is located within one or more containers to be located externally of the body of the human, and may also be filled with dedicated material. Standardized SUs allow for measurement of absolute values of indicator fluid within the ROI of a human individual.

Changes in standardized SUs over time may refer to a graphically drawn curve illustrating clearance of indicator fluid within a selectable ROI, see FIG. 7. Clearance curves of selectable ROI are compared with clearance curves of comparable ROI from a cohort of humans, by means of said anatomical coordinate system. The dedicated material may be a dummy material having liquid properties, e.g. viscosity or molecular property, resembling standard cranio-spinal cavity liquid, or having semi-solid material properties, e.g. density or molecular property, resembling standard properties of standard brain tissue.

We derived the various features of Aspect 4 from in-vivo studies in humans. The following paragraphs provide information about observations in these studies; the imaging modality used was MRI. However, in this context, other image modalities such as PET, SPECT and scintigraphy may as well be used with several advantages. The observations presented here illustrate that implementation of the features of Aspect 4 is feasible, and provides solutions to problems previously not solved.

FIG. 22 demonstrates that in the presence of gadobutrol (i.e. one example of an indicator fluid) within a cranio-spinal cavity, changes in MRI SUs (i.e. one example of an indication signal) appear within ROIs of brain tissue compartment and lymphatic pathways (i.e. cervical LNs) at the same time. In addition, the use of a reference indicator fluid is illustrated. In this study, T1-weighted MRI sequences were done with gadobutrol present within the CSF compartment. FIG. 22*a* shows an axial T1-weighted MRI; the average of indication signals within the selected ROI 2201 was 80 SU, while imaging of reference indicator fluid 2202 showed 699 SU. When gadobutrol gad been present for four hours intrathecal, the axial MRI (FIG. 22*b*) showed an increased to 83 SU within the selected ROI 2203 of brain tissue, and 700 SU within reference indicator fluid 2204. MRI of the neck region (FIG. 22*c*) at that time revealed the following indication signal levels: ROI within the cervical LN 2205 100 SU, reference muscle 2206 94 SU, and within reference indicator fluid 2207 700 SU. After gadobutrol had been present for 24 hours (FIG. 22*d*), the indication signal had increased to 103 SU (i.e. 29% increase as compared without contrast) within the selected brain tissue ROI 2208, while being roughly unchanged of 701 SU within reference indicator fluid 2209. As illustrated in FIG. 22*e*, within the cervical lymph node 2210, indication signal had increased to 141 SU (i.e. 41% increase from foregoing MRI) while the increase was minor within the reference muscle 2211 (98 SU; i.e. 4% increase from foregoing MRI) and the reference indicator fluid 2212 (701 SU, i.e. <1% change). After gadobutrol had been present for 48 hours (FIG. 22*f*), the ROI within the brain tissue 2213 showed still high indication signal with 107 SU, while unaltered indication signals of 702 SU within the reference indicator fluid 2214. Taken together, the in-vivo measurements revealed that change in SUs within brain tissue ROIs occurred within the same time frame as the change in SUs within the cervical lymph nodes. This observation further suggests that indicator fluid within the CSF compartment passes through the paravascular pathways (causing contrast enhancement within brain tissue ROIs), lymphatic vessels of cranio-spinal cavity before entering the extra-cranial lymphatic pathways, including cervical lymph nodes. From there, indicator fluid is transported to blood circulation and kidneys.

FIG. 23 also illustrates some elements of Aspect 4 of the present invention. FIG. 23a-b shows a T2-weighted MRI sequence. Using this sequence, the CSF compartment 2301 is shown with high image signal intensity (bright) while the brain tissue compartment 2302 has low intensity (dark). FIG. 23a shows the part of the brain that is revealed in FIG. 23c and FIG. 23e as T1-weighted MRI sequences. FIG. 23b shows the part of the neck region wherein a cervical lymph node 2303 is identified, and further shown in more detail in FIG. 23d and FIG. 23f. It should be noted that the T2 sequences (FIG. 23b) causes the lymph node to be highlighted, while they have low intensity on T1 sequences (FIG. 23d, 23f). The cranio-caudal diameter of this lymph node is about 2.3 cm. Hence, in this example, a T2-weighted sequence was used to aid in identifying the cervical lymph nodes (FIG. 23b), other MRI sequences may be used as well to identify LNs and other lymphatic pathways. In the absence of gadobutrol, T1 MRI sequences of the brain (FIG. 23c) showed indication signals of 7 SU within the CSF compartment 2304 (CSF of Sylvian fissure) and 77 SU within the brain tissue compartment 2305 (brain tissue of FGI), while neck MRI (FIG. 23d) revealed 106 SU within ROI of cervical LN 2306. When gadobutrol had been present within the cranio-spinal compartment for 24 hours, the brain MRI (FIG. 23e) revealed indication signals of 163 SU within CSF compartment 2307 and 136 SU (i.e. increase of 77%) within brain tissue compartment 2308. Neck MRI (FIG. 23f) showed an increase in indication signal within ROI of LN 2309 to 138 SU (i.e. increase of 30%). This case illustrates that for MRI other sequences may be added to identify LNs and other lymphatic pathways. It also illustrates that the increase in indication signal within brain tissue is accompanied with increase in indication signal within the nearby CSF compartment. Finally, the increase in indication signals (SUs) within brain tissue and extra-cranial LN parallel in time.

Table 6 shows the change in SUs after 24 hours within different compartments (CSF of Sylvian fissure nearby IFG, brain tissue of IFG, tissue of cervical LN, neck muscle reference tissue and change in SU of LN relative to brain tissue or CSF). Comparing the changes in SUs within brain tissue and LN tissue showed that after 24 hours the SU enhancement within cervical LNs was about 40% of that in the brain. These observations demonstrate that removal of the contrast agent gadobutrol with MW 605 Da occurred slowly in the human brain. Our observations support the present inventive steps, namely that most of the contrast agent passes through the brain and entering the LNs. These observations were part of the basis for the inventions of Aspects 1 and 4. Hence, the time points for blood and/or urine samples of the features of Aspect 1 should preferably be after several hours, though the present invention does not put a restriction as to the frequency or timing for retrieving samples.

It has for long been an unanswered question how a molecular substance escapes from the CSF of the craniospinal compartment to the dural lymphatics and further to extracranial lymph nodes in humans. Experimental studies in animals have indicated a role of lymphatic vessels in dura mater, but this has yet to be shown in human subjects. The present invention addresses removal of molecular substances from the craniospinal compartment in humans. Basis for the various aspects of the invention are novel observations made by the inventors regarding transport of indicator fluids from CSF to lymphatic structures in dura. The inventors have provided novel observations using time series of MRI T1 black-blood sequences after intrathecal administration of the MRI contrast agent gadobutrol. These observations are commented on as they shed light on how molecular substances move from the CSF to the extra-cranial lymphatic structures.

Figure 23A:
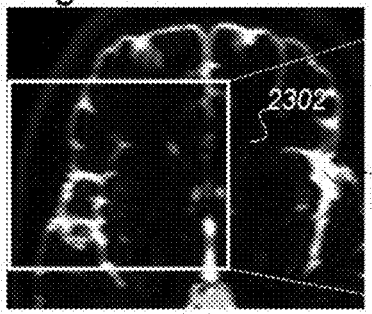
FIG. 23a-w illustrates MRI demonstrating synchronous contrast agent enhancement in brain tissue (c and e) and extra-cranial neck LN (d and f), where larger overviews of the current regions are given in FIG. 23a and FIG. 23b, respectively. In addition, contrast enhancement within parasagittal dura at different time points is presented (g-w)
Figure 23C:
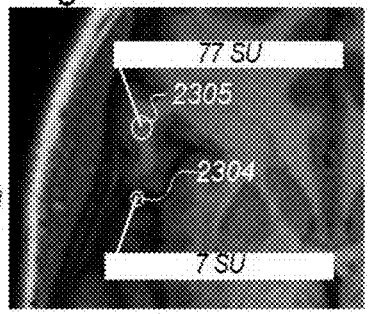
Figure 23E:
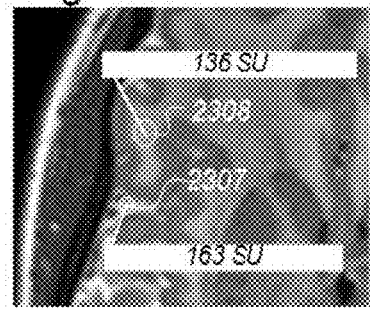
Figure 23B:
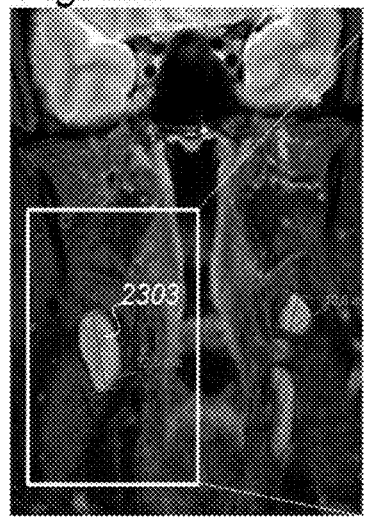
Figure 23D:
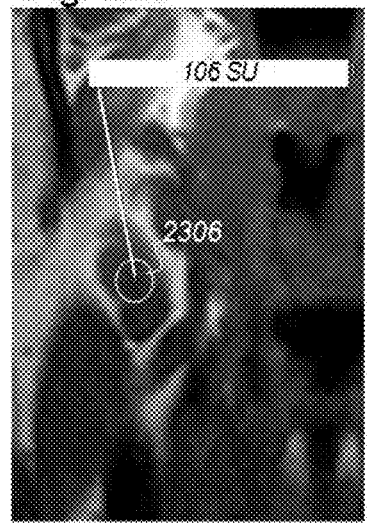
Figure 23F:
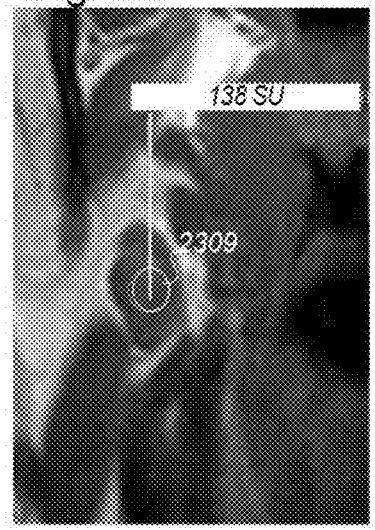
Figure 23G:
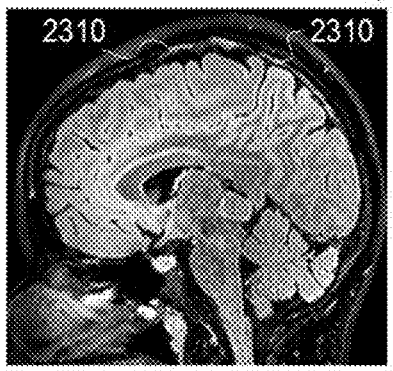
Figure 23H:
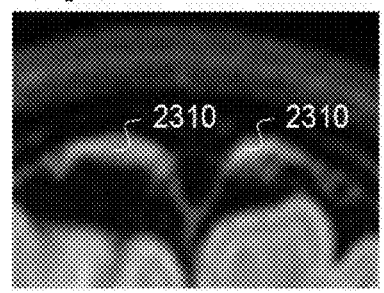
Figure 23I:
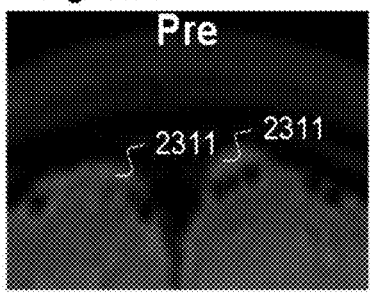
Figure 23J:
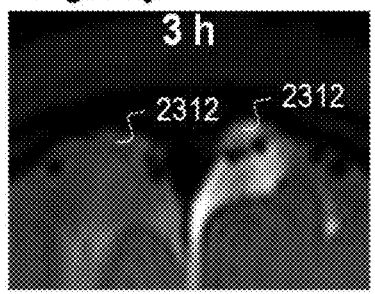
Figure 23K:
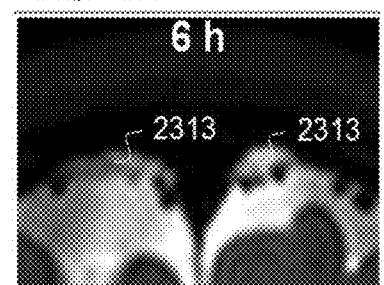
Figure 23L:
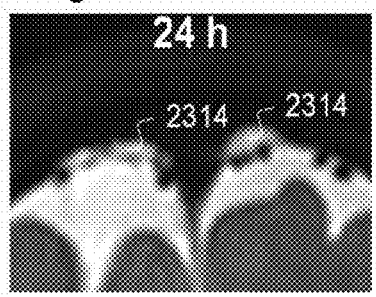
Figure 23M:
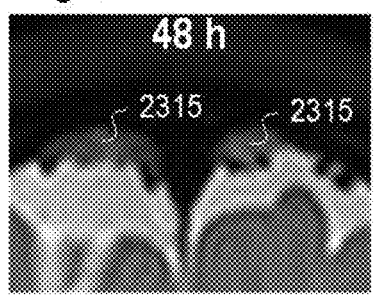
Figure 23N:
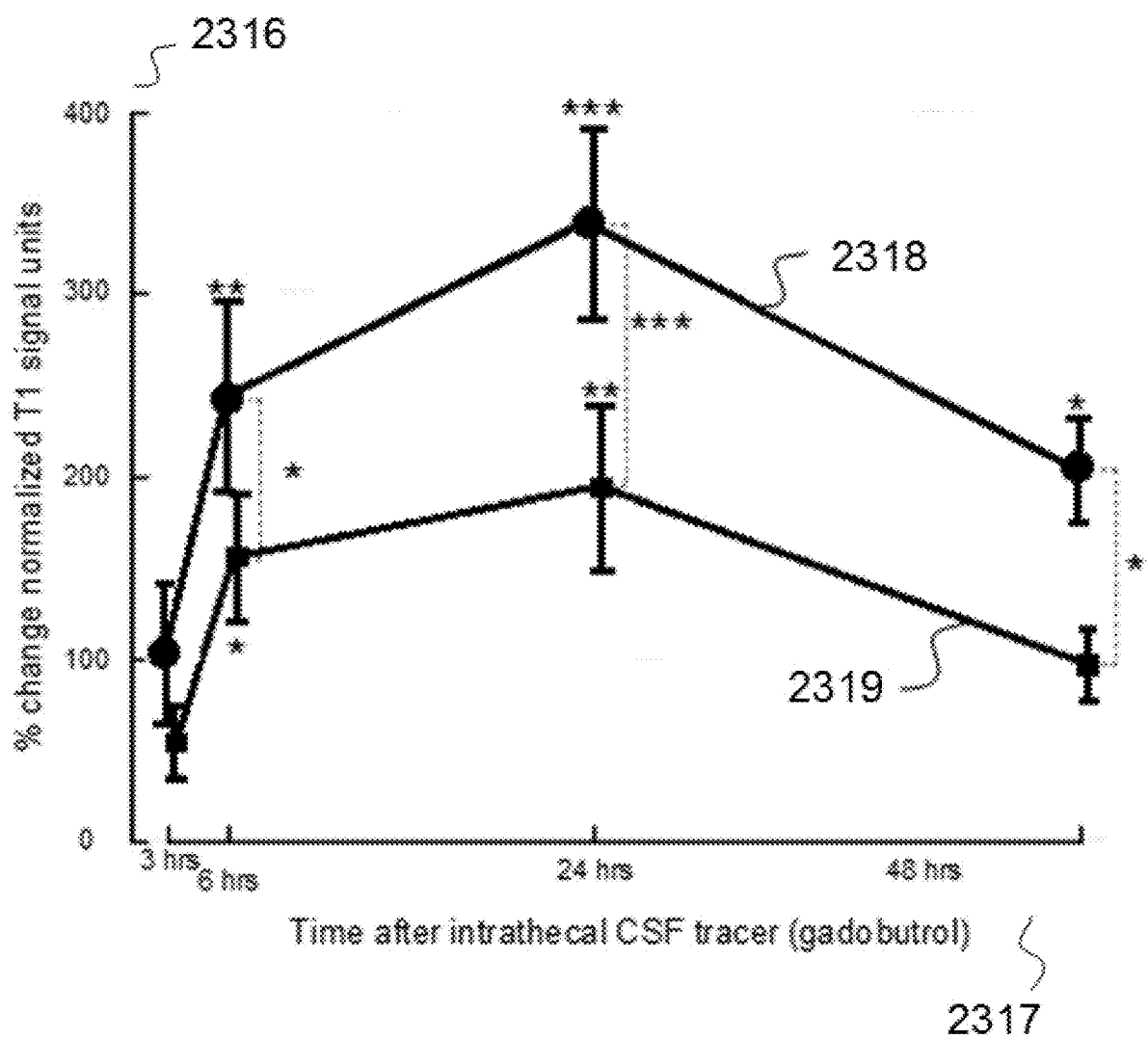

With reference FIG. 23g-w, novel information about indicator fluid movement from CSF to parasagittal dura in humans is provided. FIG. 23g presents sagittal (left) and coronal (right) T2-FLAIR MR images, respectively, demonstrating the typical longitudinal extension of parasagittal dura (PSD) with high signal 2310. In FIG. 23h, section of coronal T2-FLAIR demonstrates the lateral extension of the parasagittal dura 2310. FIG. 23i shows similar sections from T1-BB with change in signal intensity of parasagittal dura 2311 from before (Pre) indicator fluid being present in CSF, including change in intensity of parasagittal dura after 3 h 2312 (FIG. 23j), 6 h 2313 (FIG. 23k), 24 h 2314 (FIG. 23l) and 48 h 2315 (FIG. 23m). Moreover, in FIG. 23n is shown on the y axis the percentage change in normalized T1-BB signal units 2316, and on the x axis the time 2317 after indicator fluid or CSF tracer, i.e. the MRI contrast agent gadobutrol, was administered intrathecal. For a cohort of 18 individuals examined by the inventors, the trend plots of percentage change in signal unit ratio in CSF 2318 and parasagittal dura 2319 are shown. The cohort of 18 individuals consisted of 13 females and 5 males who together had a mean age of 39±16 years. In other words, there was a more marked enrichment of indicator fluid in CSF nearby dura than in the parasagittal dura itself. Notably, signal change peaked at 24 h in both CSF and parasagittal dura. The percentage change of signal unit ratio was highly significant in both locations (linear mixed model analysis; *$P<0.05$, $P<0.01$, *$P<0.001$) and was largest within the CSF. Taken together, these observations provide evidence that molecular substances within the CSF of the craniospinal compartment may move directly from the CSF space to the parasagittal dura, which is an integral part of dura. The parasagittal dura is suggested to pass to the lymphatic vessels of the dura.

Figure 23O:
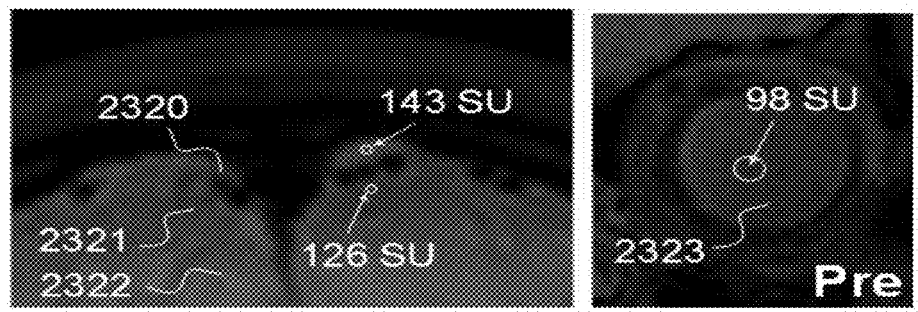
Figure 23P:
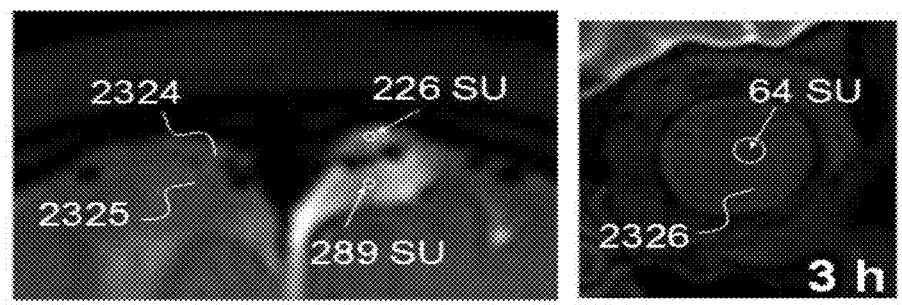
Figure 23Q:
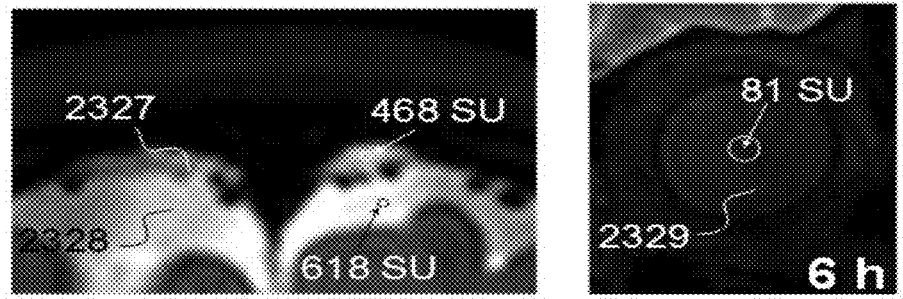
Figure 23R:
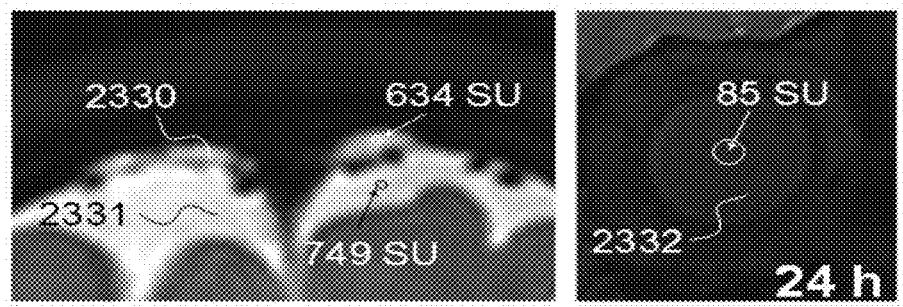
Figure 23S:
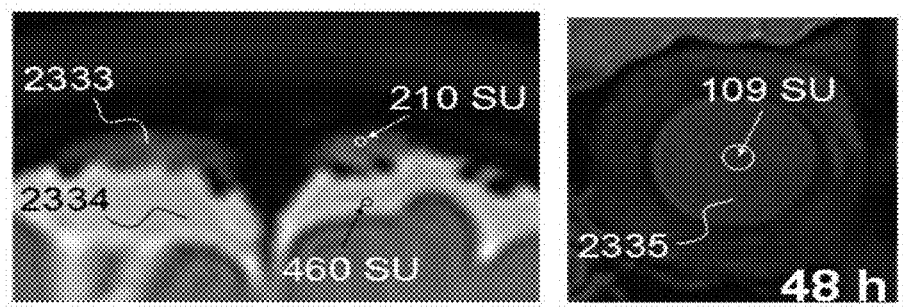

FIG. 23o-s illustrate the determination of signal unit ratios, which is particularly useful when measuring indication signals from MRI. Enrichment of indicator fluid is measured as change in T1-BB signal units. The images represent coronal sections from one individual obtained before intrathecal injection of the indicator fluid gadobutrol (FIG. 23o), and after 3 h (FIG. 23p), 6 h (FIG. 23q) 24 h (FIG. 23r) and 48 h (FIG. 23s). FIG. 23o presents information before CSF tracer is present in the CSF space. The left image presents the parasagittal dura 2320 and nearby CSF space 2321, brain compartment 2322. The reference location, i.e. the vitreous body of the ocular bulb 2323, is shown to the right. The enrichment of CSF tracer is quantified as change in signal units (SU) within the regions of interest that are marked by an open circle. The measured signal units were normalized against the reference to correct for any baseline shift of image greyscale between time points. FIG. 23p shows change in signal units after 3 hours in parasagittal dura 2324, nearby CSF space 2325 and vitreous body of the ocular bulb 2326. FIG. 23q shows change in signal units after 6 hours in parasagittal dura 2327, nearby CSF space 2328 and vitreous body of the ocular bulb 2329. FIG. 23r shows change in signal units after 24 hours in parasagittal dura 2330, nearby CSF space 2331 and vitreous body of the ocular bulb 2332. FIG. 23s shows change in signal units after 48 hours in parasagittal dura 2333, nearby CSF space 2334 and vitreous body of the ocular bulb 2335. The signal unit ratio is the dividend between signal units within the region of interest and the reference location.

The enrichment of indicator fluid within the parasagittal dura is dependent on the enrichment of indicator fluid within the CSF spaces. FIG. 23*t-w* present correlation plots with percentage change in normalized T1 signal units in CSF 2336 on y axis and percentage change in normalized T1 signal units in parasagittal dura 2337 on the x axis. FIG. 23*t* presents a trend plot 2338 that reveals a highly significant positive correlation between indicator fluid availability within nearby CSF spaces and enrichment of indicator fluid within parasagittal dura 3 hours after indicator fluid was present in the CSF space. The Pearson correlation coefficient (R) is highly significant (R=0.93; P<0.001). FIG. 23*u* presents a trend plot 2339 that reveals a highly significant positive correlation between availability of indicator fluid within nearby CSF spaces and enrichment of indicator fluid within parasagittal dura 6 hours after indicator fluid was present in the CSF space. The Pearson correlation coefficient (R) is highly significant (R=0.85; P<0.001). FIG. 23*v* presents a trend plot 2340 that reveals a highly significant positive correlation between enrichment of indicator fluid within CSF spaces nearby dura and indicator fluid enrichment within parasagittal dura 24 hours after indicator fluid was present in the CSF space. The Pearson correlation coefficient (R) is highly significant (R=0.92; P<0.001). FIG. 23*w* presents a trend plot 2341 that reveals a highly significant positive correlation between indicator fluid enrichment within CSF spaces nearby dura and indicator fluid enrichment within parasagittal dura 48 hours after indicator fluid was present in the CSF space. The Pearson correlation coefficient (R) is highly significant (R=0.72; P=0.001).

Dysfunction of parasagittal dura may result in failure of transport of molecular substances from CSF spaces of craniospinal compartment to dural lymphatic vessels, which may halt clearance of molecular substances from the craniospinal compartment. Tentative causes may be inflammation of dura or mechanical obstruction from bleeds or infection.

In FIG. 7 is provided a schematic illustration of a clearance illustrating curve. The morphology of such a clearance curve depends on various factors, such as the location of the ROI (e.g. type of tissue or fluid for measurements), type of indicator fluid, time-frame of samples, as well as the image modality (MRI versus CT, PET, SPECT or scintigraphy). To further illustrate the variation regarding clearance illustrating curves, FIG. 24 presents clearance curves of 8 different individuals, which are all based on MRI and determining changes in SU as one way of assessing indication signals. While FIG. 7 provides a schematic illustration of a clearance curve; FIG. 24 provides in-vivo clearance curves from eight individuals, and three different ROIs in each. For some ROI locations, no obvious clearance curve is created, while for other curves, only the enhancement phase is visualized. Obviously, the curve shape depends on the frequency of observations and the duration of observations. Since a clearance curve is ended when indication signals have returned to the curve baseline, measurements over a required time frame is needed for establishing a complete clearance illustrating curve. It should be noted, however, that instead of establishing a complete clearance curve, measurement of indication signal level at one single time may as well be optional. A point measurement may be preferable in some situations. Even though a complete clearance curve is not created, point measurements may as well provide information about the removal ability of a cranio-spinal cavity, and be useful for comparison between individuals. Hence, point measurements represent one embodiment of this invention.

The variability of clearance curves is illustrated for 8 individual patients, which is commented on in consecutive order:

In FIG. 24*a* the SUs 2401 are plotted against time 2402 for Patient 1, demonstrating changes of SUs over time for ROI within CSF nearby IFG 2403, brain tissue of IFG 2404 and tissue of cervical LN 2405. The time to first enhancement 2406 is indicated and is denoted the spinal transit time. For the clearance curve of CSF nearby IFG 2403, a maximum level of SU 2407 is indicated. Further documentation of the clearance phase would require more observations at later time points. For the brain tissue IFG curve 2404, only the start of enhancement phase is shown: more observations would be required to visualize maximum SU value and the clearance phase. Obviously, the exact shape of the clearance curve depends on the frequency and the time-span of observations.

In FIG. 24*b* the SUs 2408 are plotted against time 2409 for Patient 2, demonstrating changes of SUs over time for ROI within CSF nearby IFG 2410, brain tissue of IFG 2411 and tissue of cervical LN 2412. In Patient 2, the time to first enhancement 2413 within CSF was markedly shorter than time to first enhancement 2406 for Patient 1. For the clearance curve of CSF nearby IFG 2410, a maximum 2414 is indicated, while further documentation of the clearance phase would require more observations at a later stage. The profile of change in SU within brain tissue IFG 2411 and cervical LN 2412 is comparable. However, for both curves 2411 and 2412 only the start of enhancement phase is shown. More observations would be required to get maximum value and the clearance phase. The clearance curves 2410, 2411 and 2412 for the various ROIs illustrate the time aspect of clearance, i.e. the human brain's ability to remove substances from the cranio-spinal cavity.

In FIG. 24*c* the SUs 2415 are plotted against time 2416 for Patient 3, demonstrating changes of SUs over time for ROI within CSF nearby IFG 2417, brain tissue of IFG 2418 and tissue of cervical LN 2419. In Patient 2, a complete clearance curve 2417 for CSF nearby IFG was created, including start 2420, maximum 2421, and minimum 2422 of the curve. Maximum 2423 for brain tissue IFG clearance curve 2418 and maximum 2424 for LN curve 2419 was shown. Again, the profile of change in SU within brain tissue IFG 2418 and cervical LN 2419 is comparable, and highly different from the CSF clearance curve 2417. Comparing the three clearance curves 2417, 2418 and 2419 is consistent with the view that substances move from CSF compartment, via brain tissue paravascular pathways to lymphatic pathways. Moreover, comparing clearance curves of different individuals show a great variability, which may suggest variability concerning the ability of the craniospinal cavity to remove substances.

In FIG. 24*d* the SUs 2425 are plotted against time 2426 for Patient 4, demonstrating changes of SUs over time for ROI within CSF nearby IFG 2427, brain tissue of IFG 2428 and tissue of cervical LN 2429. It should be noted that maximum 2430 for brain tissue IFG clearance curve 2428 and maximum 2431 for LN curve 2429 occurred at the same time. Again, the profile of change in SU within brain tissue IFG 2428 and cervical LN 2429 are comparable, and highly different from the CSF clearance curve 2427.

Figure 24E:
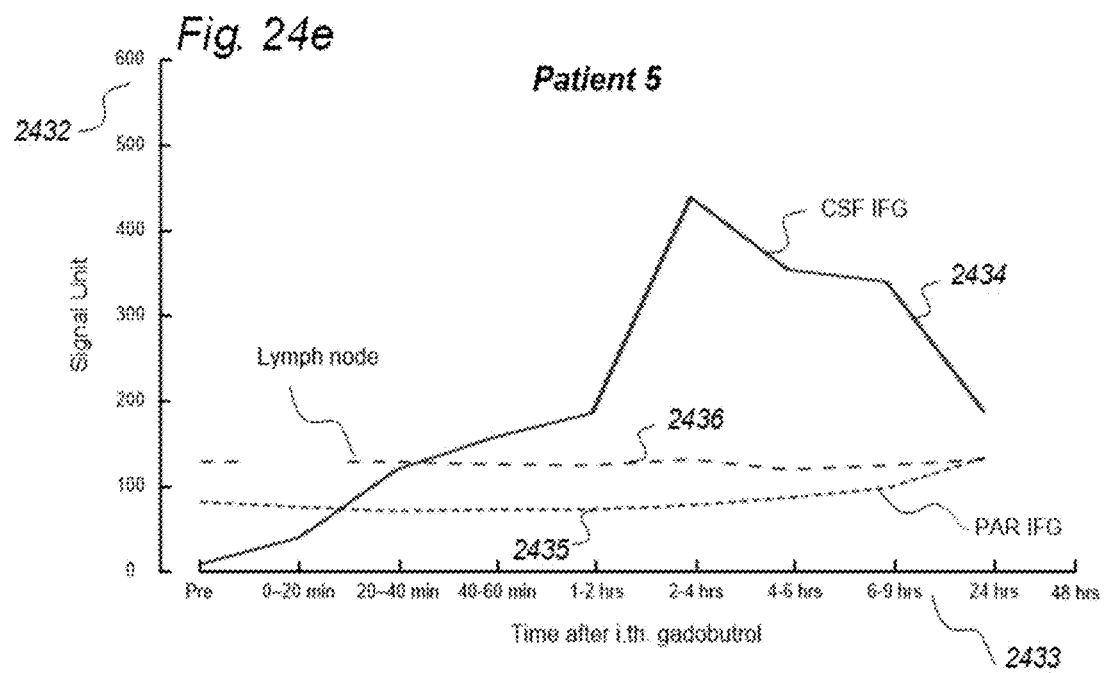
FIG. 24a-n illustrate time series of change in SUs within CSF nearby IFG (CSF IFG), brain tissue of IFG (PAR IFG) and tissue of LN (Lymph node) when there was no contrast agent within CSF (Pre) and after when gadobutrol was present within CSF in individuals named Patients 1, 2, 3, 4, 5, 6, 7 and 8, respectively. In addition, trend plots of percentage change in signal unit ratios (presentations of mean and standard deviation) for a cohort of 19 individuals are presented for three regions, namely CSF nearby IFG (CSF IFG), brain tissue of IFG (PAR IFG) and tissue of LN (Lymph node). Further, different relationships between concentrations of indicator fluid in blood versus CT indication signals are given (l-n).

In FIG. 24e the SUs 2432 are plotted against time 2433 for Patient 5, demonstrating changes of SUs over time for ROI within CSF nearby IFG 2434, brain tissue of IFG 2435 and tissue of cervical LN 2436. For the brain tissue IFG clearance curve 2435 only the start of enhancement phase is indicated, while no obvious clearance curve for cervical lymph node 2436 is present. The reason may be that regional differences may be present regarding which LNs that drain the specific structures of the cranio-spinal cavity. In this regard, other imaging modalities, such as PET, SPECT and scintigraphy, may be even more useful than MRI as they may be more sensitive to detect change in indication signals, and thus presence of indicator fluid, in cervical lymph nodes.

Figure 24F:
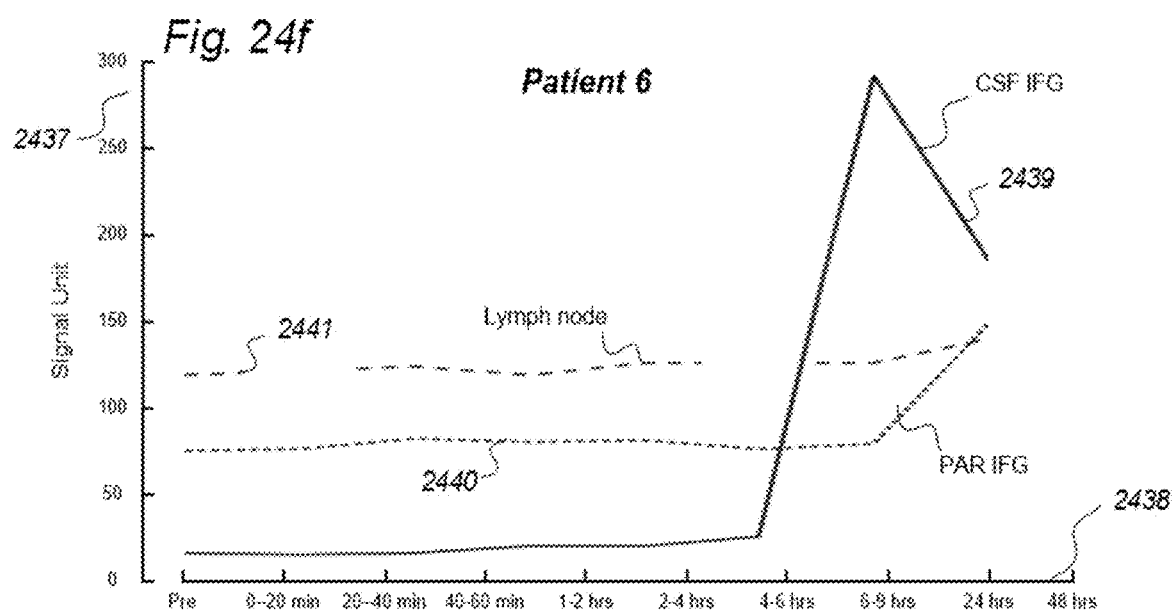

In FIG. 24f the SUs 2437 are plotted against time 2438 for Patient 6, demonstrating changes of SUs over time for ROI within CSF nearby IFG 2439, brain tissue of IFG 2440 and tissue of cervical LN 2441. For the brain tissue IFG clearance curve 2440 only the start of enhancement phase is indicated; a better characterization of the clearance curve would require more observations over a longer time span.

In FIG. 24g the SUs 2442 are plotted against time 2443 for Patient 7, demonstrating changes of SUs over time for ROI within CSF nearby IFG 2444, brain tissue of IFG 2445 and tissue of cervical LN 2446.

In FIG. 24h the SUs 2447 are plotted against time 2448 for Patient 8, demonstrating changes of SUs over time for ROI within CSF nearby IFG 2449, brain tissue of IFG 2450 and tissue of cervical LN 2451. While the clearance illustrating curve 2449 for CSF nearby IFG shows a clear profile, this is less evident for clearance curves of brain tissue of IFG 2450 and cervical LN 2451. Both the curves 2450 and 2451 had similar maximum at the same time 2452.

Taken together, FIG. 24a-h illustrates that clearance illustrating curves (see FIG. 7) may be created for ROIs in different locations using MRI. The clearance curves show a great degree of inter-individual variation. Further, the time profile varies.

The clearance curves of FIG. 24a-h highlights as well why the establishment of clearance curves may not be a requirement. Instead, single measurements of indication signals may be done once with indicator fluid present. For example, with reference to the clearance curves shown in FIG. 24a-h, single measurements after 24 hours and/or 48 hours might be done instead of repeated measurements that are required for establishing clearance curves.

TABLE 6

Signal units of T1 image without gadobutrol (Pre), and change after gadubutrol had been present for 24 hours.

| Pat | Per | CSF inferior frontal gyrus (IFG) Change after 24 hours | Per | Brain tissue of inferior frontal gyrus (IFG) Change after 24 hours | Per | Tissue of cervical lymph node (LN) Change after 24 hours | Per | Muscels reference tissue Change after 24 hours | Index of enhancement in lymph node (LN) relative to: Parenchyma IFG | CSF IFG |
|---|---|---|---|---|---|---|---|---|---|---|
| 1 | 14 | 237 (1693%) | 81 | 63 (%) | 113 | 12 (%) | 105 | 6 (%) | 0.19 | 0.05 |
| 2 | 6 | 122 (2025%) | 80 | 57 (%) | 112 | 23 (%) | 125 | −5 (%) | 0.40 | 0.19 |
| 3 | 6 | 100 (1667%) | 79 | 26 (%) | 110 | 15 (%) | 13 | −1 (%) | 0.58 | 0.15 |
| 4 | 6 | 271 (4517%) | 65 | 79 (%) | 107 | −1 (%) | 93 | 8 (%) | −0.01 | 0.00 |
| 5 | 8 | 179 (2238%) | 82 | 52 (%) | 129 | 3 (%) | 121 | 1 (1%) | 0.06 | 0.02 |
| 6 | 17 | 169 (994%) | 76 | 4 (%) | 120 | 21 (%) | 119 | 2 (2%) | 0.28 | 0.12 |
| 7 | 7 | 33 (471%) | 87 | 16 (18%) | 136 | 6 (%) | 122 | 8 (7%) | 0.38 | 0.18 |
| 8 | 8 | 138 (1725%) | 82 | 53 (65%) | 106 | 32 (%) | 111 | 5 (5%) | 0.60 | 0.23 |

IFG: Inferior frontal gyrus. Change in SU at 24 hours relative to re is given as numberical change (percentage change in parenthesis). Bold font for individuals with ≥10% increase of SU within cervical LNs 24 hours after gadobutrol. *Index of parenchymal change CLN/InFG indicated by proportion of change in absolute numbers (and percentage change).

Figure 24I:
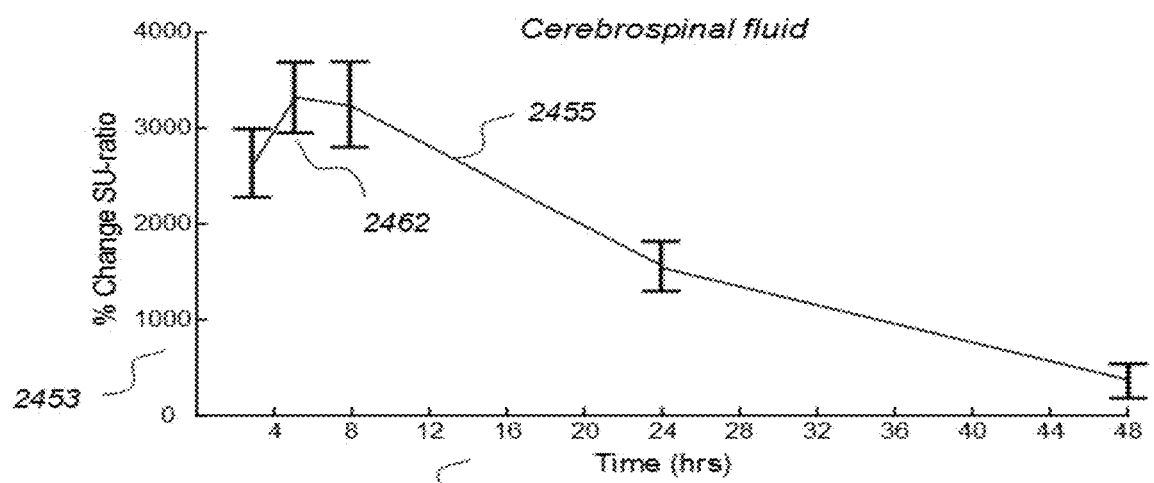
Figure 24J:
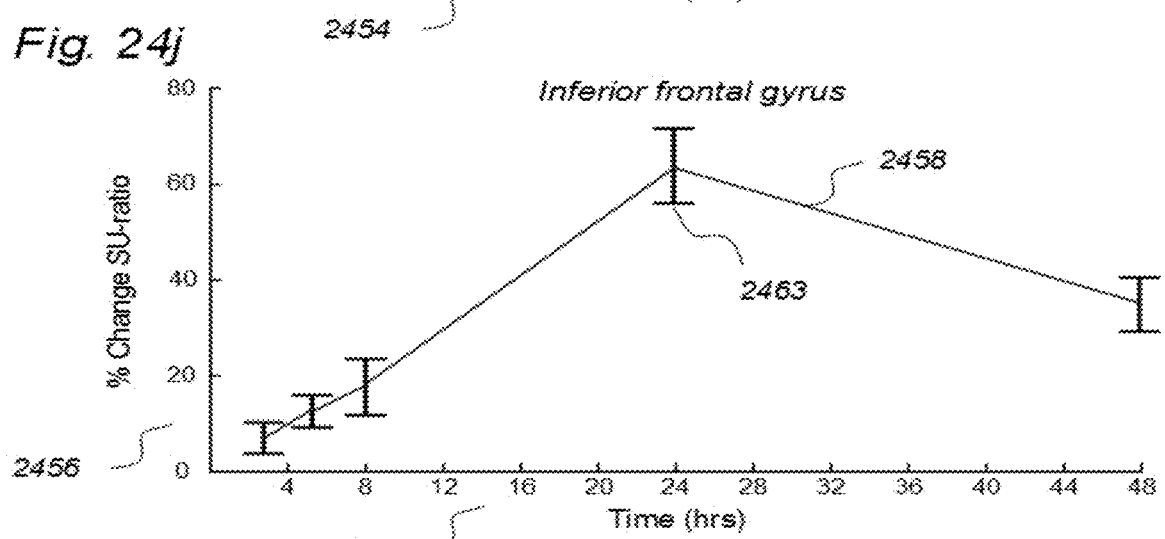
Figure 24K:
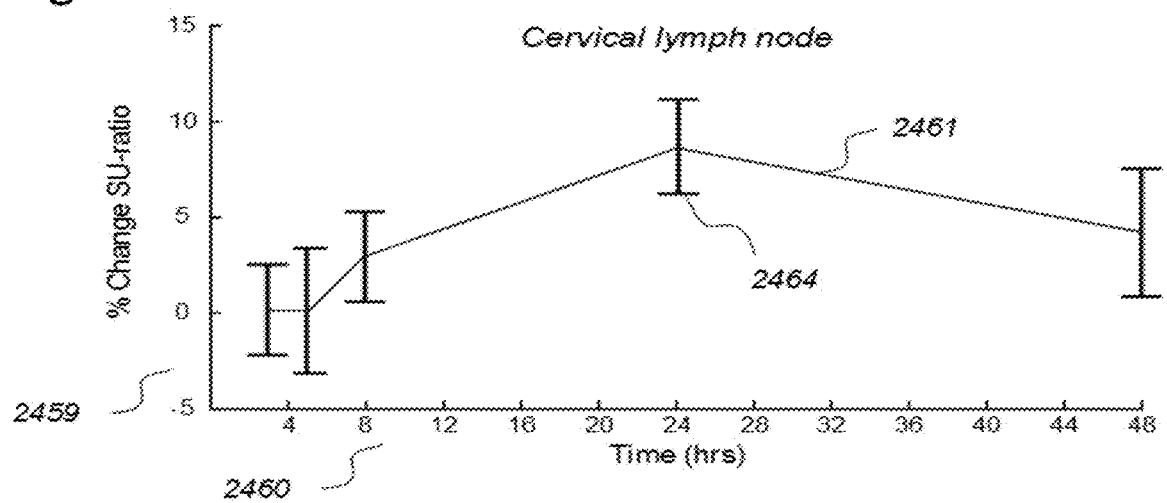

While FIG. 24a-h present data from individual patients, FIG. 24i-k show trend plots of percentage change in signal unit ratios at different time points after intrathecal CSF tracer (gadobutrol) in a cohort of 19 individuals. Each bar shows the mean±standard error. The following paragraphs describe the cohort including 19 individuals who underwent MRI of the head (intracranial) and neck regions, where we utilized the contrast agent gadobutrol as CSF tracer, and in whom a cervical lymph node with largest diameter >1.5 cm was identified. For CSF tracer enrichment within the CSF compartment (FIG. 24i), percentage change in signal unit ratio is shown along y-axis 2453, and time at x-axis, 2454 with the trend plot 2455 showing change in signal unit ratio over time. The CSF tracer enrichment within the brain parenchyma (inferior frontal gyrus; FIG. 24j) was shown as percentage change in signal unit ratio is shown along y-axis 2456, and time at x-axis, 2457 with the trend plot 2458 showing change in signal unit ratio over time. Moreover, the CSF tracer enrichment within cervical lymph nodes (FIG. 24k) was shown as percentage change in signal unit ratio is shown along y-axis 2459, and time at x-axis, 2460 with the trend plot 2461 showing change in signal unit ratio over time. As can be seen in FIG. 24i, tracer in CSF peaked after 4-6 hours 2462 and had declined at 24 hours. Moreover, the results of these 19 individuals show that peak enhancement of the tracer within brain parenchyma (inferior frontal gyrus; FIG. 24j) 2463 coincides in time with peak tracer enhancement within cervical lymph nodes (FIG. 24k) 2464. As can be see, both peaked at 24 hours 2463, 2464. At the individual level in this cohort, peak tracer enhancement occurred in CSF after 4-6 hours in 8/19 individuals (42%) and after 6-9 hours in 7/19 individuals (37%), while after 24-48 hours in only 1/19 individuals (5%). In comparison, after 24-48 hours peak enhancement occurred in 18/18 (100%) in parenchyma of inferior frontal gyms, and within the cervical lymph node, enhancement peaked after 24-48 hours in 11/17 individuals (65%) with a positive change in signal unit ratio after intrathecal gadobutrol. While the timing of peak enhancement within CSF and cervical lymph node differed significantly, the time point of peak enhancement within brain parenchymal regions and cervical lymph node did not differ significantly.

Referring to FIG. 7b-e, each region of interest provides the mean signal intensity from the image greyscale, and was normalized to reference tissue to compare values between time points. All regions of interest were fitted to local anatomical landmarks to avoid partial volume effects from neighboring tissue or CSF. For each exam, the following four regions of interest were used: 1) CSF nearby inferior frontal gyrus (average of left and right sides). 2) Parenchyma of inferior frontal gyrus (average of left and right sides). 4) Blood of sagittal sinus within a predefined region above the venous confluence served as reference for measurements in brain parenchyma. 5) Parenchyma of deep cervical lymph node. If a lymph node was identified on the left and right side, we selected the one with largest enhancement following contrast agent, and examined the same lymph node over time. 6) Medial pterygoid muscle as reference tissue for lymph node measurements to correct for any baseline variations in displayed signal intensity values between scans. To limit possible partial volume averaging effects, all ROIs were placed well within the borders of the defined tissue or fluid compartment.

Tables 7-9 present the signal units from the locations at study and of the reference tissues, as well as the normalized signal unit ratios for the 19 individuals at the various time points. The results demonstrate how indication signals may be presented.

TABLE 7

Overview of signal units within cerebrospinal fluid and reference tissue including normalized signal unit ratios

| | No intrathecal contrast | | | 2-4 hours | | | 4-6 hours | | | 6-9 hours | | | 24 hours | | |
|---|---|---|---|---|---|---|---|---|---|---|---|---|---|---|---|
| Patient | $SU_{CSF}$ | $SU_{REF}$ | Ratio | $SU_{CSF}$ | $SU_{REF}$ | Ratio | $SU_{CSF}$ | $SU_{REF}$ | Ratio | $SU_{CSF}$ | $SU_{REF}$ | Ratio | $SU_{CSF}$ | $SU_{REF}$ | Ratio |
| 1 | 14 | 42 | 0.3 | 308 | 37 | 8.3 | 360 | 42 | 8.6 | | | | 251 | 44 | 5.7 |
| 2 | 6 | 31 | 0.2 | 262 | 34 | 7.7 | 272 | 28 | 9.7 | 294 | 29 | 10.1 | 128 | 30 | 4.3 |
| 3 | 6 | 45 | 0.1 | 156 | 39 | 4.0 | 201 | 41 | 4.9 | | | | 106 | 42 | 2.5 |
| 4 | 17 | 27 | 0.6 | 27 | 25 | 1.1 | 293 | 27 | 10.9 | | | | 186 | 28 | 6.6 |
| 5 | 8 | 38 | 0.2 | 402 | 34 | 11.8 | 414 | 34 | 12.2 | 383 | 32 | 12.0 | 146 | 32 | 4.6 |
| 6 | 7 | 42 | 0.2 | 235 | 35 | 6.7 | 296 | 27 | 11.0 | 311 | 37 | 8.4 | 201 | 36 | 5.6 |
| 7 | 20 | 32 | 0.6 | 338 | 26 | 13.0 | 273 | 26 | 10.5 | 323 | 30 | 10.8 | 90 | 33 | 2.7 |
| 8 | 8 | 29 | 0.3 | 325 | 26 | 12.5 | 338 | 29 | 11.7 | | | | 97 | 27 | 3.6 |
| 9 | 12 | 30 | 0.4 | 310 | 26 | 11.9 | 331 | 26 | 12.7 | | | | 237 | 30 | 7.9 |
| 10 | 22 | 38 | 0.6 | 337 | 34 | 9.9 | 363 | 34 | 10.7 | 367 | 34 | 10.8 | 128 | 37 | 3.5 |
| 11 | 6 | 33 | 0.2 | 170 | 28 | 6.1 | 275 | 35 | 7.9 | | | | 277 | 33 | 8.4 |
| 12 | 8 | 35 | 0.2 | 345 | 35 | 9.9 | 355 | 33 | 10.8 | 341 | 35 | 9.7 | 187 | 35 | 5.3 |
| 13 | 7 | 38 | 0.2 | 47 | 42 | 1.1 | 98 | 41 | 2.4 | 143 | 41 | 3.5 | 40 | 46 | 0.9 |
| 14 | 7 | 43 | 0.2 | 35 | 42 | 0.8 | 128 | 44 | 2.9 | 188 | 40 | 4.7 | 29 | 44 | 0.7 |
| 15 | 8 | 28 | 0.3 | 278 | 30 | 9.3 | 326 | 30 | 10.9 | 277 | 33 | 8.4 | 250 | 30 | 8.3 |
| 16 | 22 | 86 | 0.3 | 667 | 60 | 11.1 | 856 | 77 | 11.1 | | | | 285 | 84 | 3.4 |
| 17 | 48 | 152 | 0.3 | 559 | 138 | 4.1 | 644 | 129 | 5.0 | 691 | 131 | 5.3 | 291 | 131 | 2.2 |
| 18 | 15 | 142 | 0.1 | 291 | 134 | 2.2 | 623 | 131 | 4.8 | 712 | 141 | 5.0 | 194 | 123 | 1.6 |
| 19 | 38 | 110 | 0.3 | 523 | 103 | 5.1 | 709 | 103 | 6.9 | 742 | 104 | 7.1 | 298 | 104 | 2.9 |
| Mean ± STD | 15 ± 12 | 54 ± 39 | 0.3 ± 0.2 | 296 ± 170 | 49 ± 35 | 7 ± 4 | 377 ± 197 | 49 ± 34 | 9 ± 3 | 398 ± 203 | 57 ± 42 | 8 ± 3 | 180 ± 85 | 51 ± 33 | 4 ± 2 |

SU = signal unit; CSF = CSF within Sylvian fissure close to frontal inferior gyrus; REF = blood of superior sagittal sinus; Ratio = signal units within CSF divided by signal units within REF; STD = standard deviation.

TABLE 8

Overview of signal units within parenchyma of inferior frontal gyrus and reference tissue including normalized signal unit ratios

| | No intrathecal contrast | | | 2-4 hours | | | 4-6 hours | | | 6-9 hours | | | 24 hours | | |
|---|---|---|---|---|---|---|---|---|---|---|---|---|---|---|---|
| Patient | $SU_{IFG}$ | $SU_{REF}$ | Ratio | $SU_{IFG}$ | $SU_{REF}$ | Ratio | $SU_{IFG}$ | $SU_{REF}$ | Ratio | $SU_{IFG}$ | $SU_{REF}$ | Ratio | $SU_{IFG}$ | $SU_{REF}$ | Ratio |
| 1 | 81 | 42 | 1.93 | 82 | 37 | 2.22 | 89 | 42 | 2.12 | | | | 144 | 44 | 3.27 |
| 2 | 80 | 31 | 2.58 | 79 | 34 | 2.32 | 82 | 28 | 2.93 | 95 | 29 | 3.28 | 137 | 30 | 4.57 |
| 3 | 79 | 45 | 1.76 | 73 | 39 | 1.87 | 78 | 41 | 1.90 | | | | 105 | 42 | 2.50 |
| 4 | 76 | 27 | 2.81 | 77 | 25 | 3.08 | 80 | 27 | 2.96 | | | | 150 | 28 | 5.36 |
| 5 | 82 | 38 | 2.16 | 87 | 34 | 2.56 | 88 | 34 | 2.59 | 107 | 32 | 3.34 | 135 | 32 | 4.22 |
| 6 | 89 | 42 | 2.12 | 84 | 35 | 2.40 | 85 | 27 | 3.15 | 91 | 37 | 2.46 | 144 | 36 | 4.00 |
| 7 | 86 | 32 | 2.69 | 87 | 26 | 3.35 | 90 | 26 | 3.46 | 94 | 30 | 3.13 | 129 | 33 | 3.91 |
| 8 | 83 | 29 | 2.86 | 81 | 26 | 3.12 | 83 | 29 | 2.86 | | | | 91 | 27 | 3.37 |
| 9 | 75 | 30 | 2.50 | 79 | 26 | 3.04 | 85 | 26 | 3.27 | | | | 172 | 30 | 5.73 |
| 10 | 86 | 38 | 2.26 | 85 | 34 | 2.50 | 90 | 34 | 2.65 | 114 | 34 | 3.35 | 144 | 37 | 3.89 |
| 11 | 65 | 33 | 1.97 | 68 | 28 | 2.43 | 81 | 35 | 2.31 | | | | 144 | 33 | 4.36 |
| 12 | 82 | 35 | 2.34 | 78 | 35 | 2.23 | 87 | 33 | 2.64 | 98 | 35 | 2.8 | 134 | 35 | 3.83 |
| 13 | 87 | 38 | 2.29 | 82 | 42 | 1.95 | 82 | 41 | 2.00 | 87 | 41 | 2.12 | 103 | 46 | 2.24 |
| 14 | 83 | 43 | 1.93 | 78 | 42 | 1.86 | 84 | 44 | 1.91 | 85 | 40 | 2.13 | 96 | 44 | 2.18 |
| 15 | 85 | 28 | 3.04 | 77 | 30 | 2.57 | 83 | 30 | 2.77 | 86 | 33 | 2.61 | 162 | 30 | 5.40 |
| 16 | 221 | 86 | 2.57 | 280 | 60 | 3.47 | 254 | 77 | 3.30 | | | | 331 | 84 | 3.94 |
| 17 | 256 | 152 | 1.68 | 223 | 138 | 1.62 | 235 | 129 | 1.82 | 268 | 131 | 2.05 | 335 | 131 | 2.56 |
| 18 | 257 | 142 | 1.81 | 232 | 134 | 1.73 | 242 | 131 | 1.85 | 248 | 141 | 1.76 | 323 | 123 | 2.63 |
| 19 | 195 | 110 | 1.77 | 194 | 103 | 1.88 | 200 | 103 | 1.94 | 223 | 104 | 2.14 | 298 | 104 | 2.87 |

TABLE 8-continued

Overview of signal units within parenchyma of inferior frontal gyrus and reference tissue including normalized signal unit ratios

| | | | | Time after intrathecal gadobutrol | | | | | | | | | | | |
|---|---|---|---|---|---|---|---|---|---|---|---|---|---|---|---|
| | No intrathecal contrast | | | 2-4 hours | | | 4-6 hours | | | 6-9 hours | | | 24 hours | | |
| Patient | $SU_{IFG}$ | $SU_{REF}$ | Ratio | $SU_{IFG}$ | $SU_{REF}$ | Ratio | $SU_{IFG}$ | $SU_{REF}$ | Ratio | $SU_{IFG}$ | $SU_{REF}$ | Ratio | $SU_{IFG}$ | $SU_{REF}$ | Ratio |
| Mean ± STD | 113 ± 65 | 54 ± 39 | 2.3 ± 0.4 | 108 ± 57 | 49 ± 35 | 2.4 ± 0.6 | 116 ± 63 | 49 ± 34 | 2.5 ± 0.6 | 133 ± 70 | 57 ± 42 | 2.6 ± 0.6 | 172 ± 82 | 51 ± 33 | 3.7 ± 1.1 |

SU = signal unit; IFG = brain tissue of inferior frontal gyrus; REF = blood of superior sagittal sinus; Ratio = signal units within IFG divided by signal units within REF; STD = standard deviation.

TABLE 9

Overview of signal units within cervical lymph node and reference tissue including normalized signal unit ratios

| | | | | Time after intrathecal gadobutrol | | | | | | | | | | | |
|---|---|---|---|---|---|---|---|---|---|---|---|---|---|---|---|
| | No intrathecal contrast | | | 2-4 hours | | | 4-6 hours | | | 6-9 hours | | | 24 hours | | |
| Patient | $SU_{CLN}$ | $SU_{REF}$ | Ratio | $SU_{CLN}$ | $SU_{REF}$ | Ratio | $SU_{CLN}$ | $SU_{REF}$ | Ratio | $SU_{CLN}$ | $SU_{REF}$ | Ratio | $SU_{CLN}$ | $SU_{REF}$ | Ratio |
| 1 | 113 | 105 | 1.08 | 111 | 102 | 1.09 | 112 | 105 | 1.07 | | | | 125 | 111 | 1.13 |
| 2 | 112 | 125 | 0.90 | 102 | 112 | 0.91 | 117 | 116 | 1.01 | 111 | 118 | 0.94 | 135 | 120 | 1.13 |
| 3 | 110 | 103 | 1.07 | 98 | 113 | 0.87 | 103 | 106 | 0.97 | | | | 125 | 102 | 1.23 |
| 4 | 120 | 119 | 1.01 | | | | 127 | 121 | 1.05 | | | | 141 | 121 | 1.17 |
| 5 | 106 | 111 | 0.95 | 108 | 116 | 0.93 | 110 | 110 | 1.00 | 113 | 119 | 0.95 | 138 | 116 | 1.19 |
| 6 | 101 | 110 | 0.92 | 99 | 108 | 0.92 | 100 | 107 | 0.93 | 114 | 115 | 0.99 | 105 | 113 | 0.93 |
| 7 | 124 | 98 | 1.27 | 125 | 97 | 1.29 | 119 | 98 | 1.21 | 122 | 98 | 1.24 | 135 | 95 | 1.42 |
| 8 | 112 | 110 | 1.02 | 126 | 123 | 1.02 | 131 | 121 | 1.08 | | | | 125 | 113 | 1.11 |
| 9 | 121 | 112 | 1.08 | 119 | 116 | 1.03 | 118 | 108 | 1.09 | | | | 130 | 113 | 1.15 |
| 10 | 124 | 124 | 1.00 | 121 | 101 | 1.20 | 134 | 103 | 1.30 | 130 | 105 | 1.24 | 129 | 111 | 1.16 |
| 11 | 107 | 93 | 1.15 | 106 | 103 | 1.03 | 73 | 112 | 0.65 | | | | 106 | 101 | 1.05 |
| 12 | 129 | 121 | 1.07 | 132 | 122 | 1.08 | 120 | 116 | 1.03 | 125 | 118 | 1.06 | 132 | 122 | 1.08 |
| 13 | 136 | 122 | 1.11 | 129 | 126 | 1.02 | 128 | 123 | 1.04 | 131 | 120 | 1.09 | 142 | 130 | 1.09 |
| 14 | 117 | 117 | 1.00 | 114 | 121 | 0.94 | 118 | 117 | 1.01 | 119 | 122 | 0.98 | 122 | 127 | 0.96 |
| 15 | 142 | 106 | 1.34 | 127 | 107 | 1.19 | 142 | 105 | 1.35 | 150 | 104 | 1.44 | 143 | 108 | 1.32 |
| 16 | 228 | 223 | 1.02 | 277 | 241 | 1.15 | 233 | 233 | 1.00 | | | | 305 | 250 | 1.22 |
| 17 | 277 | 263 | 1.05 | 219 | 175 | 1.25 | 254 | 223 | 1.14 | 230 | 221 | 1.04 | 273 | 248 | 1.10 |
| 18 | 205 | 230 | 0.89 | 224 | 241 | 0.93 | | | | 232 | 245 | 0.95 | 274 | 240 | 1.14 |
| 19 | 209 | 204 | 1.02 | 234 | 221 | 1.06 | 224 | 218 | 1.03 | 223 | 236 | 0.94 | 229 | 226 | 1.01 |
| Mean ± STD | 142 ± 50 | 137 ± 51 | 1.05 ± 0.11 | 143 ± 55 | 136 ± 49 | 1.05 ± 0.12 | 137 ± 49 | 130 ± 44 | 1.05 ± 0.15 | 150 ± 48 | 143 ± 55 | 1.07 ± 0.16 | 159 ± 61 | 140 ± 54 | 1.14 ± 0.12 | signal unit; CLN = cervical lymph node; REF = medial pterygoid muscle; Ratio = signal units within CLN divided by signal units within REF; STD = standard deviation.

In the following paragraphs, the combination of features of Aspect 1 with other Aspects of the invention is described in more detail. The determination of concentrations of indicator fluid in blood or urine may be combined with measurements of indication signals within regions of interest using imaging modalities such as MRI, CT, PET, SPECT or scintigraphy imaging. Here, the combination with CT is commented on.

In one embodiment of the invention the indicator fluid 201 is a CT contrast agent that is measurable in blood or urine and that may be measured as indication signals using CT scanning. The indicator fluid has molecular properties enabling movement from a cerebrospinal fluid compartment of a cranio-spinal cavity. Parameters of removal of molecular substances 203 may be a function of at least one of: measured and analyzed level or change in level of indicator fluid concentration in urine or blood 204, and removal of indicator fluid in urine or blood versus time. The molecular properties of the indicator fluid 201 allow levels or change in level 205 of the indicator fluid in the urine or blood samples subsequently to be measured and analyzed once or at selectable time intervals 204 to determine said parameters of removal 203. The parameters of removal 203 are a function of ability of the cranio-spinal cavity to clear molecular substances from the cerebrospinal fluid compartment or the brain or spinal cord compartment to blood and urine. The ability of the cranio-spinal cavity to remove molecular substances also refers to clearance of waste solutes from the cerebrospinal fluid, brain or spinal cord compartment. The indicator fluid 201 may be a CT contrast agent, and it may be selected from one of: iohexol, iodixanol, iomeprol, ioversol, and iobitridol.

The indicator fluid 201 may be combined to both measure indicator fluid indication signals within regions of interest of a cerebrospinal fluid, brain or spinal cord compartment, and may be measured as level or change in level within blood or urine. Removal of indicator fluid in urine or blood versus time may thus be related to change in indication signals within regions of interest.

Different kinds of relationships between removal of indicator fluid to blood or urine and from regions of interest may be determined, such as concentration levels in blood or urine versus levels of indication signals, measured by CT.

The indicator fluid for measurements in blood or urine may thus be combined with an indicator fluid being measured as indication signals within regions of interest. In this regard, the indicator fluid 501 may comprise a computed tomography (CT) contrast agent, wherein the indicator fluid 501 is configured to assist in assessing movement of molecular substances from a cerebrospinal fluid compartment to a nearby brain or spinal cord compartment of a cranio-spinal cavity of a human. The indicator fluid may also assist in assessing ability of a cranio-spinal cavity of the human, i.e. the brain or the spinal cord compartment, to remove molecular substances 202. The indicator fluid 501 is movable along a movement path of said molecular substances. The indicator fluid 501 upon movement from a cerebrospinal fluid compartment may provide indicator fluid indication signals that are measurable at least once within regions of interest of the cerebrospinal fluid, brain or spinal cord compartment 502. Measurements are to be made of indication signals from the cerebrospinal fluid compartment or simultaneously both from the cerebrospinal fluid compartment and said brain or spinal cord compartment 502. Enhancement phase parameters and/or parameters of removal 503 of the indicator fluid from said cranio-spinal cavity are provided, and the enhancement phase parameters and/or parameters of removal 503 may be based on at least one of change in one of levels or change in levels in indication signals, and being indicative of ability of said cranio-spinal cavity to remove molecular substances 504. The ability to remove molecular substances refers to clearance of waste solutes from the cerebrospinal fluid, brain or spinal cord compartment. The parameters of removal 503 may be a function of ability of the cranio-spinal cavity to clear molecular waste solutes from the cerebrospinal fluid, the brain or the spinal cord compartment to blood and urine.

The timing of either measurements of blood levels and indication signals is selectable but should preferably be done between 0 hours to 72 hours after the indicator fluid is present in the CSF. The inventors have in tests studied performed measurements at various time points, for example when the indicator fluid has been present in the cerebrospinal fluid for a period of any one of 4-6, 6-9, 24 and 48 hours.

The movement of the indicator fluid 201, 501 to, within or from a cerebrospinal fluid, brain or spinal cord compartment may be a function of ability of: a) movement of molecular substances between individual cerebrospinal fluid compartments, e.g. cerebral ventricles within the craniospinal cavity, or b) removal of molecular substances via the brain or spinal cord compartment from said cranio-spinal cavity 504, or c) removal of molecular substances from cerebrospinal fluid compartment to blood or urine.

The levels of indicator fluid in blood or urine and the levels of indicator fluid indication signals within regions of interest of said cerebrospinal fluid, brain or spinal cord compartment are comparable against said levels from a reference cohort.

The invention also describes a system combining the measurements of indicator fluid levels in blood or urine and measurement of indication signals based on CT. The system enables comparisons of removal parameters based on blood or urine concentration levels and parameters of movement of indicator fluid. The system 301 enables assessment of ability of a cranio-spinal cavity of a human, i.e. the brain or the spinal cord compartment, to remove molecular substances therefrom, upon presence of the indicator fluid 302 in movement from a cerebrospinal fluid compartment of said cranio-spinal cavity, the indicator fluid comprising a computed tomography (CT) contrast agent. The system comprises: a) a sampling device 303 that is configured to sample and measure levels of said indicator fluid in blood or urine at selectable time intervals 304. The system further comprises: b) an analyzer 305 being configured to analyze amount of indicator fluid level 306 in said blood or urine samples 304 to determine parameters of removal 307 of said indicator fluid from said cranio-spinal cavity, and c) an analyzer output 308 to provide a presentation of said parameters of removal 307. The parameters of removal 307 may be at least one of:—level or change in level of indicator fluid concentration in blood or urine 306, and coefficient of indicator fluid removal (clearance) versus time in blood or urine. The parameters of removal 307 are indicative of ability of said cranio-spinal cavity, i.e. the brain or the spinal cord compartment, to remove said indicator fluid 309, and thereby being a function of ability of clearance of any waste solutes of molecular substances from the cerebrospinal fluid, brain or spinal cord compartment of said cranio-spinal cavity, and wherein said parameters of removal 307 being a function of ability of the cranio-spinal cavity to clear molecular waste solutes from the cerebrospinal fluid compartment or the brain or spinal cord compartment to blood and urine. The CT contrast agent of the system may be a selected one of: iohexol, iodixanol, iomeprol, ioversol, and iobitridol. Moreover, the system may be configured to compare said levels against levels from a reference cohort. The storage means 310 of the system may be provided to store parameters of removal 307 which are determined for a cohort of human individuals, and wherein a comparator 311 is provided to compare parameters of removal 307 obtained from at least one individual human against said stored parameters of removal 307 of said cohort of humans.

In combination with measurements of indicator fluid in blood or urine, the system 601 also comprises: a) an apparatus 602 configured for computed tomography (CT) to be interactive with an indicator fluid comprising a CT contrast agent detectable by the computed tomography (CT), b) a detector device 604 and a sampling device 605 configured to measure at least once indicator fluid indication signals 606 from the cranio-spinal cavity as provided by use of said apparatus 602 within regions of interest of said cerebrospinal fluid, brain or spinal cord compartment. The measuring is to be made of indication signals from the cerebrospinal fluid compartment or simultaneously both from the cerebrospinal fluid compartment and said brain or spinal cord compartment 607. The system 601 is configured to assess movement of molecular substances within, to or from a cerebrospinal fluid compartment to a nearby brain or spinal cord compartment of a cranio-spinal cavity of a human, with assistance from a selectable indicator fluid movable along a movement path of said molecular substances. c) An analyzer 608 can determine any sampled and detected change in indication signals 609 over time within selectable fluid compartments of said cranio-spinal cavity, said changes in indication signals being indicative of said movement of indicator fluid within, to or from said cerebrospinal fluid, brain or spinal cord compartment of said cranio-spinal cavity. d) An analyzer output 610 is capable of providing a presentation of said changes in indication signals 609 as enhancement phase parameters and/or parameters of removal of the indicator fluid 611 as a function of ability of:—movement of molecular substances between individual cerebrospinal fluid compartments, e.g. cerebral ventricles within the cranio-spinal cavity, or—removal of molecular substances via the cerebrospinal fluid, brain or spinal cord compartment from said cranio-spinal cavity 612, or—clearance of molecular waste solutes from the cerebrospinal fluid compartment or the brain or spinal cord compartment. The ability of movement or removal of molecular substances 612 refers to and is a function of clearance of molecular waste solutes.

The levels or change in levels measured by the system are to be measured and analyzed when the indicator fluid has been present in the cerebrospinal fluid for a period of any one of 4-6, 6-9, 24 and 48 hours. Other time points may as well be analyzed.

In this system 601, change in indication signals 609 may be measured over time, and may refer to parameters extracted from a graphically drawn curve 703 illustrating clearance of indicator fluid. A clearance illustrating curve 703 may be representative of parameters being at least one of: a) enhancement phase 708 with attributes selectable from: time to peak, maximum increase of indication signals and enhancement coefficient, and b) clearance phase 712 with attributes selectable from: decline time, maximum decrease of indication signals, clearance coefficient, parameter area being present under said curve, and indicator fluid half-time.

The system 601 may be applied onto multiple ones of human individuals to determine indication signals through use of said imaging within regions of interest in order to determine changes in indication signals over time within said regions of interest. The system may have a transfer device 613 capable of transferring said regions of interest of said imaging acquisition to an anatomical coordinate system 614, the anatomical coordinate system 614 being configured to enable segmentation of selectable anatomic regions. The system 601 may have a comparator 615 enabling a comparison of said change in indication signals over time 607, 609 between indication signal changes in a single human individual and changes in said multiple ones of human individuals 616. The comparator output 617 may be configured to provide a presentation of any deviation in movement of molecular substances in as measured and acquired from a single human individual compared to average movement of molecular substances in said multiple ones of human individuals 616. In this system 601, curves of clearance 703 of selectable regions of interest are compared with curves of clearance of comparable regions of interest from a cohort of humans 616, by means of said anatomical coordinate system 614. The system may be configured to compare said levels against levels from a reference cohort.

Another embodiment of an aspect of the invention is related to computer-aided methods for parameters of removal of molecular substances based on measurements of concentrations in blood or urine and measurements of indicator fluid in regions of interest. The computer assisted method 401 may enable assessment of ability of a cranio-spinal cavity of a human, i.e. the brain or the spinal cord compartment, to remove molecular substances therefrom, upon presence of an indicator fluid 402 in movement from a cerebrospinal fluid compartment of said cranio-spinal cavity. The indicator fluid 402 may comprise at least one of: a computed tomography (CT) contrast agent, and a magnetic resonance imaging (MRI) contrast agent. The method may further comprise: a) measuring once or at selectable time intervals by means of detectors 403 operatively linked to a computer a1) levels of said indicator fluid in blood or urine 404, b) analyzing by means of the computer 406 said levels of the indicator fluid 407 to determine parameters of removal 408 of said indicator fluid 402 from said cranio-spinal cavity, and c) presenting said parameters of removal 408 as delivered from a computer output 409. The parameters of removal 408 may be at least one of:—level or change in level of indicator fluid concentration in blood or urine 407, and—coefficient of contrast agent removal (clearance) versus time in blood or urine. Said presented parameters of removal 408 are indicative of ability of said cranio-spinal cavity, i.e. a cerebrospinal fluid, the brain or the spinal cord compartment, to remove said indicator fluid therefrom 410. Said parameters of removal 408 may be a function of ability of the cranio-spinal cavity to clear molecular waste solutes from the cerebrospinal fluid compartment or the brain or the spinal cord compartment to blood and urine.

Parameters of removal 408 may be determined for a cohort of human individuals and stored in a computer storage device 411, and wherein parameters of removal 408 associated with a further human individual are compared with said stored parameters of removal. The CT contrast agent is a selected one of: iohexol, iodixanol, iomeprol, ioversol, and iobitridol. The ability of a cranio-spinal cavity to remove molecular substances 410 refers to clearance of waste solutes from the cerebrospinal fluid, brain or spinal cord compartment.

The measurement of concentrations in blood or urine may be combined with measurement of indication signals within regions of interest using a computer aided method. Said method aided by a computer 801 can assess movement of molecular substances from a cerebrospinal fluid compartment to a nearby brain or spinal cord compartment of a cranio-spinal cavity of a human, or within, to or from a cerebrospinal fluid, brain or spinal cord compartment of a cranio-spinal cavity of a human, with assistance from a selectable indicator fluid movable from a cerebrospinal fluid compartment along a movement path of said molecular substances. The indicator fluid comprises a computed tomography (CT) contrast agent, and the method using the computer 801 comprises: a) measuring at least once indicator fluid indication signals 802 by use of a detector device 803 and a sampling device 804 linked to the computer 801 and provided by use of computed tomography (CT), as related to a selected indicator fluid 806, within regions of interest of said cranio-spinal cavity. Said measuring is to be made of indication signals 802 from the cerebrospinal fluid compartment or simultaneously both from the cerebrospinal fluid compartment and said brain or spinal cord compartment 807. b) A determining section 808 in the computer 801 determines changes in indication signals 809 over time within selectable regions of said cranio-spinal cavity. The change in indication signals 809 is indicative of said ability of movement of indicator fluid within, to or from said regions of said cranio-spinal cavity. c) An output of an analyzer section 810 in the computer presents enhancement phase parameters and/or parameters of removal 811 of the indicator fluid 806 from said cranio-spinal cavity, and said enhancement phase parameters and/or parameters of removal 811 are based on at least one of said changes in indication signals 809, and are indicative of ability of said cranio-spinal cavity to remove molecular substances 812. The ability is a function of clearance of waste solutes from compartments of the cranio-spinal cavity. Said presented parameters 811 are indicative of ability of said cranio-spinal cavity, i.e. a cerebrospinal fluid, brain or spinal cord compartment, to remove said indicator fluid therefrom 410. The change in indication signals may be related to clearance of waste solutes from the cerebrospinal fluid compartment or the brain or spinal cord compartment.

According to the method aided by the computer 801 said change in indication signals are to be measured and analyzed when the indicator fluid has been present in the cerebrospinal fluid for a period of any one of 4-6, 6-9, 24 and 48 hours. Other time points may as well be used.

Parameters of removal 811 may be determined for a cohort of human individuals and parameters of removal 811 associated with a further human individual are compared with said stored parameters of removal.

Said movement of the indicator fluid 806 within, to or from a cerebrospinal fluid compartment may be a function of ability of: a) movement of molecular substances between individual cerebrospinal fluid compartments, or b) removal of molecular substances via the cerebrospinal fluid, brain or spinal cord compartment from said cranio-spinal cavity 812. The cerebrospinal fluid compartments of feature a) are cerebral ventricles within the cranio-spinal cavity. The CT contrast agent may be a selected one of: iohexol, iodixanol, iomeprol, ioversol, and iobitridol.

The method may be applied onto multiple ones of human individuals to determine indication signals through use of said imaging within regions of interest in order and to determine changes in indication signals over time within said regions of interest. The regions of interest of said imaging acquisition may be transferred by a transfer section 813 to an anatomical coordinate system 814, which is configured to enable segmentation of selectable anatomic regions. A comparison by a comparator section 815 of said change in indication signals over time can be made between indication signal changes in a single human individual and changes in a database 816 related to multiple ones of human individuals. Moreover, a presentation by means of a comparator output section 817 can be provided of any deviation in movement of molecular substances as measured and imaged from a single human individual compared to average movement of molecular substances in said multiple ones of human individuals as derivable from the database 816. Said levels may be compared against levels from a reference cohort.

FIG. 24*l*-n provide some examples how change in blood concentration level of an indicator fluid may be related to change in indication signals of the indicator fluid. These examples are provided for illustration purpose and represent no limitation of the invention. The level 2465 of indicator fluid in blood is given along the y axis as well as the level 2466 of indication signals measured by CT. Along the x-axis, the time 2467 from CT indicator being present in CSF is given. The time point Pre denotes time prior to indicator fluid being present in CSF.

In FIG. 24*l*, the trend plot 2468 of blood concentration of the indicator fluid is shown, including time 2469 to maximum blood concentration level (enhancement phase), maximum level 2470 of indicator fluid in blood, and coefficient 2471 of enhancement phase (maximum level versus time to peak). For the clearance phase, the time 2472 from maximum level to minimum level is indicated, the decline 2473 in blood concentration from maximum to minimum, and the clearance phase coefficient 2474 is indicated. Regarding CT indication signals measured by CT, the trend plot 2475 is shown, also including time 2476 to maximum indication signal level (enhancement phase), maximum level 2477 of indication signal, and coefficient 2478 of maximum indication signal level versus time to peak of enhancement phase. During the clearance phase, the time 2479 from maximum level to minimum indication signal level is indicated, as well as the reduction 2480 in indication signal level from maximum to minimum, and the clearance phase coefficient 2481. Comparisons between blood concentration levels 2468 and indication signal levels 2475 may be done at various levels, such as the following:

relationships between time 2469, 2476 to peak during enhancement phase,
relationships between maximum levels 2470 of blood concentrations and indication signal levels 2477,
relationships between coefficient 2471 of enhancement phase blood concentration levels and coefficient 2478 of indication signal levels,
relationships between time 2472 from maximum to minimum (clearance phase) of blood concentration versus indication signal level 2479,
relationship between decrease 2473 in blood concentration from maximum to minimum and reduction 2480 in indication signal level from maximum to minimum,
relationship between blood concentration level 2468 and indication signal level 2475 at any single time point, including individual time points 2467 such as 2 h, 4 h, 6 h, 8 h, 24 h, and 48 h. Of note regarding the case in FIG. 24*l* is that blood concentration reaches high maximum value early with a rapid decline, providing both a steep coefficient 2471 during the enhancement phase 2469 and a steep coefficient 2474 during the clearance phase 2472. The CT indication signal level, on the other hand, reached a maximum level later, and with a modest maximum indication signal level, which gave a lower value of coefficient of enhancement phase 2478, as well as a lower clearance phase coefficient 2481. This situation may be seen when a molecular substance is being removed very fast from the craniospinal compartment.

Another situation is illustrated in FIG. 24*m*. The y axes revealing the concentrations levels 2465 of indicator fluid in blood and the magnitude 2466 of CT indication signals and the x-axis representing the time 2467 from CT indicator being present in CSF. The trend plot 2482 of concentration of the indicator fluid in blood is presented with time 2483 to maximum blood concentration level (enhancement phase), and with maximum blood concentration 2484 of indicator fluid, and with coefficient 2485 of enhancement phase (maximum level versus time to peak). The time 2486 from maximum level to minimum level of clearance phase is indicated with the decline 2487 in blood concentration from maximum to minimum, and the clearance phase coefficient 2488. The trend plot 2489 of CT indication signals is presented with time 2490 to maximum indication signal level (enhancement phase), and the maximum level 2491 of indication signal, and coefficient 2492 of maximum indication signal level versus time to peak of enhancement phase. Moreover, the time 2493 from maximum level to minimum indication signal level during the clearance phase is shown, as well as the reduction 2494 in indication signal level from maximum to minimum, and the clearance phase coefficient 2495. Comparable to that shown in FIG. 24*l*, a variety of comparisons between blood concentration levels 2482 and indication signal levels 2489 may be done, exemplified by the following:

relationships between time 2483, 2490 to peak during enhancement phase,
relationships between maximum levels 2484 of blood concentrations and maximum indication signal levels 2491,
relationships between coefficient 2485 of enhancement phase blood concentration levels and coefficient 2492 of indication signal levels,
relationships between time 2486 from maximum to minimum (clearance phase) of blood concentration versus indication signal level 2493,
relationship between decrease 2487 in blood concentration from maximum to minimum and reduction 2494 in indication signal level from maximum to minimum,
relationship between blood concentration level 2482 and indication signal level 2489 at any single time point, including individual time points 2467 such as 2 h, 4 h, 6 h, 8 h, 24 h, and 48 h. The situation shown in FIG. 24m illustrates blood concentrations reaching a rather low maximum value, occurring late, and with a low blood concentration at 24 h. The CT indication signal level 2489, on the other hand, reached a late maximum level later, even later than maximum blood concentration. This situation may be seen when a molecular substance is being removed very slow from the craniospinal compartment. Notably, this is only one example, and should not be considered as a limitation of the invention.

A third example to illustrate how blood concentrations may compare with indication signal levels is illustrated in FIG. 24n. As for FIG. 24l and FIG. 24m, the y axes show the concentrations 2465 of indicator fluid in blood and the magnitude 2466 of CT indication signals and the x-axis representing the time 2467 from CT indicator being present in CSF. The trend plot 2495 of concentration of indicator fluid in blood is presented with time 2496 to maximum blood concentration level (enhancement phase), and maximum blood concentration of indicator fluid 2497, and the enhancement phase coefficient (maximum level versus time to peak) 2498. The time 2499 from maximum level to minimum level of clearance phase is indicated with the decline 24100 in blood concentration from maximum to minimum, and the clearance phase coefficient 24101. The trend plot 24102 of CT indication signals is presented with time 24103 to maximum indication signal level (enhancement phase), and the maximum level 24104 of indication signal, and coefficient 24105 of maximum indication signal level versus time to peak of enhancement phase. The time 24106 from maximum level to minimum indication signal level during the clearance phase is shown, as well as the reduction 24107 in indication signal level from maximum to minimum, and the clearance phase coefficient 24108. Comparable to that shown in FIG. 24l and FIG. 24m several comparisons may be done between blood concentration levels 2495 and indication signal levels 24102, and some examples are given:

relationships between times 2496, 24103 to peak during enhancement phase, relationships between maximum levels 2497 of blood concentrations and maximum indication signal levels 24104, relationships between coefficient 2498 of enhancement phase blood concentration levels and coefficient 24105 of indication signal levels, relationships between time 2499 from maximum to minimum (clearance phase) of blood concentration versus indication signal level 24106, relationship between decrease 24100 in blood concentration from maximum to minimum and reduction 24107 in indication signal level from maximum to minimum, relationship between blood concentration level 2495 and indication signal level 24102 at any single time point, including individual time points 2467 such as 2 h, 4 h, 6 h, 8 h, 24 h, and 48 h. In FIG. 24n is shown a situation where maximum value 2497 of blood concentrations and maximum CT indication signal level 24104 occurs at the same time. It can further be noted that both the enhancement phase coefficients 2498 of blood concentration and indication signal level 24105 are comparable, as well as the clearance phase coefficient 24101 of blood and coefficient 24108 of CT indication signal. A similar situation may be observed in an ordinary state with proper removal of molecular substances from the craniospinal compartment.

While the trend plots of blood concentrations and CT indication levels presented in FIGS. 24l, 24m, and 24n refer to repeated measurements, these examples represent no limitation of the invention. It may as well be preferable to perform single measurements at selectable time points, for example 6-9 hours, after 23-26 hours, or after 46-49 hours after the indicator fluid is present in CSF. With single measurements, comparisons may be done towards reference values. When single measurements are done, relationships are determined between single observations of blood or urine concentrations of indicator fluid and indication signal levels of said indicator fluid. Hence, at a given time the blood or urine concentration may be higher or lower and the indication signal level higher or lower, as would be expected in the given situation.

In situations where measurements are done repeatedly, providing for a trend plot, the area under curve may be computed. The strategy, however, requires a certain number of measurements to provide reliable information.

Figure 25A:
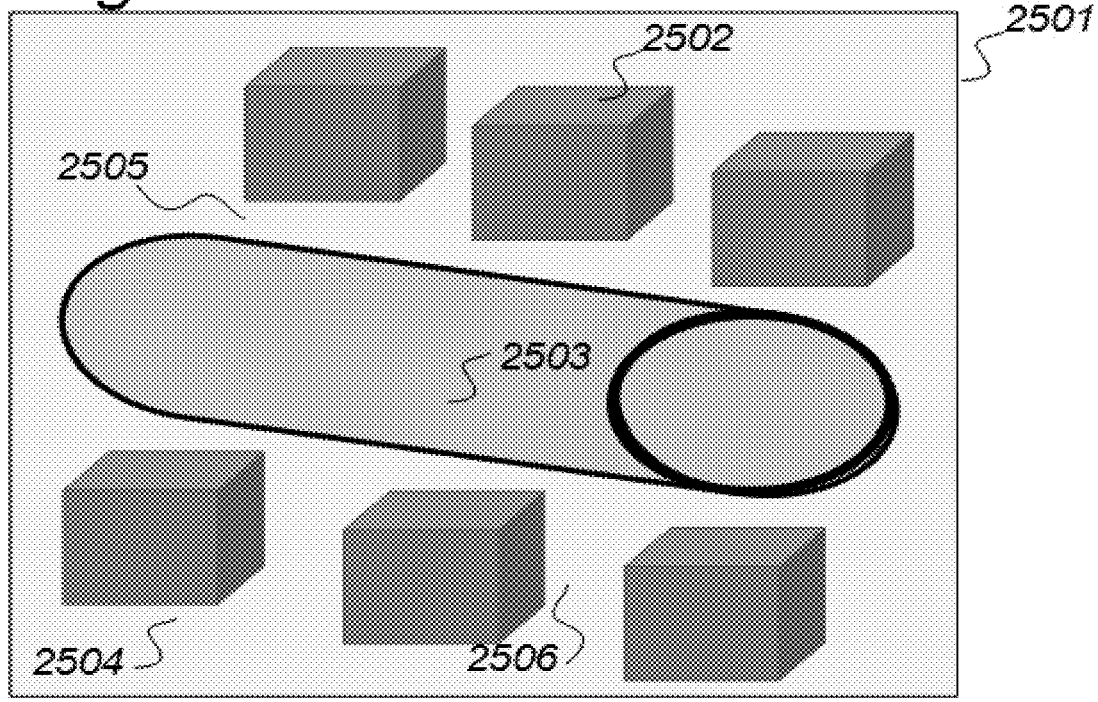
FIG. 25a-f illustrate the differences between the vascular (i.e. intra-vascular) and extra-vascular compartments, and how the structural and dimensional properties of restricted or occluded extra-vascular space may be visualized according to the invention.
Figure 25B:
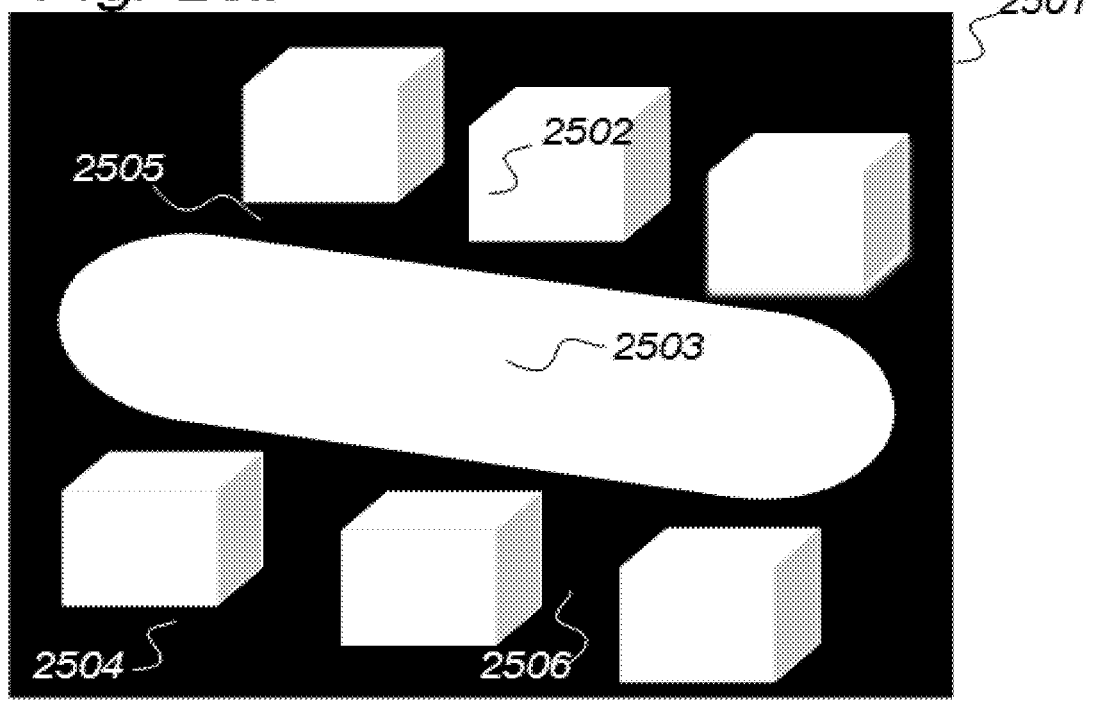

In the following, Aspect 5 of the invention is described, which provides means (indicator fluid, system, computer-aided method) for determining the dimensional properties of the extravascular space of the brain and spinal cord compartment of a cranio-spinal cavity of a human. The differences between vascular and extra-vascular compartments are schematically illustrated in FIG. 25a-b. With reference to FIG. 25a, within the brain and spinal cord tissue compartment 2501, the major elements are the brain cells and their processes 2502, the blood circulating within the blood vessels 2503. The space between the cells (primarily neurons, glia cells and cell processes) and the blood vessels constitute the extra-vascular space 2504. The extra-vascular space also includes the paravascular space 2505 along the blood vessels. The blood vessels within the brain structure 2501 consist of arteries, capillaries and veins. Within the human brain, the vasculature constitutes only about 3% of the volume. The paravascular space at the capillary level it primarily includes the basement membrane, which is a loose matrix between the capillary wall (endothelial cells and pericytes) and the end-feet of the astrocyte processes. However, the present definition of the extra-vascular space, a macro-anatomic perspective is taken. The extra-vascular space refers to the space outside the blood circulating within the blood vessels 2503 and outside the cell structures 2502 of the brain and spinal cord tissue compartment 2501. Using imaging with modalities such as CT, MRI, PET, SPECT and scintigraphy, the vascular compartment 2503 can be visualized with applying contrast agents detectable by the respective image modalities. Imaging of the dimensional properties of the extra-vascular brain and spinal cord compartment has previously not been done. The differentiation between vascular and extra-vascular spaces is further illustrated in FIG. 25b, showing that within the brain and spinal cord tissue compartment 2501, removing the cell structures 2502 and the blood contained within the blood vessels 2503 leaves the extra-vascular space 2504, wherein the paravascular space 2505 is a part. Aspect 5 of the present invention deals with tools to assess the structural dimensions as well as the functionality of the extra-vascular space. The extra-vascular space 2504 incorporates both the paravascular space 2505 and the interstitial space 2506. The paravascular fluid within the paravascular space 2505 and the interstitial fluid (ISF) between cells 2506 are in free communication, and being a part of the extravascular fluid within the extra-vascular space 2504.

Figure 25C:
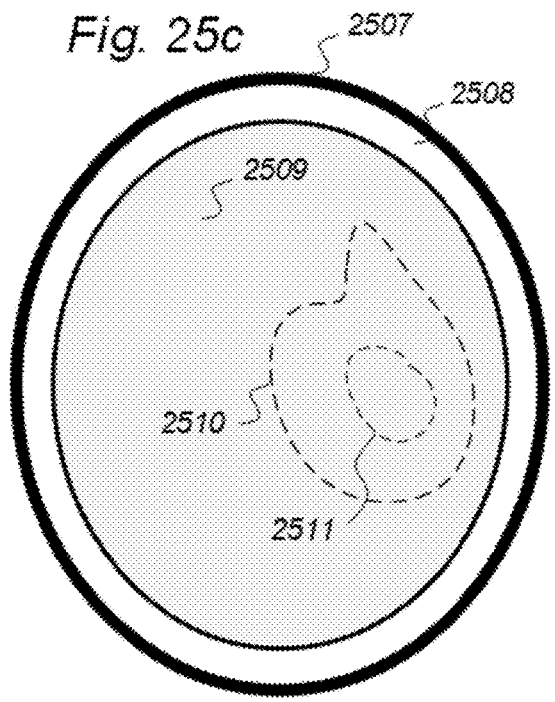
Figure 25D:
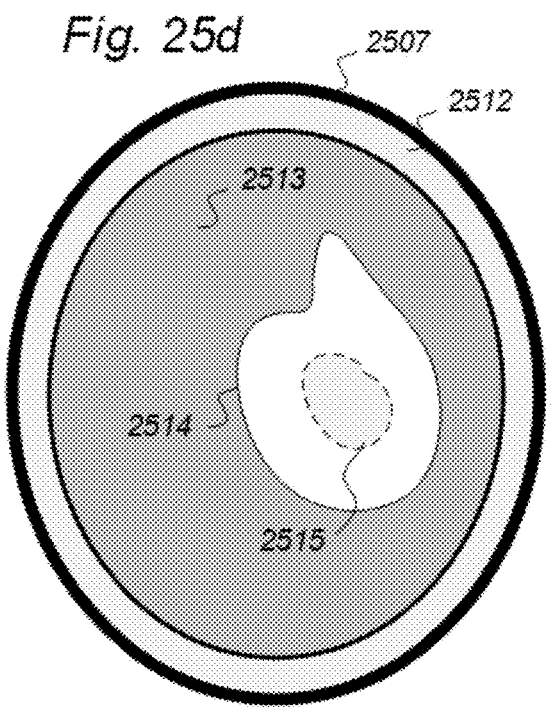

FIG. 25c-f illustrate how this aspect of the invention may be applied to visualize structural dimensional properties of the extra-vascular space. FIG. 25c provides a schematic illustration of a cranium 2507, enclosing a CSF compartment 2508, which is surrounding a brain compartment 2509. Within the brain compartment, there is a region wherein the extra-vascular space is restricted or occluded, which is marked with stippled line 2510. Moreover, inside the area with occluded extra-vascular space 2510, there is a region with breakdown of BBB 2511. There are many reasons for restriction or occlusion of the extra-vascular space that also may include areas with BBB damage. However, prior art provides limited tools for assessing the structural and dimensional properties of the extra-vascular space. The present invention provides novel tools for solving this problem. In FIG. 25d, an indicator fluid is present within the CSF compartment 2512, thus changing the indication signals from the CSF compartment 2512. This may result in change of indication signals within the brain compartment 2513. Since the indicator fluid distributes within the extra-vascular space, the indicator fluid does not distribute to the area with restricted or occluded extravascular space 2514, even though the indicator fluid potentially may distribute to areas with BBB breakdown 2515. This may happen if the extra-vascular compartment is restricted, though not fully occluded. Passage of indicator fluid passes through the BBB, may cause entrance of some indicator fluid to the vascular space. In one embodiment, the indicator fluid has been present within the CSF compartment for several hours, e.g. 24 hours. In another embodiment indication signals are measured repeatedly. This example (FIG. 25d) illustrates how an indicator fluid present within CSF may be used to visualize the extra-vascular space.

Figure 25E:
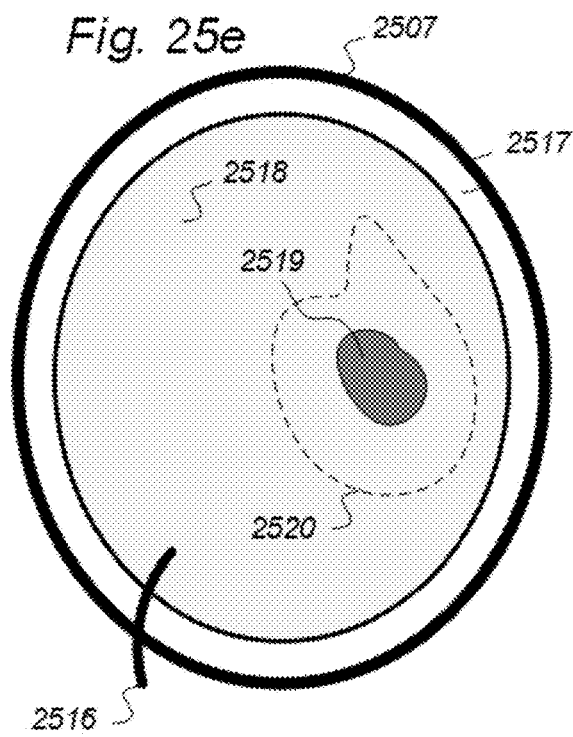

The present invention also describes how presence of indicator fluid within different compartments (CSF versus intravenous) may be assessed at the same time. FIG. 25e illustrates how the indicator fluid may be administrable to the vascular space, e.g. intravenously 2516. Indicator fluid within the intra-vascular compartment does not pass to the CSF compartment 2517, neither to the extra-vascular space of the brain compartment 2518 because of the BBB. On the other hand, indicator fluid will pass unto the extra-vascular space in an area with breakdown of the BBB 2519. If the BBB is intact, an intravenous indicator fluid will not be able to visualize extra-vascular regions with restricted or blocked extra-vascular space 2520. For example, today's practice with intravenous contrast-enhanced CT or MRI relies on administering the contrast agent intravenously that results in contrast-enhancement of areas with breakdown of BBB. Contrast-enhancement of the extra-vascular space for assessment of its dimensional properties is not used or described in prior art.

Figure 25F:
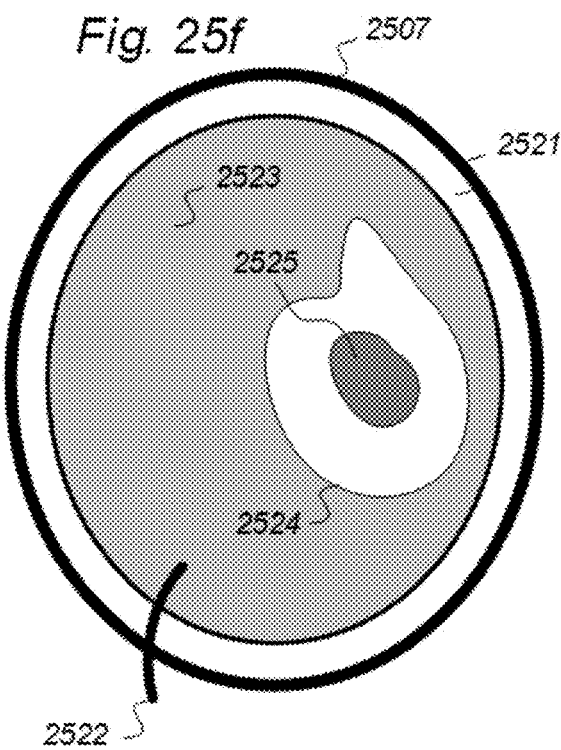

As illustrated in FIG. 25f, one inventive step is to combine indicator fluids administrable to both the CSF space 2521 and the vascular system, e.g. intravenous 2522. The different administrations of indicator fluid may be separated in time. Notably, the administration step itself is not part of the invention, as the invention comes to play when an indicator fluid is present within the craniospinal cavity, or in combination with indicator fluid present within intravenous compartment. For example, imaging may be done at a time when indicator fluid having been administered to a CSF compartment 2521 about 24 hours earlier. This results in passage of indicator fluid to the extra-vascular space of brain compartment 2523, but not to the region with restricted or occluded extra-vascular space 2524. Indicator fluid may also have been administered to the vascular compartment, e.g. intravenous, 2522 at another time, which causes passage of indicator fluid to area with BBB damage 2525. The combined indicator fluid within the CSF compartment 2521 and intravenous 2522 will give estimation of the area with restricted or occluded extra-vascular space 2524. Moreover, subtraction of indication signals from the extra-vascular and vascular compartments may aid in assessing the dimensional and structural properties of the extra-vascular space.

Figure 26:
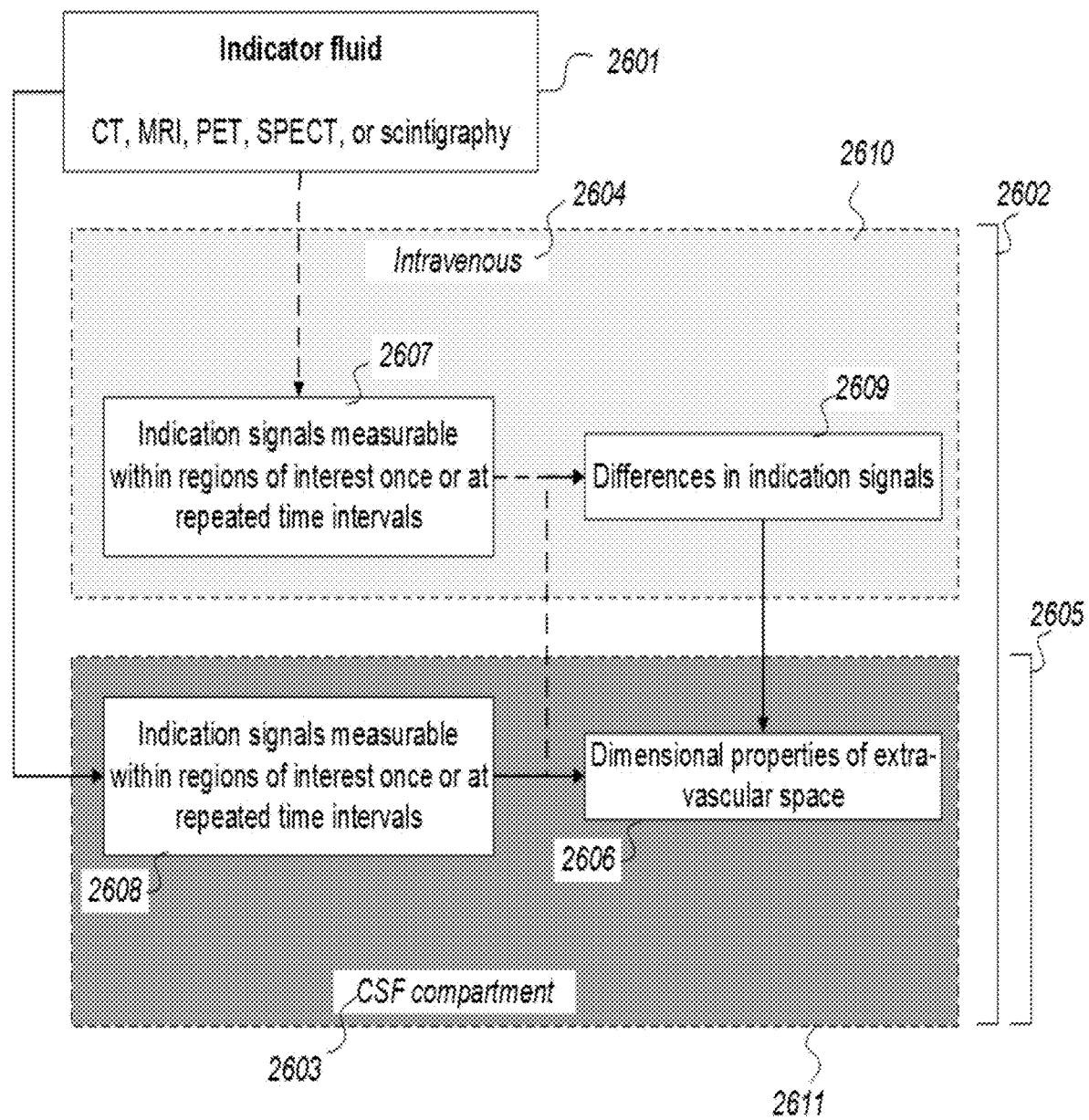
FIG. 26 illustrates usage of an indicator fluid to assess the dimensional properties of extra-vascular space of a brain and/or spinal cord compartment of a cranio-spinal cavity of a human. The upper (dark grey) bar indicates the vascular (intra-vascular) compartment, whereas the lower (light grey) bar indicates the extra-vascular compartment. The compartments are separated by the BBB.

A first feature of Aspect 5 is illustrated in FIG. 26. This first feature discloses an indicator fluid 2601 comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, wherein the indicator fluid 2601 is of a type to be movable, in a mode a) 2602 selectively from a cerebrospinal fluid compartment of a cranio-spinal cavity 2603 and intravenously 2604 of a human, or in a mode b) 2605 from a cerebrospinal fluid compartment of the cranio-spinal cavity of a human, to assist in assessing dimensional properties of extra-vascular space of a brain or spinal cord compartment 2606 of a cranio-spinal cavity of the human. The indicator fluid 2601 indication signals 2607, 2608 being measurable at least once within regions of interest of said brain or spinal cord compartment of the cranio-spinal cavity, and either wherein in indicator fluid mode a) 2602 said dimensional properties of the extra-vascular space of said brain or spinal cord compartment 2606 is a function of a determined difference in indicator fluid indication signals of similar regions of interest 2609, or wherein in indicator fluid mode b) 2605 said dimensional properties of the extra-vascular space of said brain or spinal cord compartment 2606 is a function of determined indicator fluid indication signals of regions of interest 2608.

The notation indication signal 2607, 2608 has a broad meaning, and depends on imaging modality. CT refers to Hounsfield Units (HU), MRI refers to SU and PET, SPECT and scintigraphy refer to Standard Uptake Value (SUV). An indication signal 2607, 2608 is thus a measurable feature derived from a specific imaging modality, where the indication signal level may be influenced by presence of indicator fluid 2601. Indication signals 2607, 2608 may though be measured both in the presence and absence of indicator fluid. This inventive step thus renders for secondary use of contrast agents and radioisotopes by exploiting their ability to provide information of extra-vascular space dimensional properties 2606 outside the intact BBB, when having been administered to CSF.

When moving from a CSF compartment 2603, an indicator fluid 2601 with suitable molecular size will, like other substances with similar properties, enter paravascular spaces 2505 along the outside of vessels penetrating through the surface of the brain and spinal cord tissue compartment 2501. The BBB will prevent the indicator fluid 2601 from leaking into the blood circulation 2503, and thus be confined to the extra-vascular compartment 2504 before it is further cleared to lymphatic pathways including LNs, and thereafter to blood and urine. Presence, or absence, of indicator fluid 2601, visualized as indication signals 2608 on CT, MRI, PET, SPECT or scintigraphy at certain time points will provide for information about dimensional properties of the extra-vascular space 2606 of the brain and spinal cord tissue compartments.

The extra-vascular compartment 2504, including the paravascular space 2505, is the scene of numerous disease processes in the brain, such as neoplastic, inflammatory and degenerative processes, and of a much larger size than the vascular compartment 2503, in which the blood circulation occurs.

The indicator fluid 2601 serve as an example of a substance. In this context, the term "substance" has a wide meaning. It may be small molecules [e.g. water ($H_2O$) molecule, MW 18 gr/mole (=18 Da)], macromolecules (e.g. the contrast agents gadobutrol (Gadovist™; MW 605 Da) and iohexol (Omnipaque™, MW 821 Da), peptides (e.g. amyloid-β protein fragment 1-42, MW 4 514 Da), proteins (e.g. Tau-protein, MW 55-62 000 Da), and antibodies (e.g. immunoglobulin G, MW 150 kDa). Obviously, the movement of a substance within or from a craniospinal cavity depends on the size of the substance.

The indicator fluid 2601 may contain a CT contrast agent, or MRI contrast agent, or a substance exhibiting recognized pharmacokinetic properties. The CT contrast agent may be a selected one of: iohexol, iodixanol, iomeprol, ioversol, and iobitridol, and the MRI contrast agent either gadobutrol or gadoteric acid.

The indicator fluid 2601 may be a radioactive ligand suitable for PET, SPECT or scintigraphy imaging tied to or chelated with a CT or MRI contrast agent substance or a substance exhibiting recognized pharmacokinetic properties. The radioactive ligand may be a selectable tracer material from at least one of: $^{89}$Zirconium, $^{99m}$Tc-DTPA, and $^{111}$In-DTPA. The indicator fluid 2601 may contain a radioactive ligand which is chelated with material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques. The indicator fluid 2601 may also be a CT or an MRI contrast agent coupled with one or more of: large-molecule biotechnology based products, antibodies, monoclonal antibodies, recombinant proteins, and antisense or gene therapeutics means.

Further, an MRI contrast agent may be a dendrimer based macromolecular MRI contrast agent of size sufficiently high to be retained outside the BBB.

The indicator fluid 2601 may have affinity to inflammatory cells or tumor cells, and being a contrast agent conjugated with antibodies or with avidin, or wherein the indicator fluid 2601 contains a substance having fibrinolytic properties.

The indication fluid 2601 may have affinity to certain proteins presented along the paravascular spaces in the brain and spinal cord tissue, such as aquaporin-4 (AQP4), being water channels that regulate transport of water in the brain, or AQP4 anchoring proteins.

The indicator fluid 2601 may be configured to be delivered to said CSF compartment by spinal puncture and intrathecal injection, even though delivery procedure itself is not part of the invention.

Figure 27:
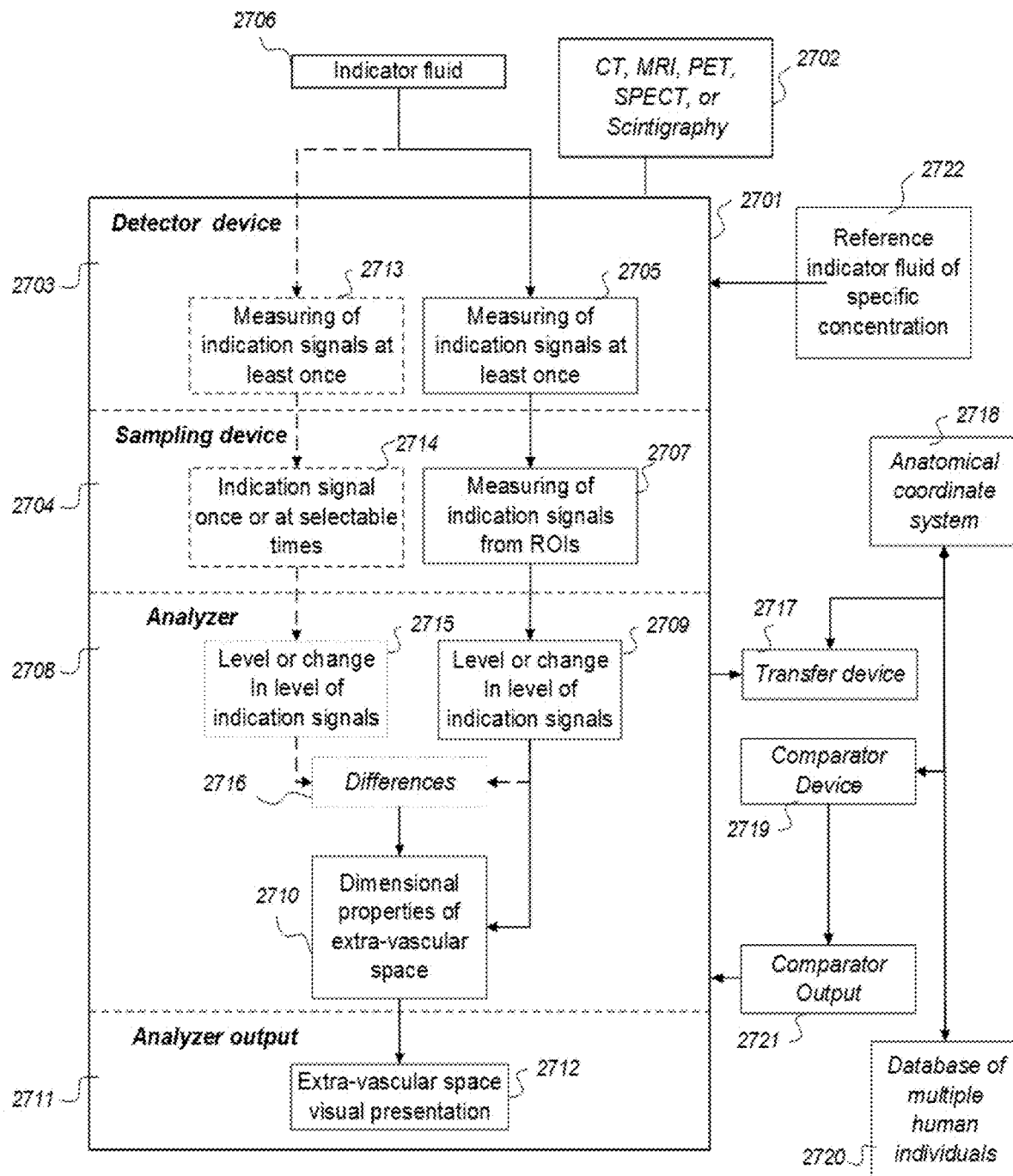
FIG. 27 illustrates a system to assess dimensional properties of extra-vascular space of a brain and/or spinal cord compartment of a cranio-spinal cavity of a human.

In a second feature of Aspect 5 is described a system to assist in assessing dimensional properties of extra-vascular space of a brain or spinal cord compartment of a craniospinal cavity of a human, upon an indicator fluid being in movement in the body of the human, the indicator fluid comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging, and a substance exhibiting recognized pharmacokinetic properties, exhibiting recognized pharmacokinetic properties. FIG. 27 provides an overview of the system 2701, which comprises:

- an apparatus 2702 configured for imaging by one of computed tomography (CT), magnetic resonance imaging (MRI), positron emission tomography (PET), single photon emission computed tomography (SPECT), and scintigraphy imaging,
- a detector device 2703 and a sampling device 2704 to measure indicator fluid indication signals 2705 within regions of interest as indicator fluid 2706 flows from a cerebrospinal fluid compartment of the cranio-spinal cavity, to
- a1) measure at least once indication signals 2707 through use of imaging acquisition of brain or spinal cord compartment, and
- an analyzer 2708 capable of assessing any sampled and detected indication signals 2705, 2707, said analyzer 2708 being configured:
- a2) to determine, based on said imaging acquisition, value of level of indication signal or value of change in level of indication signals 2709 over time within said brain or spinal cord compartment of said cranio-spinal cavity, and
- to assess said dimensional properties of said extra-vascular space of said brain or spinal cord compartment 2710 as a function of indication signals of regions of interest 2709 as determined by feature a2),
- and
- an analyzer output 2711 to provide an extra-vascular enhanced visual presentation of assessed dimensional properties of said extra-vascular space of said brain or spinal cord compartment 2712.

The detector device 2703 and sampling device 2704 of said system 2701 may in addition be configured to:

b1) measure at least once indicator fluid indication signals 2713, 2714 through use of imaging acquisition of brain or spinal cord compartment as indicator fluid 2706 flows intravenously, wherein the analyzer 2708 in addition being configured to:

b2) determine, based on said imaging acquisition, value of level or change in level of indication signals 2715 over time within said brain or spinal cord compartment of said craniospinal cavity, and assess said dimensional properties of said extra-vascular space of said brain or spinal cord compartment 2710 as a function of difference 2716 in indication signals of similar regions of interest as determined by features b2) and a2), and wherein the analyzer output 2711 in addition is configured to provide an extra-vascular enhanced visual presentation 2712 of dimensional properties of said extra-vascular space of said brain or spinal cord compartment 2710 based on such a difference in indication signals 2716.

Said extra-vascular space 2504 of a brain and/or spinal cord tissue compartment is represented by the entire volume outside vessel walls and cell structure walls of the craniospinal cavity.

Imaging according to the system 2701 may be an MRI or PET-MRI acquisition, which incorporates T1 weighted sequences with selectable and standardized imaging parameters being at least echo and repetition time, flip angle, matrix, and field of view. Further, all parameters essential to a T1 weighted image should be standardized as far as possible to enable for the highest reproducibility of T1 SUs, both between different time points in single human subjects, but also between subjects, and between different MRI scanners. Other MRI sequences that may show useful are T1-mapping, susceptibility weighted imaging, and FLAIR. Assessment of indication signals from this system may also be combined with other MRI sequences such as diffusion weighted imaging, T2 weighted imaging and T1 weighted imaging utilizing intravenous MRI contrast agents. Such combinations could be co-registration of images to render for overlay- and subtraction images, or combinations of image parameters.

The system may incorporate different operational modes. One operational mode may be features a1) and a2), which is referred to as mode b) 2605. Another operational mode, which is referred to as mode a) 2602, may imply that features b1) and b2) are time separated by a selectable number of hours or a selectable number of days. The difference in indication signals 2716 represents subtraction of indication signal values from comparable imaging acquisitions according to one mode a1), a2) 2605 and another mode b1), b2) 2602. Said comparable acquisitions are related to aligning acquired images of a human.

The indicator fluid 2706 in operational mode a) 2602 may be administrable to both the CSF compartment of craniospinal cavity by spinal puncture and intrathecal injection, and through intravenous injection. The indicator fluid 2706 in operational mode b) 2605 may be administrable to the CSF compartment of cranio-spinal cavity by spinal puncture and intrathecal injection. Neither the administration or injection procedures are part of the invention.

The indicator fluid 2706 used by the system 2701 may contain a CT contrast agent, or a MRI contrast agent, or a substance exhibiting recognized pharmacokinetic properties. The CT contrast agent may be a selected one of: iohexol, iodixanol, iomeprol, ioversol, and iobitridol, and the MRI contrast agent either gadobutrol or gadoteric acid.

In another embodiment, the system 2701 applies an indicator fluid 2706 may be a radioactive ligand suitable for PET, SPECT or scintigraphy imaging tied to or chelated with a contrast agent substance or a substance exhibiting pharmacokinetic properties. The radioactive ligand may be a selectable tracer material from at least one of: $^{89}$Zirconium, $^{99m}$Tc-DTPA, and $^{111}$In-DTPA.

Furthermore, the indicator fluid 2706 may contain a radioactive ligand, which is chelated with material being at least one of: large-molecule biotechnology based products, antibodies, monoclonal antibodies, recombinant proteins, and antisense or gene therapeutics means. The material chelated with said ligand has at least a partial property of making a bond to tumor cells or inflammation cells or amyloid beta plaques.

The indicator fluid 2706 may also be a CT or an MRI contrast agent coupled with one or more of: large-molecule biotechnology based products, antibodies, monoclonal antibodies, recombinant proteins, and antisense or gene therapeutics means.

The MRI contrast agent may be a dendrimer based macromolecular MRI contrast agent of size sufficiently high to be retained outside the BBB.

The indicator fluid 2706 may have affinity to inflammatory cells or tumor cells, and be a contrast agent conjugated with antibodies or with avidin. In another embodiment, the indicator fluid may contain a substance having fibrinolytic properties.

The indication fluid 2706 may have affinity to certain proteins presented along the paravascular spaces in the brain and spinal cord tissue, such as AQP4, being water channels that regulate transport of water in the brain, or AQP4 anchoring proteins.

The system according to Aspect 5 may have functionality to compare individuals with a cohort. In this regard, the system 2701 may be applied onto multiple ones of human individuals using a detector device 2703 and sampling device 2704 to measure indication signals 2705, 2707, 2713, 2714 through use of said imaging within ROIs determine levels or changes in levels of 2709, 2715 indication signals over time within said ROI. The system 2701 may have a transfer device 2717 capable of transferring said ROIs of said imaging acquisition to an anatomical coordinate system 2718, the anatomical coordinate system being configured to enable segmentation of selectable anatomic regions. The system may have a comparator device 2719 enabling a comparison of said change in indication signals over time between indication signal changes in a single human individual and changes in said multiple ones of human individuals, using database information 2720. Further, a comparator output 2721 is configured to provide a presentation of any deviation in movement of substances in as measured and imaged from a single human individual compared to average movement of substances in said multiple ones of human individuals (2720).

Concerning MRI, the system may be cooperative with an MRI SU standardization device to cause said indication signals being SUs to be standardized SUs. The standardization device may comprise an extra-body device containing at least one reference indicator fluid of specific concentration 2722, wherein said at least one reference indicator fluid 2722 is located within one or more containers to be located externally of the body of the human. The containers may also be filled with dedicated material having liquid properties, e.g. viscosity or molecular property, resembling standard cranio-spinal cavity liquid, or having semi-solid material properties, e.g. density or molecular property, resembling standard properties of standard brain tissue. Thereby, standardized SUs allow for measurement of absolute values of indicator fluid within the ROI of a human individual.

Figure 28:
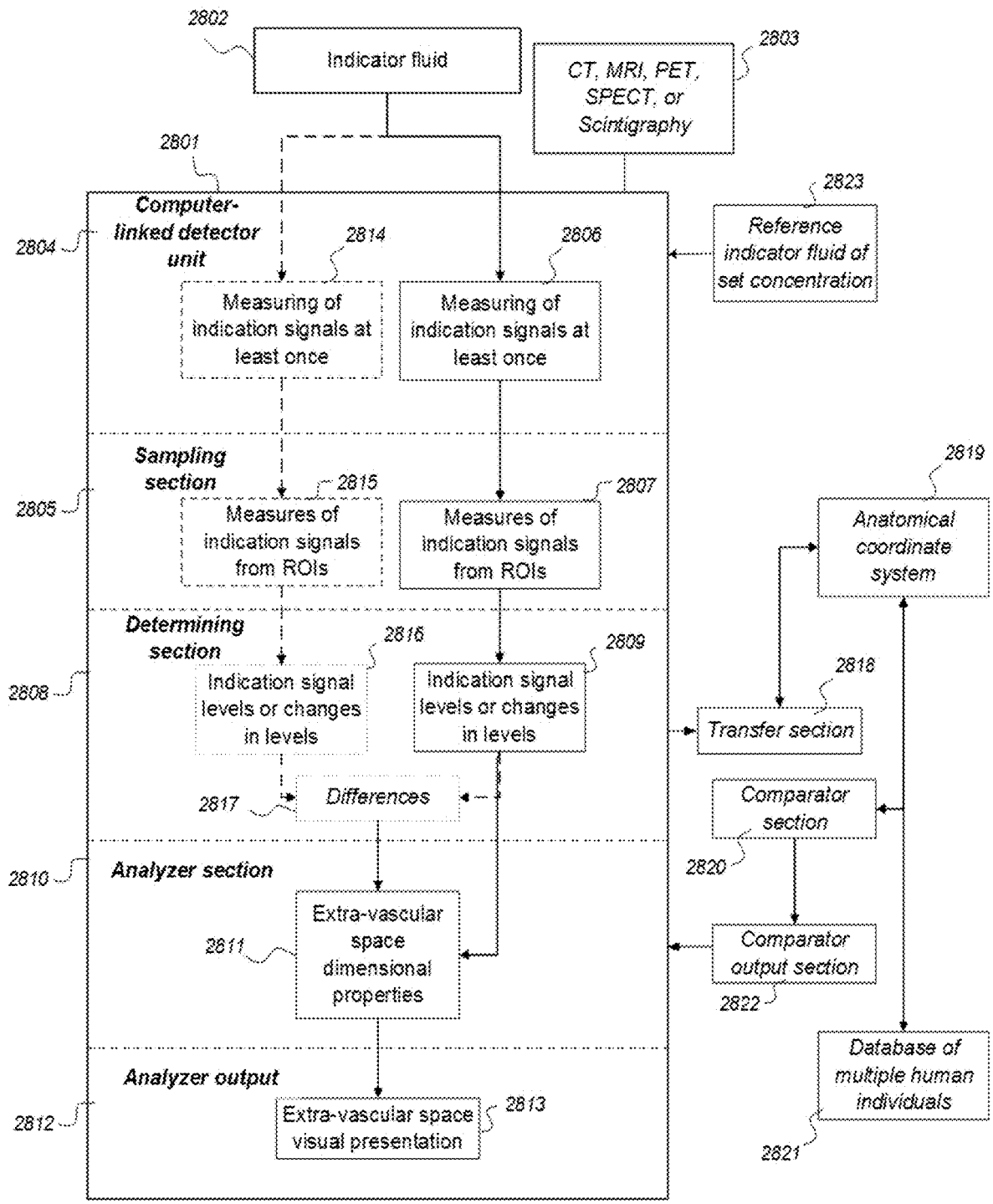
FIG. 28 illustrates a computer-aided method to assess dimensional properties of extra-vascular space of a brain and/or spinal cord compartment of a cranio-spinal cavity of a human.

A third feature of Aspect 5 is illustrated in FIG. 28, disclosing a computer aided method 2801 to assist in assessing dimensional properties of extra-vascular space of a brain or spinal cord compartment of a cranio-spinal cavity of a human, upon an indicator fluid 2802 being in movement in the body of the human, the indicator fluid 2802 comprising one or more of: a CT contrast agent detectable by computed tomography (CT), an MRI contrast agent detectable by magnetic resonance imaging (MRI), a radioactive ligand detectable by one of positron emission tomography (PET), single photon emission computed tomography (SPECT), and scintigraphy imaging 2803, and a substance exhibiting recognized pharmacokinetic properties. The computer aided method 2801 comprises:

a1) measuring at least once, using a detector device 2804 and a sampling device 2805 linked to the computer 2801, indicator fluid indication signals 2806, 2807 through use of imaging acquisition 2803 of brain or spinal cord compartment upon indicator fluid 2802 flow movement from a cerebrospinal compartment of said cranio-spinal cavity and a2) determining, by use of a determining section 2808 in the computer 2801, based on said imaging acquisition, value of indication signal level or change in value of indication signal levels 2809 over time within said brain or spinal cord compartment of said cranio-spinal cavity, the measuring of indication signals 2806, 2807 in feature a1) being provided by a selected one of CT, MRI, PET, SPECT, and scintigraphy imaging 2803, assessing, by use of an analyzer section 2810 in the computer 2801, said dimensional properties of extra-vascular space of said brain or spinal cord compartment 2811 as a function of indication signal 2809 of regions of interest as determined by said feature a2), and providing from an analyzer output 2812 an extra-vascular enhanced visual presentation 2813 of assessed dimensional properties of said extra-vascular space of said brain or spinal cord compartment 2811.

The computer aided method 2801 may further comprise:

b1) measuring at least once, using a detector device 2804 and a sampling device 2805 linked to the computer 2801 indicator fluid indication signals 2814, 2815 through use of imaging acquisition 2803 of brain or spinal cord compartment, upon said indicator fluid 2802 having an intravenous flow movement, and b2) determining, by use of a determining section 2808 in the computer 2801, based on said imaging acquisition, value of indication signal level or change in value of indication signal levels 2816 over time within said brain or spinal cord compartment of said cranio-spinal cavity, said feature b1) and b2) being provided by one of CT, MRI, PET, SPECT, and scintigraphy imaging 2803, assessing, by use of an analyzer section 2810 in the computer 2801, said dimensional properties of extra-vascular space of said brain or spinal cord compartment 2811 as a function of difference in indication signals of regions of interest 2817 as determined by features a2) and b2), and providing from an analyzer output 2812 an extra-vascular enhanced visual presentation 2813 of assessed dimensional properties of said extra-vascular space 2811 of said brain or spinal cord compartment based on features a2) and b2).

The notation indication signal 2806, 2807, 2809, 2814, 2815, 2816 has a broad meaning, and depends on imaging modality. CT refers to Hounsfield Units (HU), MRI refers to SU and PET, SPECT and scintigraphy refer to Standard Uptake Value (SUV). An indication signal 2806, 2807, 2809, 2814, 2815, 2816 is thus a measurable feature derived from an imaging modality, where the indication signal level may be influenced by presence of indicator fluid. Indication signals 2806, 2807, 2809, 2814, 2815, 2816 may be measured both in the presence and absence of indicator fluid 2803.

According to this computer aided method 2801, the extra-vascular space of a brain or spinal cord compartment 2811 is represented by the entire volume outside vessel walls of the cranio-spinal cavity.

When the method 2801 applies MRI, imaging may incorporate T1 weighted sequences with selectable and standardized imaging parameters being at least echo and repetition time, flip angle, matrix, and field of view. Further, all parameters essential to a T1 weighted image should be standardized as far as possible to enable for the highest reproducibility of T1 SU, both between different time points in single human subjects, but also between subjects, and between different MRI scanners. Other MRI sequences that may show useful are T1-mapping, susceptibility weighted imaging, and FLAIR. Assessment of indication signals from this system may also be combined with other MRI sequences such as diffusion weighted imaging, T2 weighted imaging and T1 weighted imaging utilizing intravenous MRI contrast agents. Such combinations could be co-registration of images to render for overlay- and subtraction images, or combinations of image parameters. Information from different imaging modalities may also be combined, such as PET-MRI.

According to this method 2801, one mode may comprise features a1) and a2), which was referred to as mode b) 2605. Another mode, which was referred to as mode a) 2602, may comprise features b1) and b2) that are time separated by a selectable number of hours or a selectable number of days. The difference 2817 in indication signals represents subtraction of indication signal values from comparable imaging acquisitions according a mode b) 2605 comprising features a1) and a2) and another mode a) 2602 comprising features bland b2). Said comparable acquisitions may be related to aligning acquired images of a human.

In one embodiment, assessment of the dimensional properties according to the method incorporates estimation of change, and is indicative of the ability of removal of substances, which refers to removal of waste solutes.

The indicator fluid 2802 used with this method may contain a CT contrast agent, or an MRI contrast agent, or a substance exhibiting recognized pharmacokinetic properties. The CT contrast agent may be a selected one of: iohexol, iodixanol, iomeprol, ioversol, and iobitridol, and a MRI contrast agent either gadobutrol or gadoteric acid.

The indicator fluid 2802 may be a radioactive ligand suitable for PET, SPECT or scintigraphy imaging tied to or chelated with being a contrast agent substance or a substance exhibiting recognized pharmacokinetic properties. For example, the radioactive ligand may be a selectable tracer material from one or more of: $^{89}$Zirconium, $^{99m}$Tc-DTPA, and $^{111}$In-DTPA.

In one embodiment, the indicator fluid 2802 may contain a radioactive ligand, which is chelated with material being at least one of: large-molecule biotechnology based products, antibodies, monoclonal antibodies, recombinant proteins, and antisense or gene therapeutics means. The material may be chelated with said ligand having at least a partial property of making a bond to tumor cells or inflammation cells or amyloid beta plaques.

The MRI contrast agent may be a dendrimer based macromolecular MRI contrast agent of size sufficiently high to be retained outside the BBB.

The indicator fluid 2802 may also be a CT or an MRI contrast agent coupled with one or more of: large-molecule biotechnology based products, antibodies, monoclonal antibodies, recombinant proteins, and antisense or gene therapeutics means.

Further, the indicator fluid 2802 may have affinity to inflammatory cells or tumor cells, and may be a contrast agent conjugated with antibodies or with avidin. In another embodiment, the indicator fluid 2802 may contain a substance having fibrinolytic properties. The indicator fluid 2802 may also contain substances of other therapeutic means.

The indication fluid 2802 may have affinity to certain proteins presented along the paravascular spaces in the brain and spinal cord tissue, such as AQP4, being water channels that regulate transport of water in the brain, or AQP4 anchoring proteins.

Using this method, the indicator fluid 2802 may be configured to be delivered to said cranio-spinal cavity by spinal puncture and intrathecal injection, though the delivery procedure itself is not part of the invention.

According to this method 2801, comparisons may be done between individuals and a cohort of individuals. The method 2801 may be applied onto multiple ones of human individuals to determine indication signals through use of said imaging within ROIs with an indicator fluid present within the CSF compartment to determine changes in indication signals over time within said ROI, wherein said ROIs of said imaging acquisition are transferred by transfer means 2818 to an anatomical coordinate system 2819. The anatomical coordinate system 2819 may be configured to enable segmentation of selectable anatomic regions, wherein a comparison by comparator means 2820 of said levels or change in levels of indication signals 2809, 2816 over time is made between indication signal changes in a single human individual and changes in said multiple ones of human individuals using database 2821 information. A presentation by comparator output 2822 is provided for any deviation in movement of substances as measured and imaged from a single human individual compared to average movement of substances in said multiple ones of human individuals.

Concerning MRI, the method allows that the indication signals are MRI SUs, which may be made into standardized SUs through use of a standardization device comprising an extra-body device containing at least one reference indicator fluid of specific concentrations 2823. At least one reference indicator fluid 2823 is located within one or more containers to be located externally of the body of the human, and may also be filled with dedicated material being a dummy material having liquid properties, e.g. viscosity or molecular property, resembling standard cranio-spinal cavity liquid, or having semi-solid material properties. e.g. density or molecular property, resembling standard properties of standard brain tissue. Standardized SUs allow for measurement of absolute values of indicator fluid within the ROI of a human individual.

Previous MRI techniques utilizing contrast enhancement have applied intravenous contrast agents. Due to the BBB, the contrast agent does not escape from the blood circulation confined to blood vessels 2503 since the tight-junctions between endothelial cells prevent large molecules from escaping from the lumen of the blood vessels. Therefore, intravenous contrast agents provide for visualization of the vascular spaces 2503 of the brain tissue compartment 2501. The present invention utilizes contrast agents having been administered to the CSF compartment, allowing for contrast distribution within the extra-vascular spaces 2504 of the brain and/or spinal cord tissue compartment. In this situation, the intact BBB serves as an advantage since it prevents the contrast agent from directly leaking over to blood vessels 2503, and thus confines the contrast agent to the extra-vascular space 2504. Thus, as opposed to the techniques revealing contrast agent distribution within intact brain and spinal cord blood vessels 2503, or outside disrupted brain blood vessels, the present invention relates to contrast agent distribution outside all brain and spinal cord blood vessels, i.e. the extra-vascular spaces 2504. Even though the latter space is much larger than the intravascular space, it has yet been explored to a very limited degree, and until now the extra-vascular brain and spinal cord compartments have been accessed with contrast agents only when the BBB is disrupted, and intravenous contrast agent escapes the intra-vascular space and leaks into the extra-vascular space. The extra-vascular space outside the intact BBB has, however, not been accessible for contrast agents being present intravenous only.

The intra-vascular compartment 2503 of a brain compartment (may also be denoted vascular space) can be visualized by contrast agent confined to the blood circulation. For example, intravenous gadobutrol visualizes the intra-vascular compartment on MRI. Leakage of contrast agent from intra-vascular compartment through the BBB may cause efflux of contrast agent to outside the vascular bed, i.e. extra-vascular, but then because of disease process. Intravenous contrast agents used for CT or MRI visualizes the vascular compartment 2503.

In comparison, a contrast agent present within the CSF compartment, e.g. gadobutrol having been administered intrathecally, causes distribution outside the vascular compartment, such as the brain paravascular compartment 2505 and within the interstitial space 2506 (i.e. space between the cells). The extra-vascular space 2504 incorporates both the paravascular space 2505 and the interstitial space 2506. Hence, the paravascular fluid within the paravascular space 2505 and the interstitial fluid (ISF) between cells 2506 communicate, and being a part of the extravascular fluid within the extra-vascular space 2504. Aspect 5 of the invention relates both to the visualization of the dimensional properties of the extra-vascular space (i.e. assessment of anatomical and structural characteristics), and quantifying removal of substances from the extravascular compartment (i.e. assessment of functional characteristics).

The extra-vascular compartment may be obstructed by inflammatory cells (such as in multiple sclerosis), or by tumor cells (such as in malignant gliomas), or by amyloid-$\beta$ plaques (such as in Alzheimer's). The degree to which the extra-vascular space is occupied may be quantified by determined absolute amounts of contrast agent, using the device described in Aspect 7 of the invention. While automated detection of impaired extra-vascular contrast agent enhancement may be most precise, the invention also provides for qualitative assessment of enrichment of contrast agent within the extra-vascular compartment. Such qualitative assessment may be visual image analysis, and may include e.g. utilizing tools such as comparing SU measurements in ROIs from different part of the brain and spinal cord.

In the following, Aspect 6 of the invention is described, namely an indicator fluid. In one embodiment, said indicator fluid allows for attachment of other molecules (ligands) to the indicator fluid. Thereby the indicator fluid becomes a carrier for, or is carried by, other molecules.

Figure 29:
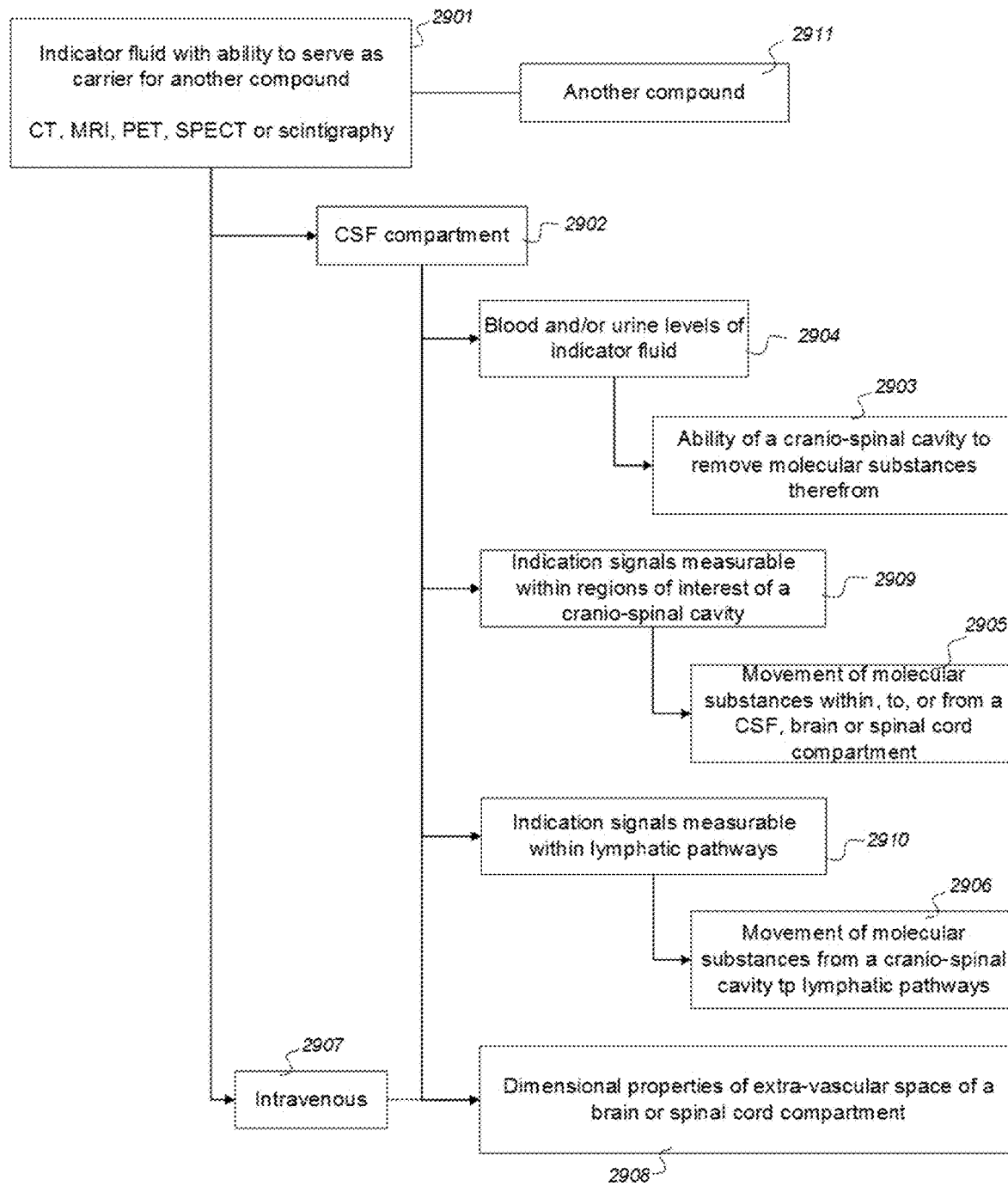
FIG. 29 illustrates usage of an indicator fluid for use in a human for a selected one of: CT, MRI, PET, SPECT, and scintigraphy, wherein the indicator fluid may be a contrast agent serving as a carrier for another compound.

In another embodiment of this invention, we describe Aspect 6. Aspect 6 is illustrated in FIG. 29 and describes an indicator fluid 2901 for use in a human, the indicator fluid 2901 comprising a contrast agent being one or more of:

a computed tomography (CT) contrast agent selected from one of iohexol, iodixanol, iomeprol, ioversol and iobitridol, a magnetic resonance imaging (MRI) contrast agent being one of gadobutrol, gadoteric acid, and a dendrimer based macromolecular magnetic resonance imaging contrast agent of size sufficiently high to be retained outside the blood-brain-barrier, a radioactive ligand suitable for positron emission tomography (PET), single photon emission computed tomography (SPECT) or scintigraphy, and a substance exhibiting recognized pharmacokinetic properties, for a selected and related one of: CT, MRI, PET, SPECT, and scintigraphy, wherein the indicator fluid 2901 is of a type to be movable from a cerebrospinal compartment 2902 of a crania-spinal cavity of the human and thus when present in a human body to contribute to one of:

a) assessing ability of a cranio-spinal cavity of the human to remove molecular substances therefrom 2903, and levels of the indicator fluid to be measured subsequently once or at selectable time intervals in blood or urine of the human 2904, b) assessing movement of molecular substances within, to or from a cerebrospinal fluid, brain or spinal cord compartment of a cranio-spinal cavity of the human 2905, and c) assessing movement of molecular substances from a cranio-spinal cavity to lymphatic pathways 2906, e.g. cervical or neck lymph nodes, or kidneys of a human, or wherein the indicator fluid 2901 is of a type to be movable intravenously 2907 as well as from a cerebrospinal compartment 2902 of a crania-spinal cavity of the human, and thus when present in the human body to contribute to:

d) assessing dimensional properties of extra-vascular space of a brain or spinal cord compartment of a crania-spinal cavity of a human 2908.

Regarding movement of molecular substances within, to, or from a CSF, brain or spinal cord compartment 2905, the indicator fluid 2901 may provide for indication signals that are measurable within regions of interest of the cranio-spinal cavity 2909. Moreover, the indicator fluid 2901 may provide for indication signals that are measurable within lymphatic pathways 2910 for assessing movement of molecular substances from a cranio-spinal cavity to lymphatic pathways.

An inventive step of said Aspect 6 is that the indicator fluid 2901 may be a contrast agent serving as a carrier for another compound 2911.

With regard to another compound 2911, it may have affinity to inflammatory cells or tumor cells or amyloid beta plaques, and wherein the contrast agent may be conjugated with antibodies or with avidin. In another embodiment, said another compound 2911 may have fibrinolytic properties.

The indicator fluid 2901 may be of a CT or an MRI contrast agent coupled with one or more of: large-molecule biotechnology based products, antibodies, monoclonal antibodies, recombinant proteins, and antisense or gene therapeutics means 2911.

The indication fluid 2901 may have affinity to certain proteins 2911 presented along the paravascular spaces in the brain and spinal cord tissue, such as AQP4, being water channels that regulate transport of water in the brain, or AQP4 anchoring proteins.

In still another embodiment, the indicator fluid 2901 may be a radioactive ligand suitable for PET, SPECT or GCI imaging tied to or chelated with the contrast agent substance or with a substance having pharmacokinetic properties 2911. The radioactive ligand may be a selectable tracer material from at least one of: $^{89}$Zirconium, $^{99m}$Tc-DTPA, and $^{111}$In-DTPA. Further, the indicator fluid 2901 may contain a radioactive ligand, which is chelated with material being selected from one or more of: large-molecule biotechnology based products, antibodies, monoclonal antibodies recombinant proteins, and antisense or gene therapeutics means 2911. The material chelated with said ligand has at least a partial property of making a bond to tumor cells or inflammation cells or amyloid beta plaques.

The indicator fluid 2901 may be configured to be delivered to said CSF compartment by spinal puncture and intrathecal injection. Notably, the delivery procedure itself is not part of the present invention, as this invention comes into play after delivery has taken place.

Said ability of a cranio-spinal cavity to remove 2903 or move 2905 substances is described by parameters of removal 2905 and refer to clearance of indicator fluid 2901 from the CSF compartment or the brain or spinal cord compartment and being a function of removal or movement of waste solutes.

When being present within a CSF compartment, an indicator fluid 2901 with suitable molecular size will, like other substances with similar properties, enter paravascular spaces 2505 along the outside of vessels 2503 penetrating through the surface of the brain and spinal cord. The BBB will prevent the indicator fluid from leaking into the blood circulation, and thus be confined to the extra-vascular compartment 2504 before it is further cleared to LNs, blood and urine. Presence, or absence, of indicator fluid at certain time points after having been administered to the CSF compartment will therefore provide for information about dimensional properties of the extra-vascular brain and spinal cord compartments. The extra-vascular compartment 2504 is the scene of numerous disease processes in the brain, such as neoplastic, inflammatory and degenerative processes, and of a much larger quantity than the intra-vascular compartment.

A wide range of other molecules, also referred to as another compound 2911, may be attached to an indicator fluid 2901 (e.g. gadolinium-based MRI contrast agent) to allow for co-infusion of substances to the paravascular and interstitial space. For example, an MRI contrast agent 2901 may become both a carrier and visualizer on MRI for another compound 2911, i.e. other molecules of various functions. The advantage is that distribution of the other molecules (i.e. another compound 2911) may be traced within the paravascular and interstitial spaces in e.g. T1 weighted images due to the paramagnetic effect of the contrast agent. Concerning the present invention of imaging extra-vascular compartment circulation (see Aspect 5), there are different possibilities.

In comparison, a wide range of PET ligands have been developed. The ligand may be connected to the isotope that is used for visualization. Regarding the present invention, the contrast agent, e.g. gadobutrol, provides for the signal and visualization, while the ligand (or another compound 2911) addresses the function to be studied.

Some examples of another compound attachment 2911 may be highlighted. Molecules with affinity to tumor cells may reveal the spread of tumor cells within the paravascular and extracellular spaces. One example relates to gliomas, which are malignant tumors with poor prognosis. The tumor cells spread along the blood vessels, and along the paravascular/glymphatic pathway. The present invention provides a solution for imaging the spread of tumor cells. It would be expected that enrichment of indicator fluid 2901 is hampered in the areas with tumor infiltration of the extracellular space, however, when disease targeting compounds 2911 are attached to indicator fluids 2901, enrichment of indicator fluid 2901 may be enhanced at the site of pathology.

Other compounds 2911 such as molecules with affinity to inflammatory cells would reveal the distribution of inflammatory changes, which is applicable for a wide range of diseases. For example, inflammatory changes appear along the small vessels of the brain in the clinical state multiple scleroses. The paravascular pathway is probably the major transport pathway for inflammatory cells. By connecting molecules with affinity for inflammatory cells as another compound 2911 to indicator fluid 2901 such as contrast agent, we may assess distribution of inflammation as well as the integrity of the paravascular pathways. Other compounds 2911 may be molecules with affinity to molecular products of neurodegeneration, such as amyloid-β plaques. For example, antibodies with affinity to amyloid-β plaques 2911 may be attached to an MRI contrast agent 2901.

Molecules 2911 known to improve neurological function may be connected to the indicator fluid serving as contrast agent 2901. Various therapeutic molecules are deliverable to the CSF compartment, for example intrathecal or intraventricular. By binding of therapeutic molecules 2911 to contrast agents 2901, the distribution and metabolism within the paravascular and interstitial compartments may be explored. For example, brain-derived neurotrophic factor (BDNF) given to the entorhinal cortex of monkeys improves neurological function. Connecting BDNF as another compound 2911 to contrast agent 2901 may be used for drug function targeting. However, the present invention is not for diagnosis or treatment of disease.

In another embodiment, molecules may be attached 2911 to contrast agent 2901 to enhance the extra-vascular compartment and assess clearance of substances from the brain. One obvious candidate is the molecule albumin 2911, which tends to escape from the extracellular compartment through the blood vessels along with water. Another example of another compound 2911, is the water channel aquaporin-4 (AQP4), which is bound to α-syntropin and dystrophin-71 (Dp71) within the dystrophin-associated protein complex (DAPC).

Aspect 6 of the invention does not relate to the chemical process of attaching ligands 2911 to MRI contrast agents 2901, but to area of using contrast agents 2901 with attached ligands 2911 according to the first, second, third and fifth aspects of the present invention.

In the following, Aspect 7 of this invention is described, which include indicator fluid for standardization of values of detected SUs measurable through use of imaging of human body ROI by use of MRI.

Figure 30:
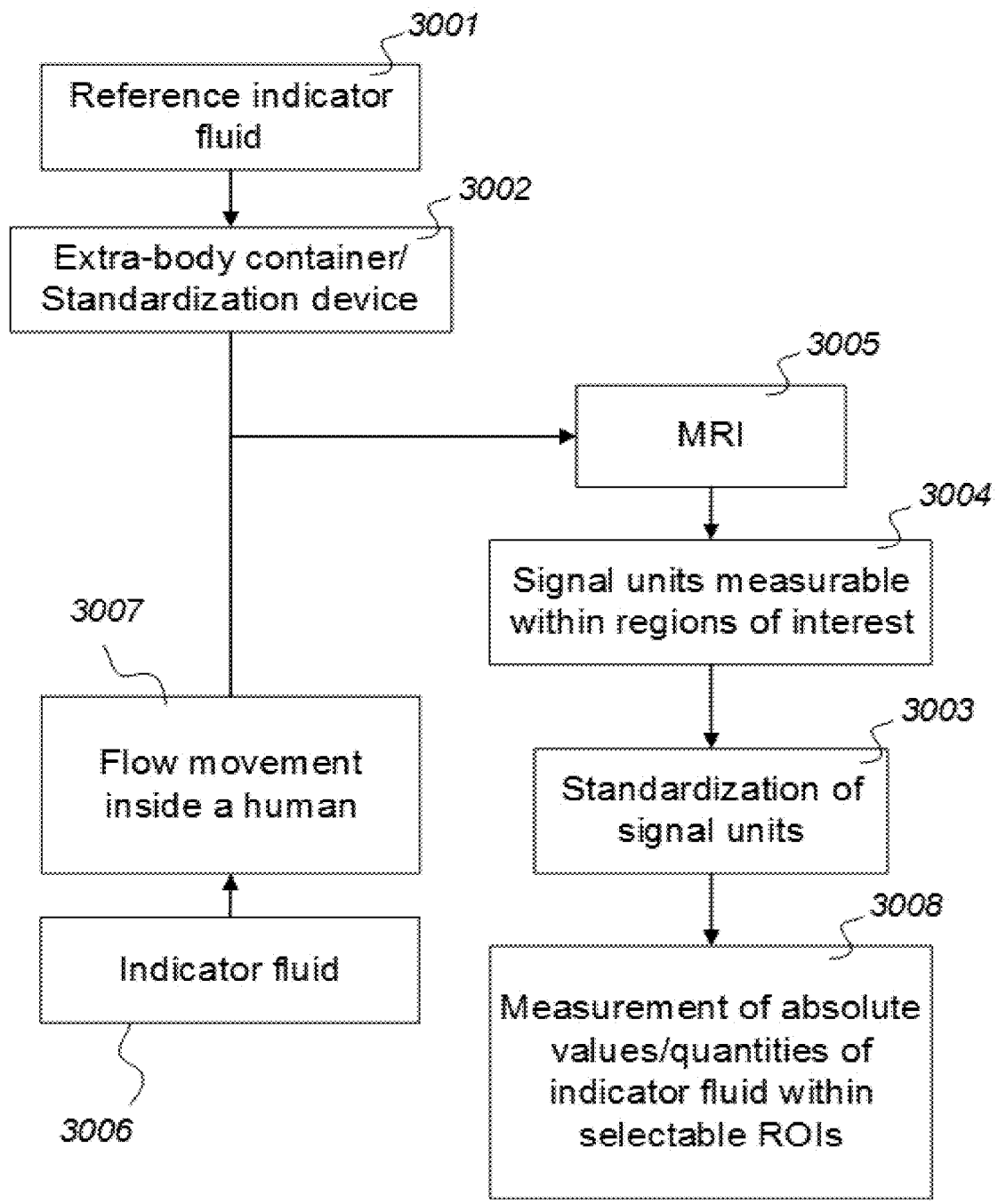
FIG. 30 illustrates usage of a reference indicator fluid to be used with a standardization device to standardize values of detected SUs measurable through use of MRI.

A sole feature of Aspect 7 is illustrated in FIG. 30, and discloses a reference indicator fluid 3001, configured to be used with a standardization device 3002 having at least one reference indicator fluid housing locatable on an exterior surface of a human body, to standardize values of detected signal units 3003 measurable through use of imaging of human body regions of interest 3004 by use of magnetic resonance imaging (MRI) 3005 and in interaction with a matching indicator fluid 3006 to be in flow movement inside a human 3007, the reference indicator fluid providing for MRI signal unit values measured 3004 through use of MRI imaging 3005 of said human and based on said indicator fluid 3006 in flow movement inside the human to be standardized 3003 through a calibration against reference values of signal units measured from the reference indicator fluid 3001, wherein the reference indicator fluid 3001 is MRI compatible and being a contrast agent of a type of said matching indicator fluid and selected from one of: gadobutrol, gadoteric acid, and a dendrimer based macromolecular magnetic resonance imaging contrast agent of molecular size sufficiently large to be retained outside a blood-brain-barrier of the human body.

In one embodiment, at least two containers are provided by the device 3002, each container housing a reference indicator fluid 3001 having a unique fluid concentration. The container housing 3002 the reference indicator fluid 3001 may be filled with a dedicated material being a liquid or a semi-solid material. The dedicated material may be a dummy material having liquid properties, e.g. viscosity or molecular property of standard cranio-spinal cavity liquid or having semi-solid material properties. e.g. density or molecular property, compatible with standard material property of brain tissue, LN tissue or kidney tissue.

Concerning the device 3002 to which the reference indicator fluid 3001 is to be used, at least one container may be located externally of the body of the human. SUs are standardized or normalized 3003 through use of the device 3002 to allow for measurement of absolute values/quantities of indicator fluid for any ROI of said assessment 3008.

Figure 31:
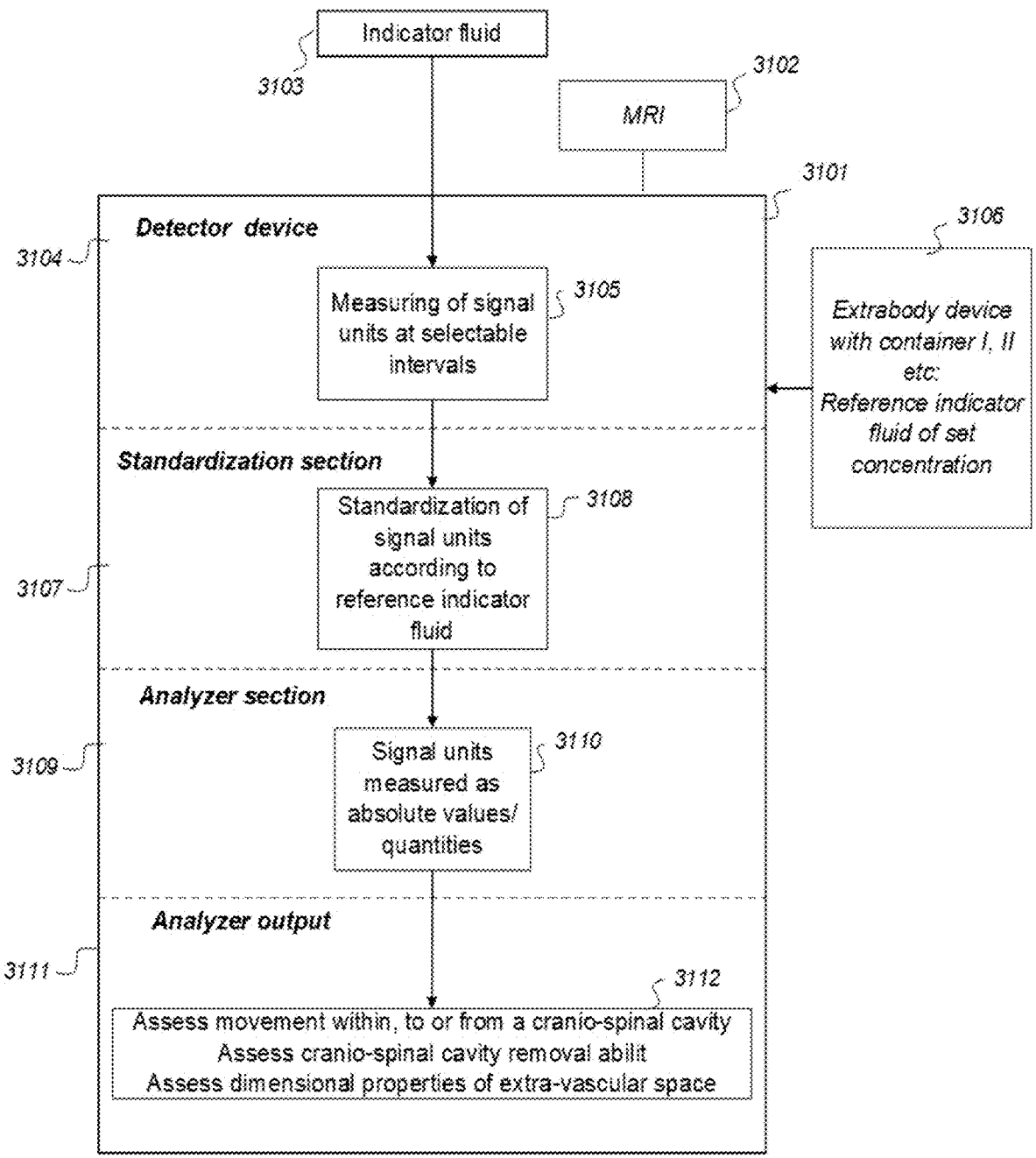
FIG. 31 illustrates a measurement standardization method for use with a system to assess movement of substances within, to or from a CSF, brain or spinal cord compartment of a cranio-spinal cavity to assess cranio-spinal cavity removal ability, and to assess dimensional properties of extra-vascular space of a human.

FIG. 31 illustrates a measurement standardization method for use with a system for:

a) assessing movement of substances within, to or from a CSF, brain or spinal cord compartment of a cranio-spinal cavity of a human using an indicator fluid 3112, or b) assessing movement of substances from a cranio-spinal cavity to kidneys and/or lymphatic pathways, e g. LNs, or kidneys of a human 3112, or c) for assessing dimensional properties of extra-vascular space of a brain or spinal cord compartment of a cranio-spinal cavity of a human 3112.

As further illustrated in FIG. 31, the standardization method for use with a system 3101 comprises an apparatus configured for MRI acquisition 3102, and operative with a detector device 3104 to measure MRI SUs 3105 by use of said apparatus 3102 within ROIs of said assessing, with the indicator fluid 3103 present within the CSF compartment, which is a contrast agent suitable for MRI or PET-MRI acquisition. During MRI, SUs is standardized through use of an extra-body device having one container or a plurality of containers 3106. The container containing at least one specific reference indicator fluid of set concentration 3106. Using a standardization section 3107, detected SUs thereby standardized or normalized 3108 with reference to said reference indicator fluid provided at the extra-body device 3106. By means of an analyzer section 3109, this procedure allows for quantification or measurement of absolute values of indicator fluid within said ROI 3110. Using an analyzer output section 3111, the standardization method is used for: a) assessing movement of substances within, to or from a CSF compartment, a brain or a spinal cord compartment, of a cranio-spinal cavity of a human 3112, orb) assessing movement of substances from a cranio-spinal cavity to kidneys and/or lymphatic pathways, e g. LNs, or kidneys of a human 3112, or c) for assessing dimensional properties of extra-vascular space of a brain or spinal cord compartment of a cranio-spinal cavity of a human 3112.

According to this method, at least one container of the standardization device 3106 may be configured to be located externally of the body of the human. At least two containers are provided, each container housing a reference indicator fluid 3106 having a unique fluid concentration. Further, container housing said reference indicator fluid 3106 is additionally filled with a dedicated material. Said dedicated material may be a dummy material having liquid properties, e.g. viscosity or molecular property of standard cranio-spinal cavity liquid or having semi-solid material properties, e.g. density or molecular property, resembling standard material property of brain tissue, LN tissue or kidney tissue. The container may be located externally of the body of the human.

Using this method, SUs standardized or normalized 3108 through use of said extra-body device 3106 may allow for measurement of absolute values of indicator fluid for any ROI of said assessing 3110. The concept of allowing for two or more containers with inside of each MRI contrast agents in different, but preset concentrations, allows for estimation of the change in SUs as a function of change of contrast agent concentration. This allows for extracting parameters, such as a constant, which can be applied to assess contrast agent concentration in a fluid cavity and/or body tissue quantitatively, or semi-quantitatively.

The reference indicator fluid 3103 may be MRI compatible and being a contrast agent selected from one of: gadobutrol, gadoteric acid, and a dendrimer based macromolecular MRI contrast agent of size sufficiently high to be retained outside the BBB. Gadolinium-diethylenetriamine (Gd-DTPA) is another MRI contrast agent that may be used; however, it is less preferable than gadobutrol and gadoteric acid since it is chemically less stable.

Figure 32:
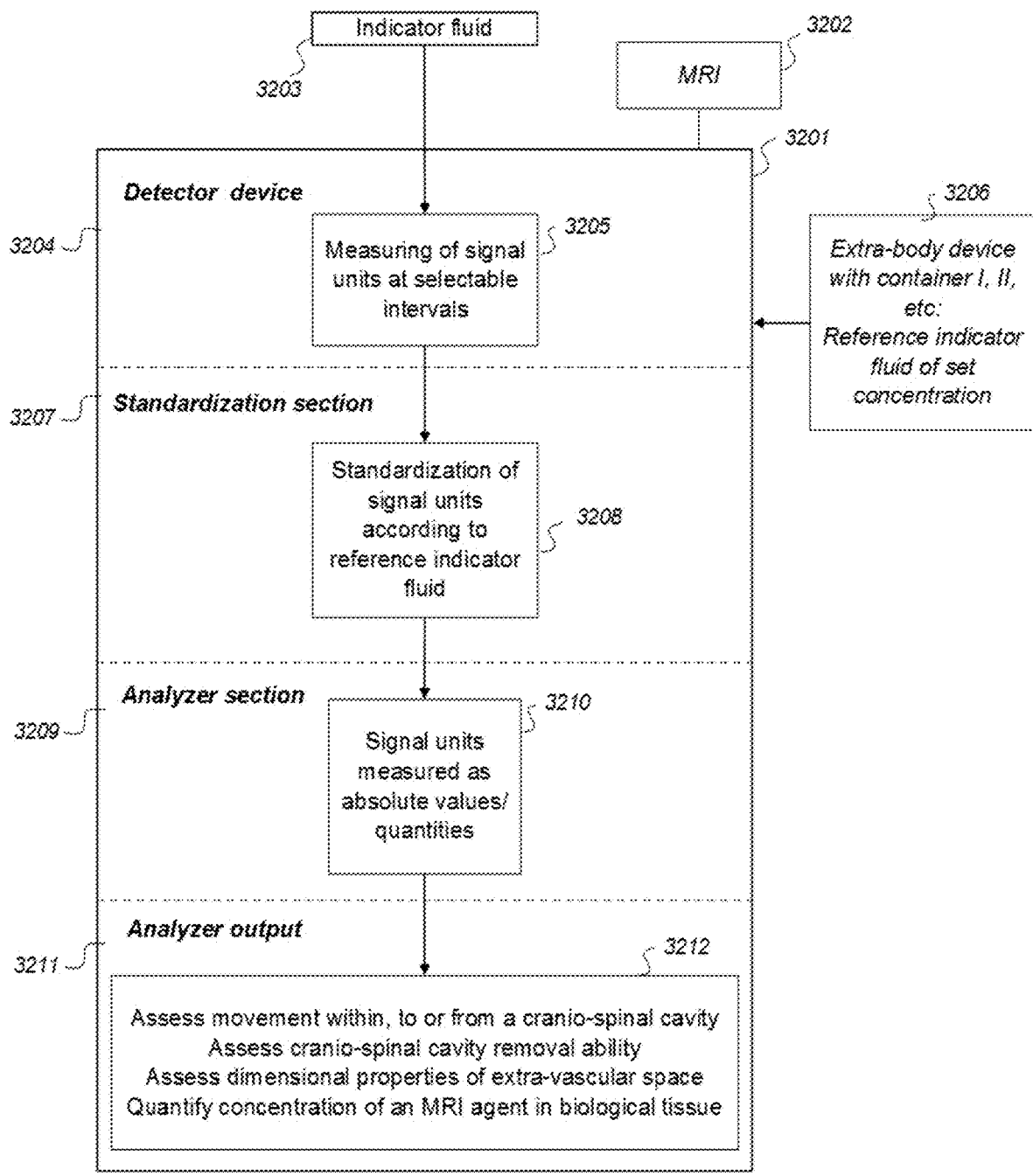
FIG. 32 illustrates a measurement standardization device for use with a system to assess movement of substances within, to or from a CSF, brain or spinal cord compartment of a cranio-spinal cavity, to assess cranio-spinal cavity removal ability, and to assess dimensional properties of extra-vascular space of a human.

FIG. 32 illustrates a measurement standardization device 3201 for use with a system configured for a selected one of:
a) assessing movement of substances within, to or from a CSF, brain or spinal cord compartment of a craniospinal cavity of a human using an indicator fluid 3212,
b) assessing movement of substances from a cranio-spinal cavity to kidneys and/or lymphatic pathways, e g. LNs, of a human 3212,
c) assessing dimensional properties of extra-vascular space of a brain or spinal cord compartment of a cranio-spinal cavity of a human 3212, and
d) quantifying concentration of an MRI contrast agent in biological tissue 3212.

The standardization device 3201 for use with a system comprises an apparatus for MRI acquisition 3202, and operates with a detector device 3204 to measure MRI SUs 3205, by use of said apparatus 3202 within ROIs with indicator fluid 3203 present within the CSF compartment, which is a contrast agent suitable for one of MRI or PET-MRI acquisition. The standardization device 3201 may be configured to enable said measuring of MRI SUs 3205 to be standardized against a reference, said device being an extra-body device exhibiting one container or a plurality of containers 3206. The container contains at least one specific MRI reference indicator fluid of a set concentration 3206.

Regarding the device 3201, at least two containers are provided, each container housing a reference indicator fluid having a unique fluid concentration 3201. The container housing the reference indicator fluid 3201 may also be filled with a dedicated material being a liquid or a semi-solid material. At least one container may be located externally of the body of the human. The dedicated material may be a dummy material having liquid properties, e.g. viscosity or molecular property, resembling standard cranio-spinal cavity liquid or having semi-solid material properties, e.g. density or molecular property, resembling standard material property of brain tissue, LN tissue or kidney tissue. One of the containers may not contain MRI contrast agent. One of the containers may be filled with water, or a fluid resembling CSF.

The concept of allowing for two or more containers 3206 with inside of each MRI contrast agents in different, but preset concentrations, allows for, by use of an analyzer section 3209, estimation of the change in SUs as a function of change of contrast agent concentration 3210. The analyzer output 3211 of the device 3201 allows for extracting parameters, such as a constant, which can be applied to assess contrast agent concentration in a fluid cavity and/or body tissue quantitatively, or semi-quantitatively 3212.

The SUs standardized or normalized through use of said extra-body device allow for measurement of absolute values of indicator fluid for any ROI of said assessing 3212.

Figure 33A:
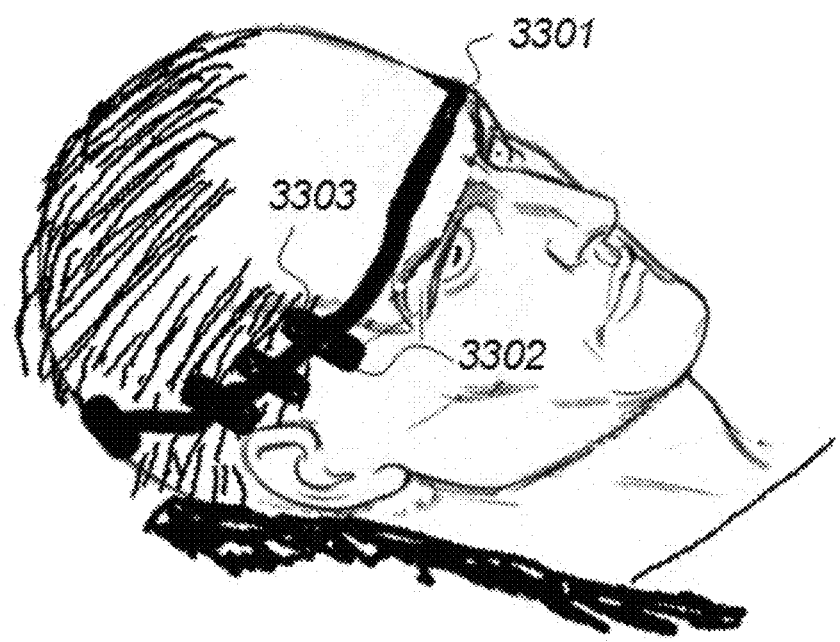
FIGS. 33a and 33b illustrate a standardization device, on FIG. 33a attached to the head of a human, to normalize values of detected SUs measurable through use of imaging of human body ROI by use of MRI, and in interaction with a matching indicator fluid. Such a standardization device to be used within MRI scanners contains one or more containers, as shown on the two views of FIG. 33b, with selectable concentrations of a selected MRI contrast agent. It can be attached to the patient, for example by a strap around the head. Thereby the SUs of the T1 signal of the particular MRI scanner may be calibrated, allowing for accurate comparison of T1 SUs between MRI scanners.
Figure 33B:
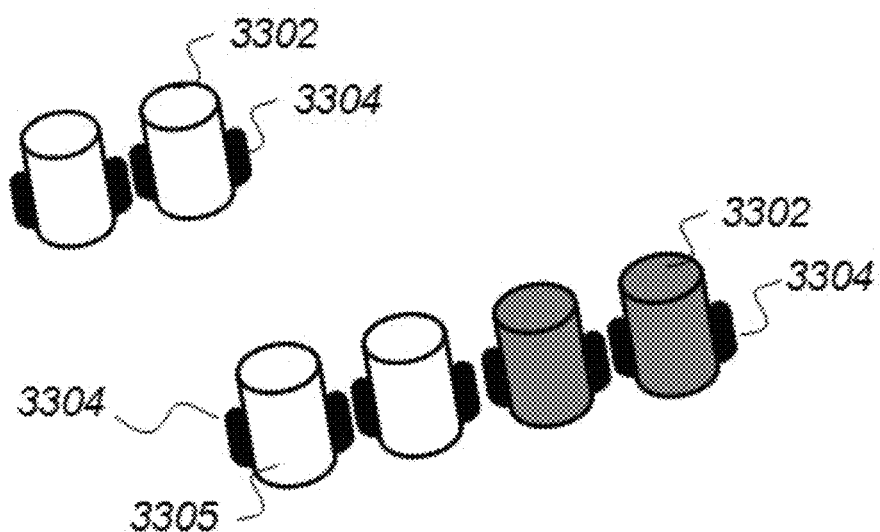

According to this device 3201, the reference indicator fluid 3203 may be MRI compatible and being a contrast agent selected from one of: gadobutrol, gadoteric acid, and a dendrimer based macromolecular MRI contrast agent of molecular size sufficiently large to be retained outside the BBB. Gadolinium-diethylenetriamine (Gd-DTPA) is another MRI contrast agent that may be used; however, it is less preferable than gadobutrol and gadoteric acid since it is chemically less stable FIG. 33 illustrates possible structural issues of a measurement standardization device. The main elements of the device have been shown in FIG. 32. Further details are provided in FIG. 33a-b. The device is used to standardize values of detected MRI SUs 3205 measurable through use of imaging of human body ROI by use of MRI 3202, and in interaction with an MRI indicator fluid 3203 administrable to the human body. The device 3201 exhibits at least one container configured to house a specimen of said indicator fluid to constitute a reference indicator fluid therein having a specific concentration 3206. Further, the device 3201 provides for MRI SU values measured through use of said imaging 3205 of said human and based on indicator fluid after having been administered to the human to be standardized through a calibration against reference values of SUs measured from container contents in said device. The device 3201 is made from a material having a low-magnetic or non-magnetic property and being at least partly flexible, and includes attachment means enabling the device to be detachably attachable to an exterior region of said human.

Further details are provided in FIG. 33a-b. The attachment means 3301 for attachment to the head of a human may be a band or web to be wrapped around the head of a human, thereby providing for attachment of a selectable number of containers 3302 to head region by said band 3301. The head region 3303 is a side region of the head. FIG. 33b illustrates attachment means 3304 of the containers 3302 with reference indicator fluid 3206.

In another embodiment, the attachment means 3304 allows for connection to a head or neck coil of an MRI machine, which allows for a selectable number of containers 3302, 3305 to have close contact with the head of the human.

The device 3201 may be arranged so that said container is subdivided into a plurality of sealed compartments 3302, 3305 containing a same plurality of mutually separated specimens of said reference indicator fluid 3206, each specimen having a specific and unique concentration, here illustrated by containers 3302 and 3305. Said specific concentration(s) of indicator fluid 3203 and reference indicator fluid 3206 are related to SUs on specific imaging acquisitions.

The inventive device is preferably of small size and should be placed nearby the head. Various modifications of the device are possible. It is possible to use one concentration of the contrast agent, while 3-5 different concentrations may be more preferable, as a curve demonstrating SU increase as function of contrast agent concentration may be created. The device may also be attached to the surface of other body regions than the head to allow for standardization of image SUs when imaging other body parts.

MRI SUs derive from the greyscale of MR images. SUs are highly dependent on image parameter settings, magnetic field strengths, and type of MRI scanner. SUs can therefore not be directly compared between different MRI acquisitions, and neither quantified directly, but relates merely to relative differences within one single image. The inventive step of the standardization device is to enable normalization, or calibration, of SUs in single MRI acquisitions, rendering for quantitative, or semi-quantitative, assessments, and by those means comparisons of SUs between different MRI acquisitions.

According to device specifications, at least two containers (FIG. 33b) are provided, each container having an indicator fluid of a unique and specific concentration being different from that of any of other of the containers. Further, at least one container is configured to additionally house a dedicated base material being a liquid or semi-solid material or a combination thereof replicating a specific body liquid or tissue properties of the human. The base materials in the containers are all of same composition.

Concerning the attachment means 3304, it is configured to be attached to one of:
the head of the human,
a head or neck coil co-operable with an apparatus for said imaging,
a lymph region, and
an exterior body part adjacent to internal organs of interest.

The concept of allowing for two or more containers with inside of each MRI contrast agents in different, but preset concentrations, allows for estimation of the change in SUs as a function of change of contrast agent concentration. This enables for extracting parameters, such as a constant, which can be applied to assess contrast agent concentration in a fluid cavity and/or body tissue quantitatively, or semi-quantitatively 3210.

Further, at least one container of the device is filled with liquid base material 3302, and configured to assist standardizing measurement of SUs within ROI of a CSF compartment 3208. Alternatively, at least one container is filled with semi-solid base material 3305, which is configured to standardize measurement of SUs within ROI of a brain or spinal cord compartment or of a lymph or kidney region 3208.

The liquid base material 3302 has liquid properties, e.g. viscosity or molecular property, resembling standard craniospinal cavity liquid. The semi-solid material 3305 has properties. e.g. density or molecular property, resembling standard properties of standard tissue in brain, spinal cord compartment, LN or kidney.

To be used with said device, the reference indicator fluid 3203 is MRI compatible and being a contrast agent selected from one of: gadobutrol, gadoteric acid, and a dendrimer based macromolecular MRI contrast agent of size sufficiently high to be retained outside the BBB. Gadolinium-diethylenetriamine (Gd-DTPA) is another MRI contrast agent that may be used; however, it is less preferable than gadobutrol and gadoteric acid since it is chemically less stable.

This invention describes a novel device for determining absolute values of SUs measured on MRI acquisitions from extra-body containers with contents of contrast agents of specific concentrations 3210.

One example is given. During MRI acquisitions, a device with gadobutrol in one or more containers with certain concentrations is placed nearby the head. The concentrations of gadobutrol correspond to a certain number of SUs in the T1 images. By comparing the SUs of the containers with the SUs of the T1 images of the cranio-spinal compartment, and assessing differences in SU of different containers as function of differences in contrast agent concentrations, accurate concentration levels of gadobutrol concentrations in body compartments may be determined.

It is important to note that SUs may vary between MRI scanners even though the same image specifications are used. To adjust for this methodological weakness, the presently described device is to be used within MRI scanners nearby a body surface during T1 MRI acquisition. This device contains one or more containers containing different concentrations of a selected contrast agent. Thereby the SUs of the T1 images of the MRI scanner may be calibrated, allowing accurate comparison of SUs between MRI scanners. In addition, the ability to describe changes in SU after contrast agent application within the cranial cavity with an extra-body device also provides the ability to determine change in contrast agent concentration within the different ROIs of the cranial cavity. Accordingly, the use of an extra-cranial device enables semi-quantification, or quantification, of contrast agent concentration. For example, the concentration of contrast agent that enhances in brain tissue may be semi-quantitatively, or quantitatively, assessed by placing the device with containers of one or more known concentrations of the contrast agent in close vicinity of the patient's head. Thereby, the SU change within the cranial cavity may be semi-quantitatively determined. The contrast agent used in the device containers is the same as applied for T1 MRI acquisition.

Although the device is here exemplified for standardization of T1 SU, this represents no limitation, and the device may be used for standardization of SUs from any MRI sequence, for example SWI, T2* and FLAIR.

The extra-body device, constituting Aspect 7 of the invention, represents a non-limiting example of an embodiment for performing the method described as Aspects 2-6 of the invention. This was further illustrated in FIG. 21a-b and FIG. 22a-f. FIG. 21a illustrated clearance curves of simultaneous measurements of change in SUs within a CSF space compartment (ROI-1) 2103, and the SUs retrieved from an extra-body compartment (ROI-2) 2106. This extra-body compartment can be the device described as Aspect 7 of the invention. For example, the device may constitute a set of two or more containers with different concentrations of the contrast agent gadobutrol. Thereby, the different SUs of the T1 images can be standardized according to the concentrations of gadobutrol. The clearance curve of ROI-2 2106 may be determined according to curve of ROI-2 as subtraction, dividend or being formula-based. In that way, the change in SU within a CSF compartment 2103 may be expressed as a function of change in SU within an extra-body compartment. Using this approach, accurate changes in SUs may be determined, allowing for accurate comparisons of specific ROIs within one individual. In addition, accurate comparisons may be done between individuals using different MRI scanners, provided similar image specifications are being used. This same aspect is illustrated within FIG. 21b, showing simultaneous measurements of change in SUs within a brain tissue compartment (ROI-1) 2109, and the SUs retrieved from an extra-body compartment (ROI-2) 2112. The extra-body compartment (ROI-2) may be the device containing different concentrations of contrast agent. Relating the clearance curve of ROI-1 2109 to the SU's corresponding to different concentrations of contrast agent of ROI-2 enables semi-quantification, or quantification, of changes in concentrations of contrast agent within the brain tissue compartment (ROI-1).

The application of an extra-body device is no requirement for the implementation of the invention, but provides clear advantages such as inter-scanner comparisons, and the opportunity for semi-quantification, or quantification. On the other hand, comparisons between repeated MRI acquisitions require the use of identical, fixed MRI sequence parameters during subsequent MRI acquisitions, as previously commented on. In addition, a robust method for alignment of repeated scans should be incorporated.

Various aspects of the present invention may find its application in humans with a wide variety of clinical conditions. Some examples are given.

The invention has numerous areas of use and represents novel methodology for visualization and characterization of events taking place outside the brain vessels, namely within the extravascular space. Quantification of movement of substances within and from the cranio-spinal cavity has relevance for several physiological processes (sleep disturbances; normal ageing) and clinical conditions (Alzheimer's and dementia in general, brain tumor, multiple sclerosis and inflammatory brain disease, stroke such as brain infarction or bleeds, neurodegenerative disease, CSF circulation disorders, traumatic brain injury, neurometabolic diseases, glaucoma, chronic headache and migraine). However, the invention does not diagnose disease.

Example #1

Alzheimer's disease and dementia in general. The present invention provides for establishing information about the ability of movement of molecular substances within and from the cranio-spinal cavity in early Alzheimer's disease, or in individuals at risk of Alzheimer's disease, and other variants of dementia. The entorhinal cortex has an important role in cognition and dementia development. Changes within the entorhinal cortex are seen early in dementia. For example, the grid cells, which were described by the 2014 Nobel Prize recipients from NTNU in Norway, are in the entorhinal cortex. The present invention explores paravascular transport within this region as a function of contrast agent within nearby CSF compartment, and as a function of values from the extra-body device. Early changes in paravascular transport within this area may be seen in early dementia development. Hence, impaired paravascular transport within the various layers of the entorhinal cortex may be a function of the available contrast within the adjacent CSF compartment. It is possible to specifically segment this area on MRI, and provide for information from a large cohort of images transferred to a coordinate system. To assess movement of molecular substances within and from the cranio-spinal cavity in Alzheimer's, with a contrast agent being moving within the CSF space, MRI T1 weighted imaging is done at selectable time points. The MRI scans may be segmented to visualize the entorhinal cortex to assess degree of paravascular flow assessed as a function of available contrast agent in CSF. The T1 weighted MRI with contrast may be related to T1 weighted MRI acquisition from another time point wherein no contrast is present. Moreover, in the individual patient, the degree of impaired paravascular transport may be compared against a reference indicator fluid or material (seventh aspect of invention). We would expect that clearance of indicator fluids from limbic structures on CSF enhanced MRI would be impaired in early Alzheimer's, and have preliminary data supporting this view. Other kinds of dementia such as iNPH may present in a similar way. Finally, it should be noted that assessment of movement of molecular substances within and from the cranio-spinal cavity in Alzheimer's might be done using MRI contrast agents with various ligands attached. Such ligands might be therapeutic agents. By using the MRI contrast agent as carrier, the distribution of the specific compounds might be examined. The present invention also provides for assessing movement of molecular substances within and from the cranio-spinal cavity in early Alzheimer's, and in individuals at risk of developing the disease, without use of imaging methods by measuring levels of indicator fluid in blood and/or urine, at certain time points after indicator fluid having been administered to the CSF compartment. It is also from prior art described that amyloid-β is cleared from the brain to neck LNs, and the invention incorporates a method to assess clearance to LNs.

Example #2

Brain tumors. The present invention provides for an alternative way of assessing brain tumor invasion. This is particularly relevant for gliomas in areas of the brain not readily detected with current MRI techniques. There are no reliable methods for in vivo characterization of spread of glioma cells. Conventional MRI may present with normal signals though tumor cells are present. Glioma cells typically spread along the outside of the vessels of the brain and within the extracellular space. Diffusion techniques have only revealed alterations in limited areas close to the tumor. Conventional techniques apply intravenous contrast agents, which are restricted to the vascular (intra-vascular) compartment because of the BBB, and only distributes in local, extra-vascular spaces when the BBB is disrupted by tumor. With the present invention (e.g. Aspect 5), we provide a method that may reveal events on the outer side of the vessels. The present invention may reveal spread of tumor over larger areas, which often is expected, but not susceptible to current imaging methods. With CSF-enhanced MRI, SU would be expected to be lower in extra-vascular space where tumor invasion is present, than in normal tissue. However, attaching compounds with affinity for tumor cells to an indicator fluid, such as an MRI contrast agent, may cause SU to increase in areas of tumor cell invasion.

Example #3

Multiple sclerosis and inflammatory brain disease. The present invention provides for a method of macroscopically imaging the integrity of paravascular fluid spaces in demyelinating disease, which is a perivascular inflammation. This seems to be a main aspect of the pathogenesis of the disease. It is expected that Gd-based contrast agents will facilitate a signal drop in T1 weighted images. Attaching compounds with affinity for inflammation cells to an indicator fluid, such as an MRI contrast agent, may cause SU to increase in areas of inflammatory cell invasion. By this method, assessment of disease load and disease activity may be provided.

Example #4

Stroke (brain infarction or bleeds). The present invention provides for a novel assessment of edema after e.g. brain infarction due to cerebral artery occlusion. CSF enhanced MbRI with intrathecal contrast may be done in patients with occluded artery providing flow to main vascular territories, such as the middle cerebral artery, to assess to which degree paravascular transport of contrast agent is restricted due to reduced artery pulsations on that side, and by that study evolvement and treatment of brain edema associated with stroke. The invention also has the ability to detect reduced craniospinal clearance of macromolecular substances after stroke in assessment of stroke-related dementia.

Example #5

Sleep disturbances. The present invention enables assessment of rate of clearance in individuals with sleep disturbances. Recent evidence from basic neurosciences show that brain extracellular spaces increase much (tenfold) during sleep. This might be due to shrinkage of brain cells including astrocytes. The increased volume of extracellular spaces during sleep may contribute to enhanced clearance of waste solutes from the brain. Thereby, it might be examined in the individual patient to which extent the sleep disturbance affects brain clearance, which might be the most severe negative consequence of sleep deprivation. The impact of sleep quality on glymphatic function may also be studied. Further, in sleep-deprived patients, efforts might be taken to enhance paravascular transport and the efficacy might be assessed by the present invention.

Example #6

Neurodegenerative disease. Some experimental evidence from the basic sciences suggests that impaired brain clearance of substances may be accompanied with neurodegeneration. In this regard, the present invention may provide a method to assess impaired clearance from brain tissue, which may be linked to hampered clearance of toxic waste solutes leading to neurodegeneration.

Example #7

CSF circulation disorders. The present invention provides for a method to differentiate between "total brain clearance" and "regional brain clearance". Many clinical conditions may be characterized by regional alterations in brain clearance, for example brain cysts, idiopathic intracranial hypertension (IIH), dementia, and non-communicating hydrocephalus (HC). All these conditions include CSF circulation disturbances. It is of interest to determine regional change in brain transport of fluid and metabolites. Overall brain clearance may be tested by measuring change in SU in draining LNs of the neck, or from blood or urine samples. In patients with CSF circulation disorders, CSF enhanced MRI may be combined with ventricular and/or lumbar infusion tests to extract information about fluid transport with pressure-volume reserve capacity.

Example #8

Traumatic brain injury. Traumatic brain injury may be associated with a wide range of events such as infarction, edema and astrogliosis, which would be expected to hamper clearance of toxic metabolites from the brain. Pathogenic mechanisms behind long-term effects of brain trauma are poorly understood.

Example #9

Neurometabolic diseases. The present invention provides for detection of compromised overall and regional clearance of toxic metabolites from the brain. Neurometabolic diseases are characterized by accumulation of toxic metabolites within the brain, which causes destruction of brain tissue. Parkinson's disease and Amyotrophic lateral sclerosis (ALS) are examples of diseases that presently are incompletely described regarding etiology, and treatment options are unsatisfactory. The present invention renders for a new approach to characterize such diseases further.

Example #10

Glaucoma. The present invention enables assessment how solutes like neurotoxins and inflammatory proteins are cleared from the ISF in the optic nerve through the glymphatic system and thereby shed light on the pathogenesis for glaucoma.

Example #11

Headache and migraine. The present invention enables assessment of how solutes like neurotoxins and inflammatory proteins are cleared from the ISF in individuals with headache and migraine.

Example #12

Ageing. The present invention provides for assessment of effects of ageing in general. Animal studies show that cerebral clearance is impaired with ageing. With an ageing population increased focus is on the effects of ageing. The present invention provides quantifying effects of ageing on brain clearance.

Although the invention provides for an improved understanding of flow or movement of substances within, to or from a CSF, brain or spinal cord compartment of a craniospinal cavity of a human, the invention does not provide for a specific diagnosis of illness or health deficiency of a type as mentioned in Examples 1-12 mentioned above, as any such diagnosis will also have to be dictated by other medical criteria. Further, the invention does not provide for any medical treatment.

APPENDIX A—ABBREVIATIONS

ALS=Amyotrophic lateral sclerosis
AQP4=Aquaporin-4
AUC=Area under curve
BBB=Blood-brain-barrier
BDNF=Brain-derived neurotrophic factor
CAT=Computerized axial tomography
CI=Confidence intervals
CNS=Central nervous system
CSF=Cerebrospinal fluid
CT=Computer tomography
Da=Dalton (=gr/mole)
DAPC=Dystrophin-associated protein complex
Dp71=Dystrophin-71
DSCE=Dynamic susceptibility weighted, contrast enhanced
DTPA=Diethylenetriaminepentaacetic acid
FDG=Fluoro-2-deoxyglucose
FE=First enhancement
FLAIR=Fluid attenuated inversion recovery
FOV=Field of view
GCI=Gamma camera imaging
Gd-DTPA=Gadolinium-diethylenetriamine
GFR=Glomerular filtration rate
HU=Hounsfield unit
ICP=Intracranial pressure
IFG=Inferior frontal gyms
iNPH=Idiopathic normal pressure hydrocephalus
ISF=Interstitial fluid
i.th.=Intrathecal
LN=Lymph node
mAbs=Monoclonal antibodies
MRI=Magnetic resonance imaging
MW=Molecular weight
Niftii=Neuroimaging informatics technology initiative
PACS=Picture archiving and communication system
PET=Positron emission tomography
REF=Reference RF=Radiofrequency
ROI=Region of interest
SPECT=Single photon emission CT
SU=Signal unit
SUV=Standard uptake value
SWI=Susceptibility weighted imaging
TTP=Time to peak
TTT=Tissue transit time
Å$^2$=Ångström

What is claimed is:

1. A method for assessing ability of a cranio-spinal cavity of a human subject to remove molecular substances therefrom, comprising:
    (a) measuring once or at selectable time intervals a concentration or radiation level of an indicator fluid in a blood or urine sample from the subject, wherein the sample has been obtained following administration of the indicator fluid to the cerebrospinal fluid compartment of the subject's cranio-spinal cavity, and wherein the indicator fluid comprises:
        (i) a computed tomography (CT) contrast agent,
        (ii) a magnetic resonance imaging (MRI) contrast agent, or
        (iii) a radioactive ligand detectable by one or more of positron emission tomography (PET), single photon emission computed tomography (SPECT), or scintigraphy imaging, and
    (b) determining a parameter of removal from the measurement that indicates the ability of the cranio-spinal cavity to remove molecular substances, wherein the parameter of removal comprises at least one of:
        (i) a concentration or a change in concentration of the indicator fluid, or a level or a change in level of nuclear radiation when the indicator fluid is a radioactive ligand,
        (ii) removal of the indicator fluid versus time, or
        (iii) half-time of the indicator fluid, or half-life when the indicator fluid is a radioactive ligand.

2. The method of claim 1, wherein the parameter of removal includes time to maximum concentration level of the indicator fluid, maximum concentration level of the indicator fluid, coefficient between maximum concentration level and time to maximum concentration level of the indicator fluid, time from maximum to minimum concentration level of the indicator fluid, decline in concentration level of the indicator fluid, and coefficient between concentration level and time from maximum to minimum concentration level of the indicator fluid.

3. The method of claim 1, wherein the parameter of removal indicates the ability of the cranio-spinal cavity to remove waste solutes from the cerebrospinal fluid, brain, or spinal cord compartment.

4. The method of claim 1, wherein the indicator fluid is non-lipophilic, does not pass the blood-brain barrier, and does not interact with other molecules or with cellular metabolism.

5. The method of claim 1, wherein the CT contrast agent comprises iohexol, iodixanol, iomeprol, ioversol, or iobitridol.

6. The method of claim 1, wherein the MRI contrast agent comprises gadobutrol or gadoteric acid.

7. The method of claim 1, wherein the radioactive ligand comprises $^{89}$Zirconium, $^{99m}$Tc-DTPA, or $^{111}$In-DTPA.

8. The method of claim 1, wherein the indicator fluid is coupled with one or more of: an antibody, monoclonal antibody, recombinant protein, or antisense or gene therapeutic.

9. The method of claim 1, wherein the indicator fluid binds to tumor cells, inflammation cells, or amyloid beta plaques.

10. The method of claim 1, further comprising comparing the parameter of removal from the subject to a corresponding parameter of removal from a reference cohort.

11. The method of claim 1, further comprising comparing the parameter of removal to an indication signal within regions of interest of a cerebrospinal fluid, brain, or spinal cord compartment in the subject obtained by MRI, CT, PET, SPECT, or scintigraphy imaging.

12. The method of claim 11, wherein the comparison comprises one or more of:
    (a) a relationship between times to peak during an enhancement phase,
    (b) a relationship between maximum levels of indicator fluid concentration and maximum indication signal level,
    (c) a relationship between coefficient of enhancement phase indicator fluid concentration and coefficient of indication signal level,
    (d) a relationship between time from maximum to minimum indicator fluid concentration versus indication signal level,
    (e) a relationship between decrease in indicator fluid concentration level from maximum to minimum and reduction in indication signal level from maximum to minimum, or
    (f) a relationship between indicator fluid concentration level and indication signal level at any single time point.

13. The method of claim 1, further comprising obtaining the blood or urine sample from the subject.

14. The method of claim 1, further comprising administering the indicator fluid to the subject.

15. The method of claim 14, wherein the indicator fluid is administered by spinal puncture, intrathecal injection, an intracisternal route, or an intraventricular route.

16. A computer-assisted method for assessing ability of a cranio-spinal cavity of a human subject to remove molecular substances therefrom, comprising:
    (a) measuring once or at selectable time intervals with a detector operatively linked to a computer a concentration or radiation level of an indicator fluid in a blood or urine sample from the subject, wherein the sample has been obtained following administration of the indicator fluid to the cerebrospinal fluid compartment of the subject's cranio-spinal cavity, and wherein the indicator fluid comprises:
        (i) a computed tomography (CT) contrast agent,
        (ii) a magnetic resonance imaging (MRI) contrast agent, or
        (iii) a radioactive ligand detectable by one or more of positron emission tomography (PET), single photon emission computed tomography (SPECT), or scintigraphy imaging, and
    (b) analyzing the blood or urine sample with a computer to determine a parameter of removal of the indicator fluid that indicates the ability of the cranio-spinal cavity to remove molecular substances, wherein the parameter of removal comprises at least one of:
        (i) a concentration or a change in concentration of the indicator fluid, or a level or a change in level of nuclear radiation when the indicator fluid is a radioactive ligand,
        (ii) removal of the indicator fluid versus time, (iii) half-time of the indicator fluid, or half-life when the indicator is a radioactive ligand, and (c) presenting the parameter of removal from a computer output.

17. The method of claim 16, further comprising comparing the parameter of removal from the subject to a corresponding parameter of removal from a reference cohort that is stored in the computer.

18. The method of claim 16, wherein the parameter of removal includes time to maximum concentration level of the indicator fluid, maximum concentration level of the indicator fluid, coefficient between maximum concentration level and time to maximum concentration level of the indicator fluid, time from maximum to minimum concentration level of the indicator fluid, decline in concentration level of the indicator fluid, and coefficient between concentration level and time from maximum to minimum concentration level of the indicator fluid.

19. The method of claim 16, wherein the parameter of removal indicates the ability of the cranio-spinal cavity to remove waste solutes from the cerebrospinal fluid, brain, or spinal cord compartment.

20. The method of claim 16, wherein the indicator fluid is non-lipophilic, does not pass the blood-brain barrier, and does not interact with other molecules or with cellular metabolism.

21. The method of claim 16, wherein the CT contrast agent comprises iohexol, iodixanol, iomeprol, ioversol, or iobitridol.

22. The method of claim 16, wherein the MRI contrast agent comprises gadobutrol or gadoteric acid.

23. The method of claim 16, wherein the radioactive ligand comprises $^{89}$Zirconium, $^{99m}$Tc-DTPA, or $^{111}$In-DTPA.

24. The method of claim 16, wherein the indicator fluid is coupled with one or more of: an antibody, monoclonal antibody, recombinant protein, or antisense or gene therapeutic.

25. The method of claim 16, wherein the indicator fluid binds to tumor cells, inflammation cells, or amyloid beta plaques.

26. The method of claim 16, further comprising comparing the parameter of removal to an indication signal within regions of interest of a cerebrospinal fluid, brain, or spinal cord compartment in the subject obtained by MRI, CT, PET, SPECT, or scintigraphy imaging.

27. The method of claim 26, wherein the comparison comprises one or more of:

(a) a relationship between times to peak during an enhancement phase, (b) a relationship between maximum levels of indicator fluid concentration and maximum indication signal level, (c) a relationship between coefficient of enhancement phase indicator fluid concentration and coefficient of indication signal level, (d) a relationship between time from maximum to minimum indicator fluid concentration versus indication signal level, (e) a relationship between decrease in indicator fluid concentration level from maximum to minimum and reduction in indication signal level from maximum to minimum, or (f) a relationship between indicator fluid concentration level and indication signal level at any single time point.

* * * * *